(12) United States Patent
Molinari et al.

(10) Patent No.: US 6,894,061 B2
(45) Date of Patent: May 17, 2005

(54) SUBSTITUTED DIHYDROPHENANTHRIDINE SULFONAMIDES

(75) Inventors: Albert John Molinari, Pottstown, PA (US); Mark Antony Ashwell, Carlisle, MA (US); Brian Hugh Ridgway, Belmont, CA (US); Amedeo Arturo Failli, Princeton Junction, NJ (US); William Jay Moore, Collegeville, PA (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 10/718,461

(22) Filed: Nov. 20, 2003

(65) Prior Publication Data

US 2004/0167155 A1 Aug. 26, 2004

Related U.S. Application Data

(60) Provisional application No. 60/430,949, filed on Dec. 4, 2002.

(51) Int. Cl.[7] .................... A61K 31/473; C07D 221/12
(52) U.S. Cl. .................. 514/298; 546/108; 546/109; 546/110; 544/324; 514/269
(58) Field of Search ................ 514/298, 269; 546/108, 109, 110; 544/324

(56) References Cited

U.S. PATENT DOCUMENTS 5,153,185 A  10/1992  DiNinno et al. ........ 514/210.14

FOREIGN PATENT DOCUMENTS

| EP | 509756 A1 | 10/1992 |
|---|---|---|
| EP | 509780 A1 | 10/1992 |
| EP | 761669 A2 A3 | 3/1997 |
| FR | 5762 M | 2/1968 |
| GB | 1 135 947 A | 12/1968 |
| WO | 99/05113 A1 | 2/1999 |
| WO | 00/42018 A1 | 7/2000 |
| WO | 00/42020 A1 | 7/2000 |
| WO | 01/42219 A2 | 6/2001 |
| WO | 02/05616 A1 | 1/2002 |
| WO | 02/20463 A1 | 3/2002 |

OTHER PUBLICATIONS

Adams, M. R. et al., "Inhibition of Coronary Artery Atherosclerosis by 17–beta Estradiol in Ovariectomized Monkeys," *Arterio.*, 1990, 10(6), 1051–1057.

Alexander et. al., "Initiation of Hormone Replacement Therapy After Acute Myocardial Infarction Is Associated With More Cardiac Events During Follow–Up," *J. Am. Coll. Cardio.*, 2001, 38, 1–7.

Bauer M. A., Herrmann F., "Interleukin–6 in clinical medicine," *Ann. Hematol.*, 1991, 62, 203–210.

Cefalu, W., "The Use of Hormone Replacement Therapy in Postmenopausal Women with Type 2 Diabetes," *J Womens Health & Gender–based Med.*, 2001, 10(3), 241–255.

Chin–Chi Lin et.al., "Pulmonary function changes and increased Th–2 cytokine expression and nuclear factor kB activation in the lung after sensitization and allergen challenge in brown Norway rats," *Immunol. Lett.*, 2000, 73, 57–64.

(Continued)

*Primary Examiner*—Charanjit S. Aulakh
(74) *Attorney, Agent, or Firm*—Woodcock Washburn LLP

(57) ABSTRACT

This invention provides a compound of formulae (I) or (II) having the structure

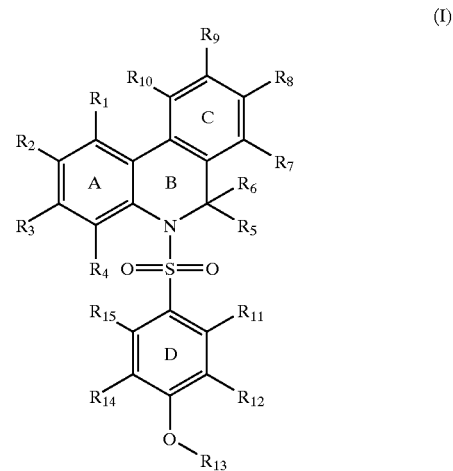

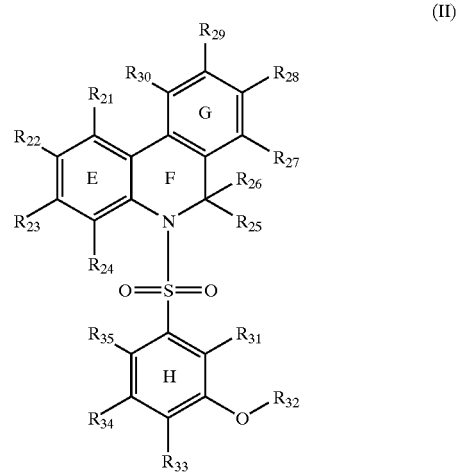

or a pharmaceutically acceptable salt thereof which are useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatiod arthritis.

29 Claims, No Drawings

OTHER PUBLICATIONS

Delyani, J. A. et al., "Protection from Myocardial Reperfusion Injury by Acute Administration of 17β–Estradiol," *J. Molec. Cell. Cardiol.*, 1996, 28, 1001–1008.

Felson, D. T. et al., "The effects of estrogen on osteoarthritis,", *Curr Opinion Rheum*, 1998, 10, 269–272.

Finkelstein, J. et al. "Derivatives of 6–Methyl–5,6–dihydrophenanthridine," *J. Am. Chem. Soc.*, 1950, 72, 3282–3.

Grigg, R. et al., "Palladium Catalysed Triscyclisation–Anion Capture Queuing Cascades," *Tetrahedron Lett.*, 1997, 38(10), 1825–1828.

Grigg, R. et al., "Phenanthrene type heterocycles via Rh(I) catalysed [2+2+2]–cycloaddition and Pd(0) catalysed arylation," *Tetrahedron Lett.*, 2000, 41(16), 3003–3006.

Grigg, R. et al., "Palladium Catalysed Intramolecular Coupling of Aryl and Benzylic Halides and Related Tandem Cyclisations," *Tetrahedron Lett.*, 1991, 32(31), 3859–3862.

Grodstein, F. et. al., "A Prospective, Observational Study of Postmenopausal Hormone Therapy and Primary Prevention of Cardiovascular Disease," *Ann. Int. Med.*, 2000, 133, 933–41.

Grodstein F. et. al., "Postmenopausal Hormone Use and Secondary Prevention of Coronary Events in the Nurses' Health Study," *Ann. Int. Med*, 2001, 135, 1–8.

Hulley, S. et. al., "Randomized Trial of Estrogen Plus Progestin for Secondary Prevention of Coronary Heart Disease in Postmenopausal Women," *J. Am. Med. Assoc.*, 1998, 280, 605–13.

Huppatz, J. L. et al., "Pschorr Reactions With Sulphonamides Derived From N–Benzyl–o–Phenylenediamine: A New Route to Phenanthridine, and a New Type of Molecular Rearrangement," *Aust. J. Chem.*, 1963, 16, 417–431.

Huppatz, J. L. et al., "Synthesis of 9–Bromophenanthridine and 7–Bromophenanthridine by Pschorr Reactions with Sulphonamides Derived from N–p–Bromobenzyl– and N–o–Bromobenzyl–o–Phenylenediamines, and a New Route to N–Sulphonylcarbazoles," *Aust. J. Chem.*, 1964, 17, 1407–1417.

Huppatz, J. L. et al., "Pschorr Reactions with Sulphonamides Derived from N–Aminobenzyl–Aniline: Synthesis of a 4–Bromophenanthridine and Formation of 6–Phenyl–7H–Dibenzo[d,f]–[1,2]–Thiazepine–5–Dioxide," *Aust. J. Chem.*, 1965, 18(2), 206–212.

Kant, J. et al., "Reissert Compound Studies. XLV. The Phenanthridine Reissert Compound," *J. Heterocycl. Chem.*, Mar.–Apr. 1984, 21, 425–427.

Kurebayashi S. et. al., "Characterization of Mechanisms of Interleukin–6 Gene Repression by Estrogen Receptor," *J. Steroid Biochem. Molec. Biol.*, 1997, 60, 11–17.

Miura, M. et al., "Oxidative Cross–Coupling of N–(2'–Phenylphenyl)benzene–sulfonamides or Benzoic and Naphthoic Acids with Alkenes Using a Palladium–Copper Catalyst System under Air," *J. Org. Chem.*, 1998, 63, (15), 5211–5215.

Nathan, L. et. al., "Estradiol Inhibits Leukocyte Adhesion and Transendothelial Migration in Rabits In Vivo," *Circ. Res.*, 1999, 85, 377–385.

Paterson et al., "Azabenzocycloheptenones. Part IV. An Azadibenzotropone," *J. Chem. Soc.*, 1962, 3468–3472.

Patra, P. K., et al., "A New Regiospecific Method for the Synthesis of Substituted Phenanthridines and Benzo[j] phenanthridines via Aromatic Annelation of 1–N–Benzenesulfonyl–3–[Bis9methylthio)methylene]–1,2,3, 4–tetrahydroquinoline–4–one," *Tetrahedron*, 1998, 54(34), 10167–10178.

Peaston, W. C. et al, "Azabenzocycloheptenones. VIII. Further observations in the dibenz[b,d]azepine–7–one field," *J. Chem. Soc.*, 1968, 19, 2481–4. Chemical Abstracts Service, HCAPLUS Accession No. 1968:496433, Document No. 69:96433 (Abstract).

Pelletier et al., "Osteoarthritis, an Inflammatory Disease," *Arthr. & Rheum.*, 2001, 44:1237–1247.

Reis et. al., "Estrogen Is Associated With Improved Survival in Aging Women With Congestive Heart Failure: Analysis of the Vesnarinone Studies," *J. Am. Coll. Cardio.*, 2000, 36, 529–33.

Roth, A. et. al., "Phytoestrogen Kaempferol (3,4,5,7–Tetrahydroxylflavone) Protects PC12 and T47D Cells From β–Amyloid–Induced Toxicity," *J. Neurosci. Res.*, 1999, 57, 399–404.

Schonknecht, P. et. al., "Reduced cerebrospinal fluid estradiol levels are associated with increased β–amyloid levels in female patients with Alzheimer's disease," *Neurosci. Lett.*, 2001, 307, 122–124.

Sullivan, T. R. et al. "Estrogen Inhibits the Response–to–Injury in a Mouse Carotid Artery Model," *J. Clin. Invst.*, 1995, 96, 2482–8.

Ulmer, L. et al., "Mono– and bisfunctionalization of fullerenes with N–containing reactants," *J. Inf. Rec.*, 1998, 24(3–4), 243–247. Chemical Abstracts Service, Accession No. 1999:251961, HCAPLUS Registry No. 226909–66–6 (Abstract).

Yuan et al., "Reversal of Obesity– and Diet–Induced Insulin Resistance with Salicylates or Targeted Disruption of Ikkβ," *Science*, 2001, 293, 1673–7.

Chemical Abstracts Service, CA Registry No. 213486–09–0.
Chemical Abstracts Service, CA Registry No. 213486–08–9.
Chemical Abstracts Service, CA Registry No. 211621–30–6.
Chemical Abstracts Service, CA Registry No. 211621–27–1.
Chemical Abstracts Service, CA Registry No. 211621–26–0.
Chemical Abstracts Service, CA Registry No. 211621–25–9.
Chemical Abstracts Service, CA Registry No. 211621–24–8.
Chemical Abstracts Service, CA Registry No. 211621–23–7.
Chemical Abstracts Service, CA Registry No. 211621–22–6.
Chemical Abstracts Service, CA Registry No. 211621–21–5.
Chemical Abstracts Service, CA Registry No. 211621–20–4.
Chemical Abstracts Service, CA Registry No. 91871–03–3.
Chemical Abstracts Service, CA Registry No. 19711–96–7.
Chemical Abstracts Service, CA Registry No. 2608–29–9.
Chemical Abstracts Service, CA Registry No. 1096–83–9.
Chemical Abstracts Service, CA Registry No. 279680–75–0.
Chemical Abstracts Service, CA Registry No. 279680–74–9.
Chemical Abstracts Service, CA Registry No. 226909–66–6.
Chemical Abstracts Service, CA Registry No. 226909–63–3.
Chemical Abstracts Service, CA Registry No. 213486–15–8.
Chemical Abstracts Service, CA Registry No. 213486–14–7.
Chemical Abstracts Service, CA Registry No. 213486–13–6.
Chemical Abstracts Service, CA Registry No. 213486–12–5.
Chemical Abstracts Service, CA Registry No. 213486–11–4.
Chemical Abstracts Service, CA Registry No. 213486–10–3.
Chemical Abstracts Service, CA Registry No. 213486–07–8.

Chemical Abstracts Service, CA Registry No. 213486–05–6.
Chemical Abstracts Service, CA Registry No. 213486–04–5.
Chemical Abstracts Service, CA Registry No. 188755–32–0.
Smith, M. B.; March, J. March's Advanced Organic Chemistry: Reactions, Mechanisms, and Structure, 5th ed.; John Wiley & Sons: New York, 2001.

Greene, T. W.; Wuts, P. G. M. Protective Groups in Organic Synthesis, 3rd ed.; John Wiley & Sons: New York, 1999.
Ulmer, L. et al., "Preparation and Characterization of Sulfonyl–Azafulleroid and Sulfonylaziridino–Fullerene Derivatives," *Eur. J. Org. Chem.,* 2003, No. 15, pp. 2933–2940.

SUBSTITUTED DIHYDROPHENANTHRIDINESULFONAMIDES

CROSS REFERENCE TO RELATED APPLICATIONS

This application claims the benefit of U.S. Provisional Application Ser. No. 60/430,949, filed Dec. 4, 2002, which is incorporated herein by reference in its entirety.

BACKGROUND OF THE INVENTION

This invention relates to ligands for the estrogen receptor (ER), and specifically relates to substituted dihydrophenanthridinesulfonamides useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatoid arthritis.

The ability of ligands for the estrogen receptor to inhibit inflammatory gene expression causing a reduction of cytokines, chemokines, adhesion molecules and inflammatory enzymes provides a means to treat the inflammatory component of diseases such as atherosclerosis, myocardial infarction (MI), congestive heart failure (CHF), inflammatory bowel disease and arthritis. Other potential therapeutic indications for these type of molecules include type II diabetes (Cefalu, *J Womens Health & Gender-based Med.*, 2001, 10, 241 & Yuan et al., *Science*, 2001, 293, 1673), osteoarthritis (Pelletier et al., *Arthr. & Rheum.*, 2001, 44:1237 and Felson et al., *Curr Opinion Rheum*, 1998, 10, 269) asthma (Chin-Chi Lin et. al., *Immunol. Lett.*, 2000, 73, 57), Alzheimer's disease (Roth, A. et. al.; *J. Neurosci. Res.*, 1999, 57, 399) and autoimmune diseases such as multiple sclerosis and rheumatoid arthritis.

A common component of these chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.*, 1991, 62, 203). Synthesis of the IL-6 gene is induced by the transcription factor, nuclear factor κB (NF-κB). Interference at this step in the inflammatory process can effectively regulate the uncontrolled proliferative process that occurs in these chronic conditions.

In endothelial cells, 17β-estradiol (E2) inhibits IL-1β induced NF-κB reporter activity and IL-6 expression in an ER dependent fashion (Kurebayashi S. et. al., *J. Steroid Biochem. Molec. Biol.*, 1997, 60, 11). This correlates with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.*, 1990, 1051, Sullivan, T. R. et al. *J. Clin. Invst.*, 1995, 96, 2482, Nathan, L. et. al., *Circ. Res.*, 1999, 85, 377). Similar effects of estrogen on the vascular wall have also been demonstrated in animal models of myocardial infarction (Delyani, J. A. et al., *J. Molec. Cell. Cardiol.*, 1996, 28, 1001) and congestive heart failure. Clinically, estrogen replacement therapy (ERT) has been demonstrated to reduce the risk of mortality in patients with both CHF (Reis et. al., *J. Am. Coll. Cardio.*, 2000, 36, 529) and MI (Grodstein, F. et. al., *Ann. Int. Med.*, 2000, 133, 933, Alexander et. al., *J. Am. Coll. Cardio.*, 2001, 38, 1 and Grodstein F. et. al., *Ann. Int. Med*, 2001, 135, 1). In ERT, clinical studies demonstrated an influence of E2 on the decrease in the production. of β-amyloid 1–42 (Aβ42), a peptide central for the formation of senile plaques in Alzheimer's disease (Schonknecht, P. et. al., *Neurosci. Lett.*, 2001, 307, 122).

However, 17-β-estradiol also strongly stimulates creatine kinase expression. Thus, in ERT some potential unwanted side effects, such as an increase risk of cardiovascular events in the first year of use, have been demonstrated (Hulley, S. et. al., *J. Am. Med. Assoc.*, 1998, 280, 605) as well as proliferative effects on uterine and breast tissue.

DETAILED DESCRIPTION OF ILLUSTRATIVE EMBODIMENTS

The invention provides substituted dihydrophenanthridinesulfonamides represented by the general formulae (I) and (II) that are useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatoid arthritis.

This invention provides novel compounds of formulae (I) or (II) having the structure

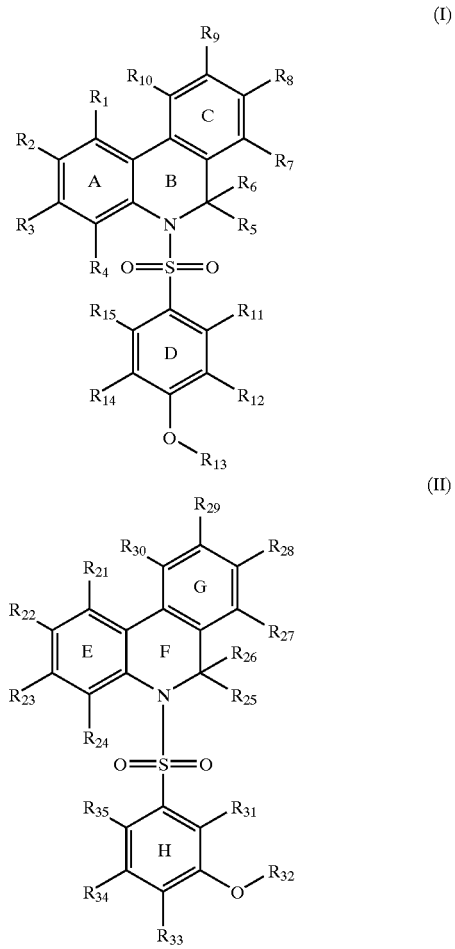

wherein
$R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either $R_{p+1}$ or $R_{p-1}$ linked with an -alkylene-, or —X-alkylene- group;

$R_5$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, —CR(O), —CO$_2$R, or —C(O)N(R)$_2$; or $R_5$ may be taken together with either $R_6$ or $R_7$ and linked with an -alkylene- or —X-alkylene- group;

$R_6$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, —CR(O), —CO$_2$R, or —C(O)N(R)$_2$; or $R_6$ may be taken together with either $R_5$ or $R_7$ and linked with an -alkylene- or —X-alkylene- group;

$R_{13}$ is R, $R_{17}$—X—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_2$-C$_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

X is O, —NR—, —S(O)$_m$—, —C(O)—, —OC(O)—, —C(O)O—, —NRC(O)—, or —C(O)NR—;

m is 0, 1, or 2;

p is 2, 3, 6, 7, 8, 9, 12, 13, or 14;

$R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either $R_{q+1}$ or $R_{q-1}$ linked with an -alkylene-, or —Y-alkylene- group;

$R_{25}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{25}$ may be taken together with either $R_{26}$ or $R_{27}$ and linked with an -alkylene- or —Y-alkylene- group;

$R_{26}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{26}$ may be taken together with either $R_{25}$ or $R_{27}$ and linked with an -alkylene- or —Y-alkylene- group;

$R_{32}$ is R, $R_{17}$—Y—$R_{16}$—, $R_{17}$—S(O)—, $R_{17}$—S(O)$_2$—, —SO$_3$R, —S(O)$_2$N(R)$_2$, or D-glucuronidate;

Y is O, —NR—, —S(O)$_n$—, —C(O)—, —OC(O)—, —C(O)O—, —NRC(O)—, or —C(O)NR—;

n is 0, 1, or 2;

q is 22, 23, 26, 27, 28, 29, 32, 33, or 34;

or pharmaceutically acceptable salts thereof.

The term "alkyl", employed alone, is defined herein as, unless otherwise stated, either a (C$_1$-C$_{20}$) straight chain or (C$_3$-C$_{20}$) branched-chain monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like. It is preferred that straight chain alkyl moieties have 1–6 carbon atoms, and branched alkyl moieties have 3–8 carbon atoms.

The term "alkenyl", employed alone, is defined herein as, unless otherwise stated, either a (C$_2$-C$_{20}$) straight chain or (C$_3$-C$_{20}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like. It is preferred that straight chain alkenyl moieties have 2–7 carbon atoms, and branched alkenyl moieties have 3–8 carbon atoms.

The term "alkynyl", employed alone, is defined herein as, unless otherwise stated, either a (C$_2$-C$_{20}$) straight chain or (C$_3$-C$_{20}$) branched-chain monovalent hydrocarbon moiety containing at least one triple bond. Examples of alkynyl moieties include, but are not limited to, chemical groups such as ethynyl, 1-propynyl, 1-(2-propynyl), 3-butynyl, and higher homologs, isomers, and the like. It is preferred that straight chain alkynyl moieties have 2–7 carbon atoms, and branched alkynyl moieties have 3–8 carbon atoms.

The term "alkylene", employed alone or in combination with other terms, is defined herein as, unless otherwise stated, either a (C$_1$-C$_{20}$) straight chain or (C$_2$-C$_{20}$) branched-chain bivalent hydrocarbon moiety derived from an alkane; or a (C$_2$-C$_{20}$) straight chain or branched-chain bivalent hydrocarbon moiety derived from an alkene. Such hydrocarbon alkylene moieties may be fully saturated, or mono or polyunsaturated, and may exist in the E or Z configurations. The compounds of this invention are meant to include all possible E and Z configurations. Examples of saturated and unsaturated hydrocarbon alkylene moieties include, but are not limited to, bivalent chemical groups such as —CH$_2$—, —CH$_2$CH$_2$—, —CH$_2$CH$_2$CH$_2$—, —CH$_2$CH$_2$CH$_2$CH$_2$—, —CH=CH—, —CH=CHCH=CH—, vinylidene, and higher homologs, isomers, and the like. Preferred alkylene chains have 2–7 carbon atoms.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3–10 carbon atoms, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The term "cycloalkenyl", employed alone or in combination with other terms, is defined herein as, unless otherwise stated, a monocyclic, bicyclic, tricyclic, fused, bridged, or spiro monovalent unsaturated hydrocarbon moiety of 3–10 carbon atoms containing at least one double bond, wherein the carbon atoms are located inside or outside of the ring system. Any suitable ring position of the cycloalkenyl moiety may be covalently linked to the defined chemical structure. Examples of cycloalkenyl moieties include, but are not limited to, chemical groups such as cyclopropenyl, cyclopropenylmethyl cyclobutenyl, cyclopentenyl, cyclohexenyl, cyclohexenylmethyl, cyclohexenylethyl, cycloheptenyl, norbornenyl, and homologs, isomers, and the like.

The term "cycloalkylene", employed alone, is defined herein as, unless otherwise stated, a bivalent moiety of 3–10 carbon atoms derived from a monocyclic, bicyclic, tricyclic, fused, bridged, or spiro hydrocarbon. Such hydrocarbon cycloalkylene moieties may be fully saturated, or mono or polyunsaturated, and may exist in the E or Z configurations. The compounds of this invention are meant to include all possible E and Z configurations. Any suitable ring position of the cycloalkylene moiety may be covalently linked to the defined chemical structure. Examples of saturated and unsaturated hydrocarbon cycloalkylene moieties include, but are not limited to, bivalent chemical groups such as cyclopropylene, cyclopentylene, cyclohexylene, cyclohexenylene, trans-decahydronaphthalenylene, spiro[3.3]heptenylene, and higher homologs, isomers, and the like.

The terms "halo" or "halogen", employed alone or in combination with other terms, is defined herein as, unless otherwise stated, a fluorine, chlorine, bromine, or iodine atom.

The term "monofluoroalkyl", employed alone, is defined herein as, unless otherwise stated, either a $(C_1–C_{10})$ straight chain or $(C_3–C_{10})$ branched-chain monovalent saturated hydrocarbon moiety containing only one fluorine atom. Examples of monofluoroalkyl moieties include, but are not limited to, chemical groups such as —$CH_2F$, —$CH_2CH_2F$, —$CH(CH_3)CH_2CH_2F$, and higher homologs, isomers, and the like. Preferred chain lengths are from 1–6 carbon atoms for straight chains and from 3–8 carbon atoms for branched chains.

The term "monofluoroalkenyl", employed alone, is defined herein as, unless otherwise stated, either a $(C_2–C_{10})$ straight chain or $(C_3–C_{10})$ branched-chain monovalent unsaturated hydrocarbon moiety, containing only one fluorine atom and at least one double bond. Examples of monofluoroalkenyl moieties include, but are not limited to, chemical groups such as —$CH=CH_2F$, —$CH_2CH=CH_2F$, —$CH=CHCH_2F$, —$C(CH_3)=CHF$ and higher homologs, isomers, and the like. Preferred chain lengths are from 2–7 carbon atoms for straight chains and from 3–8 carbon atoms for branched chains.

The term "perfluoroalkyl", employed alone or in combination with other terms, is defined herein as, unless otherwise stated, either a $(C_1–C_{10})$ straight chain or $(C_3–C_{10})$ branched-chain monovalent saturated hydrocarbon moiety containing two or more fluorine atoms. Examples of perfluoroalkyl moieties include, but are not limited to, chemical groups such as trifluoromethyl, —$CH_2CF_3$, —$CF_2CF_3$, and —$CH(CF_3)_2$, and homologs, isomers, and the like. Preferred chain lengths are from 1–7 carbon atoms for straight chains and from 3–8 carbon atoms for branched chains.

The term "aryl", employed alone or in combination with other terms, is defined herein as, unless otherwise stated, an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. It is preferred that the aryl moiety contain 6–14 carbon atoms.

The term "arylalkyl", employed alone or in combination with other terms, is defined herein as, unless otherwise stated, an aryl group, as herein before defined, suitably substituted on any open ring position with an alkyl moiety wherein the alkyl chain is either a $(C_1–C_6)$ straight or $(C_2–C_7)$ branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "heteroaryl", employed alone or in combination with other terms, is defined herein as, unless otherwise stated, an aromatic heterocyclic ring system, which may be a single ring (monocyclic) or multiple rings (bicyclic, up to three rings) fused together or linked covalently. The rings may contain from one to four hetero atoms selected from nitrogen (N), oxygen (O), or sulfur (S), wherein the nitrogen or sulfur atom(s) are optionally oxidized, or the nitrogen atom(s) are optionally substituted or quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole, 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like.

The term "heteroarylalkyl", employed alone or in combination with other terms, is defined herein as, unless otherwise stated, a heteroaryl group, as herein before defined, suitably substituted on any open ring position with an alkyl moiety, wherein the alkyl chain is either a $(C_1–C_6)$ straight or $(C_2–C_7)$ branched-chain saturated hydrocarbon moiety. Examples of heteroarylalkyl moieties include, but are not limited to, chemical groups such as furanylmethyl, thienylethyl, indolylmethyl, and the like.

Heteroaryl chemical groups, as herein before defined, also include saturated or partially saturated heterocyclic rings. Examples of saturated or partially saturated heteroaryl moieties include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "acyl", employed alone or in combination with other terms, is defined herein as, unless otherwise stated, either an alkyl, arylalkyl, heteroarylalkyl, ($C_2$–$C_{10}$) straight chain, or ($C_4$–$C_{11}$) branched-chain monovalent hydrocarbon moiety; wherein the carbon atom, covalently linked to the defined chemical structure, is oxidized to the carbonyl oxidation state. Such hydrocarbon moieties may be mono or polyunsaturated, and may exist in the E or Z configurations. The compounds of this invention are meant to include all possible E and Z configurations. Examples of acyl moieties include, but are not limited to, chemical groups such as acetyl, propionyl, butyryl, 3,3-dimethylbutyryl, trifluoroacetyl, pivaloyl, hexanoyl, hexenoyl, decanoyl, benzoyl, nicotinyl, isonicotinyl, and homologs, isomers, and the like.

The term "hydroxyalkyl", employed alone or in combination with other terms, is defined herein as, unless otherwise stated, a ($C_1$–$C_{10}$) straight chain hydrocarbon, terminally substituted with a hydroxyl group. Examples of hydroxyalkyl moieties include chemical groups such as —$CH_2OH$, —$CH_2CH_2OH$, —$CH_2CH_2CH_2OH$, and higher homologs.

The term "alkoxy", employed alone or in combination with other terms, is defined herein as, unless otherwise stated, either a ($C_1$–$C_{10}$) straight chain or ($C_3$–$C_{10}$) branched-chain hydrocarbon covalently bonded to an oxygen atom. Examples of alkoxy moieties include, but are not limited to, chemical groups such as methoxy, ethoxy, isopropoxy, sec-butoxy, tert-butoxy, decanoxy, and homologs, isomers, and the like.

The terms "aryloxy" or "heteroaryloxy", employed alone or in combination with other terms, or unless otherwise stated, are aryl or heteroaryl groups, as herein before defined, which are further covalently bonded to an oxygen atom. Examples of aryloxy, or heteroaryloxy moieties include, but are not limited to, chemical groups such as $C_6H_5O$—, 4-pyridyl-O—, and homologs, isomers, and the like.

The term "carbonyl", employed alone or in combination with other terms, is defined herein as, unless otherwise stated, a bivalent one-carbon moiety further bonded to an oxygen atom with a double bond. An example is

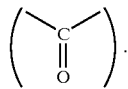

The term "alkoxycarbonyl", employed alone or in combination with other terms, is defined herein as, unless otherwise stated, an alkoxy group, as herein before defined, which is further bonded to a carbonyl group to form an ester moiety. Examples of alkoxycarbonyl moieties include, but are not limited to, chemical groups such as methoxycarbonyl, ethoxycarbonyl, isopropoxycarbonyl, sec-butoxycarbonyl, tert-butoxycarbonyl, decanoxycarbonyl, and homologs, isomers, and the like.

The term "alkylthio", employed alone or in combination with other terms, is defined herein as, unless otherwise stated, either a ($C_1$–$C_{10}$) straight chain or ($C_3$–$C_{10}$) branched-chain hydrocarbon moiety covalently bonded to a sulfur atom. Examples of alkylthio moieties include, but are not limited to, chemical groups such as methylthio, ethylthio, isopropylthio, sec-butylthio, tert-butylthio, decanylthio, and homologs, isomers, and the like. It is preferred that straight chain alkylthio moieties have 1–6 carbon atoms, and branched alkylthio moieties have 3–8 carbon atoms.

The terms "arylthio" or "heteroarylthio", employed alone or in combination with other terms, or unless otherwise stated, are aryl or heteroaryl groups, as herein before defined, which are further covalently bonded to a sulfur atom. Examples of arylthio or heteroarylthio moieties include, but are not limited to, chemical groups such as $C_6H_5S$—, 4-pyridyl-S—, and homologs, isomers, and the like.

The terms "alkoxyalkyl" or "alkylthioalkyl", employed alone or in combination with other terms, are an alkoxy or alkylthio group, as herein before defined, which is further covalently bonded to an unsubstituted ($C_1$–$C_{10}$) straight chain or unsubstituted ($C_2$–$C_{10}$) branched-chain hydrocarbon. Examples of alkoxyalkyl or alkylthioalkyl moieties include, but are not limited to, chemical groups such as, methoxymethyl, methylthioethyl, ethylthioethyl, isopropylthiomethyl, sec-butylthioethyl, —$CH_2CH(CH_3)$ $OCH_2CH_3$, and homologs, isomers, and the like. It is preferred that straight chain alkoxyalkyl or alkylthioalkyl moieties have 1–6 carbon atoms, and branched alkoxyalkyl or alkylthioalkyl moieties have 3–8 carbon atoms.

The terms "aryloxyalkyl", "heteroaryloxyalkyl", "arylthioalkyl", or "heteroarylthioalkyl", employed alone or in combination with other terms, or unless otherwise stated, are aryloxy, heteroaryloxy, arylthio, or heteroarylthio groups, as herein before defined, which are further covalently bonded to an unsubstituted ($C_1$–$C_{10}$) straight chain or unsubstituted ($C_2$–$C_{10}$) branched-chain hydrocarbon. Examples of aryloxyalkyl, heteroaryloxyalkyl, arylthioalkyl, or heteroarylthioalkyl moieties include, but are not limited to, chemical groups such as $C_6H_5OCH_2$—, $C_6H_5OCH(CH_3)$—, 4-pyridyl-O—$CH_2CH_2$—, $C_6H_5SCH_2$—, $C_6H_5SCH(CH_3)$—, 4-pyridyl-S—$CH_2CH_2$—, and homologs, isomers, and the like. It is preferred that straight chain aryloxyalkyl, heteroaryloxyalkyl, arylthioalkyl, or heteroarylthioalkyl moieties have 1–6 carbon atoms, and branched aryloxyalkyl, heteroaryloxyalkyl, arylthioalkyl, or heteroarylthioalkyl moieties have 3–8 carbon atoms.

The term "alkylamino", employed alone or in combination with other terms, or unless otherwise stated, is a moiety with one alkyl group, wherein the alkyl group is an unsubstituted ($C_1$–$C_6$) straight chain hereunto before defined alkyl group or an unsubstitued ($C_3$–$C_8$) hereunto before defined cycloalkyl group. Examples of alkylamino moieties include, but are not limited to, chemical groups such as —$NH(CH_3)$, —$NH(CH_2CH_3)$, —NH-cyclopentyl, and homologs, and the like.

The term "dialkylamino", employed alone or in combination with other terms, or unless otherwise stated, is a moiety with two independent alkyl groups, wherein the alkyl groups are unsubstitued ($C_1$–$C_6$) straight chain hereunto before defined alkyl groups or unsubstitued ($C_3$–$C_8$) hereunto before defined cycloalkyl groups. Two groups may be linked to form an unsubstituted ($C_1$–$C_6$)-alkylene- group. Examples of dialkylamino moieties include, but are not limited to, chemical groups such as —$N(CH_3)_2$, —$N(CH_2CH_3)_2$, —$NCH_3(CH_2CH_3)$,

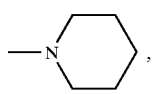

and homologs, and the like.

The term "alkylaminoalkyl" employed alone or in combination with other terms, or unless otherwise stated, is an alkylamino moiety, as herein before defined, which is further covalently bonded to a straight chain alkyl group of 1–6 carbon atoms. Examples of alkylaminoalkyl moieties include, but are not limited to, chemical groups such as —CH$_2$NH(CH$_3$), —CH$_2$CH$_2$NH(CH$_2$CH$_3$), —CH$_2$CH$_2$CH$_2$NH(CH$_2$CH$_3$), and homologs, and the like.

The term "dialkylaminoalkyl" employed alone or in combination with other terms, or unless otherwise stated, is a dialkylamino moiety, as herein before defined, which is further covalently bonded to a straight chain alkyl group of 1–6 carbon atoms. Examples of dialkylaminoalkyl moieties include, but are not limited to, chemical groups such as —CH$_2$N(CH$_3$)$_2$, —CH$_2$CH$_2$N(CH$_2$CH$_3$)$_2$, —CH$_2$CH$_2$CH$_2$NCH$_3$(CH$_2$CH$_3$), and homologs, and the like.

The terms "alkylaminocarbonyl" or "dialkylaminocarbonyl", employed alone, or unless otherwise stated, are alkylamino or dialkylamino moieties, as herein before defined, which are further bonded to a carbonyl group. Examples of alkylaminocarbonyl or dialkylaminocarbonyl moieties include, but are not limited to, chemical groups such as —C(O)NH(CH$_3$), —C(O)N(CH$_2$CH$_3$)$_2$, —C(O)NCH$_3$(CH$_2$CH$_3$), and homologs, and the like.

Each of the above terms (e.g., alkyl, aryl, heteroaryl) includes unsubstituted, monosubstituted, and polysubstituted forms of the indicated radical or moiety. Substituents for each type of moiety are provided below.

Substituents for alkyl, alkenyl, alkynyl, cycloalkyl, cycloalkenyl, alkylene, cycloalkylene, the alkyl portion of arylalkyl and heteroarylalkyl, saturated or partially saturated heterocyclic rings, and acyl or carbonyl moieties are, employed alone or in combination with other terms, selected from the group consisting of —R', OR', =O, =NR', =N—OR', —NR'R", —SR', halo, trifluoromethyl, trifluoromethoxy, —OC(O)R', —CO$_2$R', —C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', —S(O)$_2$R', —S(O)$_2$NR'R", cyano, and nitro; wherein, R' or R" are each, independently, hydrogen, unsubstituted (C$_1$–C$_6$)alkyl, unsubstituted (C$_3$–C$_7$)cycloalkyl, aryl, aryl-(C$_1$–C$_3$)alkyl, aryloxy-(C$_1$–C$_3$)alkyl, arylthio-(C$_1$–C$_3$)alkyl, heteroaryl, heteroaryl-(C$_1$–C$_3$)alkyl, heteroaryloxy-(C$_1$–C$_3$)alkyl, or heteroarylthio-(C$_1$–C$_3$)alkyl groups; or if optionally taken together may be linked as an alkylene- group to form a ring.

The aryl or heteroaryl moieties, employed alone or in combination with other terms, may be optionally mono-, di- or tri-substituted with substituents selected from the group consisting of —R', —OR', —SR', —C(O)R', —CO$_2$R', -alkoxyalkyl, alkoxyalkyloxy, cyano, halogen, nitro, trifluoromethyl, trifluoromethoxy, —NR'R", alkylaminoalkyl, dialkylaminoalkyl, hydroxyalkyl, —S(O)R', —S(O)$_2$R', —SO$_3$R', —S(O)$_2$NR'R", —CO$_2$R', —C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', and —S(O)$_2$R'; wherein, R' or R" are each, independently, hydrogen, (C$_1$–C$_6$)alkyl, (C$_3$–C$_7$)cycloalkyl, aryl, aryl-(C$_1$–C$_3$)alkyl, aryloxy-(C$_1$–C$_3$)alkyl, arylthio-(C$_1$–C$_3$)alkyl, heteroaryl, heteroaryl-(C$_1$–C$_3$)alkyl, heteroaryloxy-(C$_1$–C$_3$)alkyl, or heteroarylthio-(C$_1$–C$_3$)alkyl groups; or if optionally taken together may be linked as an -alkylene- group to form a ring.

A pro-drug is defined as a compound which is convertible by in vivo enzymatic or non-enzymatic metabolism (e.g. hydrolysis) to a compound of Formula (I) or Formula (II); wherein, R$_{13}$ or R$_{32}$ respectively is a hydrogen atom.

The compounds of the present invention may contain an asymmetric atom, and some of the compounds may contain one or more asymmetric atoms or centers, which may thus give rise to optical isomers (enantiomers) and diastereomers. While shown without respect to the stereochemistry in Formula (I) or (II), the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers may be obtained in pure form by standard procedures known to those skilled in the art, and include, but are not limited to, diasteromeric salt formation, kinetic resolution, and asymmetric synthesis. It is also understood that this invention encompasses all possible regioisomers, and mixtures thereof, which may be obtained in pure form by standard separation procedures known to those skilled in the art, and include, but are not limited to, column chromatography, thin-layer chromatography, and high-performance liquid chromatography.

The compounds of the present invention may contain isotopes of atoms for diagnostic, therapeutic, or metabolic purposes. Such isotopes may or may not be radioactive.

The compounds of this invention include racemates, enantiomers, geometric isomers, or pro-drugs of the compounds shown by formulae (I) or (II).

Pharmaceutically acceptable salts of the compounds of Formula (I) and Formula (II) with an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

As used in accordance with this invention, the term "providing," with respect to providing a compound or substance covered by this invention, means either directly administering such a compound or substance, or administering a pro-drug, derivative, or analog which will form the effective amount of the compound or substance within the body. This invention also covers providing the compounds of this invention to treat the disease states disclosed herein that the compounds are useful for treating.

Preferred compounds of this invention include those in which:

(A). the compound is of formula (II),
where the remaining substituents are as defined above.
Preferred compounds of this invention include those of
(A) in which:
(B). R$_{32}$ is hydrogen,
where the remaining substituents are as defined above.
Preferred compounds of this invention include those of
(B) in which:

(C). $R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are each, independently, hydrogen, $R_{17}$, aryl-$R_{16}$—, $R_{17}$—Y—$R_{16}$—, hydroxyalkyl, HO—$R_{16}$—, halogen, —OR, —COR, or —CO$_2$R;

$R_{25}$ and $R_{26}$ are each, independently, hydrogen or $R_{17}$;

$R_{16}$ is -alkylene-;

$R_{17}$ is alkyl, aryl, heteroaryl, or perfluoroalkyl;

R is hydrogen or alkyl;

where the remaining substituents are as defined above.

Most preferred compounds of this invention include those in which:

(D). the compound is of formula (I), where the remaining substituents are as defined above.

Most preferred compounds of this invention include those of (D) in which:

(E). $R_{13}$ is hydrogen, where the remaining substituents are as defined above.

Most preferred compounds of this invention include those of (E) in which:

(F). $R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, aryl-$R_{16}$—, $R_{17}$—X—$R_{16}$—, hydroxyalkyl, HO—$R_{16}$—, halogen, —OR, —COR, or —CO$_2$R;

$R_5$, and $R_6$, are each, independently, hydrogen or $R_{17}$;

$R_{16}$ is -alkylene-;

$R_{17}$ is alkyl, aryl, heteroaryl, or perfluoroalkyl;

R is hydrogen or alkyl;

where the remaining substituents are as defined above.

The compounds of the present invention can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. Although not limited to any one or several sources, classic texts such as Smith, M. B.; March, J. March's Advanced Organic Chemistry: Reactions, Mechanisms, and Structure, 5th ed.; John Wiley & Sons: New York, 2001; and Greene, T. W.; Wuts, P. G. M. Protective Groups in Organic Synthesis, 3rd ed.; John Wiley & Sons: New York, 1999 are useful and recognized reference textbooks of organic synthesis known to those in the art. The following synthetic schemes are designed to illustrate, but not limit, general procedures for the preparation of compounds of Formula (I) and Formula (II). An exemplary general procedure for the convenient preparation of such poly-substituted, dihydrophenanthridines is shown in the following schemes:

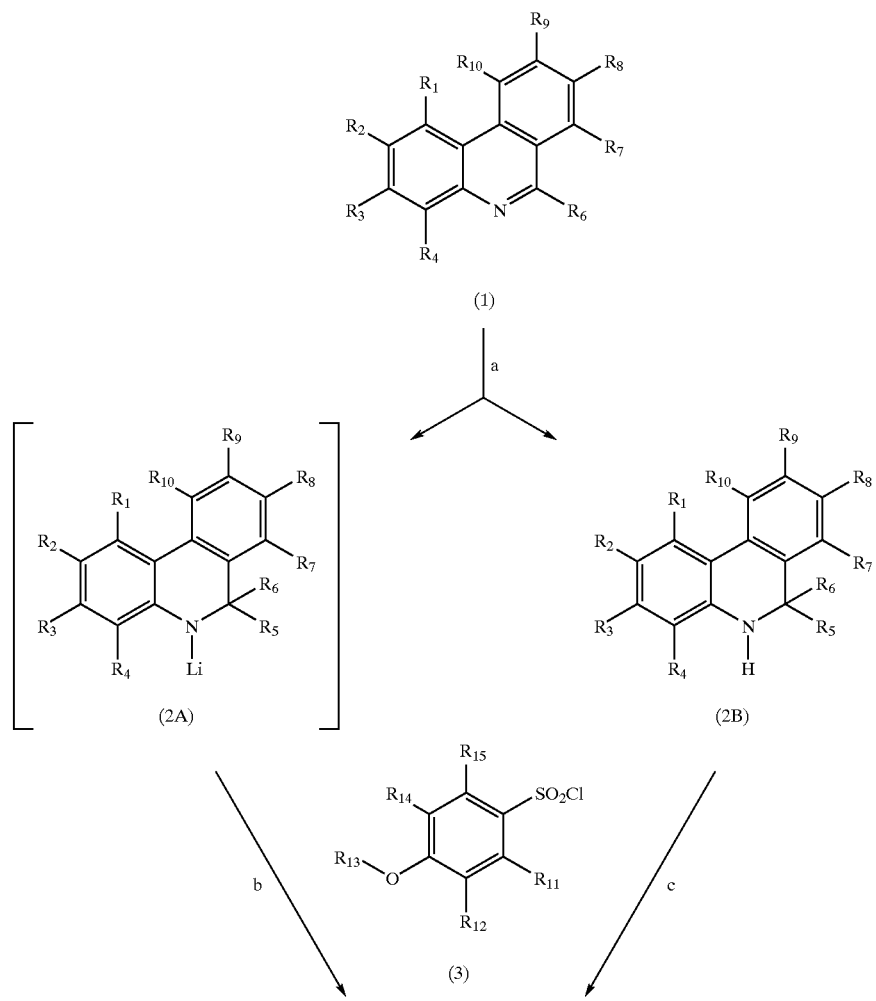

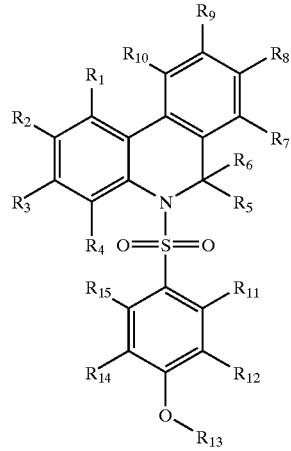

(4)

↓ d

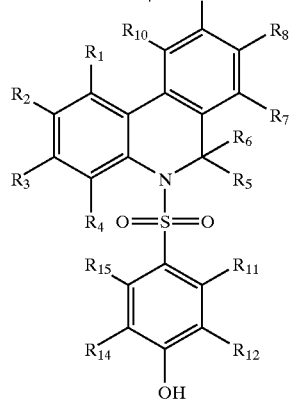

(5)

a. R$_5$Li, ether solvent, −78° C. to RT; b. (3) at −78° C. to RT; c. (3), pyridine, 80° C.;
d. When R$_{13}$ is methyl: BBr$_3$, cyclohexene, methylene chloride, 2–24 h., or when OR$_{13}$ is carbonate: 1N NaOH, methanol (1:1), 75° C., 12 h.

In scheme 1, step a, a suitably substituted phenanthridine (1), either commercially available, known in the literature, or prepared according to methods known and established for the preparation of said phenanthridines, including the schemes described below; wherein, R$_1$ through R$_{10}$ are herein before defined, is reacted with an R$_5$—Li reagent, either commercially available, known in the literature, or prepared according to methods known and established for the formation of lithium reagents, in a suitable solvent, such as diethyl ether, tetrahydrofuran, 1,4-dioxane, or the like, at temperatures between −78° C. and room temperature. The lithium amide salt (2A) is reacted in situ with a suitably substituted sulfonyl chloride (3), either commercially available, known in the literature, or prepared according to methods known and established for the preparation of said sulfonyl chlorides, including the schemes VII, VIII, IX, X, and XI described below, and exemplified in the experimental section at temperatures between −78° C. and room temperature. Alternatively, the suitably substituted dihydrophenanthridine (2B) can be isolated and reacted in a separate step with a suitable sulfonyl chloride (3), as previously described, in a non-reactive solvent, such as diethyl ether, tetrahydrofuran, 1,4-dioxane, chloroform, 1,2-dichloroethane, or typically dichloromethane, and the like, at temperatures between −78° C. and room temperature.

A methyl ether (4); wherein, R$_{13}$ is a methyl group, can be de-methylated in step d to the corresponding phenol (5) by contacting (4) with boron tribromide in the presence of an excess of olefin or cycloolefin, such as cyclohexene, acting as a bromine and hydrogen bromide scavenger, in a suitably halogenated solvent such as chloroform, 1,2-dichloroethane, or dichloromethane, and the like. Alternatively, the methyl ether (4) can be de-methylated to phenol (5) by contacting (4) with boron trichloride, in the presence of quaternary ammonium iodides, such as tetrabutylammonium iodide, in a suitably halogenated solvent, such as chloroform, 1,2-dichloroethane, or dichloromethane, and the like, at temperatures between −78° C. and room temperature for two to twenty-four hours.

If R$_{13}$ is a benzyl or diphenylmethyl protecting group, removal by suitably compatible hydrogenolysis techniques, known in the literature for effecting such transformations, such as hydrogen and 5% palladium-on-carbon catalysts will afford the desired phenol (5).

If —OR$_{13}$ is a carbonate moiety, treatment of (4) with a 1 N sodium hydroxide solution in methanol at typically 40° C. to 75° C., for a length of time, typically about twelve hours, will remove the protecting group to afford the desired phenol (5).

Scheme II
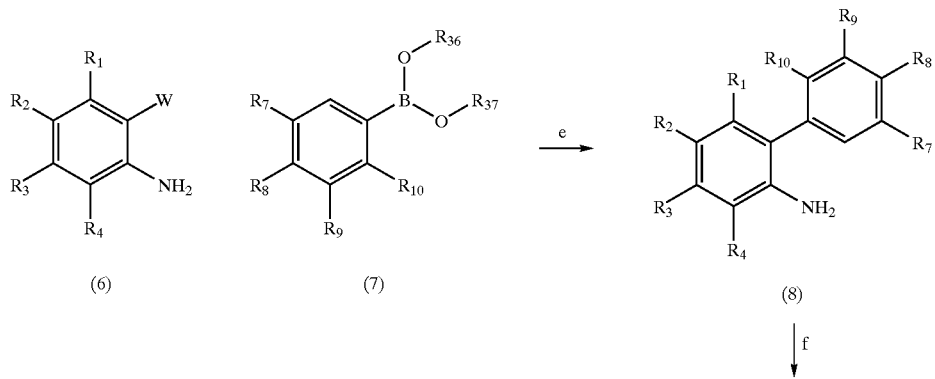
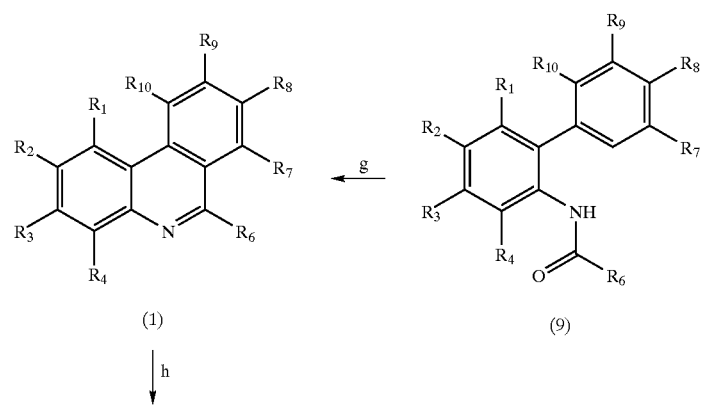
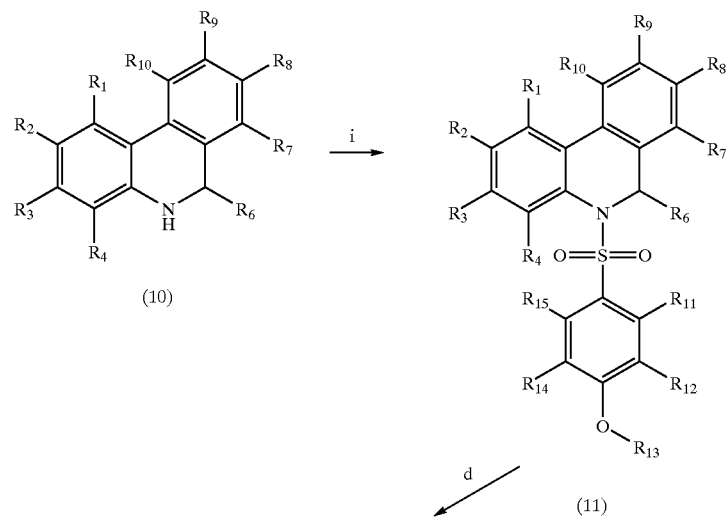

-continued

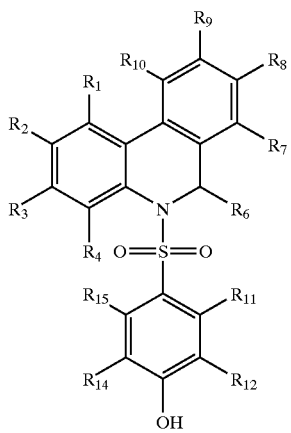

(12)

e. Pd(dppf)Cl$_2$, 5 mole %, THF, 5N NaOH, 23–70° C., 6–12 h.; f. R$_6$COCl or (R$_6$CO)$_2$O, CH$_2$Cl$_2$, 2–12 h.; g. POCl$_3$, acetonitrile, 85° C., 3 h., or polyphosphoric acid, 120° C., 24–48 h.; h. NaBH$_4$ (8 eq), trifluoroacetic acid (2 eq), THF, reflux, 8–16 h.; i. (3), triethylamine, CH$_2$Cl$_2$, 4–48 h.; or (3), pyridine, 80° C.; d. When R$_{13}$ is methyl: BBr$_3$, cyclohexene, dichloromethane, 2–24 h., or when OR$_{13}$ is carbonate: 1N NaOH, methanol (1:1), 75° C., 12 h.

In scheme II, step e, a suitably substituted haloaniline (6); wherein, W is a chlorine, bromine, or iodine atom, or triflate (—OSO$_2$CF$_3$) moiety, either commercially available, known in the literature, or prepared according to methods known and established for the preparation of said haloanilines or triflates, including procedures exemplified in the experimental section of this application; wherein, R$_1$ through R$_4$ are herein before defined, is reacted with a suitably substituted phenylboronic acid or ester (7), either commercially available, known in the literature, or prepared according to methods known and established for the preparation of said phenylboronic acids; wherein, R$_7$ through R$_{10}$ are herein before defined, and R$_{36}$ and R$_{37}$, are independently, hydrogen or (C$_1$–C$_4$) lower straight chain or (C$_3$–C$_6$) branched chain alkyl moieties, such as methyl, ethyl, and isopropyl, or where R$_{36}$ and R$_{37}$ are taken together, a pinacol moiety, in the presence of a coupling catalyst. The biphenylamine (8) is reacted in step f with an acid chloride or anhydride, wherein; R$_6$ is herein before defined, in a suitable solvent such as chloroform, 1,2-dichloroethane, or dichloromethane, and the like, optionally in the presence of an acid scavenger such as triethylamine, diisopropylethylamine, pyridine, or potassium carbonate, and the like, and further optionally in the presence of a known acylation promoter or catalyst, such as 4-(N,N-dimethylamino)pyridine at −20° C. to room temperature for several hours. In step g, treatment of the acylated biphenylamine (9) with phosphorous oxychloride in acetonitrile at 85° C. for typically three hours or treatment with polyphosphoric acid (neat) at 120° C. for typically 24–48 hours afforded phenanthridine (1). The phenanthridine (1) may be reduced in step h to the corresponding dihydrophenanthridine (10) with various reducing agents, such as sodium borohydride in the presence of an acid promoter or catalyst such as acetic acid, or trifluoroacetic acid, and the like, and in a suitable solvent, such as tetrahydrofuran, at an elevated temperature for eight to sixteen hours. The dihydrophenanthridine (10) may also be known in the literature, or prepared according to methods known and established for preparing said dihydrophenanthridines. The dihydrophenanthridine (10) may be sulfonylated to the sulfonamide (11) by contacting (10) with a sulfonyl chloride (3) in the presence of an acid scavenger such as triethylamine, diisopropylethylamine, or pyridine, and the like, in a suitable solvent such as chloroform, 1,2-dichloroethane, or dichloromethane from 4–48 hours at room temperature. Alternatively, the dihydrophenanthridine (10) and sulfonyl chloride (3) may be heated at 80° C. in pyridine for several hours to afford the sulfonamide (11). The protected phenol may be de-protected to phenol (12) as previously described for step d.

Scheme III

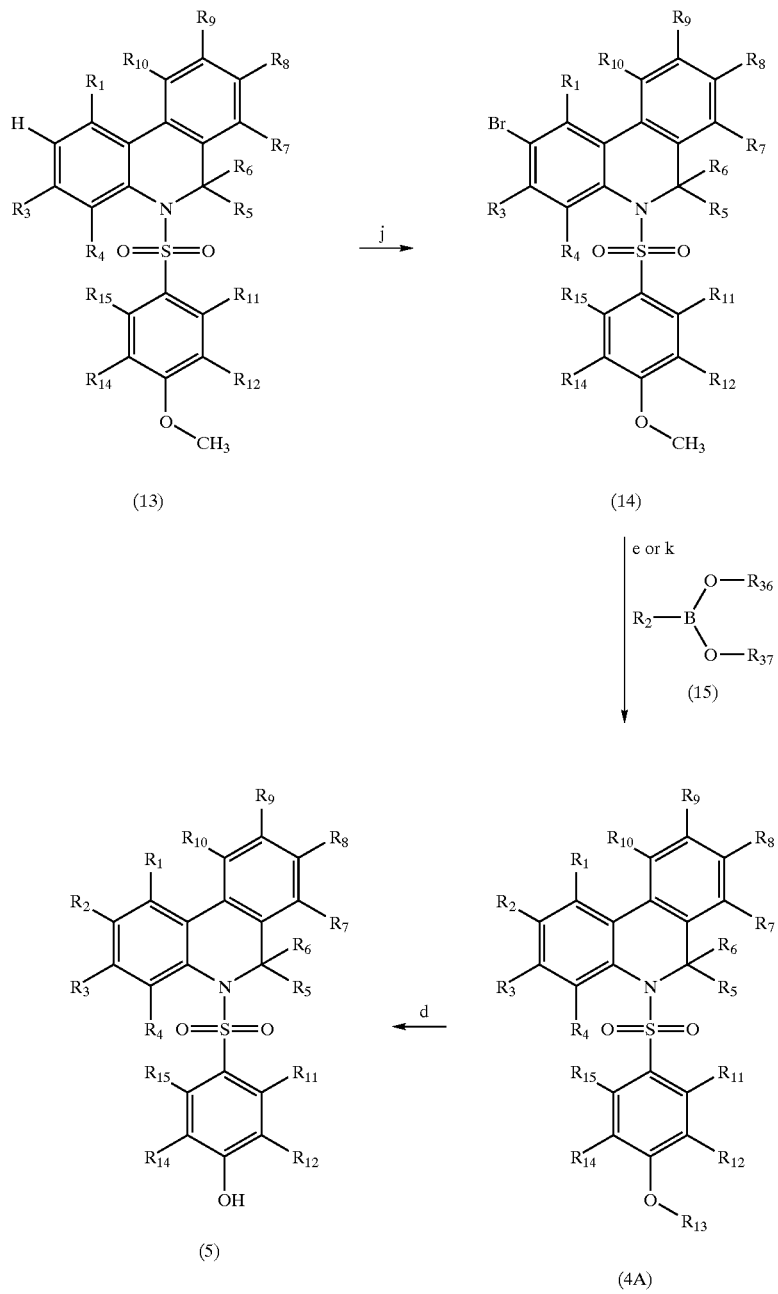

j. Excess bromine added over 7 hours, acetic acid, 50° C.; e. Pd(dppf)Cl$_2$, 5 mole %, THF, 5N NaOH, 23–70° C., 6–12 h. or k. tetrakis(triphenylphosphine)palladium (0), 15 mole %, R$_2$—B(OR$_{36}$)(OR$_{37}$) (2 equiv.) (15), 2M Na$_2$CO$_3$ (3 equiv.), 1,4-dioxane, 100° C., 1–6 hours; d. BBr$_3$, cyclohexene, dichloromethane, −30° C. to room temperature, 2–24 h.

In scheme III, the sulfonamide (13) may be brominated in step j with excess bromine in glacial acetic acid at 50° C. to afford (14), followed by a Suzuki reaction in steps e or k with (15); wherein, R$_2$ is herein before defined, in the presence of 1–10% coupling catalyst, such as [1,1'-bis (diphenylphosphino)ferrocene]dichloropalladium (II), complex with dichloromethane (1:1) in tetrahydrofuran with two equivalents of a 5 N sodium hydroxide solution at room temperature to 70° C. for 6–12 hours to afford (4A). Alternatively, (14) may be reacted with two equivalents of (15) in the presence of 1–15% coupling catalyst, such as tetrakis(triphenylphosphine)palladium (0) and a 2 M aqueous sodium carbonate solution in 1,4 dioxane at 100° C. for 1–6 hours. The protected phenol (4A) may be de-protected to phenol (5) as previously described for step d.

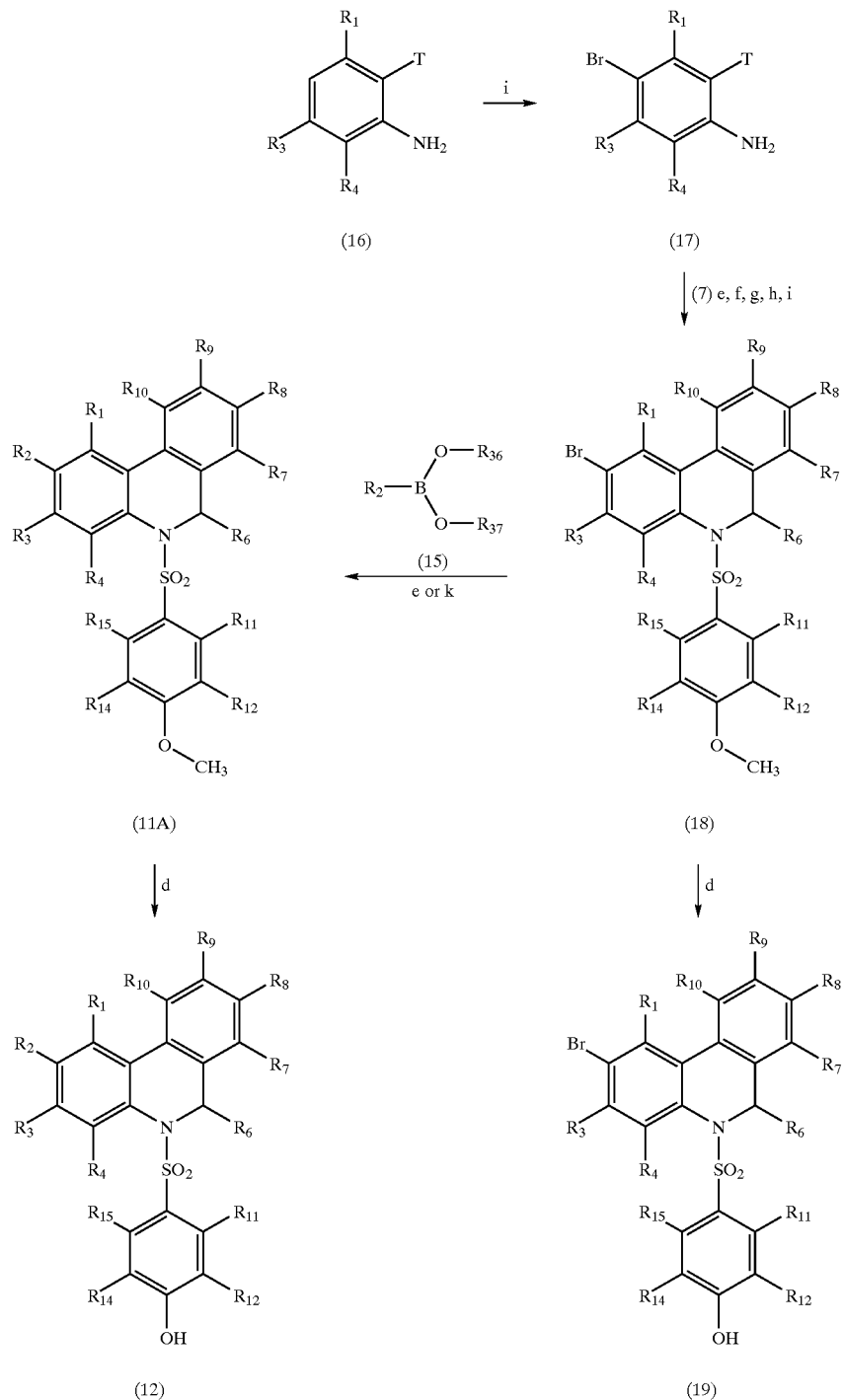

l. KBr (1.2 equiv.), (NH$_4$)$_6$Mo$_7$O$_{24}$·4H$_2$O (1 mole %), sodium perborate (1.1 equiv.); . Pd(dppf)Cl$_2$, 5 mole %, THF, 5N NaOH, 23–70° C., 6–12 h. or
k. tetrakis(triphenylphosphine)palladium (0), 15 mole %, R$_2$—B(OR$_{36}$)(OR$_{37}$) (2 equiv.) (15), 2M Na$_2$CO$_3$ (3 equiv.), 1,4-dioxane, 100° C., 1–6 hours; f. R$_6$COCl or (R$_6$CO)$_2$O, CH$_2$Cl$_2$, 2–12 h.; g. POCl$_3$, acetonitrile, 85° C., 3 h., or polyphosphoric acid, 120° C., 24–48 h.; h. NaBH$_4$ (8 eq), trifluoroacetic acid (2 equiv.), THF, reflux, 8–16 h.; i. (3B) (Scheme VII), triethylamine, CH$_2$Cl$_2$, 4–48 h.; or (3B) (Scheme VII), pyridine, 80° C.; d. BBr$_3$, cyclohexene, dichloromethane, 2–24 h.

In scheme IV, step I, a suitably substituted aniline (16); wherein, T is an iodine atom, or a triflate (—OSO$_2$CF$_3$) moiety, either commercially available, known in the literature, or prepared according to methods known and established for the preparation of said haloanilines or triflates, including procedures exemplified in the experimental section of this application; wherein, $R_1$, $R_3$, and $R_4$ are herein before defined, is reacted with potassium bromide, ammonium molybdate tetrahydrate, and sodium perborate in glacial acetic acid at room temperature for approximately three hours to afford the corresponding 4-bromoaniline (17). Coupling haloaniline (17) with a phenylboronic acid (7), as herein before defined, according to the previously described steps e, f, g, h, and i, will afford the 2-bromo dihydrophenanthridinesulfonamide (18). Further coupling of (18) with the boronic acid or ester (15), as herein before defined, according to the previously described steps e or k will afford the corresponding $R_2$-substituted dihydrophenanthridinesulfonamide (11A). The protected phenols (11A) or (18) may be de-protected to the corresponding phenols (12) or (19) as previously described for step d.

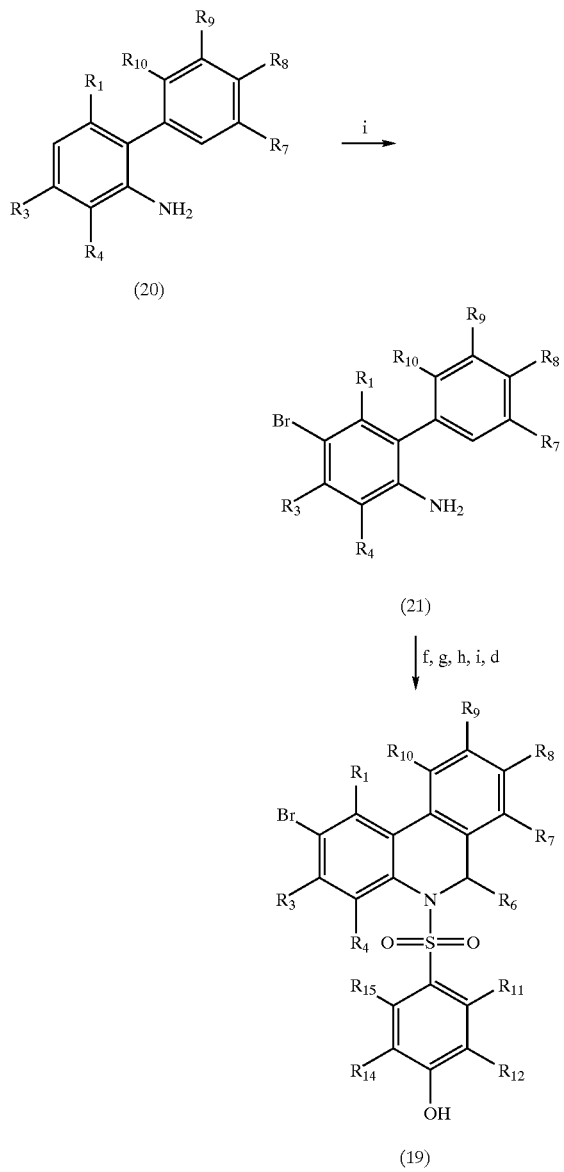

1. KBr (1.2 equiv.), $(NH_4)_6Mo_7O_{24} \cdot 4H_2O$ (1 mole %), sodium perborate (1.1 equiv.);
f. $R_6COCl$ or $(R_6CO)_2O$, $CH_2Cl_2$, 2–12 h.; g. $POCl_3$, acetonitrile, 85° C., 3 h., or polyphosphoric acid, 120° C., 24–48 h.; h. $NaBH_4$ (8 eq), trifluoroacetic acid (2 equiv.), THF, reflux, 8–16 h.; i. (3B), triethylamine, $CH_2Cl_2$, 4–48 h.; or (3B) (Scheme VII), pyridine, 80° C.; d. $BBr_3$, cyclohexene, dichloromethane, 2–24 h.

As an alternative to scheme IV, scheme V may be employed; wherein, the pre-formed biphenylamine (20), is brominated according to the previously described step I, followed by the previously described steps f, g, h, i, and optionally d to afford the protected phenol (18) or de-protected phenol (19).

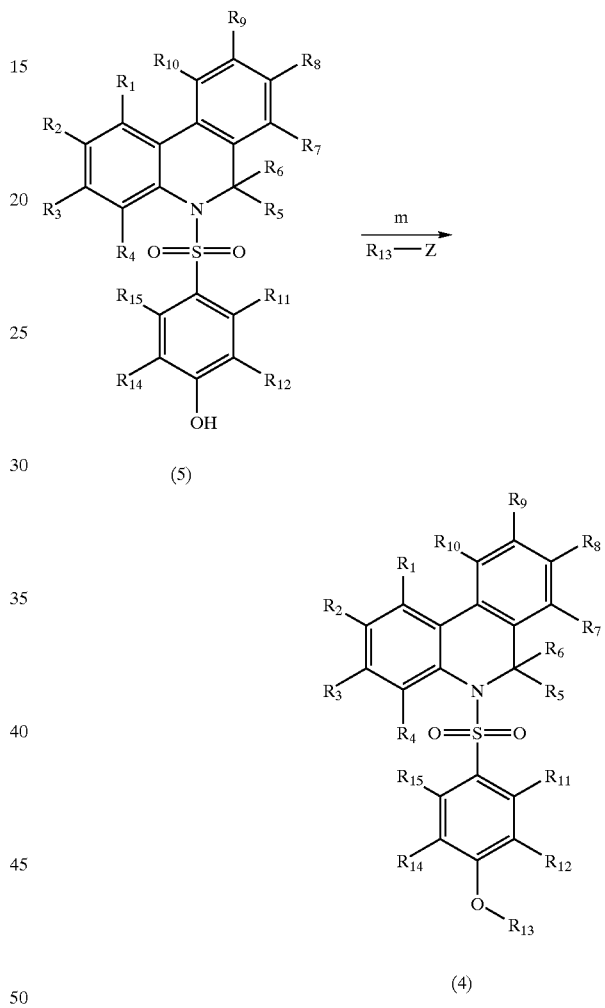

m. $R_{13}$—Z, base, solvent

A pro-drug is a compound of Formula (I) or Formula (II) that could facilitate absorption, inhibit or facilitate metabolism, affect distribution, or alter excretion of the pharmaceutically active agent. A pro-drug may be converted to the active pharmaceutical species by hydrolytic, enzymatic, or metabolic transformations. In scheme VI, the desired phenol (5) may be protected by alkylation or acylation of phenol (5) to prepare (4). This could be for the purpose of further synthetic elaboration, or for the reason of preparing pro-drugs, metabolites, or conjugates of (5). Consequently, $R_{13}$—Z; wherein, $R_{13}$ is as herein before defined, and Z is a leaving group, such as, but not limited to, a chlorine, bromine, or iodine atom, or a triflate (—$OSO_2CF_3$) or anhydride moiety, or a hydroxy (such as in Mitsunobu chemistry) moiety, is reacted under alkylating or acylating conditions with (5), optionally in the presence of a base, such as, but not limited to, triethylamine, diisopropylethylamine, pyridine, triphenylphosphine, or potassium carbonate, and the like, and further optionally in the presence of a known promoter or catalyst, such as 4-(N,N-dimethylamino)pyridine at −78° C. to 80° C. for several hours to afford the protected phenol (4).

Scheme VII

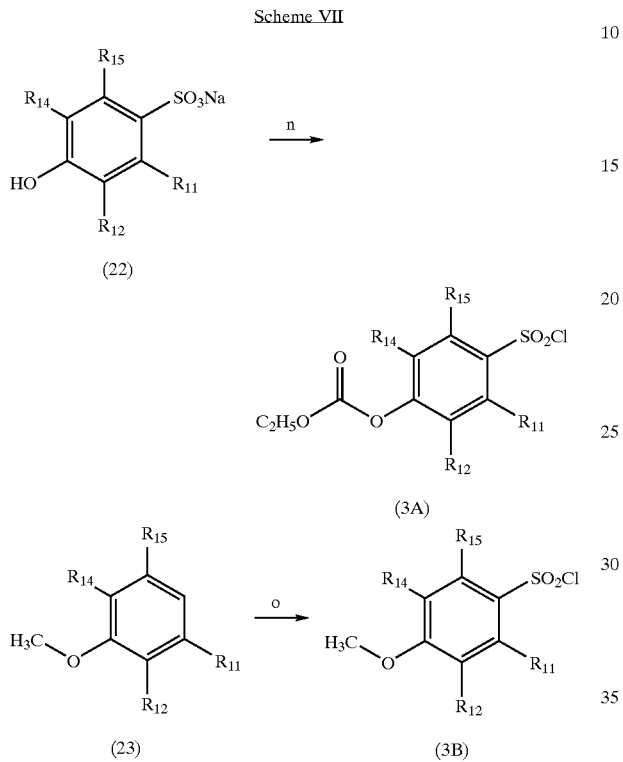

n. a. NaOH, ethyl chloroformate, water, 12 h., b. dimethylformamide, thionyl chloride, toluene, 100° C., 12 h.; o. chlorosulfonic acid (2 equiv.), 0° C. to room temperature, 12 h.

In scheme VII, step n, a suitably substituted sulfonic acid (22), either commercially available, known in the literature, or prepared according to methods known and established for the preparation of said sulfonic acids, including procedures exemplified in the experimental section of this application; wherein, $R_{11}$, $R_{12}$, $R_{14}$, and $R_{15}$ are herein before defined, is reacted with a base such as sodium or potassium hydroxide and an alkyl chloroformate in water for up to 12 hours, followed by thionyl chloride in an aromatic hydrocarbon such as toluene at up to 100° C. for up to 12 hours to afford the corresponding sulfonyl chloride (3A). Alternatively, in scheme VII, step o, a suitably substituted anisole (23), either commercially available, known in the literature, or prepared according to methods known and established for the preparation of said anisoles, including procedures exemplified in the experimental section of this application; wherein, $R_{11}$, $R_{12}$, $R_{14}$, and $R_{15}$ are herein before defined, is reacted with two equivalents of chlorosulfonic acid at 0° C. and allowed to stir at room temperature for up to 12 hours to afford the corresponding sulfonyl choride (3B). The structures (3A) and (3B) are specific embodiments of structure (3) and may be substituted for the more general (3) in schemes where appropriate.

Scheme VIII

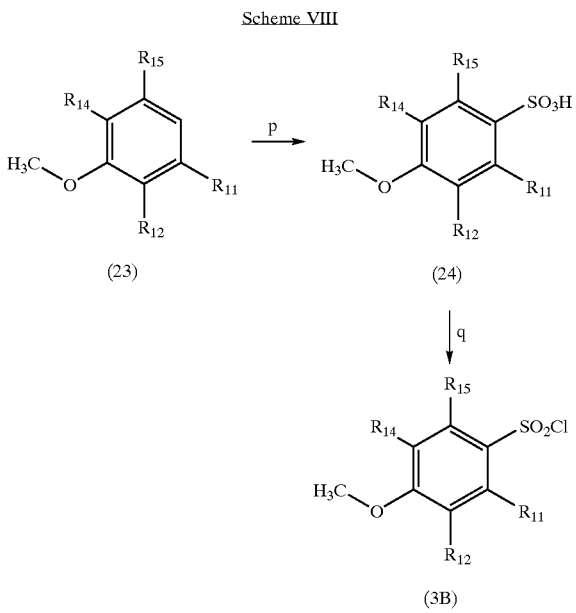

p. $H_2SO_4$, 20% $SO_3$, 100° C.; q. $PCl_5$ or dimethylformamide, thionyl chloride, toluene, 100° C.

Similarly, in scheme VIII, step p, the anisole (23) is reacted with concentrated sulfuric acid—20% sulfur trioxide complex at 100° C., followed in step q by phosphorus pentachoride or dimethylformamide and thionyl chloride in an aromatic hydrocarbon such as toluene at 100° C. to also afford (3B).

Scheme IX

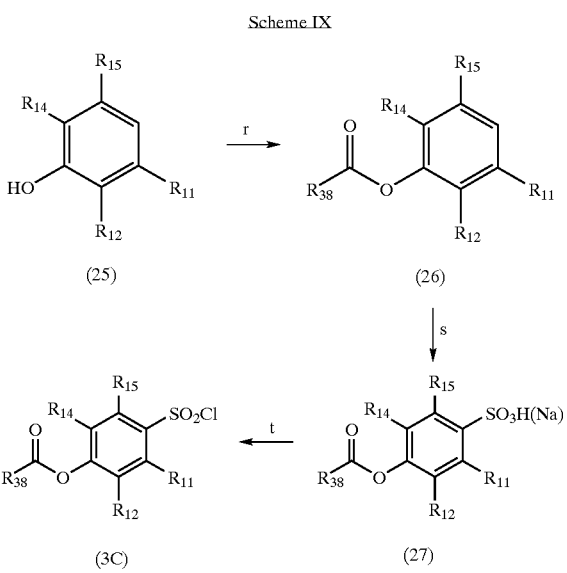

r. $R_{38}$—$CO_2H$, trifluoroacetic anhydride, trifluoroacetic acid, 0–5° C.; s. a. oleum (18–24%), trifluoroacetic anhydride (2 equiv.), trifluoroacetic acid, 0–5° C., b. $Na_2CO_3$, water (for salt formation); t. dimethylformamide, thionyl chloride, toluene, 100° C., 12 h.

In scheme IX, step r, a suitably substituted phenol (25), either commercially available, known in the literature, or prepared according to methods known and established for the preparation of said phenols, including procedures exemplified in the experimental section of this application; wherein, $R_{11}$, $R_{12}$, $R_{13}$, $R_{14}$, and $R_{15}$ are herein before defined, is reacted with an organic acid, $R_{38}$—$CO_2H$; wherein, $R_{38}$ is the above defined R or $R_{17}$—X—$R_{16}$—, and trifluoroacetic anhydride in trifluoroacetic acid at 0 to 5° C. to afford the corresponding (26). Treatment of (26) in step s with oleum (18–24%) and trifluoroacetic anhydride (2 equivalents) in trifluoroacetic acetic acid at 0 to 5° C., followed optionally by sodium or potassium carbonate in water, affords the free sulfonic acid or its corresponding sodium or potassium salt (27). Treatment of (27) in step t with dimethylformamide and thionyl chloride in an aromatic hydrocarbon solvent such as toluene at up to 100° C. for up to 12 hours affords the acylated sulfonyl chloride (3C). The acylated moiety (3C) is a specific embodiment of structure (3) and may be substituted for the more general (3); where appropriate, to form protected phenols and pro-drugs according to Formula (I).

Scheme X

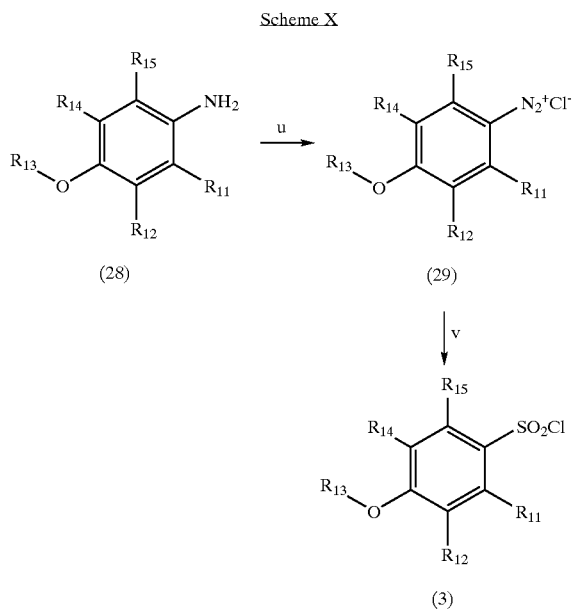

(28)　　　(29)

(3)

u. $NaNO_2$, HCl, −10° C.; v. Sulfur dioxide, copper (I) chloride, acetic acid, HCl, −10–+10° C.

In scheme X, step u, a suitably substituted para-anisidine (28), either commercially available, known in the literature, or prepared according to methods known and established for the preparation of said para-anisidines, including procedures exemplified in the experimental section of this application; wherein, $R_{11}$, $R_{12}$, $R_{13}$, $R_{14}$, and $R_{15}$ are herein before defined, is reacted with sodium nitrite and hydrochloric acid at −10° C. to form the corresponding diazonium salt (29). Treatment of (29) in step v with sulfur dioxide and copper (I) chloride in acetic acid and hydrochloric acid at −10 to +10° C. affords the corresponding sulfonyl chloride (3).

Scheme XI

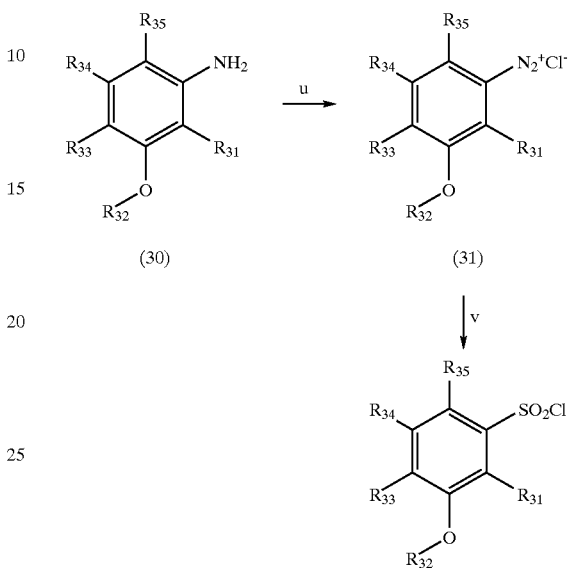

(30)　　　(31)

(32)

u. $NaNO_2$, HCl, −10° C.; v. Sulfur dioxide, copper (I) chloride, acetic acid, HCl, −10–+10° C.

In analogous fashion, compounds of Formula (II) may be prepared following all the above schemes with the appropriately substituted starting materials and reagents. In particular, following again steps u and v in scheme XI, a suitably substituted meta-anisidine (30), either commercially available, known in the literature, or prepared according to methods known and established for the preparation of said meta-anisidines, including procedures exemplified in the experimental section of this application; wherein, $R_{31}$, $R_{32}$, $R_{33}$, $R_{34}$, and $R_{35}$ are herein before defined, is reacted with sodium nitrite and hydrochloric acid at −10° C. to form the corresponding diazonium salt (31). Treatment of (31) in step v with sulfur dioxide and copper (I) chloride in acetic acid and hydrochloric acid at −10 to +10° C. affords the corresponding sulfonyl chloride (32). Sulfonyl chloride (32) may be substituted for sulfonyl chloride (3) in any scheme to afford the corresponding meta-substituted phenols or protected phenols of Formula (II).

Scheme XII

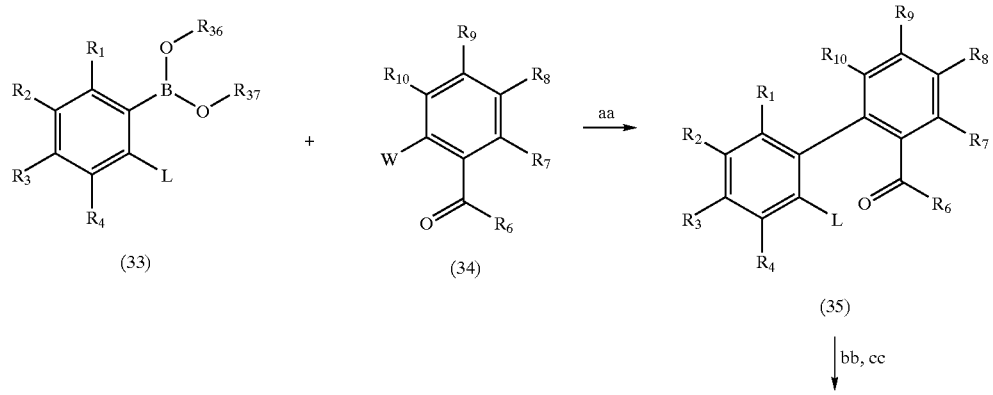

(33)　　+　　(34)　　→　　(35)

↓ bb, cc

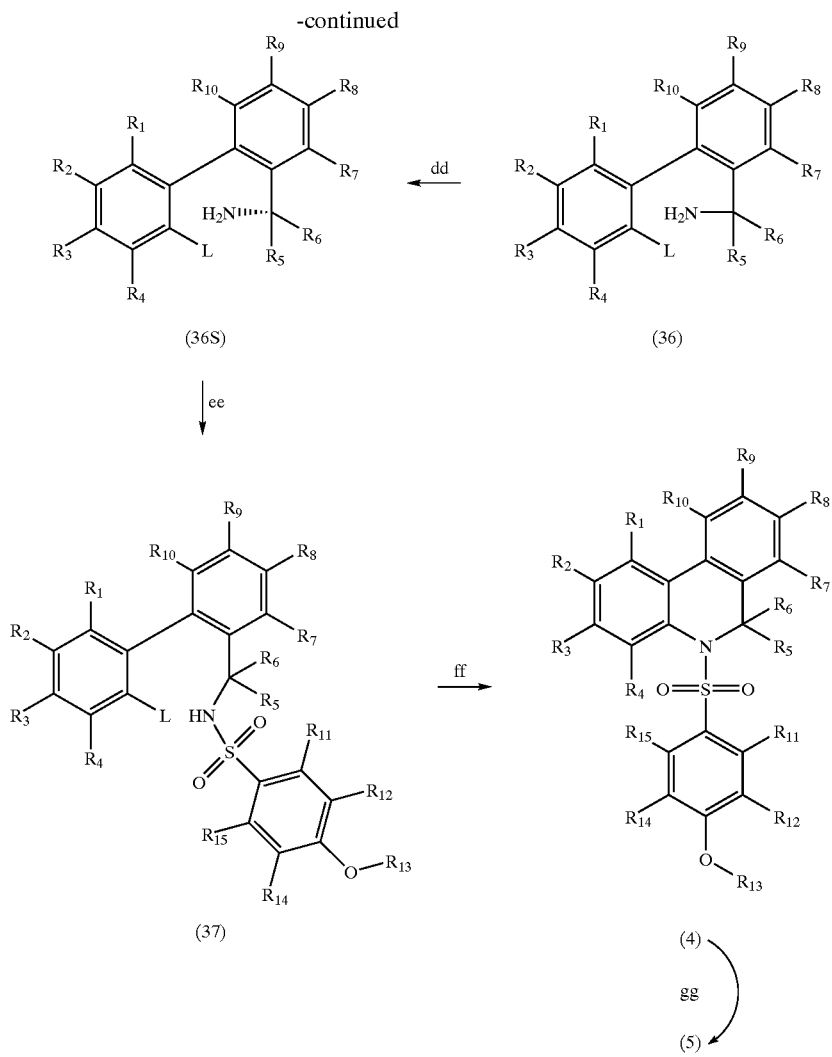

aa. Pd(OAc)$_2$, K$_2$CO$_3$, tetrabutylammonium bromide, THF, 60° C., 2–12 h; bb. NH$_4$OAc, MeOH, 60° C.; cc. When R$_5$ is hydrogen, NaCNBH$_3$, MeOH, 60° C., 12 h; dd. (R)-(+)-2-hydroxy-4-(2-methoxyphenyl)-5,5-dimethyl-1,3,2-dioxaphosphorinane, 2-butanone; e (3) or (32) wherein R$_{13}$ or R$_{32}$ is methyl: triethylamine, CH$_2$Cl$_2$, 2–12 h; ff. K$_2$CO$_3$, DMF, 100° C., 12 h; gg. When R$_{13}$ or R$_{32}$ is methyl: BBr$_3$, cyclohexene, dichloromethane, 2–24 h.

In Scheme XII, step aa, a suitably substituted arylboronic acid or ester (33), either commercially available, known in the literature, or prepared according to methods known and established for the preparation of said arylboronic acids or esters, including procedures exemplified in the experimental section of this application; wherein, L is a fluorine or chlorine atom, R$_1$ through R$_4$, and R$_{36}$ and R$_{37}$ are herein before defined, in the presence of a coupling catalyst, is reacted with a suitably substituted alkyl aryl ketone (34), either commercially available, known in the literature, or prepared according to methods known and established for the preparation of said alkyl aryl ketones, including procedures exemplified in the experimental section of this application; wherein, W and R$_6$ through R$_{10}$ are herein before defined. The biphenylketone (35) is reacted in step bb with an ammonium source, such as ammonium chloride or ammonium acetate, and the like, either commercially available, or known in the literature, in a suitable solvent such as methanol, toluene, tetrahydrofuran, 1,2-dichloroethane, and the like, optionally in the presence of an acid catalyst such as p-toluenesulfonic acid or pyridinium p-toluenesulfonate, followed in a second step cc by reduction of the intermediate imine with an acceptable hydride source, such as sodium cyanoborohydride, sodium borohydride, lithium aluminum hydride, or diisobutylaluminum hydride, or the like. The intermediate imine can be isolated or not isolated. The conjugate base of a suitable, nucleophilic R$_5$, such as methyllithium, tert-butyllithium, and the like, may be substituted for the hydride source to afford a tertiary biphenylamine as the product of step cc. The biphenylamine (36) can be separated into it's respective enantiomers (36S) and (36R) by subjecting (36) to either an analytical chiral separation, an enzymatic or chemical resolution, or a de novo enantiospecific synthesis of either (36S) or (36R) according to methods known and established in the literature for the enantiospecific synthesis of benzylic amines. The chemical resolution in step dd is carried out by employing a suitable chiral acid, either commercially available or known in the literature, according to methods known and established for the resolution of benzylic amines. The biphenylamine, either as the racemate or enantiomerically pure, is then reacted in step ee with (3) or (32) or an anhydride, in a suitable solvent such as acetonitrile, 1,2-dichloroethane, or dichloromethane, and the like, optionally in the presence of an acid scavenger such as triethylamine, diisopropylethylamine, pyridine, or potassium carbonate, and the like, and further optionally in the presence of a known acylation promoter or catalyst, such as 4-(N,N-dimethylamino)pyridine at −20° C. to room temperature for several hours. In step ff, treatment of the sulfonamide (37) with potassium carbonate in N,N-dimethylformamide at 100° C. for 24–48 hours affords the phenanthridine (4), or optionally a solution can be heated with microwave irradiation for typically seven to ten minutes in suitable solvents conducive to microwave-assisted reactions. The protected phenol may be de-protected in step gg to phenol (5) as previously described.

The compounds of this invention are useful in the treatment of the inflammatory component of diseases and are therefore particularly useful in treating atherosclerosis, myocardial infarction, congestive heart failure, arthritis, inflammatory bowel disease, type II diabetes, osteoarthritis, asthma and any other autoimmune disease in humans or other mammals which comprises administering to a human or other mammal an antiinflammatory effective amount of a compound of the present invention.

Representative compounds of this invention were evaluated in the following standard pharmacological test procedures which demonstrated the antiinflammatory activity for the compounds of this invention. The test procedures used and the results obtained are briefly described below.

Test Procedures:
a) Cells

T-175 flasks of 100% confluent HAECT-1 cells (immortalized human aortic endothelial cells) were washed with 8 mL of HBSS (HEPES buffered saline solution) and infected for four hours with 6 mL of a 1:10 dilution of Ad5-wt-hERα virus (an adenovirus transfection vector that mediates CMV promoter driven expression of human ERα) in phenol red free Endothelial Cell Basal medium (Clonetics, San Diego Calif., Catalog # CC-3129) containing 0.25% bovine serum albumin (EBM-BSA). After four hours, cells were washed with EBM-BSA and incubated overnight in the same medium. Following overnight incubation, cells were washed with EBM-BSA and infected for 2 hours with 6 mL of a 1:10 dilution of Ad5-3x(NFκB) .Luc virus (Adenovirus luciferase expression vector driven by 3 repeats of the MHC NFκb site 5' to the thymidine kinase promoter) in EBM-BSA. After two hours, cells were washed and incubated at 34° C. for 1 hour. Cells were then washed, trypsinized, counted and resuspended in 95% FBS/5% dimethylsulfoxide at a concentration of $4 \times 10^6$ cells/mL, frozen as 1 or 5 mL aliquots in cryo-vials and stored at −150°

C. Control (no ER infection) cells were processed as above without Ad5-wt-hERα virus infection.

IL-6 and Creatine Kinase (CK) Test Procedure

ERα infected HAECT-1 cells or control cells were thawed, diluted 42× in warm EBM-BSA, plated into 96-well plates at 0.1 mL/well and incubated for 4 hours at 34° C. Test compounds were added to the cells as 2× stocks in EBM-BSA containing 2 ng/mL IL-1β (R&D Systems) and the 96-well plates were returned to the incubator (34° C.). After 15–20 hours, 100 μL aliquots of media were removed from the cells and assayed for IL-6 content using a BioSource human IL-6 ELISA Kit. Cells were subsequently washed with 300 μL of Dulbecco's phosphate buffered saline and lysed in 50 μL of Cell Culture Lysis Reagent (Promega). Luciferase was determined on a Wallac Victor² Luminometer (Gaithersburg, Md.) using 10 μL of lysate and mixing with 100 μL of Promega Luciferase Assay reagent. Creatine kinase was determined from the rate of increase in $A_{340}$ following addition of 100 μL of CK assay reagent (Sigma, cat. No 47–10) to the remainder of the cell lysate.

Data Analyses

For $IC_{50}$ and $EC_{50}$ calculations, mean IL-6, luciferase or CK values versus $\log_{10}$ of the compound concentration were fitted to a four parameter logistic equation. The $IC_{50}/EC_{50}$ value, 'Hill slope', upper and lower limits of the curve were iteratively estimated.

Mice

Ovariectomized C57BL/6 mice (16–20 g) (Taconic) were separated into groups of eight mice each. After 5–7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

II. RNA Analysis

Liver total RNA was prepared by using Trizol reagent (BRL). Estrogen and compound regulation of NF-□B target genes were verified by real time reverse transcriptase-polymerase chain reaction (RT-PCR) using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

The following table summarizes the results obtained in the standard pharmacological test procedures described above.

TABLE 1

Effects of tested compounds on ER/NF-κB, IL-6 and CK expression in Ad5-wt-ERα infected HAECT-1 cells.

| Example # | ER/NFκB | | Interleukin-6 | | Creatin Kinase | |
|---|---|---|---|---|---|---|
| | $IC_{50}$ (nM) | Efficacy (%)* | $IC_{50}$ (nM) | Efficacy (%) | $EC_{50}$ (nM) | Efficacy (%) |
| 1 | 422 | 94 | ND** | ND | 1004 | 39 |
| 2 | 40 | 103 | ND | ND | 420 | 28 |
| 3 | 1512 | 97 | ND | ND | <35% @10 μM | |
| 4 | 54 | 101 | ND | ND | 48 | 23 |
| 5 | 433 | 102 | ND | ND | <35% @10 μM | |
| 6 | 474 | 92 | ND | ND | <35% @10 μM | |
| 7 | 470 | 07 | ND | ND | <35% @10 μM | |
| 8 | 672 | 89 | ND | ND | <35% @10 μM | |
| 9 | 125 | 89 | ND | ND | 455 | 26 |

TABLE 1-continued

Effects of tested compounds on ER/NF-κB, IL-6 and CK expression in Ad5-wt-ERα infected HAECT-1 cells.

| Example # | ER/NFκB IC$_{50}$ (nM) | Efficacy (%)* | Interleukin-6 IC$_{50}$ (nM) | # | Creatin Kinase IC$_{50}$ (nM) | Efficacy (%)* |
|---|---|---|---|---|---|---|
| 10 | 61 | 95 | ND | ND | | <35% @10 μM |
| 11 | 168 | 115 | ND | ND | 117 | 37 |
| 12 | 682 | 93 | ND | ND | | <35% @10 μM |
| 13 | >10,000 | | ND | ND | | <35% @10 μM |
| 14 | 108 | 105 | ND | ND | 757 | 50 |
| 15 | 16 | 99 | ND | ND | | <35% @10 μM |
| 16 | 2276 | 89 | ND | ND | 3160 | 15 |
| 17 | 58 | 76 | ND | ND | | <35% @10 μM |
| 18 | 529 | 76 | ND | ND | | <35% @10 μM |
| 19 | 186 | 80 | ND | ND | | <35% @10 μM |
| 20 | >10,000 | | ND | ND | | <35% @10 μM |
| 21 | 831 | 85 | ND | ND | | <35% @10 μM |
| 22 | 163 | 96 | ND | ND | | <35% @10 μM |
| 23 | >10,000 | | ND | ND | | <35% @10 μM |
| 26 | >10,000 | | ND | ND | | <35% @10 μM |
| 27 | >10,000 | | ND | ND | | <35% @10 μM |
| 28 | 76 | 98 | ND | ND | | <35% @10 μM |
| 29 | 234 | 86 | ND | ND | | <35% @10 μM |
| 30 | 53 | 76 | ND | ND | | <35% @10 μM |
| 31 | 254 | 108 | ND | ND | | <35% @10 μM |
| 32 | 96 | 96 | ND | ND | 302 | 26 |
| 33 | 33 | 99 | 23.4 | 108 | 91 | 21 |
| 34 | 2845 | 89 | | 35 | | <35% @10 μM |
| 35 | 707 | 94 | ND | ND | | <35% @10 μM |
| 36 | 690 | 60 | ND | ND | | <35% @10 μM |
| 38 | >10,000 | | ND | ND | | <35% @10 μM |
| 39 | >10,000 | | ND | ND | | <35% @10 μM |
| 40 | 27 | 99 | ND | ND | | <35% @10 μM |
| 41 | 815 | 75 | ND | ND | 429 | 24 |
| 42 | 83 | 99 | ND | ND | | <35% @10 μM |
| 43 | >10,000 | | ND | ND | | <35% @10 μM |
| 44 | 85 | 94 | ND | ND | | <35% @10 μM |
| 45 | 357 | 92 | ND | ND | | <35% @10 μM |
| 46 | >10,000 | | ND | ND | | <35% @10 μM |
| 47 | 60 | 89 | ND | ND | | <35% @10 μM |
| 48 | 525 | 107 | ND | ND | | <35% @10 μM |
| 49 | >10,000 | | ND | ND | | <35% @10 μM |
| 50 | >10,000 | | ND | ND | | <35% @10 μM |
| 51 | 56 | 106 | ND | ND | 77 | 27 |
| 52 | 68 | 95 | ND | ND | | <35% @10 μM |
| 53 | 764 | 76 | ND | ND | | <35% @10 μM |
| 54 | 423 | 87 | ND | ND | 839 | 24 |
| 55 | >10,000 | | ND | ND | 239 | 32 |
| 56 | 1436 | 100 | ND | ND | 750 | 34 |
| 57 | >10,000 | | ND | ND | | <35% @10 μM |
| 58 | >10,000 | | ND | ND | | <35% @10 μM |
| 59 | 1723 | 102 | ND | ND | 2929 | 22 |
| 60 | 257 | 95 | ND | ND | | <35% @10 μM |
| 62 | 120 | 90 | ND | ND | | <35% @10 μM |
| 63 | 335 | 89 | ND | ND | | <35% @10 μM |
| 65 | 241 | 93 | ND | ND | | <35% @10 μM |
| 67 | 245 | 79 | ND | ND | | <35% @10 μM |
| 69 | 235 | 90 | ND | ND | | <35% @10 μM |
| 70 | 463 | 90 | ND | ND | | <35% @10 μM |
| 73 | 52 | 56 | ND | ND | | <35% @10 μM |
| 74 | 434 | 96 | ND | ND | | <35% @10 μM |
| 75 | 3928 | 116 | ND | ND | | <35% @10 μM |
| 76 | 1184 | 67 | ND | ND | | <35% @10 μM |
| 78 | 771 | 79 | ND | ND | | <35% @10 μM |
| 79 | 226 | 86 | ND | ND | | <35% @10 μM |
| 84 | 447 | 80 | ND | ND | | <35% @10 μM |
| 90 | 2550 | 108 | ND | ND | | <35% @10 μM |
| 94 | 382 | 105 | ND | ND | | <35% @10 μM |
| 95 | 678 | 89 | ND | ND | | <35% @10 μM |
| 99 | ND** | ND | 341 | 139 | ND | ND |
| 100 | ND | ND | 6.9 | 196 | ND | ND |
| 101 | ND | ND | 1281 | 74 | ND | ND |
| 102 | ND | ND | 5.4 | 156 | ND | ND |
| 103 | ND | ND | 47 | 141 | 85 | 9 |
| 104 | ND | ND | 171 | 43 | | 9 |

TABLE 1-continued

Effects of tested compounds on ER/NF-κB, IL-6 and CK
expression in Ad5-wt-ERα infected HAECT-1 cells.

| | | | | | | |
|---|---|---|---|---|---|---|
| 105 | ND | ND | 92 | >100 | 32 | 17 |
| 106 | ND | ND | 43 | 104 | 1418 | 22 |
| 107 | ND | ND | 1329 | 79 | 110 | 20 |
| 108 | ND | ND | 43 | 92 | 152 | 11 |
| 109 | ND | ND | ND | ND | ND | ND |
| 110 | ND | ND | 2340 | 38 | 954 | −7 |
| 111 | ND | ND | 22 | 114 | 102 | 33 |
| 112 | ND | ND | 175 | 100 | 337 | 1 |
| 113 | ND | ND | 173 | 100 | 284 | 40 |
| 114 | ND | ND | 78 | 98 | | 23 |
| 115 | ND | ND | 81 | 102 | 102 | 16 |
| 116 | ND | ND | 130 | 99 | 326 | 23 |
| 117 | ND | ND | 104 | 101 | 40 | 8 |
| 118 | ND | ND | 96 | 103 | | −16 |
| 119 | ND | ND | 18 | 35 | | 21 |
| 120 | ND | ND | 6 | 153 | | 10 |
| 121 | ND | ND | 30 | 113 | 107 | 29 |
| 122 | ND | ND | 464 | 37 | 805 | 14 |
| 123 | ND | ND | 7 | 154 | | 2 |
| 124 | ND | ND | 224 | 19 | 624 | 4 |
| 125 | ND | ND | 54 | 94 | | 22 |
| 126 | ND | ND | 40 | 99 | 661 | 61 |
| 127 | ND | ND | ND | ND | ND | ND |

E2 inhibits NF-κB and IL-6 expression in Ad5-wt-ER infected HAECT-1 cells with an $IC_{50}$ value around 1 nM and induces expression of creatine kinase in the same cells with similar potency (5.8 nM) (Table 1). In contrast, compounds of the present invention potently and efficaciously inhibit NF-κB and IL-6 expression in Ad5-wt-ER infected HAECT-1 cells but do not induce CK expression (Table 1) in an ER-dependent manner. The ability of compounds of the present invention to inhibit NF-κB and IL-6 expression without inducing CK activity (Table 1) is demonstrates anti-inflammatory activity in the absence of classic estrogenic activity.

Based on the results obtained in the standard pharmacological test procedures, the compounds of this invention are selective antiinflammatory compounds described herein useful for the treatment and prevention of chronic inflammatory diseases without stimulating uterine and breast cell proliferation as found with classic estrogens.

Accordingly, the compounds of this invention are useful in treating or inhibiting osteoporosis and in the inhibition of bone demineralization, which may result from an imbalance in an individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those conditions described above, these compounds can be used in treatment or inhibition of osteoarthritis, hypocalcemia, hypercalcemia, Paget's disease, osteomalacia, osteohalisteresis, multiple myeloma and other forms of cancer having deleterious effects on bone tissues.

The compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lipoprotein (a) (Lp(a)), and low density lipoprotein (LDL) levels; inhibiting or treating hypercholesteremia, hyperlipidemia, cardiovascular disease, atherosclerosis, acute coronary syndrome, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis, psoriatic arthritis, juvenile arthritis), pleurisy, ischemia/reperfusion injury (e.g. stroke, transplant rejection, myocardial infarction, etc.), asthma, chronic obstructive pulmonary disease, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as disorders of lipid metabolism, appetite (e.g. anorexia nervosa and bulimia), or type-II diabetes.

Compounds in this invention are also useful in treating or inhibiting bleeding disorders such as hereditary hemorrhagic telangiectasia, dysfunctional uterine bleeding, and combating hemorrhagic shock.

The compounds of this invention are useful in disease states where amenorrhea is advantageous, such as leukemia, endometrial ablations, chronic renal or hepatic disease or coagulation diseases or disorders.

It is understood that the effective dosage of the active compounds of this invention may vary depending upon the particular compound utilized, the mode of administration, the condition, and severity thereof, of the condition being treated, as well as the various physical factors related to the individual being treated. It is projected that compounds of this invention will be administered at an oral daily dosage of from about 0.05 mg to about 30 mg per kilogram of body weight, preferably administered in divided doses two to six times per day, or in a sustained release form. For most large mammals, the total daily dosage is from about 3.5 mg to about 2100 mg, preferably from about 3.5 to about 5 mg. In the case of a 70 kg human adult, the total daily dose will generally be from about 3.5 mg to about 2100 mg and may be adjusted to provide the optimal therapeutic result.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, sweetening agents, lubricants, solubilizers, suspending agents, fillers, glidants, compression aids, binders, or tablet-disintegrating agents; it can also be an encapsulating material. In powders, the carrier is a finely divided solid which is in admixture with the finely divided active ingredient.

Solid dosage unit forms or compositions such as tablets, troches, pills, capsules, powders, and the like, may contain a solid carrier binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both.

Liquid carriers are used in preparing liquid dosage forms such as solutions, suspensions, dispersions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution); alcohols, including monohydric alcohols such as ethanol and polyhydric alcohols such as glycols and their derivatives; lethicins, and oils such as fractionated coconut oil and arachis oil. For parenteral administration, the liquid carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

A liquid pharmaceutical composition such as a syrup or elixir may contain, in addition to one or more liquid carriers and the active ingredients, a sweetening agent such as sucrose, preservatives such as methyl and propyl parabens, a pharmaceutically acceptable dye or coloring agent, or a flavoring agent such as cherry or orange flavoring.

Liquid pharmaceutical compositions which are sterile solutions or suspensions can be administered intraocularly or parenterally, for example, by intramuscular, intraperitoneal or subcutaneous injection. Sterile solutions can also be administered intravenously. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under the conditions of manufacture and storage and must be preserved against the contaminating action of microorganisms such as bacteria and fungi. The carrier can be a solvent or dispersion medium containing a liquid carrier, for example, water, ethanol, polyol (e.g. glycerol, propylene glycol and liquid polyethylene glycol), suitable mixtures thereof, and vegetable oils. The liquid carrier may be suitably mixed with a surfactant such as hydroxypropylcellulose.

The compounds of the present invention may also be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may be administered topically, or also transdermally through the use of a transdermal patch containing the active compound and a carrier that is inert to the active compound, which is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The following describes the preparation of representative compounds of this invention. Compounds described as homogeneous were determined to be 98% or greater a single peak (exclusive of enantiomers) by analytical reverse phase chromatographic analysis with 254 nM UV detection. Melting points are reported as uncorrected in degrees centigrade. The infrared data is reported as wavenumbers at maximum absorption, $v_{max}$, in reciprocal centimeters, $cm^{-1}$. Mass spectral data is reported as the mass-to-charge ratio, m/z; and for high resolution mass spectral data, the calculated and experimentally found masses, $[M+H]^+$, for the neutral formulae M are reported. Nuclear magnetic resonance data is reported as δ in parts per million (ppm) downfield from the standard, tetramethylsilane; along with the solvent, nucleus, and field strength parameters. The spin-spin homonuclear coupling constants are reported as J values in hertz; and the multiplicities are reported as a: s, singlet; d, doublet; t, triplet; q, quartet; quintet; or br, broadened. Italicized elements or groups are those responsible for the chemical shifts. $^{13}$C NMR chemical shift assignments were made by reasonable comparison to a full chemical shift assignment determination for Example 1, Step a. The yields given below are for informational purposes and may vary according to experimental conditions or individual techniques.

EXAMPLE 1

Step a)

5-[(4-Methoxyphenyl)sulfonyl]-6-methyl-5,6-dihydrophenanthridine

A stirred solution of phenanthridine (3.58 g, 20 mmol) in anhydrous diethyl ether (20 mL) was cooled to −30° C. and treated drop-wise under nitrogen via syringe with a solution of 1.4 M methyllithium in diethyl ether (14.5 mL, 20.3 mmol). The yellow solution was warmed to room temperature and stirred for 15 minutes. The mixture was cooled to −78° C. and treated with 4-methoxybenzenesulfonyl chloride (4.12 g, 20 mmol), as a solid, in a single aliquot. The reaction mixture was warmed slowly to room temperature over one hour, poured into 1 N aqueous sodium hydroxide, and extracted with ethyl acetate. The organic phase was washed sequentially with water, a 1 N hydrochloric acid solution, and a saturated, aqueous sodium chloride solution. After drying over anhydrous sodium sulfate, the organic phase was filtered through a short column of silica gel, and the filtrate evaporated in vacuo to yield a crude yellow oil (5.3 g, 73%). The crude oil was purified by preparative chromatography on a Biotage® 40 Mi column of pre-packed silica gel (90 g), eluting with a mixture of methyl tert-butyl ether-hexane (15:85) at a flow rate of 40 mL/min to afford, after evaporation of the solvent, a colorless oil. Crystallization of the colorless oil from a mixture of diethyl ether-hexane yielded the title compound (2.02 g, 5.6 mmol, 28%) as a homogeneous, colorless, crystalline solid, m.p. 167–169° C.;

MS [(+ESI), m/z]: 366 [M+H]$^+$;

IR (Solid), $v_{max}$: 1595, 1585, 1495, 1430, 1330, 1260, 1160, 1080, 770, 720 cm$^{-1}$;

$^1$H NMR (500 MHz, DMSO-d$_6$) δ: 7.77 (dd, J=7.6, 1.4 Hz, 1H, ArH-1), 7.62 (dd, J=7.8, 1.4 Hz, 1H, ArH-4), 7.43 (d, J=7.6 Hz, 1H, ArH-10), 7.42 (td, J=7.8, 1.5 Hz, 1H, ArH-3), 7.38 (td, J=7.5, 1.4 Hz, 1H, ArH-2), 7.23 (dd, J=7.3, 1.1, Hz, 1H, ArH-7), 7.17 (td, J=7.3, 1.2 Hz, 1H, ArH-8), 7.12 (td, J=7.5, 1.1 Hz, 1H, ArH-9), 6.94 (ddd, J=8.9, 2.9, 2.0 Hz, 2H, ArH'-2',6'), 6.54 (ddd, J=9.0, 2.9, 2.0 Hz, 2H, ArH'-3',5'), 5.42 (q, J=6.9 Hz, 1H, H-6), 3.62 (s, 3H, —OCH$_3$-4'), 1.14 (d, J=7.0 Hz, 3H, —CH$_3$-6);

$^{13}$C NMR (125 MHz, DMSO-d$_6$) δ: 162.2 (s, 1C, ArC'-4'), 136.3 (s, 1C, ArC-6a), 132.5 (s, 1C, ArC-4a), 129.3 (s, 1C, ArC-10b), 128.8 (s, 1C, ArC-4), 128.6 (s, 2C, ArC'-2',6'), 128.4 (s, 1C, ArC'-1'), 128.3 (s, 1C, ArC-10a), 128.2 (s, 1C, ArC-3), 128.1 (s, 1C, ArC-8), 127.5 (s, 1C, ArC-2), 127.4 (s, 1C, ArC-9), 126.0 (s, 1C, ArC-7), 123.7 (s, 1C, ArC-1), 123.1 (s, 1C, ArC-10), 113.4 (s, 2C, ArC'-3',5'), 55.5 (s, 1C, —OCH$_3$-4'), 53.9 (s, 1C, C-6), 21.7 (s, 1C, —CH$_3$-6);

Additional NMR experiments (NOE, COSY, HSQC, HMBC) confirmed the structural assignments and chemical shifts;

Anal. calcd for C$_{21}$H$_{19}$NO$_3$S: C, 69.02; H, 5.24; N, 3.83. Found: C, 69.19; H, 5.24; N, 3.82.

Step b)

4-[(6-Methylphenanthridin-5(6H)-yl)sulfonyl]phenol

A stirred suspension of 5-[(4-methoxyphenyl)sulfonyl]-6-methyl-5,6-dihydrophenanthridine (0.73 g, 2.0 mmol) and cyclohexene (3.28 g, 40 mmol) was treated at room temperature under nitrogen with a solution of 1.0 M boron tribromide in dichloromethane (12 mL, 12 mmol). After stirring for approximately four hours at room temperature, the reaction was quenched with methanol (20 mL) and diluted with dichloromethane. The mixture was washed sequentially with an aqueous potassium carbonate solution, a saturated, aqueous sodium chloride solution, and water. The organic phase was dried over anhydrous sodium sulfate, filtered through a short column of silica gel, and eluted with ethyl acetate. The ethyl acetate phase was evaporated in vacuo to a crude residue (1.0 g). The crude residue was purified by preparative chromatography on a Biotage® 40 Mi column of pre-packed silica gel (90 g) with gradient elution of between 10% to 30% methyl tert-butyl ether in hexane at a flow rate of 50 mL/min and afforded, after evaporation of the solvent, a colorless oil. Crystallization of the colorless oil from a mixture of diethyl ether-hexane yielded the title compound (0.525 g, 1.5 mmol, 75%) as a homogeneous, colorless, crystalline solid, m.p. 196–198° C.;

MS [(−ESI), m/z]: 350 [M−H]$^-$;

IR (Solid), $v_{max}$: 3360, 1600, 1585, 1430, 1325, 1150, 1080, 830, 730 cm$^{-1}$;

$^1$H NMR (500 MHz, DMSO-d$_6$) δ: 10.17 (br s, 1H, —OH-4'), 7.77 (dd, J=7.6, 1.5 Hz, 1H, ArH-1), 7.62 (dd, J=7.8, 1.4 Hz, 1H, ArH-4), 7.47 (d, J=7.4 Hz, 1H, ArH-10), 7.41 (td, J=7.5, 1.5 Hz, 1H, ArH-3), 7.36 (td, J=7.5, 1.4 Hz, 1H, ArH-2), 7.22 (dd, J=7.3, 1.2, Hz, 1H, ArH-7), 7.18 (td, J=7.3, 1.2 Hz, 1H, ArH-8), 7.13 (td, J=7.3, 1.5 Hz, 1H, ArH-9), 6.84 (ddd, J=8.9, 2.9, 2.0 Hz, 2H, ArH'-2',6'), 6.33 (ddd, J=8.9, 2.9, 2.0 Hz, 2H, ArH'-3',5'), 5.40 (q, J=7.0 Hz, 1H, H-6), 1.12 (d, J=7.0 Hz, 3H, —CH$_3$-6);

$^{13}$C NMR (125 MHz, DMSO-d$_6$) δ: 161.0 (s, 1C, ArC'-4'), 136.5 (s, 1C, ArC-6a), 132.6 (s, 1C, ArC-4a), 129.3 (s, 1C, ArC-10b), 128.8 (s, 1C, ArC-4), 128.7 (s, 2C, ArC'-2',6'), 128.3 (s, 1C, ArC'-1'), 128.2 (s, 1C, ArC-10a), 128.0 (s, 1C, ArC-3), 127.4 (s, 1C, ArC-8), 127.3 (s, 1C, ArC-2), 126.8 (s, 1C, ArC-9), 125.9 (s, 1C, ArC-7), 123.6 (s, 1C, ArC-1), 123.0 (s, 1C, ArC-10), 114.5 (s, 2C, ArC'-3',5'), 53.8 (s, 1C, C-6), 21.8 (s, 1C, —CH$_3$-6);

Anal. calcd for C$_{20}$H$_{17}$NO$_3$S: C, 68.36; H, 4.88; N, 3.99. Found: C, 68.05; H, 4.84; N, 3.88.

EXAMPLE 2

Step a)

(S)-5-[(4-Methoxyphenyl)sulfonyl]-6-methyl-5,6-dihydrophenanthridine*

The enantiomers of 5-[(4-methoxyphenyl)sulfonyl]-6-methyl-5,6-dihydrophenanthridine, prepared in Example 1, were separated by automated preparative normal phase chiral chromatography on a Chiralpak AD® (25 cm×5 cm) column, eluting with 10% 2-propanol in hexane at a flow rate of 20 mL/min. After evaporation of the solvent in vacuo, peak one with a retention time at 10.2 minutes, monitored at 254 nm, was isolated to yield (S)-5-[(4-methoxyphenyl)sulfonyl]-6-methyl-5,6-dihydrophenanthridine* as a white, solid, single enantiomer, m.p. 183–185° C.;

$T_R$=10.2 minutes

[α]$_D^{25}$=+242.9° (c=1% solution, CHCl$_3$);

MS [(+ESI), m/z]: 366 [M+H]$^+$;

$^1$H NMR (500 MHz, DMSO-d$_6$) δ: 7.77 (dd, J=7.8, 1.1 Hz, 1H, ArH-1), 7.62 (dd, J=7.8, 1.0 Hz, 1H, ArH-4), 7.44–7.36 (m, 3H, ArH-2,3,10), 7.23 (d, J=7.4 Hz, 1H,

ArH-7), 7.17 (t, J=7.3 Hz, 1H, ArH-8), 7.12 (t, J=7.3 Hz, 1H, ArH-9), 6.94 (d, J=9.0 Hz, 2H, ArH'-2',6'), 6.54 (d, J=8.9 Hz, 2H, ArH'-3',5'), 5.41 (q, J=6.8 Hz, 1H, H-6), 3.62 (s, 3H, —OCH$_3$-4'), 1.13 (d, J=7.0 Hz, 3H, CH$_3$-6);

Anal. calcd for $C_{21}H_{19}NO_3S$: C, 69.02; H, 5.24; N, 3.83. Found: C, 68.97; H, 5.26; N, 3.59.

*The stereochemical configuration is not absolute and was assigned arbitrarily.

Step b)

4-{[(S)-6-Methylphenanthridin-5(6H)-yl]sulfonyl}phenol*

The title compound was prepared from (S)-5-[(4-methoxyphenyl)sulfonyl]-6-methyl-5,6-dihydrophenanthridine (0.32 g, 1.02 mmol), cyclohexene (0.26 mL, 2.54 mmol), and 1.0 M boron tribromide in dichloromethane (6.1 mL, 6.1 mmol) according to the procedure and in the same manner as described in Example 1, step b. The crude product was purified by column chromatography on silica gel, eluting with dichloromethane, to yield 4-{[(S)-6-methylphenanthridin-5(6H)-yl]sulfonyl}phenol* (0.25 g, 0.72 mmol, 71%) as a white, solid, single enantiomer, m.p. 176–178° C.;

$[\alpha]_D^{25}$=+298.0° (c=1% solution, CHCl$_3$);

MS [(–ESI), m/z]: 350 [M–H]$^-$;

$^1$H NMR (500 MHz, DMSO-d$_6$) δ: 10.15 (s, 1H, OH-4'), 7.78 (d, J=7.8 Hz, 1H, ArH-1), 7.61 (d, J=7.8 Hz, 1H, ArH-4), 7.48 (d, J=7.5 Hz, 1H, ArH-10), 7.42–7.35 (m, 2H, ArH-2,3), 7.23–7.12 (m, 3H, ArH-7,8,9), 6.84 (d, J=8.7 Hz, 2H, ArH'-2',6'), 6.33 (d, J=8.7 Hz, 2H, ArH'-3',5'), 5.40 (q, J=7.0 Hz, 1H, H-6), 1.13 (d, J=7.0 Hz, 3H, —CH$_3$-6);

Anal. calcd for $C_{20}H_{17}NO_3S\cdot0.30H_2O$: C, 67.32; H, 4.97; N, 3.93. Found: C, 67.09; H, 4.94; N, 3.70.

*The stereochemical configuration is not absolute and was assigned arbitrarily.

EXAMPLE 3

Step a)

(R)-5-[(4-Methoxyphenyl)sulfonyl]-6-methyl-5,6-dihydrophenanthridine*

The enantiomers of 5-[(4-methoxyphenyl)sulfonyl]-6-methyl-5,6-dihydrophenanthridine, prepared in Example 1, were separated by automated preparative normal phase chiral chromatography on a Chiralpak AD® (25 cm×5 cm) column, eluting with 10% 2-propanol in hexane at a flow rate of 20 mL/min. After evaporation of the solvent in vacuo, peak two with a retention time at 12.5 minutes, monitored at 220 nm, was isolated to yield (R)-5-[(4-methoxyphenyl)sulfonyl]-6-methyl-5,6-dihydrophenanthridine* as a white, solid, single enantiomer, m.p. 183–185° C.;

T$_R$=12.5 minutes $[\alpha]_D^{25}$=–239.02° (c=1% solution, CHCl$_3$);

MS [(+ESI), m/z]: 366 [M+H]$^+$;

$^1$H NMR (500 MHz, DMSO-d$_6$) δ: 7.77 (d, J=7.6 Hz, 1H, ArH-1), 7.62 (d, J=7.6 Hz, 1H, ArH-4), 7.44–7.36 (m, 3H, ArH-2,3,10), 7.23 (d, J=7.3 Hz, 1H, ArH-7), 7.17 (t, J=7.3 Hz, 1H, ArH-8), 7.12 (t, J=7.4 Hz, 1H, ArH-9), 6.94 (dd, J=11.4, 2.7 Hz, 2H, ArH'-2',6'), 6.54 (d, J=8.9 Hz, 2H, ArH'-3',5'), 5.41 (q, J=6.9 Hz, 1H, H-6), 3.62 (s, 3H, —OCH$_3$-4'), 1.13 (d, J=7.0 Hz, 3H, —CH$_3$-6);

Anal. calcd for $C_{21}H_{19}NO_3S$: C, 69.02; H, 5.24; N, 3.83. Found: C, 69.34; H, 5.51; N, 3.6.

*The stereochemical configuration is not absolute and was assigned arbitrarily.

Step b)

4-{[(R)-6-Methylphenanthridin-5(6H)-yl]sulfonyl}phenol*

The title compound was prepared from (R)-5-[(4-methoxyphenyl)sulfonyl]-6-methyl-5,6-dihydrophenanthridine (0.38 g, 1.04 mmol), cyclohexene (0.27 mL, 2.61 mmol), and 1.0 M boron tribromide in dichloromethane (6.27 mL, 6.27 mmol) according to the procedure and in the same manner as described in Example 1, step b. The crude product was purified by flash column chromatography on silica gel, eluting with dichloromethane, to yield 4-{[(R)-6-methylphenanthridin-5(6H)-yl]sulfonyl}phenol* (0.26 g, 0.74 mmol, 71%) as a white, solid, single enantiomer, m.p. 181–183° C.;

$[\alpha]_D^{25}$=–287.07° (c=4.33 mg/50 mL, CHCl$_3$);

MS [(–ESI), m/z]: 350 [M–H]$^-$;

MS [(+ESI), m/z]: 352 [M+H]$^+$;

$^1$H NMR (500 MHz, DMSO-d$_6$) δ: 10.17 (s, 1H, OH-4'), 7.78 (d, J=7.8 Hz, 1H, ArH-1), 7.61 (d, J=7.8 Hz, 1H, ArH-4), 7.48 (d, J=7.5 Hz, 1H, ArH-10), 7.42–7.35 (m, 2H, ArH-2,3), 7.23–7.12 (m, 3H, ArH-7,8,9), 6.84 (d, J=8.7 Hz, 2H, ArH'-2',6'), 6.33 (d, J=8.7 Hz, 2H, ArH'-3',5'), 5.40 (q, J=7.0 Hz, 1H, H-6), 1.13 (d, J=7.0 Hz, 3H, —CH$_3$-6);

Anal. calcd for $C_{20}H_{17}NO_3S\cdot0.50H_2O$: C, 66.65; H, 5.03; N, 3.89. Found: C, 66.60; H, 4.77; N, 3.61.

*The stereochemical configuration is not absolute and was assigned arbitrarily.

EXAMPLE 4

Step a)

2-Bromo5-[(4-methoxyphenyl)sulfonyl]-6-methyl-5,6-dihydrophenanthridine

A stirred suspension of 5-[(4-methoxyphenyl)sulfonyl]-6-methyl-5,6-dihydrophenanthridine (0.73 g, 2.0 mmol) was heated to 50° C. in glacial acetic acid 20 mL) and treated drop-wise over seven hours with excess bromine (1.92 g, 12 mmol). After cooling to room temperature, the reaction mixture was diluted with ethyl acetate and the precipitate filtered. The organic phase filtrate was washed sequentially with a saturated, aqueous sodium thiosulfate solution, a 1 N hydrochloric acid solution, and water. The organic phase was further washed sequentially with a 2.5 N aqueous sodium hydroxide solution until a basic extract was obtained, water, and a saturated aqueous sodium chloride solution. The organic phase was dried over anhydrous sodium sulfate, filtered through a short column of silica gel, and the solvent removed in vacuo to afford a crude yellow solid (0.75 g, 1.7 mmol, 85%). The crude solid was purified by preparative chromatography on a Biotage® 40 Mi column of pre-packed silica gel (90 g), eluting with a mixture of methyl tert-butyl ether-hexane (15:85) at a flow rate of 40 mL/min to afford, after evaporation of the solvent, a solid. Crystallization of the solid from a mixture of diethyl ether-hexane yielded the title compound (0.43 g, 0.97 mmol, 48%) as a homogeneous, colorless, crystalline solid, m.p. 192–194° C.;

MS [(+ESI), m/z]: 444/446 [M+H]$^+$, contains one bromine atom;

IR (Solid), $\nu_{max}$: 1595, 1585, 1495, 1440, 1330, 1260, 1160, 1080 cm$^{-1}$;

¹H NMR (500 MHz, DMSO-d₆) δ: 7.99 (d, J=2.3 Hz, 1H, ArH-1), 7.62 (dd, J=8.6, 2.1 Hz, 1H, ArH-3), 7.57 (d, J=8.6 Hz, 1H, ArH-4), 7.52 (d, J=7.6 Hz, 1H, ArH-10), 7.26 (dd, J=7.5, 1.1, Hz, 1H, ArH-7), 7.22 (td, J=7.3, 1.1 Hz, 1H, ArH-8), 7.14 (td, J=7.3, 1.1 Hz, 1H, ArH-9), 7.01 (ddd, J=8.9, 2.9, 2.0 Hz, 2H, ArH'-2',6'), 6.58 (ddd, J=8.9, 2.9, 2.0 Hz, 2H, ArH'-3',5'), 5.44 (q, J=7.0 Hz, 1H, H-6), 3.64 (s, 3H, —OCH₃-4'), 1.15 (d, J=7.0 Hz, 3H, —CH₃-6);

¹³C NMR (125 MHz, DMSO-d₆) δ: 162.4 (s, 1C, ArC'-4'), 136.4 (s, 1C, ArC-6a), 131.8 (s, 1C, ArC-4a), 131.5 (s, 1C), 131.0 (s, 1C), 130.8 (s, 1C), 128.8 (s, 1C), 128.7 (s, 2C, ArH'-2',6'), 128.2 (s, 1C, ArC'-1'), 127.5 (s, 1C), 127.0 (s, 1C), 126.4 (s, 1C), 126.1 (s, 1C), 123.5 (s, 1C), 120.4 (s, 1C), 113.6 (s, 2C, ArC'-3',5'), 55.5 (s, 1C, —OCH₃-4'), 53.8 (s, 1C, C-6), 21.8 (s, 1C, —CH₃-6);

Anal. calcd for $C_{21}H_{18}BrNO_3S$: C, 56.76; H, 4.08; N, 3.15. Found: C, 56.77; H, 4.04; N, 2.97.

Step b)

4-[(2-Bromo-6-methylphenanthridin-5(6H)-yl) sulfonyl]phenol

A stirred suspension of 2-bromo-5-[(4-methoxyphenyl) sulfonyl]-6-methyl-5,6-dihydrophenanthridine (333 mg, 0.75 mmol) and cyclohexene (1.64 g, 20 mmol) was treated at room temperature under nitrogen with a solution of 1.0 M boron tribromide in dichloromethane (5 mL, 5 mmol). After stirring for approximately four hours at room temperature, the reaction was quenched with methanol (20 mL) and diluted with dichloromethane. The mixture was washed sequentially with an aqueous potassium carbonate solution, a saturated, aqueous sodium chloride solution, and water. The organic phase was dried over anhydrous sodium sulfate, filtered through a short column of silica gel, and eluted with ethyl acetate. The ethyl acetate phase was evaporated in vacuo to a crude orange residue (0.5 g). The crude residue was purified by preparative chromatography on a Biotage® 40 Mi column of pre-packed silica gel (90 g) with gradient elution of between 10% to 30% methyl tert-butyl ether in hexane at a flow rate of 50 mL/min; and afforded, after evaporation of the solvent, a colorless oil. Crystallization of the colorless oil from a mixture of diethyl ether-hexane yielded the title compound (0.220 g, 0.51 mmol, 68%) as a homogeneous, off-white, crystalline solid, m.p. 201–203° C.;

MS [(-ESI), m/z]: 428/430 [M-H]⁻, contains one bromine atom;

IR (Solid), $v_{max}$: 3390, 1600, 1585, 1495, 1430, 1325, 1150, 1130, 1080, 1070, 830 cm⁻¹;

¹H NMR (500 MHz, DMSO-d₆) δ: 10.21 (br s, 1H, —OH-4'), 7.97 (d, J=2.1 Hz, 1H, ArH-1), 7.59 (dd, J=8.6, 2.1 Hz, 1H, ArH-3), 7.54 (d, J=8.6 Hz, 2H, ArH-4,10), 7.24 (dd, J=7.4, 1.6, Hz, 1H, ArH-7), 7.21 (td, J=7.4, 1.0 Hz, 1H, ArH-8), 7.14 (td, J=7.3, 1.4 Hz, 1H, ArH-9), 6.89 (ddd, J=8.8, 2.9, 2.0 Hz, 2H, ArH'-2',6'), 6.36 (ddd, J=8.7, 2.9, 2.0 Hz, 2H, ArH'-3',5'), 5.41 (q, J=7.0 Hz, 1H, H-6), 1.13 (d, J=7.0 Hz, 3H, —CH₃-6);

¹³C NMR (125 MHz, DMSO-d₆) δ: 161.2 (s, 1C, ArC'-4'), 136.6 (s, 1C, ArC-6a), 132.0 (s, 1C, ArC-4a), 131.4 (s, 1C), 130.9 (s, 1C), 130.7 (s, 1C), 128.8 (s, 1C), 128.7 (s, 2C, ArC'-2',6'), 127.5 (s, 1C), 127.1 (s, 1C), 126.6 (s, 1C), 126.3 (s, 1C), 126.0 (s, 1C), 123.4 (s, 1C), 120.2 (s, 1C), 114.7 (s, 2C, ArC'-3',5'), 53.7 (s, 1C, C-6), 21.8 (s, 1C, —CH₃-6);

Anal. calcd for $C_{20}H_{16}BrNO_3S$: C, 55.82; H, 3.75; N, 3.25. Found: C, 55.85; H, 3.63; N, 3.15.

EXAMPLE 5

Step a)

5-[(4-Methoxy-3-methylphenyl)sulfonyl]-6-methyl-5,6-dihydrophenanthridine

The title compound was prepared from phenanthridine (1.79 g, 10 mmol), 1.4 M methyllithium in diethyl ether (7.25 mL, 10.15 mmol), and 4-methoxy-3-methyl-benzenesulfonyl chloride (2.21 g, 10 mmol) according to the procedure and in the same manner as described in Example 1, step a; and yielded after chromatographic purification and crystallization from a mixture of ethyl acetate-hexane, 5-[(4-methoxy-3-methylphenyl)sulfonyl]-6-methyl-5,6-dihydrophenanthridine (2.1 g, 5.5 mmol, 55/o) as a homogeneous, colorless, crystalline solid, m.p. 171–173° C.;

MS [(+ESI), m/z]: 380 [M+H]⁺;

IR (Solid), $v_{max}$: 1600, 1580, 1490, 1440, 1330, 1270, 1165, 1124, 1080, 910, 770, 725 cm⁻¹;

¹H NMR (500 MHz, DMSO-d₆) δ: 7.75 (dd, J=7.6, 1.6 Hz, 1H, ArH-1), 7.60 (dd, J=7.6, 1.5 Hz, 1H, ArH-4), 7.44–7.35 (m, 3H, ArH-2,3,10), 7.22 (dd, J=7.4, 1.5, Hz, 1H, ArH-7), 7.17 (td, J=7.4, 1.2 Hz, 1H, ArH-8), 7.10 (td, J=7.5, 1.5 Hz, 1H, ArH-9), 6.80 (dd, J=8.7, 2.2 Hz, 1H, ArH'-6'), 6.75 (dd, J=2.3, 0.7 Hz, 1H, ArH'-2'), 6.53 (d, J=8.7 Hz, 1H, ArH'-5'), 5.39 (q, J=7.0 Hz, 1H, H-6), 3.65 (s, 3H, —OCH₃-4'), 1.77 (s, 3H, —CH₃-3'), 1.12 (d, J=7.1 Hz, 3H, —CH₃-6);

¹³C NMR (125 MHz, DMSO-d₆) δ: 160.4 (s, 1C, ArC'-4'), 136.3 (s, 1C, ArC-6a), 132.7 (s, 1C, ArC-4a), 129.5 (s, 1C, ArC-10b), 128.8 (s, 1C, ArC-4), 128.6 (s, 1C), 128.2 (s, 2C), 127.9 (s, 1C), 127.5 (s, 1C), 127.4 (s, 1C), 127.3 (s, 1C), 126.7 (s, 1C), 126.0 (s, 1C), 125.8 (s, 1C), 123.7 (s, 1C, ArC-1), 123.0 (s, 1C, ArC-10), 109.3 (s, 1C, ArC'-5'), 55.6 (s, 1C, —OCH₃-4'), 53.9 (s, 1C, C-6), 21.7 (s, 1C, —CH₃-6), 15.5 (s, 1C, CH₃-3');

Anal. calcd for $C_{22}H_{21}NO_3S$: C, 69.63; H, 5.58; N, 3.69. Found: C, 69.72; H, 5.33; N, 3.5.

Step b)

2-Methyl-4-[(6-methylphenanthridin-5(6H)-yl) sulfonyl]phenol

The title compound was prepared from 5-[(4-methoxy-3-methylphenyl)sulfonyl]-6-methyl-5,6-dihydrophenanthridine (0.758 g, 2 mmol), cyclohexene (3.28 g, 40 mmol), and 1.0 M boron tribromide in dichloromethane (10 mL, 10 mmol) according to the procedure and in the same manner as described in Example 1, step b; and yielded, after chromatographic purification and crystallization from a mixture of diethyl ether-hexane, 2-methyl-4-[(6-methylphenanthridin-5(6H)-yl)sulfonyl]phenol (0.577 g, 1.58 mmol, 79%) as a homogeneous, colorless, crystalline solid, m.p. 186–188° C.;

MS [(+ESI), m/z]: 366 [M+H]⁺;

MS [(-ESI), m/z]: 364 [M-H]⁻;

IR (Solid), $v_{max}$: 3410, 1590, 1500, 1325, 1310, 1160, 1120, 1080, 725 cm⁻¹;

¹H NMR (500 MHz, DMSO-d₆) δ: 10.06 (br s, 1H, —OH-4'), 7.75 (dd, J=7.6, 1.4 Hz, 1H, ArH-1), 7.59 (dd, J=7.9, 1.4 Hz, 1H, ArH-4), 7.44 (d, J=7.6 Hz, 1H, ArH-10), 7.39 (td, J=7.5, 1.5 Hz, 1H, ArH-3), 7.35 (td, J=7.5, 1.4 Hz, 1H, ArH-2), 7.23 (dd, J=7.3, 1.1, Hz, 1H, ArH-7), 7.18 (td, J=7.3, 1.1 Hz, 1H, ArH-8), 7.12 (td, J=7.6, 1.4 Hz, 1H, ArH-9), 6.71 (d, J=2.0 Hz, 1H, ArH'-2'), 6.64 (dd, J=8.6, 2.3 Hz, 1H, ArH'-6'), 6.33 (d, J=8.6 Hz, 1H, ArH'-5'), 5.38 (q, J=6.9 Hz, 1H, H-6), 1.74 (s, 3H, —CH₃-3'), 1.12 (d, J=7.0 Hz, 3H, —CH₃-6);

$^{13}$C NMR (125 MHz, DMSO-d$_6$) δ: 159.2 (s, 1C, ArC'-4'), 136.5 (s, 1C, ArC-6a), 132.8 (s, 1C, ArC-4a), 129.4 (s, 1C, ArC-10b), 129.3 (s, 1C), 128.7 (s, 1C, ArC-4), 128.3 (s, 1C), 128.1 (s, 1C), 127.8 (s, 1C), 127.3 (s, 1C), 127.2 (s, 1C), 126.3 (s, 1C), 126.2 (s, 1C), 126.0 (s, 1C, ArC-7), 124.0 (s, 1C), 123.6 (s, 1C, ArC-1), 123.0 (s, 1C, ArC-10), 113.3 (s, 1C, ArC'-5'), 53.8 (s, 1C, C-6), 21.7 (s, 1C, —CH$_3$-6), 15.4 (s, 1C, —CH$_3$-3');

Anal. calcd for C$_{21}$H$_{19}$NO$_3$S: C, 69.02; H, 5.24; N, 3.83. Found: C, 69.00; H, 5.20; N, 3.83.

EXAMPLE 6

Step a)

2-Bromo-5-[(4-methoxy-3-methylphenyl)sulfonyl]-6-methyl-5,6-dihydrophenanthridine The title compound was prepared from 5-[(4-methoxy-3-methylphenyl)sulfonyl]-6-methyl-5,6-dihydrophenanthridine (1.4 g, 3.7 mmol) and bromine (4.0 g, 25.0 mmol) according to the procedure and in the same manner as described in Example 4, step a; and yielded, after chromatographic purification and crystallization from a mixture of ethyl acetate-hexane, 2-bromo-5-[(4-methoxy-3-methylphenyl)sulfonyl]-6-methyl-5,6-dihydrophenanthridine (1.0 g, 2.2 mmol, 59%) as a homogeneous, colorless, crystalline solid, m.p. 219–221° C.;

MS [(+ESI), m/z]: 458/460 [M+H]$^+$, contains one bromine atom;

IR (Solid), ν$_{max}$: 1590, 1580, 1490, 1480, 1440, 1330, 1260, 1170, 1130 cm$^{-1}$;

$^1$H NMR (500 MHz, DMSO-d$_6$) δ: 7.96 (d, J=2.1 Hz, 1H, ArH-1), 7.60 (dd, J=8.6, 2.3 Hz, 1H, ArH-3), 7.53 (d, J=8.6 Hz, 1H, ArH-4), 7.49 (d, J=7.6 Hz, 1H, ArH-10), 7.25 (dd, J=7.5, 1.1 Hz, 1H, ArH-7), 7.21 (td, J=7.2, 1.0, Hz, 1H, ArH-8), 7.11 (td, J=7.6, 1.4 Hz, 1H, ArH-9), 6.84 (dd, J=8.6, 2.3 Hz, 1H, ArH'-6'), 6.82 (d, J=2.3 Hz, 1H, ArH'-2'), 6.59 (d, J=8.6 Hz, 1H, ArH'-5'), 5.41 (q, J=7.0 Hz, 1H, H-6), 3.66 (s, 3H, —OCH$_3$-4'), 1.79 (s, 3H, —CH$_3$-3'), 1.13 (d, J=7.0 Hz, 3H, —CH$_3$-6);

$^{13}$C NMR (125 MHz, DMSO-d$_6$) δ: 160.5 (s, 1C, ArC'-4'), 136.5 (s, 1C, ArC-6a), 132.0 (s, 1C, ArC-4a), 131.6 (s, 1C, ArC-10b), 130.9 (s, 1C), 130.8 (s, 1C), 128.6 (s, 2C), 127.5 (s, 1C), 127.4 (s, 1C), 127.0 (s, 1C), 126.7 (s, 1C), 126.3 (s, 1C), 126.1 (s, 1C), 126.0 (s, 1C), 123.4 (s, 1C, ArC-1), 120.4 (s, 1C, ArC-10), 109.4 (s, 1C, ArC'-5'), 55.7 (s, 1C, —OCH$_3$-4'), 53.8 (s, 1C, C-6), 21.7 (s, 1C, —CH$_3$-6), 15.6 (s, 1C, —CH$_3$-3');

Additional NMR experiments (NOE) confirmed the $^1$H NMR structural assignments and chemical shifts;

Anal. calcd for C$_{22}$H$_{20}$BrNO$_3$S: C, 57.65; H, 4.40; N, 3.06. Found: C, 57.67; H, 4.21; N, 2.94.

Step b)

4-[(2-Bromo-6-methylphenanthridin-5(6H)-yl)sulfonyl]-2-methylphenol

The title compound was prepared from 2-bromo-5-[(4-methoxy-3-methylphenyl)sulfonyl]-6-methyl-5,6-dihydrophenanthridine (0.535 g, 1.17 mmol), cyclohexene (2.46 g, 30 mmol), and 1.0 M boron tribromide in dichloromethane (8 mL, 8.0 mmol) according to the procedure and in the same manner as described in Example 4, step b; and yielded, after chromatographic purification and crystallization from a mixture of diethyl ether-hexane, 4-[(2-bromo-6-methylphenanthridin-5(6H)-yl)sulfonyl]-2-methylphenol (0.348 g, 0.78 mmol, 67%) as a homogeneous, colorless, crystalline solid, m.p. 193–195° C.;

MS [(+ESI), m/z]: 444/446 [M+H]$^+$, contains one bromine atom;

MS [(-ESI), m/z]: 442/444 [M-H]$^-$, contains one bromine atom;

IR (Solid), ν$_{max}$: 3420, 1605, 1590, 1500, 1440, 1325, 1280, 1160, 1120 cm$^{-1}$;

$^1$H NMR (500 MHz, DMSO-d$_6$) δ: 10.13 (br s, 1H, —OH-4'), 7.96 (d, J=2.3 Hz, 1H, ArH-1), 7.58 (dd, J=8.6, 2.3 Hz, 1H, ArH-3), 7.53 (d, J=8.6 Hz, 1H, ArH-4), 7.51 (d, J=7.5 Hz, 1H, ArH-10), 7.26 (dd, J=7.5, 1.2 Hz, 1H, ArH-7), 7.22 (td, J=7.3, 0.9, Hz, 1H, ArH-8), 7.13 (td, J=7.8, 1.4 Hz, 1H, ArH-9), 6.77 (d, J=2.3 Hz, 1H, ArH'-2'), 6.68 (dd, J=8.6, 2.3 Hz, 1H, ArH'-6'), 6.37 (d, J=8.6 Hz, 1H, ArH'-5'), 5.40 (q, J=7.0 Hz, 1H, H-6), 1.75 (s, 3H, —CH$_3$-3'), 1.12 (d, J=7.0 Hz, 3H, —CH$_3$-6);

$^{13}$C NMR (125 MHz, DMSO-d$_6$) δ: 159.4 (s, 1C, ArC'-4'), 136.6 (s, 1C, ArC-6a), 132.1 (s, 1C, ArC-4a), 131.5 (s, 1C, ArC-10b), 130.9 (s, 1C), 130.7 (s, 1C), 129.3 (s, 1C), 128.5 (s, 1C), 127.5 (s, 1C), 127.0 (s, 1C), 126.3 (s, 1C), 126.2 (s, 1C), 126.1 (s, 1C), 126.0 (s, 1C), 124.2 (s, 1C), 123.4 (s, 1C, ArC-1), 120.2 (s, 1C, ArC-10), 113.4 (s, 1C, ArC'-5'), 53.8 (s, 1C, C-6), 21.8 (s, 1C, —CH$_3$-6), 15.4 (s, 1C, —CH$_3$-3');

Anal. calcd for C$_{21}$H$_{18}$BrNO$_3$S: C, 56.76; H, 4.08; N, 3.15. Found: C, 56.62; H, 3.74; N, 3.02.

EXAMPLE 7

Step a)

6-Butyl-5-[(4-methoxyphenyl)sulfonyl]-5,6-dihydrophenanthridine

The title compound was prepared from phenanthridine (3.58 g, 20 mmol), 1.6 M n-butyllithium in hexanes (13.0 mL, 20.8 mmol), and 4-methoxybenzenesulfonyl chloride (4.12 g, 20 mmol) according to the procedure and in the same manner as described in Example 1, step a; and yielded, after chromatographic purification and crystallization from a mixture of diethyl ether-hexane, 6-butyl-5-[(4-methoxyphenyl)sulfonyl]-5,6-dihydrophenanthridine (5.16 g, 12.6 mmol, 63%) as a homogeneous, colorless, crystalline solid, m.p. 127–129° C.;

MS [(+ESI), m/z]: 408 [M+H]$^+$;

IR (Solid), ν$_{max}$: 1595, 1580, 1495, 1330, 1270, 1170 cm$^{-1}$;

$^1$H NMR (500 MHz, DMSO-d$_6$) δ: 7.75 (dd, J=7.6, 1.4 Hz, 1H, ArH-1), 7.62 (dd, J=7.9, 1.2 Hz, 1H, ArH-4), 7.43 (d, J=7.5 Hz, 1H, ArH-10), 7.41 (td, J=7.6, 1.4 Hz, 1H, ArH-3), 7.36 (td, J=7.5, 1.4 Hz, 1H, ArH-2), 7.20–7.15 (m, 2H, ArH-7,8), 7.11 (td, J=7.3, 1.8 Hz, 1H, ArH-9), 6.93 (ddd, J=9.0, 2.9, 2.0 Hz, 2H, ArH'-2',6'), 6.52 (ddd, J=8.9, 2.9, 2.0 Hz, 2H, ArH'-3',5'), 5.16 (dd, J=9.5, 4.6 Hz, 1H, H-6), 3.61 (s, 3H, —OCH$_3$-4'), 1.38–1.19 (m, 6H, —(CH$_2$)$_3$CH$_3$), 0.80 (t, J=7.3 Hz, 3H, —(CH$_2$)$_3$CH$_3$);

$^{13}$C NMR (125 MHz, DMSO-d$_6$) δ: 162.2 (s, 1C, ArC'-4'), 135.5 (s, 1C, ArC-6a), 132.5 (s, 1C, ArC-4a), 129.6 (s, 1C, ArC-10b), 128.7 (s, 1C, ArC-4), 128.6 (s, 2C, ArC'-2',6'), 128.5 (s, 2C, ArC-10a, ArC'-1'), 128.2 (s, 1C, ArC-3), 127.9 (s, 1C, ArC-8), 127.5 (s, 1C, ArC-2), 127.4 (s, 1C, ArC-9), 126.4 (s, 1C, ArC-7), 123.7 (s, 1C, ArC-1), 123.1 (s, 1C, ArC-10), 113.4 (s, 2C, ArC'-3',5'), 58.0 (s, 1C, C-6), 55.5 (s, 1C, —OCH$_3$-4'), 33.8 (s, 1C, —CH$_2$CH$_2$CH$_2$CH$_3$), 27.5 (s, 1C, —CH$_2$CH$_2$CH$_2$CH$_3$), 21.4 (s, 1C, —CH$_2$CH$_2$CH$_2$CH$_3$), 13.8 (s, 1C, —CH$_2$CH$_2$CH$_2$CH$_3$);

Anal. calcd for C$_{24}$H$_{25}$NO$_3$S: C, 70.73; H, 6.18; N, 3.44. Found: C, 70.65; H, 6.05; N, 3.28.

Step b)

4-[(6-Butylphenanthridin-5(6H)-yl)sulfonyl]phenol

The title compound was prepared from 6-butyl-5-[(4-methoxyphenyl)sulfonyl]-5,6-dihydrophenanthridine (0.815 g, 2 mmol), cyclohexene (3.70 g, 45 mmol), and 1.0 M boron tribromide in dichloromethane (14 mL, 14 mmol) according to the procedure and in the same manner as described in Example 1, step b; and yielded, after chromatographic purification and crystallization from a mixture of diethyl ether-hexane, 4-[(6-butylphenanthridin-5(6H)-yl)sulfonyl]phenol (0.63 g, 1.6 mmol, 80%) as a homogeneous, colorless, crystalline solid, m.p. 149–151° C.;

MS [(+ESI), m/z]: 394 [M+H]$^+$;

MS [(−ESI), m/z]: 392 [M−H]$^-$;

IR (Solid), $v_{max}$: 3320, 1600, 1590, 1500, 1430, 1310, 1280, 1130, 825, 725 cm$^{-1}$;

$^1$H NMR (500 MHz, DMSO-d$_6$) δ: 10.13 (s, 1H, —OH-4'), 7.75 (dd, J=7.6, 1.4 Hz, 1H, ArH-1), 7.60 (dd, J=7.8, 1.4 Hz, 1H, ArH-4), 7.46 (d, J=7.3 Hz, 1H, ArH-10), 7.39 (td, J=7.5, 1.4 Hz, 1H, ArH-3), 7.34 (td, J=7.6, 1.4 Hz, 1H, ArH-2), 7.20–7.11 (m, 3H, ArH-7,8,9), 6.83 (ddd, J=8.7, 2.9, 1.8 Hz, 2H, ArH'-2',6'), 6.32 (ddd, J=8.8, 2.9, 2.0 Hz, 2H, ArH'-3',5'), 5.14 (dd, J=9.3, 4.6 Hz, 1H, H-6), 1.39–1.16 (m, 6H, —(CH$_2$)$_3$CH$_3$), 0.79 (t, J=7.2 Hz, 3H, —(CH$_2$)$_3$CH$_3$);

$^{13}$C NMR (125 MHz, DMSO-d$_6$) δ: 160.9 (s, 1C, ArC'-4'), 135.7 (s, 1C, ArC-6a), 132.7 (s, 1C, ArC-4a), 129.6 (s, 1C, ArC-10b), 128.7 (s, 1C, ArC-4), 128.6 (s, 2C, ArC'-2',6'), 128.5 (s, 2C, ArC-10a, ArC'-1'), 128.1 (s, 1C), 127.8 (s, 1C), 127.4 (s, 1C), 127.3 (s, 1C), 127.1 (s, 1C), 126.3 (s, 1C, ArC-7), 123.6 (s, 1C, ArC-1), 123.0 (s, 1C, ArC-10), 114.5 (s, 2C, ArC'-3',5'), 57.9 (s, 1C, C-6), 33.9 (s, 1C, —CH$_2$CH$_2$CH$_2$CH$_3$), 27.5 (s, 1C, —CH$_2$CH$_2$CH$_2$CH$_3$), 21.3 (s, 1C, —CH$_2$CH$_2$CH$_2$CH$_3$), 13.8 (s, 1C, —CH$_2$CH$_2$CH$_2$CH$_3$);

Anal. calcd for C$_{23}$H$_{23}$NO$_3$S: C, 70.20; H, 5.89; N, 3.56. Found: C, 70.09; H, 6.06; N, 3.53.

EXAMPLE 8

Step a)

2-Bromo-6-butyl-5-[(4-methoxyphenyl)sulfonyl]-5,6-dihydrophenanthridine

The title compound was prepared from 6-butyl-5-[(4-methoxyphenyl)sulfonyl]-5,6-dihydrophenanthridine (1.22 g, 3.0 mmol) and bromine (0.96 g, 6.0 mmol) according to the procedure and in the same manner as described in Example 4, step a; and yielded, after chromatographic purification and crystallization from a mixture of diethyl ether-hexane, 2-bromo-6-butyl-5-[(4-methoxyphenyl)sulfonyl]-5,6-dihydrophenanthridine (0.72 g, 1.5 mmol, 50%) as a colorless, crystalline solid, m.p. 108–111° C.;

MS [(+ESI), m/z]: 486/488 [M+H]$^+$, contains one bromine atom;

IR (Solid), $v_{max}$: 1590, 1580, 1490, 1450, 1330, 1260, 1160 cm$^{-1}$;

$^1$H NMR (500 MHz, DMSO-d$_6$) δ: 7.96 (d, J=2.1 Hz, 1H, ArH-1), 7.60 (dd, J=8.6, 2.1 Hz, 1H, ArH-3), 7.55 (d, J=8.6 Hz, 1H, ArH-4), 7.50 (d, J=7.8 Hz, 1H, ArH-10), 7.23–7.19 (m, 2H, ArH-7,8), 7.13 (td, J=7.8, 2.0 Hz, 1H, ArH-9), 6.98 (ddd, J=8.9, 2.9, 1.8 Hz, 2H, ArH'-2',6'), 6.56 (ddd, J=8.9, 2.9, 1.8 Hz, 2H, ArH'-3',5'), 5.17 (dd, J=9.3, 4.4 Hz, 1H, H-6), 3.62 (s, 3H, —OCH$_3$-4'), 1.37–1.20 (m, 6H, —(CH$_2$)$_3$CH$_3$), 0.80 (t, J=7.2 Hz, 3H, —(CH$_2$)$_3$CH$_3$);

$^{13}$C NMR (125 MHz, DMSO-d$_6$) δ: 162.3 (s, 1C, ArC'-4'), 135.7 (s, 1C, ArC-6a), 131.8 (s, 1C, ArC-4a), 131.7 (s, 1C), 131.0 (s, 2C), 130.6 (s, 1C), 128.6 (s, 2C, ArC'-2',6'), 128.5 (s, 1C), 127.5 (s, 1C), 127.3 (s, 1C), 126.5 (s, 1C), 126.4 (s, 1C), 123.5 (s, 1C, ArC-10), 120.4 (s, 1C), 113.5 (s, 2C, ArC'-3',5'), 57.9 (s, 1C, C-6), 55.5 (s, 1C, —OCH$_3$-4'), 33.9 (s, 1C, —CH$_2$CH$_2$CH$_2$CH$_3$), 27.5 (s, 1C, —CH$_2$CH$_2$CH$_2$CH$_3$), 21.3 (s, 1C, —CH$_2$CH$_2$CH$_2$CH$_3$), 13.8 (s, 1C, —CH$_2$CH$_2$CH$_2$CH$_3$);

Anal. calcd for C$_{24}$H$_{24}$BrNO$_3$S: C, 59.26; H, 4.97; N, 2.88. Found: C, 59.00; H, 4.82; N, 2.75.

Step b)

4-[(2-Bromo-6-butylphenanthridin-5(6H)-yl)sulfonyl]phenol

The title compound was prepared from 2-bromo-6-butyl-5-[(4-methoxyphenyl)sulfonyl]-5,6-dihydrophenanthridine (0.565 g, 1.16 mmol), cyclohexene (2.46 g, 30 mmol), and 1.0 M boron tribromide in dichloromethane (8 mL, 8.0 mmol) according to the procedure and in the same manner as described in Example 4, step b; and yielded, after chromatographic purification and crystallization from a mixture of diethyl ether-hexane, 4-[(2-bromo-6-butylphenanthridin-5(6H)-yl)sulfonyl]phenol (0.404 g, 0.85 mmol, 74%) as a homogeneous, colorless, crystalline solid, m.p. 178–180° C.;

MS [(−ESI), m/z]: 470/472 [M−H]$^-$, contains one bromine atom;

IR (Solid), $v_{max}$: 3320, 1600, 1580, 1500, 1430, 1310, 1280, 1130, 1080, 830 cm$^{-1}$;

$^1$H NMR (500 MHz, DMSO-d$_6$) δ: 10.21 (br s, 1H, —OH-4'), 7.96 (d, J=2.0 Hz, 1H, ArH-1), 7.58 (dd, J=8.6, 2.1 Hz, 1H, ArH-3), 7.54 (d, J=8.6 Hz, 1H, ArH-4), 7.53 (d, J=7.8 Hz, 1H, ArH-10), 7.22–7.21 (m, 2H, ArH-7,8), 7.19–7.13 (m, 1H, ArH-9), 6.88 (d, J=8.7 Hz, 2H, ArH'-2',6'), 6.35 (d, J=8.9 Hz, 2H, ArH'-3',5'), 5.15 (dd, J=9.2, 4.1 Hz, 1H, H-6), 1.38–1.17 (m, 6H, —(CH$_2$)$_3$CH$_3$), 0.80 (t, J=7.2 Hz, 3H, —(CH$_2$)$_3$CH$_3$);

$^{13}$C NMR (125 MHz, DMSO-d$_6$) δ: 161.1 (s, 1C, ArC'-4'), 135.9 (s, 1C, ArC-6a), 132.0 (s, 1C, ArC-4a), 131.7 (s, 1C), 130.9 (s, 1C), 130.6 (s, 1C), 128.7 (s, 1C), 128.6 (s, 2C, ArC'-2',6'), 127.5 (s, 1C), 127.3 (s, 1C), 126.8 (s, 1C), 126.5 (s, 1C), 126.3 (s, 1C), 123.5 (s, 1C, ArC-1), 120.2 (s, 1C, ArC-10), 114.7 (s, 2C, ArC'-3',5'), 57.9 (s, 1C, C-6), 33.9 (s, 1C, —CH$_2$CH$_2$CH$_2$CH$_3$), 27.5 (s, 1C, —CH$_2$CH$_2$CH$_2$CH$_3$), 21.3 (s, 1C, —CH$_2$CH$_2$CH$_2$CH$_3$), 13.8 (s, 1C, —CH$_2$CH$_2$CH$_2$CH$_3$);

Anal. calcd for C$_{23}$H$_{22}$BrNO$_3$S: C, 58.48; H, 4.69; N, 2.97. Found: C, 58.65; H, 4.80; N, 2.99.

EXAMPLE 9

Step a)

5-[(4-Methoxyphenyl)sulfonyl]-6-phenyl-5,6-dihydrophenanthridine

The title compound was prepared from phenanthridine (5.37 g, 30.0 mmol), 1.8 M phenyllithium in cyclohexane-diethyl ether (70/30), (17.0 mL, 30.6 mmol), and 4-methoxybenzenesulfonyl chloride (6.20 g, 30.0 mmol) according to the procedure and in the same manner as described in Example 1, step a; and yielded, after chromatographic purification and crystallization from a mixture of diethyl ether-hexane, 5-[(4-methoxyphenyl)sulfonyl]-6-phenyl-5,6-dihydrophenanthridine (8.73 g, 20.4 mmol, 68%) as a colorless, crystalline solid, m.p. 145–147° C.

Step b)

4-[(6-Phenylphenanthridin-5(6H)-yl)sulfonyl]phenol

The title compound was prepared from 5-[(4-methoxyphenyl)sulfonyl]-6-phenyl-5,6- dihydrophenanthridine (1.07 g, 2.5 mmol), cyclohexene (4.10 g, 50 mmol), and 1.0 M boron tribromide in dichloromethane (15 mL, 15.0 mmol) according to the procedure and in the same manner as described in Example 1, step b; and yielded, after chromatographic purification and crystallization from a mixture of diethyl ether-hexane, 4-[(6-phenylphenanthridin-5(6H)-yl)sulfonyl]phenol (0.89 g, 2.15 mmol, 86%) as a homogeneous, colorless, crystalline solid, m.p. 217–220° C.;

MS [(−ESI), m/z]: 412 [M−H]⁻;

IR (Solid), $v_{max}$: 3400, 1600, 1590, 1500, 1440, 1320, 1280, 1140, 1085 cm⁻¹;

¹H NMR (500 MHz, DMSO-d₆) δ: 10.23 (br s, 1H, —OH-4'), 7.74 (d, J=7.0 Hz, 1H, ArH-1), 7.58 (d, J=8.2 Hz, 1H, ArH-10), 7.56 (dd, J=7.8, 0.8 Hz, 1H, ArH-4), 7.40 (dd, J=7.9, 1.5 Hz, 1H, ArH-7), 7.32–7.25 (m, 4H, ArH-2,3,8,9), 7.18 (dd, J=7.6, 7.2 Hz, 2H, 6-ArH"-3",5"), 7.12 (t, J=7.2 Hz, 1H, 6-ArH"-4"), 7.01 (d, J=7.6 Hz, 2H, 6-ArH"-2",6"), 6.96 (d, J=8.7 Hz, 2H, ArH'-2',6'), 6.49 (s, 1H, H-6), 6.39 (d, J=8.7 Hz, 2H, ArH'-3',5');

¹³C NMR (125 MHz, DMSO-d₆) δ: 161.2 (s, 1C, ArC'-4'), 139.2 (s, 1C, ArC-6a), 133.1 (s, 1C, ArC-4a), 132.8 (s, 1C), 129.6 (s, 2C), 128.9 (s, 2C), 128.5 (s, 1C), 128.2 (s, 4C), 128.1 (s, 2C), 127.9 (s, 1C), 127.4 (s, 1C), 127.2 (s, 1C), 126.9 (s, 2C), 123.7 (s, 1C, ArC-1), 123.4 (s, 1C, ArC-10), 114.7 (s, 2C, ArC'-3',5'), 59.7 (s, 1C, C-6);

Anal. calcd for $C_{25}H_{19}NO_3S$: C, 72.62; H, 4.63; N, 3.39. Found: C, 72.35; H, 4.78; N, 3.33.

EXAMPLE 10

Step a)

(R)-5-[(4-Methoxyphenyl)sulfonyl]-6-phenyl-5,6-dihydrophenanthridine*

The enantiomers of 5-[(4-methoxyphenyl)sulfonyl]-6-phenyl-5,6-dihydrophenanthridine (3.0 g, 7.02 mmol) were separated by automated preparative normal phase chiral chromatography on a (S,S) Whelk-O® (25 cm×2 cm) column, eluting with 20% 2-propanol in hexane at a flow rate of 20 mL/min. After evaporation of the solvent in vacuo, peak one with a retention time of 12.61 minutes was isolated as a colorless solid. Crystallization of the colorless solid from a mixture of diethyl ether-hexane yielded (R)-5-[(4-methoxyphenyl)sulfonyl]-6-phenyl-5,6-dihydrophenanthridine* (1.40 g, 3.27 mmol, 47%) as a homogeneous, colorless, crystalline single enantiomer*, m.p. 145–147° C.;

$T_R$=12.61 minutes

MS [(+ESI), m/z]: 428 [M+H]⁺;

IR (Solid), $v_{max}$: 1595, 1580, 1495, 1440, 1340, 1260, 1155, 1095, 1025 cm⁻¹;

$[\alpha]_D^{25}$=−123.4° (c=1% solution, CHCl₃);

¹H NMR (500 MHz, DMSO-d₆) δ: 7.74 (dd, J=7.6, 1.2 Hz, 1H, ArH-1), 7.56 (dd, J=7.2, 1.1 Hz, 1H, ArH-10), 7.54 (d, J=6.0 Hz, 1H, ArH-4), 7.41 (dd, J=7.6, 0.8 Hz, 1H, ArH-7), 7.33–7.22 (m, 4H, ArH-2,3,8,9), 7.18 (t, J=7.8 Hz, 2H, 6-ArH"-3",5"), 7.13 (t, J=7.2 Hz, 1H, 6-ArH"-4"), 7.06 (ddd, J=9.0, 3.1, 2.9 Hz, 2H, ArH'-2',6'), 7.02 (d, J=7.3 Hz, 2H, 6-ArH"-2",6"), 6.59 (ddd, J=9.0, 3.1, 2.9 Hz, 2H, ArH'-3',5'), 6.51 (s, 1H, H-6), 3.64 (s, 3H, —OCH₃-4');

¹³C NMR (100 MHz, DMSO-d₆) δ: 162.4 (s, 1C, ArC'-4'), 139.0 (s, 1C, ArC-6a), 133.0 (s, 1C, ArC-4a), 132.6 (s, 1C), 129.7 (s, 1C), 129.6 (s, 1C), 128.7 (s, 2C, ArC'-2',6'), 128.6 (s, 1C), 128.5 (s, 1C), 128.3 (s, 1C), 128.2 (s, 2C), 128.1 (s, 2C), 127.9 (s, 1C), 127.4 (s, 2C), 126.9 (s, 2C), 123.7 (s, 1C, ArC-1), 123.4 (s, 1C, ArC-10), 113.5 (s, 2C, ArC'-3',5'), 59.8 (s, 1C, C-6), 55.5 (s, 1C, —OCH₃-4');

Anal. calcd for $C_{26}H_{21}NO_3S$: C, 73.05; H, 4.95; N, 3.28. Found: C, 72.90; H, 5.05; N, 3.19.

*The stereochemical configuration is not absolute and was assigned arbitrarily.

Step b)

4-{[(R)-6-Phenylphenanthridin-5(6H)-yl]sulfonyl}phenol*

The title compound was prepared from (R)-5-[(4-methoxyphenyl)sulfonyl]-6-phenyl-5,6-dihydrophenanthridine* (1.35 g, 3.16 mmol), cyclohexene (6.16 g, 75 mmol), and 1.0 M boron tribromide in dichloromethane (20 mL, 20 mmol) according to the procedure and in the same manner as described in Example 1, step b; and yielded, after chromatographic purification and crystallization from diethyl ether-hexane, 4-{[(R)-6-phenylphenanthridin-5(6H)-yl]sulfonyl}phenol* (0.691 g, 1.67 mmol, 53%) as a homogeneous, colorless, crystalline, single enantiomer*, m.p. 208–210° C.;

MS [(−ESI), m/z]: 412 [M−H]⁻;

IR (Solid), $v_{max}$: 3410, 1600, 1590, 1500, 1440, 1330, 1280, 1155, 1095, 1020 cm⁻¹;

$[\alpha]_D^{25}$=−141.0° (c=1% solution, CHCl₃);

¹H NMR (500 MHz, DMSO-d₆) δ: 10.23 (br s, 1H, —OH-4'), 7.74 (d, J=7.6 Hz, 1H, ArH-1), 7.58 (d, J=8.7 Hz, 1H, ArH-10), 7.56 (dd, J=7.8, 1.1 Hz, 1H, ArH-4), 7.41 (dd, J=8.6, 2.0 Hz, 1H, ArH-7), 7.32–7.24 (m, 4H, ArH-2,3,8,9), 7.17 (dd, J=7.6, 7.2 Hz, 2H, 6-ArH"-3",5"), 7.13 (t, J=7.2 Hz, 1H, 6-ArH"-4"), 7.02 (d, J=7.6 Hz, 2H, 6-ArH"-2",6"), 6.97 (ddd, J=8.9, 2.9, 1.8 Hz, 2H, ArH'-2',6'), 6.50 (s, 1H, H-6), 6.39 (ddd, J=8.9, 2.9, 1.8 Hz, 2H, ArH'-3',5');

¹³C NMR (125 MHz, DMSO-d₆) δ: 161.2 (s, 1C, ArC'-4'), 139.2 (s, 1C, ArC-6a), 133.1 (s, 1C, ArC-4a), 132.8 (s, 1C), 129.6 (s, 2C), 128.9 (s, 2C), 128.5 (s, 1C), 128.2 (s, 4C), 128.1 (s, 2C), 127.9 (s, 1C), 127.4 (s, 1C), 127.2 (s, 1C), 126.9 (s, 2C), 123.7 (s, 1C, ArC-1), 123.4 (s, 1C, ArC-10), 114.7 (s, 2C, ArC'-3',5'), 59.7 (s, 1C, C-6);

Anal. calcd for $C_{25}H_{19}NO_3S$: C, 72.62; H, 4.63; N, 3.39. Found: C, 71.67; H, 4.80; N, 3.24.

*The stereochemical configuration is not absolute and was assigned arbitrarily.

EXAMPLE 11

Step a)

(S)-5-[(4-Methoxyphenyl)sulfonyl]-6-phenyl-5,6-dihydrophenanthridine*

The enantiomers of 5-[(4-methoxyphenyl)sulfonyl]-6-phenyl-5,6-dihydrophenanthridine (3.0 g, 7.02 mmol) were separated by automated preparative normal phase chiral chromatography on a (S,S) Whelk-O® (25 cm×2 cm) column, eluting with 20% 2-propanol in hexane at a flow rate of 20 mL/min. After evaporation of the solvent in vacuo, peak two with a retention time of 14.15 minutes was isolated as a colorless solid. Crystallization of the colorless solid from a mixture of diethyl ether-hexane yielded (S)-5-[(4-methoxyphenyl)sulfonyl]-6-phenyl-5,6-dihydrophenanthridine* as a homogeneous, colorless, crystalline, single enantiomer* (1.40 g, 3.27 mmol, 47%), m.p. 145–147° C.;

$T_R$=14.15 minutes

MS [(+ESI), m/z]: 428 [M+H]⁺;

IR (Solid), $v_{max}$: 1595, 1580, 1495, 1440, 1340, 1260, 1155, 1095, 1025 cm⁻¹;

$[\alpha]_D^{25}$=+128.2° (c=1% solution, CHCl₃);

¹H NMR (500 MHz, DMSO-d₆) δ: 7.73 (dd, J=7.6, 1.2 Hz, 1H, ArH-1), 7.56 (dd, J=7.6, 1.2 Hz, 1H, ArH-10), 7.54

(d, J=6.3 Hz, 1H, ArH-4), 7.40 (dd, J=7.5, 1.1 Hz, 1H, ArH-7), 7.33–7.22 (m, 4H, ArH-2,3,8,9), 7.18 (t, J=7.6 Hz, 2H, 6-ArH"-3",5"), 7.13 (t, J=7.3 Hz, 1H, 6-ArH"-4"), 7.06 (ddd, J=8.9, 2.9, 2.7 Hz, 2H, ArH'-2',6'), 7.02 (d, J=7.3 Hz, 2H, 6-ArH"-2",6"), 6.59 (ddd, J=8.9, 2.9, 2.7 Hz, 2H, ArH'-3',5'), 6.51 (s, 1H, H-6), 3.64 (s, 3H, —OCH$_3$-4');

$^{13}$C NMR (125 MHz, DMSO-d$_6$) δ: 162.4 (s, 1C, ArC'-4'), 139.0 (s, 1C, ArC-6a), 133.0 (s, 1C, ArC-4a), 132.6 (s, 1C), 129.7 (s, 1C), 129.6 (s, 1C), 128.7 (s, 2C, ArC'-2',6'), 128.6 (s, 1C), 128.5 (s, 1C), 128.3 (s, 1C), 128.2 (s, 2C), 128.1 (s, 2C), 127.9 (s, 1C), 127.4 (s, 2C), 127.0 (s, 2C), 123.7 (s, 1C, ArC-1), 123.4 (s, 1C, ArC-10), 113.5 (s, 2C, ArC'-3',5'), 59.8 (s, 1C, C-6), 55.6 (s, 1C, —OCH$_3$-4');

Anal. calcd for C$_{26}$H$_{21}$NO$_3$S: C, 73.05; H, 4.95; N, 3.28. Found: C, 72.66; H, 4.89; N, 3.26.

*The stereochemical configuration is not absolute and was assigned arbitrarily.

Step b)

4-{[(S)-6-Phenylphenanthridin-5 (6H)-yl]sulfonyl}phenol*

The title compound was prepared from (S)-5-[(4-methoxyphenyl)sulfonyl]-6-phenyl-5,6-dihydrophenanthridine* (1.35 g, 3.16 mmol), cyclohexene (6.16 g, 75 mmol), and 1.0 M boron tribromide in dichloromethane (20 mL, 20 mmol) according to the procedure and in the same manner as described in Example 1, step b; and yielded, after chromatographic purification and crystallization from diethyl ether-hexane, 4-{[(S)-6-phenylphenanthridin-5(6H)-yl]sulfonyl}phenol* (0.627 g, 1.52 mmol, 48%) as a homogeneous, colorless, crystalline, single enantiomer*, m.p. 210–212° C.;

MS [(–ESI), m/z]: 412 [M–H]$^-$;

IR (Solid), v$_{max}$: 3410, 1600, 1590, 1500, 1440, 1330, 1280, 1155, 1095, 1020 cm$^{-1}$;

[α]$_D^{25}$=+153.3° (c=1% solution, CHCl$_3$);

$^1$H NMR (500 MHz, DMSO-d$_6$) δ: 10.22 (br s, 1H, —OH-4'), 7.74 (dd, J=7.6, 1.4 Hz, 1H, ArH-1), 7.58 (dd, J=8.7, 1.8 Hz, 1H, ArH-10), 7.56 (dd, J=7.9, 0.9 Hz, 1H, ArH-4), 7.41 (dd, J=8.7, 2.1 Hz, 1H, ArH-7), 7.32–7.24 (m, 4H, ArH-2,3,8,9), 7.18 (dd, J=7.6, 7.0 Hz, 2H, 6-ArH"-3", 5"), 7.12 (t, J=7.0 Hz, 1H, 6-ArH"-4"), 7.02 (d, J=7.6 Hz, 2H, 6-ArH"-2",6"), 6.97 (ddd, J=8.7, 2.9, 2.7 Hz, 2H, ArH'-2',6'), 6.49 (s, 1H, H-6), 6.39 (ddd, J=8.9, 2.9, 2.7 Hz, 2H, ArH'-3',5');

$^{13}$C NMR (125 MHz, DMSO-d$_6$) δ: 161.1 (s, 1C, ArC'-4'), 139.2 (s, 1C, ArC-6a), 133.1 (s, 1C, ArC-4a), 132.8 (s, 1C), 129.6 (s, 2C), 128.9 (s, 2C), 128.5 (s, 1C), 128.2 (s, 4C), 128.1 (s, 2C), 127.9 (s, 1C), 127.3 (s, 1C), 127.2 (s, 1C), 126.9 (s, 2C), 123.7 (s, 1C, ArC-1), 123.4 (s, 1C, ArC-10), 114.7 (s, 2C, ArC'-3',5'), 59.7 (s, 1C, C-6);

Anal. calcd for C$_{25}$H$_{19}$NO$_3$S: C, 72.62; H, 4.63; N, 3.39. Found: C, 72.43; H, 4.67; N, 3.28.

*The stereochemical configuration is not absolute and was assigned arbitrarily.

EXAMPLE 12

Step a)

2-Bromo-5-[(4-methoxyphenyl)sulfonyl]-6-phenyl-5,6-dihydrophenanthridine

A stirred suspension of 5-[(4-methoxyphenyl)sulfonyl]-6-phenyl-5,6-dihydrophenanthridine (4.27 g, 10 mmol) was heated to 50° C. in glacial acetic acid (20 mL) and treated drop-wise over three hours with excess bromine (8.0 g, 50 mmol). After cooling to room temperature, the reaction mixture was diluted with ethyl acetate, and the precipitate filtered. The organic phase filtrate was washed sequentially with a saturated, aqueous, sodium thiosulfate solution, a 1 N hydrochloric acid solution, and water. The organic phase was further washed sequentially with a 2.5 N aqueous sodium hydroxide solution until a basic extract was obtained, water, and a saturated, aqueous, sodium chloride solution. The organic phase was dried over anhydrous sodium sulfate, filtered through a short column of silica gel, and the solvent removed in vacuo to afford a crude yellow solid (4.0 g, 7.9 mmol, 79%). The crude solid was purified by repetitive preparative chromatography on a Biotage® 40 Mi column of pre-packed silica gel (90 g), eluting with dichloromethane at a flow rate of 25 mL/min; to afford, after evaporation of the appropriate fractions, a monobromo compound and a dibromo compound, both as solids. Crystallization of the monobromo compound from a mixture of dichloromethane-diethyl ether-hexane yielded the title compound (1.4 g, 2.76 mmol, 28%) as a homogeneous, colorless, crystalline solid, m.p. 209–211° C.;

MS [(+ESI), m/z]: 506/508 [M+H]$^+$, contains one bromine atom;

IR (Solid), v$_{max}$: 1590, 1580, 1500, 1490, 1440, 1330, 1270, 1170, 1020 cm$^{-1}$;

$^1$H NMR (400 MHz, DMSO-d$_6$) δ: 7.94 (d, J=1.2 Hz, 1H, ArH-1), 7.62 (dd, J=7.6, 0.9 Hz, 1H, ArH-10), 7.49 (s, 2H, ArH-3,4), 7.43 (dd, J=7.4, 1.3 Hz, 1H, ArH-7), 7.30 (td, J=7.4, 1.3 Hz, 1H, ArH-8), 7.24 (td, J=7.6, 1.4 Hz, 1H, ArH-9), 7.22–7.15 (m, 3H, 6-ArH"-3",4",5"), 7.11 (ddd, J=8.9, 3.0, 2.1 Hz, 2H, ArH'-2',6'), 6.99 (dd, J=8.2, 2.1 Hz, 2H, 6-ArH"-2",6"), 6.62 (ddd, J=9.0, 3.0, 2.1 Hz, 2H, ArH'-3',5'), 6.54 (s, 1H, H-6), 3.65 (s, 3H, —OCH$_3$-4');

$^{13}$C NMR (75 MHz, DMSO-d$_6$) δ: 162.5 (s, 1C, ArC'-4'), 138.7 (s, 1C, ArC-6a), 132.7 (s, 1C, ArC-4a), 132.3 (s, 1C), 131.8 (s, 1C), 131.1 (s, 1C), 130.6 (s, 1C), 128.8 (s, 2C, ArC'-2',6'), 128.7 (s, 1C), 128.4 (s, 2C), 128.3 (s, 2C), 128.2 (s, 2C), 127.5 (s, 1C), 126.9 (s, 2C), 126.4 (s, 1C), 123.9 (s, 1C, ArC-10), 120.4 (s, 1C), 113.7 (s, 2C, ArC'-3',5'), 59.6 (s, 1C, C-6), 55.6 (s, 1C, —OCH$_3$-4');

Anal. calcd for C$_{26}$H$_{20}$BrNO$_3$S: C, 61.67; H, 3.98; N, 2.77. Found: C, 61.56; H, 4.06; N, 2.72.

Step b)

4-[(2-Bromo-6-phenylphenanthridin-5(6H)-yl)sulfonyl]phenol

A stirred suspension of 2-bromo-5-[(4-methoxyphenyl)sulfonyl]-6-phenyl-5,6-dihydrophenanthridine (1.01 g, 2.0 mmol) and cyclohexene (3.70 g, 45 mmol) was treated at room temperature under nitrogen with a solution of 1.0 M boron tribromide in dichloromethane (12 mL, 12 mmol). After stirring for approximately two hours at room temperature, the reaction was quenched with methanol (20 mL) and diluted with dichloromethane. The mixture was washed sequentially with an aqueous potassium carbonate solution, a saturated, aqueous, sodium chloride solution, and water. The organic phase was dried over anhydrous sodium sulfate, filtered through a short column of silica gel, and eluted with ethyl acetate. The ethyl acetate phase was evaporated in vacuo to a crude orange residue (1.0 g,). The crude residue was purified by preparative chromatography on a Biotage® 40 Mi column of pre-packed silica gel (90 g) with gradient elution of between 10% to 30% methyl tert-butyl ether in hexane at a flow rate of 50 mL/min; and afforded, after evaporation of the solvent, a colorless oil. Crystallization of the colorless oil from a mixture of ethyl acetate-diethyl ether-hexane yielded the title compound (0.845 g, 1.72 mmol, 86%) as a homogeneous, colorless, crystalline solid, m.p. 262–265° C.;

MS [(–ESI), m/z]: 490/492 [M–H]⁻, contains one bromine atom;

IR (Solid), $v_{max}$: 3400, 1600. 1590, 1500, 1490, 1440, 1430, 1330, 1145, 830, 760 cm⁻¹;

¹H NMR (400 MHz, DMSO-d₆) δ: 10.29 (s, 1H, —OH-4'), 7.95 (d, J=1.0 Hz, 1H, ArH-1), 7.65 (d, J=7.8 Hz, 1H, ArH-10), 7.49 (s, 2H, ArH-3,4), 7.43 (d, J=7.2 Hz, 1H, ArH-7), 7.33–7.24 (m, 2H, ArH-8,9), 7.22–7.13 (m, 3H, 6-ArH"-3",4",5"), 7.02–6.99 (m, 4H, ArH'-2',6', 6-ArH"-2",6"), 6.52 (s, 1H, H-6), 6.42 (ddd, J=8.9, 2.1, 1.9 Hz, 2H, ArH'-3',5');

¹³C NMR (75 MHz, DMSO-d₆) δ: 161.4 (s, 1C, ArC'-4'), 138.9 (s, 1C, ArC-6a), 132.9 (s, 1C, ArC-4a), 132.4 (s, 1C), 131.7 (s, 1C), 131.0 (s, 1C), 130.5 (s, 1C), 128.9 (s, 2C), 128.6 (s, 1C), 128.4 (s, 1C), 128.3 (s, 3C), 128.2 (s, 1C), 127.5 (s, 1C), 126.9 (s, 2C), 126.7 (s, 1C), 126.3 (s, 1C), 123.8 (s, 1C, ArC-10), 120.2 (s, 1C), 114.9 (s, 2C, ArC'-3',5'), 59.6 (s, 1C, C-6);

Anal. calcd for $C_{25}H_{18}BrNO_3S$: C, 60.98; H, 3.68; N, 2.84. Found: C, 60.69; H, 3.63; N, 2.72.

EXAMPLE 13

Step a)

2-Bromo-5-[(3-bromo-4-methoxyphenyl)sulfonyl]-6-phenyl-5,6-dihydrophenanthridine A stirred suspension of 5-[(4-methoxyphenyl)sulfonyl]-6-phenyl-5,6-dihydrophenanthridine (4.27 g, 10 mmol) was heated to 50° C. in glacial acetic acid (20 mL) and treated drop-wise over three hours with excess bromine (8.0 g, 50 mmol). After cooling to room temperature, the reaction mixture was diluted with ethyl acetate, and the precipitate filtered. The organic phase filtrate was washed sequentially with a saturated, aqueous, sodium thiosulfate solution, a 1 N hydrochloric acid solution, and water. The organic phase was further washed sequentially with a 2.5 N aqueous sodium hydroxide solution until a basic extract was obtained, water, and a saturated, aqueous, sodium chloride solution. The organic phase was dried over anhydrous sodium sulfate, filtered through a short column of silica gel, and the solvent removed in vacuo to afford a crude yellow solid (4.0 g, 7.9 mmol, 79%). The crude solid was purified by repetitive preparative chromatography on a Biotage® 40 Mi column of pre-packed silica gel (90 g), eluting with dichloromethane at a flow rate of 25 mL/min; to afford, a monobromo compound and a dibromo compound, both as solids. Crystallization of the dibromo compound from a mixture of ethyl acetate-hexane yielded the title compound (0.663 g, 1.13 mmol, 11%) as a homogeneous, colorless, crystalline solid, m.p. 205–207° C.;

MS [(+ESI), m/z]: 584/586/588 [M+H]⁺, contains two bromine atoms;

IR (Solid), $v_{max}$: 1580, 1480, 1440, 1330, 1270, 1170 cm⁻¹;

¹H NMR (400 MHz, DMSO-d₆) δ: 7.96 (d, J=2.1 Hz, 1H, ArH-1), 7.60 (d, J=7.6 Hz, 1H, ArH-10), 7.52 (dd, J=8.6, 2.1 Hz, 1H, ArH-3), 7.47 (d, J=8.5 Hz, 1H, ArH-4), 7.47 (d, J=8.5 Hz, 1H, ArH-7), 7.32 (td, J=7.4, 1.2 Hz, 1H, ArH-8), 7.28 (d, J=2.3 Hz, 1H, ArH'-2'), 7.24 (td, J=7.6, 1.3 Hz, 1H, ArH-9), 7.20 (td, J=7.4, 1.7 Hz, 2H, 6-ArH"-3",5"), 7.15 (tt, J=7.0, 1.3 Hz, 1H, 6-ArH"-4"), 7.07 (dd, J=8.8, 2.3 Hz, 1H, ArH'-6'), 6.99 (dd, J=7.1, 0.9 Hz, 2H, 6-ArH"-2",6"), 6.80 (d, J=8.8 Hz, 1H, ArH'-5'), 6.57 (s, 1H, H-6), 3.75 (s, 3H, —OCH₃-4');

Anal. calcd for $C_{26}H_{19}Br_2NO_3S$: C, 53.35; H, 3.27; N, 2.39. Found: C, 53.18; H, 3.24; N, 2.34.

Step b)

2-Bromo-4-[(2-bromo-6-phenylphenanthridin-5(6H)-yl)sulfonyl]phenol

A stirred suspension of 2-bromo-5-[(3-bromo-4-methoxyphenyl)sulfonyl]-6-phenyl-5,6-dihydrophenanthridine (0.527 g, 0.9 mmol) and cyclohexene (2.05 g, 25 mmol) was treated at room temperature under nitrogen with a solution of 1.0 M boron tribromide in dichloromethane (6 mL, 6 mmol). After stirring for approximately two hours at room temperature, the reaction was quenched with methanol (10 mL) and diluted with dichloromethane. The mixture was washed sequentially with an aqueous potassium carbonate solution, a saturated, aqueous, sodium chloride solution, and water. The organic phase was dried over anhydrous sodium sulfate, filtered through a short column of silica gel, and eluted with ethyl acetate. The ethyl acetate phase was evaporated in vacuo to a crude orange residue (0.5 g,). The crude residue was purified by preparative chromatography on a Biotage® 40 Mi column of pre-packed silica gel (90 g) with gradient elution of between 10% to 30% methyl t-butyl ether in hexane at a flow rate of 50 mL/min; and afforded, after evaporation of the solvent, a colorless oil. Crystallization of the colorless oil from a mixture of ethyl acetate-diethyl ether-hexane yielded the title compound (0.322 g, 0.56 mmol, 63%) as a homogeneous, colorless, crystalline solid, m.p. 237–239° C.;

MS [(–ESI), m/z]: 568/570/572 [M–H]⁻, contains two bromine atoms;

IR (Solid), $v_{max}$: 3480, 1575, 1480, 1440, 1360, 1330, 1175 cm⁻¹;

¹H NMR (400 MHz, DMSO-d₆) δ: 11.18 (s, 1H, —OH-4'), 7.97 (d, J=2.2 Hz, 1H, ArH-1), 7.64 (dd, J=7.6, 0.9 Hz, 1H, ArH-10), 7.50 (dd, J=8.6, 2.2 Hz, 1H, ArH-3), 7.47–7.45 (m, 2H, ArH-4,7), 7.33 (td, J=7.4, 1.2 Hz, 1H, ArH-8), 7.26 (td, J=7.6, 1.4 Hz, 1H, ArH-9), 7.23 (d, J=2.3 Hz, 1H, ArH'-2'), 7.20 (td, J=7.4, 1.7 Hz, 2H, 6-ArH"-3",5"), 7.16 (t, J=7.0 Hz, 1H, 6-ArH"-4"), 6.99 (dd, J=7.6, 1.4 Hz, 2H, 6-ArH"-2",6"), 6.92 (dd, J=8.6, 2.4 Hz, 1H, ArH'-6'), 6.58 (d, J=8.7 Hz, 1H, ArH'-5'), 6.54 (s, 1H, H-6);

¹³C NMR (75 MHz, DMSO-d₆) δ: 158.2 (s, 1C, ArC'-4'), 138.6 (s, 1C, ArC-6a), 132.6 (s, 1C, ArC-4a), 132.1 (s, 1C), 131.9 (s, 1C), 131.7 (s, 1C), 131.1 (s, 1C), 130.7 (s, 1C), 128.8 (s, 1C), 128.3 (s, 2C), 128.2 (s, 4C), 127.6 (s, 2C), 127.0 (s, 2C), 126.4 (s, 1C), 123.8 (s, 1C, ArC-10), 120.6 (s, 1C), 115.3 (s, 1C, ArC'-5'), 109.1(s, 1C, ArC'-3'), 59.6 (s, 1C, C-6);

Additional NMR experiments (NOE) confirmed the ¹H NMR structural assignments and chemical shifts;

Anal. calcd for $C_{25}H_{17}Br_2NO_3S$: C, 52.56; H, 3.00; N, 2.45. Found: C, 52.63; H, 3.08; N, 2.30.

EXAMPLE 14

Step a)

6-tert-Butyl-5-[(4-methoxyphenyl)sulfonyl]-5,6-dihydrophenanthridine

A stirred solution of phenanthridine (7.16 g, 40 mmol) in anhydrous tetrahydrofuran (20 mL) was cooled to –30° C., and treated drop-wise under nitrogen via syringe with a solution of 1.7 M tert-butyllithium in pentane (24 mL, 40.8 mmol). The yellow solution was warmed to room temperature and stirred for 15 minutes. The mixture was cooled to −78° C., and treated with 4-methoxybenzenesulfonyl chloride (8.27 g, 40 mmol) as a solid in a single aliquot. The reaction mixture was warmed slowly to room temperature over one hour, poured into 1 N aqueous sodium hydroxide, and extracted with ethyl acetate. The organic phase was washed sequentially with water, a 1 N hydrochloric acid solution, and a saturated, aqueous, sodium chloride solution. After drying over anhydrous sodium sulfate, the organic phase was filtered through a short column of silica gel, and the filtrate evaporated in vacuo to yield a crude yellow oil (16.2 g, 99%). The crude oil was purified by preparative chromatography on a Biotage® 40 Mi column of pre-packed silica gel (90 g), eluting with a mixture of methyl tert-butyl ether-hexane (15:85) at a flow rate of 40 mL/min to afford, after evaporation of the solvent, a colorless oil. Crystallization of the colorless oil from a mixture of diethyl ether-hexane yielded the title compound (3.7 g, 9.1 mmol, 23%) as a homogeneous, colorless, crystalline solid, m.p. 156–158° C.

Step b)

4-[(6-tert-Butylphenanthridin-5(6H)-yl)sulfonyl]phenol

The title compound was prepared from 6-tert-butyl-5-[(4-methoxyphenyl)sulfonyl]-5,6-dihydrophenanthridine (0.815 g, 2 mmol), cyclohexene (3.28 g, 40 mmol), and 1.0 M boron tribromide in dichloromethane (12 mL, 12 mmol) according to the procedure and in the same manner as described in Example 1, step b; and yielded, after chromatographic purification and crystallization from a mixture of diethyl ether-hexane, 4-[(6-tert-butylphenanthridin-5(6H)-yl)sulfonyl]phenol (0.598 g, 1.52 mmol, 76%) as a homogeneous, off-white, crystalline solid, m.p. 192–194° C.;

MS [(−ESI), m/z]: 392 [M−H]$^-$;

IR (Solid), $v_{max}$: 3420, 1600, 1580, 1500, 1480, 1430, 1420, 1320, 1280, 1140, 1130, 1090, 1060, 840, 750 cm$^{-1}$;

$^1$H NMR (400 MHz, DMSO-d$_6$) δ: 10.14 (s, 1H, —OH-4'), 7.73 (dd, J=7.8, 1.6 Hz, 1H, ArH-1), 7.64 (dd, J=7.9, 1.2 Hz, 1H, ArH-4), 7.50 (dd, J=7.8, 2.1 Hz, 1H, ArH-10), 7.38 (td, J=7.4, 1.6 Hz, 1H, ArH-3), 7.31 (td, J=7.6, 1.4 Hz, 1H, ArH-2), 7.19–7.16 (m, 3H, ArH-7,8,9), 6.84 (ddd, J=8.9, 2.1, 1.9 Hz, 2H, ArH'-2'-6'), 6.31 (ddd, J=8.7, 2.1, 1.9 Hz, 2H, ArH'-3',5'), 4.94 (s, 1H, H-6), 0.70 (s, 9H, tert-butyl);

$^{13}$C NMR (75 MHz, DMSO-d$_6$) δ: 160.9 (s, 1C, ArC'-4'), 134.9 (s, 1C, ArC-6a), 131.7 (s, 1C, ArC-4a), 130.4 (s, 1C, ArC-10b), 130.3 (s, 1C, ArC-4), 129.1 (s, 1C, ArC-10a), 128.6 (s, 2C, ArC'-2',6'), 128.2 (s, 1C, ArC'-1'), 128.0 (s, 1C, ArC-3), 127.5 (s, 1C, ArC-8), 127.0 (s, 3C, ArC-2,7,9), 123.5 (s, 1C, ArC-1), 122.8 (s, 1C, ArC-10), 114.5 (s, 2C, ArC'-3',5'), 65.4 (s, 1C, C-6), 36.8 (s, 1C, —C(CH$_3$)$_3$-6), 26.5 (s, 3C, —C(CH$_3$)$_3$-6);

Anal. calcd for C$_{23}$H$_{23}$NO$_3$S: C, 70.20; H, 5.89; N, 3.56. Found: C, 69.89; H, 6.02; N, 3.54.

EXAMPLE 15

Step a)

(R)-6-tert-Butyl-5-[(4-methoxyphenyl)sulfonyl]-5,6-dihydrophenanthridine*

The enantiomers of 6-tert-butyl-5-[(4-methoxyphenyl)sulfonyl]-5,6-dihydrophenanthridine (4.26 g, 10.45 mmol) were separated by automated, preparative, normal phase, chiral chromatography on a (S,S) Whelk-O® (25 cm×2 cm) column, eluting with 10% 2-propanol in hexane at a flow rate of 20 mL/min. After evaporation of the solvent in vacuo, peak one with a retention time at 11.88 minutes was isolated as a colorless solid. Crystallization of the colorless solid from a mixture of ethyl acetate-diethyl ether-hexane yielded (R)-6-tert-butyl-5-[(4-methoxyphenyl)sulfonyl]-5,6-dihydrophenanthridine* (1.47 g, 3.61 mmol, 35%) as a homogeneous, clear, colorless, crystalline (needles), single enantiomer*, m.p. 157–158° C.;

$T_R$=11.88 minutes

MS [(+ESI), m/z]: 408 [M+H]$^+$;

IR (Solid), $v_{max}$: 1595, 1580, 1495, 1480, 1340, 1260, 1160, 1020, 830, 740 cm$^{-1}$;

$[\alpha]_D^{25}$=−275.16° (c=5.257 mg/0.526 mL, CHCl$_3$);

Enantiomeric Purity: 99.7% by chiral HPLC;

$^1$H NMR (500 MHz, DMSO-d$_6$) δ: 7.72 (d, J=7.6 Hz, 1H, ArH-1), 7.65 (d, J=7.9 Hz, 1H, ArH-4), 7.46 (dd, J=5.7, 2.4 Hz, 1H, ArH-10), 7.40 (td, J=7.3, 0.9 Hz, 1H, ArH-3), 7.33 (t, J=7.6 Hz, 1H, ArH-2), 7.16–7.13 (m, 3H, ArH-7,8,9), 6.95 (ddd, J=8.7, 2.9, 2.7 Hz, 2H, ArH'-2'-6'), 6.52 (ddd, J=8.7, 2.9, 2.7 Hz, 2H, ArH'-3',5'), 4.95 (s, 1H, H-6), 3.61 (s, 3H, —OCH$_3$-4'), 0.71 (s, 9H, tert-butyl);

$^{13}$C NMR (125 MHz, DMSO-d$_6$) δ: 162.1 (s, 1C, ArC'-4'), 134.8 (s, 1C, ArC-6a), 131.5 (s, 1C, ArC-4a), 130.5 (s, 1C,), 130.3 (s, 1C), 129.2 (s, 1C), 128.6 (s, 1C), 128.5 (s, 2C, ArC'-2',6'), 128.3 (s, 1C), 128.1 (s, 1C), 127.5 (s, 1C), 127.2 (s, 1C), 127.1 (s, 1C), 123.5 (s, 1C, ArC-10), 122.8 (s, 1C), 113.3 (s, 2C, ArC'-3',5'), 65.5 (s, 1C, C-6), 55.5 (s, 1C, —OCH$_3$-4'), 36.8 (s, 1C, —C(CH$_3$)$_3$-6), 26.5 (s, 3C, —C(CH$_3$)$_3$-6);

Anal. calcd for C$_{24}$H$_{25}$NO$_3$S: C, 70.73; H, 6.18; N, 3.44. Found: C, 70.48; H, 6.32; N, 3.24.

*The absolute configuration was determined by a single crystal x-ray diffraction experiment.

Step b)

4-{[(R)-6-tert-Butylphenanthridin-5(6H)-yl]sulfonyl}phenol*

The title compound was prepared from (R)-6-tert-butyl-5-[(4-methoxyphenyl)sulfonyl]-5,6-dihydrophenanthridine (1.35 g, 3.31 mmol), cyclohexene (6.16 g, 75 mmol), and 1.0 M boron tribromide in dichloromethane (20 mL, 20 mmol) according to the procedure and in the same manner as described in Example 12, step b; and yielded, after chromatographic purification and crystallization from a mixture of diethyl ether-hexane, 4-{[(R)-6-tert-butylphenanthridin-5(6H)-yl]sulfonyl}phenol* (1.1 g, 2.8 mmol, 84%) as a homogeneous, colorless, crystalline, single enantiomer*, m.p. 187–189° C.;

MS [(−ESI), m/z]: 392 [M−H]$^-$;

MS [(+ESI), m/z]: 394 [M+H]$^+$;

IR (Solid), $v_{max}$: 3400, 1600, 1580, 1500, 1480, 1430, 1330, 1280, 1210, 1150, 1090, 1060, 830, 740 cm$^{-1}$;

$[\alpha]_D^{25}$=−305.4° (c=1% solution, CHCl$_3$);

Enantiomeric Purity: 99.9% by chiral HPLC;

$^1$H NMR (500 MHz, DMSO-d$_6$) δ: 10.13 (s, 1H, —OH-4'), 7.73 (d, J=7.8 Hz, 1H, ArH-1), 7.64 (d, J=7.9 Hz, 1H, ArH-4), 7.50 (dd, J=3.8, 3.2 Hz, 1H, ArH-10), 7.38 (td, J=7.5, 1.4 Hz, 1H, ArH-3), 7.31 (t, J=7.5 Hz, 1H, ArH-2), 7.19–7.16 (m, 3H, ArH-7,8,9), 6.85 (d, J=8.7 Hz, 2H, ArH'-2'-6'), 6.32 (d, J=8.7 Hz, 2H, ArH'-3',5'), 4.94 (s, 1H, H-6), 0.70 (s, 9H, tert-butyl);

$^{13}$C NMR (125 MHz, DMSO-d$_6$) δ: 160.9 (s, 1C, ArC'-4'), 134.9 (s, 1C, ArC-6a), 131.7 (s, 1C, ArC-4a), 130.4 (s, 1C, ArC-10b), 130.3 (s, 1C, ArC-4), 129.1 (s, 1C, ArC-10a), 128.6 (s, 2C, ArC'-2',6'), 128.2 (s, 1C, ArC'-1'), 128.0 (s, 1C,

ArC-3), 127.5 (s, 1C, ArC-8), 127.1 (s, 1C, ArC-2), 127.0 (s, 2C, ArC-7,9), 123.5 (s, 1C, ArC-1), 122.7 (s, 1C, ArC-10), 114.5 (s, 2C, ArC'-3',5'), 65.4 (s, 1C, C-6), 36.8 (s, 1C, —C(CH$_3$)$_3$-6), 26.5 (s, 3C, —C(CH$_3$)$_3$-6);

Anal. calcd for C$_{23}$H$_{23}$NO$_3$S: C, 70.20; H, 5.89; N, 3.56. Found: C, 70.17; H, 5.91; N, 3.42.

*The absolute configuration was assigned by comparison of the physical and optical properties of the starting materials and other optical enantiomers, and the results of single crystal x-ray diffraction experiments on both (R)-6-tert-butyl-5-[(4-methoxyphenyl)sulfonyl]-5,6-dihydrophenanthridine and 4-{[(S)-6-tert-butylphenanthridin-5(6H)-yl]sulfonyl}phenol.

EXAMPLE 16

Step a)

(S)-6-tert-Butyl-5-[(4-methoxyphenyl)sulfonyl]-5,6-dihydrophenanthridine*

The enantiomers of 6-tert-butyl-5-[(4-methoxyphenyl)sulfonyl]-5,6-dihydrophenanthridine (4.26 g, 10.45 mmol) were separated by automated preparative normal phase chiral chromatography on a (S,S) Whelk-O® (25 cm×2 cm) column, eluting with 10% 2-propanol in hexane at a flow rate of 20 mL/min. After evaporation of the solvent in vacuo, peak two with a retention time at 14.25 minutes was isolated as a colorless solid. Crystallization of the colorless solid from a mixture of ethyl acetate-diethyl ether-hexane yielded (S)-6-tert-butyl-5-[(4-methoxyphenyl)sulfonyl]-5,6-dihydrophenanthridine* (1.47 g, 3.61 mmol, 35%) as a homogeneous, colorless, crystalline (needles), single enantiomer* m.p. 156–158° C.;

T$_R$=14.25 minutes

MS [(+ESI), m/z]: 408 [M+H]$^+$;

IR (Solid), ν$_{max}$: 1595, 1580, 1495, 1480, 1340, 1260, 1160, 1020, 830, 740 cm$^{-1}$;

[α]$_D$$^{25}$=+272.81° (c=5.364 mg/0.536 mL, CHCl$_3$);

Enantiomeric Purity: 99.5% by chiral HPLC;

$^1$H NMR (500 MHz, DMSO-d$_6$) δ: 7.73 (dd, J=7.8, 1.1 Hz, 1H, ArH-1), 7.65 (dd, J=8.1, 1.1 Hz, 1H, ArH-4), 7.46 (dd, J=5.5, 2.9 Hz, 1H, ArH-10), 7.40 (td, J=7.5, 1.4 Hz, 1H, ArH-3), 7.33 (td, J=7.6, 1.2 Hz, 1H, ArH-2), 7.17–7.13 (m, 3H, ArH-7,8,9), 6.95 (d, J=9.0 Hz, 2H, ArH'-2'-6'), 6.51 (d, J=9.0 Hz, 2H, ArH'-3',5'), 4.95 (s, 1H, H-6), 3.61 (s, 3H, —OCH$_3$-4'), 0.71 (s, 9H, tert-butyl);

$^{13}$C NMR (125 MHz, DMSO-d$_6$) δ: 162.1 (s, 1C, ArC'-4'), 134.8 (s, 1C, ArC-6a), 131.5 (s, 1C, ArC-4a), 130.5 (s, 1C), 130.3 (s, 1C), 129.2 (s, 1C), 128.6 (s, 1C), 128.5 (s, 2C, ArC'-2',6'), 128.3 (s, 1C), 128.1 (s, 1C), 127.5 (s, 1C), 127.2 (s, 1C), 127.1 (s, 1C), 123.5 (s, 1C, ArC-10), 122.8 (s, 1C), 113.3 (s, 2C, ArC'-3',5'), 65.5 (s, 1C, C-6), 55.5 (s, 1C, —OCH$_3$-4'), 36.8 (s, 1C, —C(CH$_3$)$_3$-6), 26.5 (s, 3C, —C(CH$_3$)$_3$-6);

Anal. calcd for C$_{24}$H$_{25}$NO$_3$S: C, 70.73; H, 6.18; N, 3.44. Found: C, 70.69; H, 6.04; N, 3.27.

*The absolute configuration was determined by a single crystal x-ray diffraction experiment.

Step b)

4-{[(S)-6-tert-Butylphenanthridin-5(6H)-yl]sulfonyl}phenol*

The title compound was prepared from (S)-6-tert-butyl-5-[(4-methoxyphenyl)sulfonyl]-5,6-dihydrophenanthridine (1.35 g, 3.31 mmol), cyclohexene (6.16 g, 75 mmol), and 1.0 M boron tribromide in dichloromethane (20 mL, 20 mmol) according to the procedure and in the same manner as described in Example 12, step b; and yielded, after chromatographic purification and crystallization from a mixture of diethyl ether-hexane, 4-{[(S)-6-tert-butylphenanthridin-5(6H)-yl]sulfonyl}phenol* (0.975 g, 2.48 mmol, 75%) as a homogeneous, colorless, crystalline (prisms), single enantiomer*, m.p. 187–189° C.;

MS [(–ESI), m/z]: 392 [M–H]$^-$;

MS [(+ESI), m/z]: 394 [M+H]$^+$;

IR (Solid), ν$_{max}$: 3470, 3400, 1600, 1580, 1500, 1480, 1430, 1320, 1280, 1160, 1150, 1090, 1060, 830, 740 cm$^{-1}$;

[α]$_D$$^{25}$=+310.5° (c=1% solution, CHCl$_3$);

Enantiomeric Purity: 100.0% by chiral HPLC;

$^1$H NMR (400 MHz, DMSO-d$_6$) δ: 10.09 (s, 1H, —OH-4'), 7.69 (dd, J=7.8, 1.4 Hz, 1H, ArH-1), 7.60 (dd, J=8.0, 1.3 Hz, 1H, ArH-4), 7.46 (dd, J=5.3, 2.0 Hz, 1H, ArH-10), 7.34 (td, J=7.5, 1.4 Hz, 1H, ArH-3), 7.27 (td, J=7.5, 1.3 Hz, 1H, ArH-2), 7.15–7.12 (m, 3H, ArH-7,8,9), 6.81 (ddd, J=8.8, 2.9, 2.0 Hz, 2H, ArH'-2'-6'), 6.28 (ddd, J=8.8, 2.9, 2.0 Hz, 2H, ArH'-3',5'), 4.90 (s, 1H, H-6), 0.67 (s, 9H, tert-butyl);

$^{13}$C NMR (100 MHz, DMSO-d$_6$) δ: 161.6 (s, 1C, ArC'-4'), 135.6 (s, 1C, ArC-6a), 132.4 (s, 1C, ArC-4a), 131.1 (s, 1C, ArC-10b), 131.0 (s, 1C, ArC-4), 129.8 (s, 1C, ArC-10a), 129.3 (s, 2C, ArC'-2',6'), 128.8 (s, 1C, ArC'-1'), 128.7 (s, 1C, ArC-3), 128.2 (s, 1C, ArC-8), 127.7 (s, 3C, ArC-2,7,9), 124.1 (s, 1C, ArC-1), 123.4 (s, 1C, ArC-10), 115.2 (s, 2C, ArC'-3',5'), 66.1 (s, 1C, C-6), 37.4 (s, 1C, —C(CH$_3$)$_3$-6), 27.2 (s, 3C, —C(CH$_3$)$_3$-6);

Anal. calcd for C$_{23}$H$_{23}$NO$_3$S: C, 70.20; H, 5.89; N, 3.56. Found: C, 70.17; H, 5.93; N, 3.46.

*The absolute configuration was determined by a single crystal x-ray diffraction experiment.

EXAMPLE 17

Step a)

2-Bromo-6-tert-butyl-5-[(4-methoxyphenyl)sulfonyl]-5,6-dihydrophenanthridine The title compound was prepared from 6-tert-butyl-5-[(4-methoxyphenyl)sulfonyl]-5,6-dihydrophenanthridine (1.43 g, 3.5 mmol) and bromine (4.0 g, 25.0 mmol) according to the procedure and in the same manner as described in Example 4, step a; and yielded, after chromatographic purification and crystallization from a mixture of ethyl acetate-diethyl ether-hexane, 2-bromo-6-tert-butyl-5-[(4-methoxyphenyl)sulfonyl]-5,6-dihydrophenanthridine (1.13 g, 2.32 mmol, 66%) as a colorless, crystalline solid, m.p. 195–198° C.;

MS [(+ESI), m/z]: 486/488 [M+H]$^+$, contains one bromine atom;

IR (Solid), ν$_{max}$: 1595, 1580, 1500, 1480, 1440, 1330, 1270, 1160 cm$^{-1}$;

$^1$H NMR (400 MHz, DMSO-d$_6$) δ: 7.94 (s, 1H, ArH-1), 7.58 (m, 2H, ArH-3,4), 7.19 (d, J=7.4 Hz, 1H, ArH-10), 7.20–7.14 (m, 3H, ArH-7,8,9), 6.99 (ddd, J=8.9, 2.9, 1.9 Hz, 2H, ArH'-2'-6'), 6.55 (ddd, J=8.9, 2.9, 1.9 Hz, 2H, ArH'-3',5'), ), 4.97 (s, 1H, H-6), 3.62 (s, 3H, —OCH$_3$-4'), 0.71 (s, 9H, tert-butyl);

$^{13}$C NMR (75 MHz, DMSO-d$_6$) δ: 162.3 (s, 1C, ArC'-4'), 134.1 (s, 1C, ArC-6a), 132.6 (s, 1C, ArC-4a), 131.6 (s, 1C, ArC-10b), 131.0 (s, 1C, ArC-4), 130.1 (s, 1C, ArC-10a), 129.3 (s, 1C, ArC'-1'), 129.0 (s, 1C, ArC-3), 128.5 (s, 2C, ArC'-2',6'), 128.4 (s, 1C, ArC-8), 127.8 (s, 1C, ArC-2), 127.7 (s, 1C, ArC-9), 126.1 (s, 1C, ArC-7), 123.2 (s, 1C, ArC-10), 120.1 (s, 1C, ArC-1), 113.5 (s, 2C, ArC'-3',5'), 65.4 (s, 1C, C-6), 55.5 (s, 1C, —OCH$_3$-4'), 36.9 (s, 1C, —C(CH$_3$)$_3$-6), 26.5 (s, 3C, —C(CH$_3$)$_3$-6);

Anal. calcd for C$_{24}$H$_{24}$BrNO$_3$S: C, 59.26; H, 4.97; N, 2.88. Found: C, 59.07; H, 5.03; N, 2.67.

Step b)

4-[(2-Bromo-6-tert-butylphenanthridin-5(6H)-yl)sulfonyl]phenol

The title compound was prepared from 2-bromo-6-tert-butyl-5-[(4-methoxyphenyl)sulfonyl]-5,6-dihydrophenanthridine (0.610 g, 1.25 mmol), cyclohexene (3.28 g, 40 mmol), and 1.0 M boron tribromide in dichloromethane (10 mL, 10 mmol) according to the procedure and in the same manner as described in Example 4, step b and yielded, after chromatographic purification and crystallization from a mixture of diethyl ether-hexane, 4-[(2-bromo-6-tert-butylphenanthridin-5(6H)-yl)sulfonyl]phenol (0.440 g, 0.93 mmol, 75%) as a homogeneous, colorless, crystalline solid, m.p. 245–247° C.;

MS [(−ESI), m/z]: 470/472 [M−H]−, contains one bromine atom;

MS [(+ESI), m/z]: 472/474 [M+H]+, contains one bromine atom;

IR (Solid), $v_{max}$: 3400, 1600, 1580, 1495, 1480, 1440, 1320, 1150, 1145, 1080, 1060, 840 cm$^{-1}$;

$^1$H NMR (400 MHz, DMSO-d$_6$) δ: 10.20 (s, 1H, —OH-4'), 7.94 (s, 1H, ArH-1), 7.58–7.55 (m, 3H, ArH-3,4,10), 7.21–7.16 (m, 3H, ArH-7,8,9), 6.89 (ddd, J=8.9, 2.9, 1.9 Hz, 2H, ArH'-2'-6'), 6.35 (ddd, J=8.9, 2.9, 1.9 Hz, 2H, ArH'-3',5'), ), 4.95 (s, 1H, H-6), 0.71 (s, 9H, tert-butyl);

$^{13}$C NMR (75 MHz, DMSO-d$_6$) δ: 161.1 (s, 1C, ArC'-4'), 134.3 (s, 1C, ArC-6a), 132.5 (s, 1C, ArC-4a), 131.7 (s, 1C, ArC-10b), 130.9 (s, 1C, ArC-4), 130.0 (s, 1C, ArC-10a), 129.2 (s, 1C, ArC'-1'), 129.0 (s, 1C, ArC-3), 128.7 (s, 2C, ArC'-2',6'), 127.7 (s, 2C, ArC-2,8), 126.8 (s, 1C, ArC-9), 126.1 (s, 1C, ArC-7), 123.1 (s, 1C, ArC-10), 119.9 (s, 1C, ArC-1), 114.7 (s, 2C, ArC'-3',5'), 65.4 (s, 1C, C-6), 36.9 (s, 1C, —C(CH$_3$)$_3$-6), 26.5 (s, 3C, —C(CH$_3$)$_3$-6);

Anal. calcd for C$_{23}$H$_{22}$BrNO$_3$S: C, 58.48; H, 4.69; N, 2.96. Found: C, 58.42; H, 4.70; N, 2.81.

EXAMPLE 18

Step a)

6-Ethyl-5-[(4-methoxyphenyl)sulfonyl]-5,6-dihydrophenanthridine

A stirred solution of phenanthridine (25 g, 139 mmol) in anhydrous diethyl ether (100 mL) was cooled to −78° C., and treated drop-wise under nitrogen via syringe with a solution of 0.62 M ethyllithium[1] in diethyl ether (225 mL, 139 mmol). The yellow solution was warmed to room temperature and stirred for three to four hours. The reaction was cooled to −78° C., and quenched with water. After warming to room temperature, the reaction mixture was extracted with diethyl ether, and the organic phase was washed sequentially with water and a saturated, aqueous, sodium chloride solution. The organic phase was dried over anhydrous sodium sulfate, filtered, and the solvent evaporated in vacuo, to yield 6-ethyl-5,6-dihydrophenanthridine as a crude solid (26 g, 124 mmol, 89%).

A solution of 6-ethyl-5,6-dihydrophenanthridine (14 g, 69.2 mmol) and 4-methoxybenzenesulfonyl chloride (17.2 g, 83 mmol) in pyridine (100 ml) was heated at 80° C. overnight. The solvent was evaporated in vacuo; and the crude product was purified by preparative column chromatography on silica gel, eluting with a gradient and mixture of dichloromethane-hexane (50:50 to 100:0). After evaporation of the solvent, the residue was crystallized from diethyl ether, yielding the title compound (22.8 g, 60.1 mmol, 87%) as a colorless, crystalline solid, which was characterized by LCMS (ES+, FA, CV=5) and $^1$H NMR.

Note 1: The ethyllithium was prepared according to the procedure described in Org. Synth., Coll. Vol. VII, 293.

Step b)

4-[(6-Ethylphenanthridin-5(6H)-yl)sulfonyl]phenol

A stirred and cooled solution of 6-ethyl-5-[(4-methoxyphenyl)sulfonyl]-5,6-dihydrophenanthridine (38 mg, 100 μmol) in dichloromethane (2 mL) was treated drop-wise under nitrogen at −30° C. with a solution of 1.0 M boron tribromide in dichloromethane (500 μL, 500 μmol). After the addition was completed, the reaction mixture was allowed to warm to room temperature and was stirred for four hours. The reaction mixture was cooled to −30° C. and quenched with methanol (600 μL). The solvent was removed in vacuo to yield the title compound (36.5 mg, 100 μmol, 100%), which was confirmed by LCMS (ES−, FA, CV=20 or 5);

LCMS [(+ESI), m/z]: 366 [M+H]+;

$^1$H NMR (300 MHz, CDCl$_3$) δ: 7.80 (dd, J=7.8, 1.5 Hz, 1H, ArH-1), 7.58 (dd, J=7.8, 2.1 Hz, 1H, ArH-4), 7.37 (td, J=7.8, 1.5 Hz, 1H, ArH-3), 7.30 (td, J=7.8, 1.5 Hz, 1H, ArH-2), 7.28 (d, J=8.1, 1.5 Hz, 1H, ArH-10), 7.20–7.04 (m, 3H, ArH-7,8,9), 6.92 (d, J=9.0 Hz, 2H, ArH'-2',6'), 6.30 (d, J=9.0 Hz, 2H, ArH'-3',5'), 5.08 (t, J=7.8 Hz, 1H, H-6), 4.96 (s, 1H, —OH), 1.48 (quintet, J=7.2 Hz, 2H, —CH$_2$CH$_3$), 1.00 (t, J=7.2 Hz, 3H, —CH$_2$CH$_3$);

EXAMPLE 19

Step a)

2-Bromo-6-ethyl-5-[(4-methoxyphenyl)sulfonyl]-5,6-dihydrophenanthridine

A stirred solution of 6-ethyl-5-[(4-methoxyphenyl)sulfonyl]-5,6-dihydrophenanthridine (6.0 g, 15.8 mmol) in dichloromethane (800 mL) was treated drop-wise with excess bromine (2.1 mL, 41 mmol). The reaction mixture was heated to reflux and additional bromine (1.0 mL, 10 mmol) was added. The reaction was cooled and stirred at room temperature overnight. The reaction mixture was washed sequentially with a saturated, aqueous sodium thiosulfate solution, water, and a saturated, aqueous, sodium chloride solution. The organic phase was dried over anhydrous magnesium sulfate, filtered through a short column of silica gel, and the solvent was removed in vacuo to afford a crude yellow solid. The crude solid was crystallized from a mixture of ethyl acetate-hexane (1:1), and yielded the title compound (6.3 g, 13.8 mmol, 87%) as a colorless, crystalline solid;

LCMS [(+ESI), m/z]: 458/460 [M+H]+, contains one bromine atom.

Step b)

4-[(2-Bromo-6-ethylphenanthridin-5(6H)-yl)sulfonyl]phenol

The title compound was prepared from 2-bromo-6-ethyl-5-[(4-methoxyphenyl)sulfonyl]-5,6-dihydrophenanthridine (45.8 mg, 100 μmol) and 1.0 M boron tribromide in dichloromethane (500 μL, 500 μmol) according to the procedure and in the same manner as described in Example 18, step b and yielded, after evaporation of the solvent in vacuo, 4-[(2-bromo-6-ethylphenanthridin-5(6H)-yl)sulfonyl] phenol (44.4 mg, 100 μmol, 100%), which was confirmed by LCMS (ES−, FA, CV=20 or 5);

$^1$H NMR (300 MHz, CDCl$_3$) δ: 7.71 (d, J=2.1 Hz, 1H, ArH-1), 7.68 (d, J=8.7 Hz, 1H, ArH-4), 7.48 (dd, J=8.7, 2.1 Hz, 1H, ArH-3), 7.26 (dd, 1H, ArH-10), 7.24–7.10 (m, 2H, ArH-8–9), 7.16 (dd, J=7.5, 2.1 Hz, 1H, ArH-7), 6.95 (d, J=9.0 Hz, 2H, ArH'-2',6'), 6.33 (d, J=9.0 Hz, 2H, ArH'-3',5'), 5.07 (t, 1H, H-6), 4.83 (s, 1H, —OH-4'), 1.45 (quintet, J=7.5 Hz, 2H, —CH$_2$CH$_3$), 0.99 (t, J=7.5 Hz, 3H, —CH$_2$CH$_3$).

EXAMPLE 20

Step a)

6-Ethyl-5-[(4-methoxy-3-methylphenyl)sulfonyl]-5,6-dihydrophenanthridine

The title compound was prepared from phenanthridine, 0.62 M ethyllithium in diethyl ether, and 4-methoxy-3-methylbenzenesulfonyl chloride according to the procedure and in the same manner as described in Example 18, step a and yielded, after chromatographic purification and crystallization from diethyl ether, 6-ethyl-5-[(4-methoxy-3-methylphenyl)sulfonyl]-5,6-dihydrophenanthridine as a colorless, crystalline, solid, which was characterized by LCMS (ES+, FA, CV=5) and $^1$H NMR.

Step b)

4-[(6-Ethylphenanthridin-5(6H)-yl)sulfonyl]-2-methylphenol

The title compound was prepared from, 6-ethyl-5-[(4-methoxy-3-methylphenyl)sulfonyl]-5,6-dihydrophenanthridine (39.3 mg, 100 μmol), and 1.0 M boron tribromide in dichloromethane (500 μL, 500 μmol) according to the procedure and in the same manner as described in Example 18, step b and yielded, after evaporation of the solvent in vacuo, 4-[(6-ethylphenanthridin-5(6H)-yl)sulfonyl]-2-methylphenol (37.9 mg, 100 μmol, 100%), which was confirmed by LCMS (ES–, FA, CV=20);

LCMS [(–ESI), m/z]: 378 [M–H]$^-$;

$^1$H NMR (300 MHz, CDCl$_3$) δ: 7.78 (dd, J=7.5, 0.9 Hz, 1H, ArH-1), 7.58 (dd, J=7.5, 2.1 Hz, 1H, ArH-4), 7.40–7.03 (m, 6H, ArH-2,3,7,8,9,10), 6.80 (d, 1H, ArH'-2'), 6.75 (dd, 1H, ArH'-6'), 6.20 (d, 1H, ArH'-5') 5.07 (t, J=7.2 Hz, 1H, H-6), 4.83 (s, 1H, —OH-4'), 1.85 (s, 3H, —CH$_3$-3'), 1.44 (quintet, 2H, —CH$_2$CH$_3$), 1.00 (t, J=7.5 Hz, 3H, —CH$_2$CH$_3$).

EXAMPLE 21

Step a)

2-Bromo-6-ethyl-5-[(4-methoxy-3-methylphenyl)sulfonyl]-5,6-dihydrophenanthridin The title compound was prepared from 6-ethyl-5-[(4-methoxy-3-methylphenyl)sulfonyl]-5,6-dihydrophenanthridine and excess bromine according to the procedure and in the same manner as described in Example 19, step a and yielded, after crystallization from a mixture of ethyl acetate-hexane, 2-bromo-6-ethyl-5-[(4-methoxy-3-methylphenyl)sulfonyl]-5,6-dihydrophenanthridine as a colorless, crystalline, solid, which was characterized by LCMS (ES+, FA, CV=5) and $^1$H NMR;

Step b)

4-[(2-Bromo-6-ethylphenanthridin-5(6H)-yl)sulfonyl]-2-methylphenol

The title compound was prepared from 2-bromo-6-ethyl-5-[(4-methoxy-3-methylphenyl)sulfonyl]-5,6-dihydrophenanthridine (47.2 mg, 100 μmol) and 1.0 M boron tribromide in dichloromethane (500 μL, 500 μmol) according to the procedure and in the same manner as described in Example 18, step b and yielded, after evaporation of the solvent in vacuo, 4-[(2-bromo-6-ethylphenanthridin-5(6H)-yl)sulfonyl]-2-methylphenol (45.8 mg, 100 μmol, 100%), which was confirmed by LCMS (ES–, FA, CV=20 or 5);

LCMS [(+ESI), m/z]: 458/460 [M+H]$^+$, contains one bromine atom.

$^1$H NMR (300 MHz, CDCl$_3$) δ: 7.71 (d, J=2.1 Hz, 1H, ArH-1), 7.67 (d, J=8.4 Hz, 1H, ArH-4), 7.48 (dd, J=8.4, 2.1 Hz, 1H, ArH-3), 7.24 (dd, 1H, ArH-10), 7.19 (td, J=7.2, 1.2 Hz, 1H, ArH-8), 7.16 (td, J=7.2, 1.2 Hz, 1H, ArH-9), 7.08 (dd, J=9.0, 1.8 Hz, 1H, ArH-7), 6.83 (d, J=2.4 Hz, 1H, ArH'-2'), 6.78 (dd, J=8.4, 2.4 Hz, 1H, ArH'-6'), 6.28 (d, J=8.1 Hz, 1H, ArH'-5'), 5.07 (t, 1H, H-6), 4.90 (s, 1H, —OH-4'), 1.87 (s, 3H, —CH$_3$-3'), 1.44 (p, J=7.5 Hz, 2H, —CH$_2$CH$_3$), 1.00 (t, J=6.9 Hz, 3H, —CH$_2$CH$_3$).

EXAMPLE 22

Step a)

5-[(4-Methoxyphenyl)sulfonyl]-{(S*)-6-[(R*)-1-methylpropyl]}-5,6-dihydrophenanthridine A stirred solution of phenanthridine (3.58 g, 20 mmol) in anhydrous diethyl ether (20 mL) was cooled to –30° C., and treated drop-wise under nitrogen via syringe with a solution of 1.3 M sec-butyllithium in cyclohexane (15.5 mL, 20.15 mmol). The yellow solution was warmed to room temperature and stirred for 15 minutes. The mixture was cooled to –78° C., and treated with 4-methoxybenzenesulfonyl chloride (4.12 g, 20 mmol) as a solid in a single aliquot. The reaction mixture was warmed slowly to room temperature over one hour, diluted with diethyl ether (80 mL), and the white precipitate (first diastereomer A) (4.0 g, 10.17 mmol, 51%) filtered.[1,3] The filtrate was poured into 1 N aqueous sodium hydroxide, and extracted with ethyl acetate. The organic phase was washed sequentially with water, a 1 N hydrochloric acid solution, and a saturated, aqueous sodium chloride solution. After drying over anhydrous sodium sulfate, the organic phase was filtered through a short column of silica gel, and the filtrate evaporated in vacuo to yield a crude yellow oil (3.87 g, 9.84 mmol, 49%). The crude oil was crystallized from diethyl ether to afford the title compound, enriched in the second diastereomer B.[2,3].

Notes:
1. The white precipitate consisted of two diastereomers in a ratio of ~88(A):12(B), and was labeled first diastereomer A, (S*)(R*).
2. The crystallized solid consisted of two diastereomers in a ratio of ~27(A):73(B), and was labeled second diastereomer B, (R*)(R*).
3. The diastereomeric ratio was determined by analytical reverse phase chromatography on a Chromolith® RP-C-18 column (4.6 mm×100 mm) eluting isocratically with 70% methanol in water with 0.1% trifluoroacetic acid. Diastereomer A, retention time at 2.36 minutes. Diastereomer B, retention time at 2.51 minutes. $^1$H NMR was also used to estimate the diastereomeric ratio.

Step b)

4{[(S*)-6-[(R*)-1-Methylpropyl]phenanthridin-5(6H)-yl]sulfonyl}phenol

The title compound was prepared from 5-[(4-methoxyphenyl)sulfonyl]-{(S*)-6-[(R*)-1-methylpropyl]}-5,6-dihydrophenanthridine (first diastereomer A, 0.814 g, 2 mmol), cyclohexene (3.69 g, 45 mmol), and 1.0 M boron tribromide in dichloromethane (12 mL, 12 mmol) according to the procedure and in the same manner as described in Example 1, step b and yielded, after chromatographic purification and crystallization from a mixture of diethyl ether-hexane, 4-{[(S*)-6-[(R*)-1-methylpropyl]phenanthridin-5(6H)-yl]sulfonyl}phenol (0.425 g, 1.08 mmol, 54%) as a colorless, crystalline solid, m.p. 115–118° C.;

MS [(−ESI), m/z]: 392 [M−H]⁻;

IR (Solid), $v_{max}$: 3430, 1595, 1580, 1500, 1480, 1440, 1320, 1130, 1090, 1075, 830, 725 cm⁻¹;

¹H NMR (500 MHz, DMSO-d₆) δ: 10.13 (s, 1H, —OH-4'), 7.76 (dd, J=7.6, 1.4 Hz, 1H, ArH-1), 7.63 (dd, J=7.8, 1.4 Hz, 1H, ArH-4), 7.46 (dd, J=7.6, 2.0 Hz, 1H, ArH-10), 7.39 (td, J=7.5, 1.4 Hz, 1H, ArH-3), 7.34 (td, J=7.5, 1.4 Hz, 1H, ArH-2), 7.19–7.14 (m, 3H, ArH-7,8,9), 6.82 (ddd, J=8.7, 2.9, 2.0 Hz, 2H, ArH'-2',6'), 6.31 (ddd, J=8.8, 2.9, 2.0 Hz, 2H, ArH'-3',5'), 4.79 (d, J=9.2 Hz, 1H, H-6), 1.26–1.21 (m, 1H, —CH(CH₃)CH₂CH₃), 1.14–1.05 (m, 2H, —CH(CH₃)CH₂CH₃), 0.86 (d, J=6.3 Hz, 3H, —CH(CH₃)CH₂CH₃), 0.69 (t, J=7.2 Hz, 3H, —CH(CH₃)CH₂CH₃);

¹³C NMR (125 MHz, DMSO-d₆) δ: 160.9 (s, 1C, ArC'-4'), 133.9 (s, 1C, ArC-6a), 133.3 (s, 1C, ArC-4a), 129.9 (s, 1C, ArC-10b), 129.1 (s, 1C, ArC-4), 128.6 (s, 2C, ArC'-2',6'), 128.2 (s, 1C, ArC'-1'), 128.1 (s, 1C, ArC-10a), 128.0 (s, 1C, ArC-3), 127.5 (s, 1C, ArC-2), 127.3 (s, 1C, ArH-8), 127.2 (s, 2C, ArC-7,9), 123.7 (s, 1C, ArC-1), 123.2 (s, 1C, ArC-10), 114.5 (s, 2C, ArC'-3',5'), 62.5 (s, 1C, C-6), 37.3 (s, 1C, —CH(CH₃)CH₂CH₃), 24.7 (s, 1C, —CH(CH₃)CH₂CH₃), 15.2 (s, 1C, —CH(CH₃)CH₂CH₃), 11.0 (s, 1C, —CH(CH₃)CH₂CH₃);

Additional NMR experiments (NOE, TOCSY) confirmed the ¹H NMR structural assignments and chemical shifts;

Anal. calcd for C₂₃H₂₃NO₃S: C, 70.20; H, 5.89; N, 3.56. Found: C, 70.22; H, 5.93; N, 3.43.

EXAMPLE 23

Step a)

5-[(3,4-Dimethoxyphenyl)sulfonyl]-6-methyl-5,6-dihydrophenanthridine

A stirred solution of phenanthridine (3.58 g, 20 mmol) in anhydrous diethyl ether (20 mL) was cooled to −30° C., and treated drop-wise under nitrogen via syringe with a solution of 1.4 M methyllithium in diethyl ether (14.5 mL, 20.3 mmol). The yellow solution was warmed to room temperature and stirred for 15 minutes. The mixture was cooled to −78° C., and treated with 3,4-dimethoxybenzenesulfonyl chloride (4.73 g, 20 mmol) as a solid in a single aliquot. The reaction mixture was warmed slowly to room temperature over one hour, poured into a 1 N aqueous sodium hydroxide solution, and extracted with ethyl acetate. The organic phase was washed sequentially with water, 1 N hydrochloric acid, and a saturated, aqueous, sodium chloride solution. After drying over anhydrous sodium sulfate, the organic phase was filtered through a short column of silica gel, and the filtrate evaporated in vacuo to yield a crude yellow solid (5.3 g, 67%). Crystallization of the solid from a mixture of diethyl ether-hexane yielded the title compound (2.93 g) and a second crop (0.8 g) (Total: 3.73 g, 9.43 mmol, 47%) as a homogeneous, off-white, crystalline solid, m.p. 131–133° C.;

MS [(+ESI), m/z]: 396 [M+H]⁺;

IR (Solid), $v_{max}$: 1590, 1505, 1440, 1330, 1275, 1230, 1160, 1130, 1080, 1020, 770, 730 cm⁻¹;

¹H NMR (500 MHz, DMSO-d₆) δ: 7.77 (dd, J=7.6, 1.2 Hz, 1H, ArH-1), 7.63 (dd, J=7.9, 1.1 Hz, 1H, ArH-4), 7.45–7.41 (m, 2H, ArH-3,10), 7.38 (td, J=7.5, 1.1 Hz, 1H, ArH-2), 7.24 (d, J=7.3 Hz, 1H, ArH-7), 7.16 (t, J=7.3 Hz, 1H, ArH-8), 7.11 (td, J=7.5, 1.1 Hz, 1H, ArH-9), 6.60 (dd, J=8.6, 2.0 Hz, 1H, ArH'-6'), 6.56 (d, J=8.6 Hz, 1H, ArH'-5'), 6.38 (d, J=2.0 Hz, 1H, ArH'-2'), 5.44 (q, J=6.9 Hz, 1H, H-6), 3.61 (s, 3H, —OCH₃-4'), 3.38 (s, 3H, —OCH₃-3'), 1.14 (d, J=7.0 Hz, 3H, —CH₃-6);

¹³C NMR (125 MHz, DMSO-d₆) δ: 152.0 (s, 1C, ArC'-4'), 147.6 (s, 1C, ArC'-3'), 136.3 (s, 1C, ArC-6a), 132.6 (s, 1C, ArC-4a), 129.5 (s, 1C, ArC-10b), 128.8 (s, 1C, ArC-4), 128.3 (s, 1C, ArC'-1'), 128.2 (s, 1C, ArC-10a), 128.0 (s, 2C, ArC-3,8), 127.5 (s, 1C, ArC-2), 127.4 (s, 1C, ArC-9), 126.0 (s, 1C, ArC-7), 123.6 (s, 1C, ArC-1), 123.0 (s, 1C, ArC-10), 120.6 (s, 1C, ArC'-6'), 110.4 (s, 1C, ArC'-2'), 108.9 (s, 1C, ArC'-5'), 55.7 (s, 1C, —OCH₃-4'), 55.0 (s, 1C, —OCH₃-3'), 53.9 (s, 1C, C-6), 21.8 (s, 1C, —CH₃-6);

Anal. calcd for C₂₂H₂₁NO₄S: C, 66.82; H, 5.35; N, 3.54. Found: C, 66.82; H, 5.27; N, 3.22.

Step b)

4-[(6-Methylphenanthridin-5(6H)-yl)sulfonyl]benzene-1,2-diol

A stirred suspension of 5-[(3,4-dimethoxyphenyl)sulfonyl]-6-methyl-5,6-dihydrophenanthridine (988 mg, 2.5 mmol) and cyclohexene (4.11 g, 50 mmol) was treated at room temperature under nitrogen with a solution of 1.0 M boron tribromide in dichloromethane (15 mL, 15 mmol). After stirring for approximately two hours at room temperature, the reaction was quenched with methanol (20 mL) and diluted with dichloromethane. The mixture was washed sequentially with an aqueous potassium carbonate solution, a saturated, aqueous, sodium chloride solution, and water. The organic phase was dried over anhydrous sodium sulfate, filtered through a short column of silica gel, and eluted with ethyl acetate. The ethyl acetate phase was evaporated in vacuo to a crude residue (1.0 g). The crude residue was purified by preparative chromatography on a Biotage® 40 Mi column of pre-packed silica gel (90 g) with gradient elution of between 10% to 70% methyl tert-butyl ether in hexane at a flow rate of 50 mL/min; and afforded, after evaporation of the solvent, a colorless solid. Crystallization of the colorless solid from a mixture of ethyl acetate-diethyl ether-hexane yielded the title compound (0.523 g, 1.42 mmol, 57%) as a colorless, amorphous solid, m.p. 163–165° C.;

MS [(−ESI), m/z]: 366 [M−H]⁻;

IR (Solid), $v_{max}$: 3400, 1610, 1595, 1520, 1480, 1430, 1340, 1290, 1150, 1075, 775, 730 cm⁻¹;

¹H NMR (500 MHz, DMSO-d₆) δ: 9.59 (br s, 1H, —OH-4'), 9.18 (bs, 1H, —OH-3'), 7.79 (d, J=7.6 Hz, 1H, ArH-1), 7.59 (d, J=7.8 Hz, 1H, ArH-4), 7.52 (d, J=7.3 Hz, 1H, ArH-10), 7.40 (t, J=7.3 Hz, 1H, ArH-3), 7.35 (t, J=7.5 Hz, 1H, ArH-2), 7.19–7.12 (m, 3H, ArH-7,8,9), 6.46 (d, J=2.1 Hz, 1H, ArH'-2'), 6.41 (dd, J=8.4, 2.1 Hz, 1H, ArH'-6'), 6.32 (d, J=8.4 Hz, 1H, ArH'-5'), 5.35 (q, J=6.9 Hz, 1H, H-6), 1.12 (d, J=6.9 Hz, 3H, —CH₃-6);

¹³C NMR (125 MHz, DMSO-d₆) δ: 149.5 (s, 1C, ArC'-4'), 144.5 (s, 1C, ArC'-3'), 136.6 (s, 1C, ArC-6a), 132.8 (s, 1C, ArC-4a), 129.2 (s, 1C, ArC-10b), 128.4 (s, 1C, ArC-4), 128.3 (s, 1C, ArC'-1'), 128.1 (s, 1C, ArC-10a), 127.9 (s, 1C, ArC-3), 127.4 (s, 1C, ArC-8), 127.1 (s, 2C, ArC-2,9), 125.9 (s, 1C, ArC-7), 123.7 (s, 1C, ArC-1), 123.0 (s, 1C, ArC-10), 119.1 (s, 1C, ArC'-6'), 114.4 (s, 1C, ArC'-2'), 113.8 (s, 1C, ArC'-5'), 53.8 (s, 1C, C-6), 21.8 (s, 1C, —CH₃-6);

Anal. calcd for $C_{20}H_{17}NO_4S$: C, 65.38; H, 4.66; N, 3.81. Found: C, 65.02; H, 4.65; N, 3.70.

EXAMPLE 24

2-Hydroxy-5-[(6-methylphenanthridin-5(6H)-yl) sulfonyl]benzoic acid

A stirred solution of phenanthridine (7.16 g, 40 mmol) in anhydrous diethyl ether (40 mL) was cooled to −30° C., and treated drop-wise under nitrogen via syringe with a solution of 1.4 M methyllithium in diethyl ether (30 mL, 42 mmol). The yellow solution was warmed to room temperature and stirred for 15 minutes. The mixture was cooled to −78° C., and treated with 5-(chlorosulfonyl)-2-hydroxybenzoic acid (9.47 g, 40 mmol) as a solid in a single aliquot. The reaction mixture was diluted with anhydrous tetrahydrofuran (40 mL), warmed to room temperature, and a solution of N,N-diisopropylethylamine (25.85 g, 200 mmol) in anhydrous dimethylformamide (40 mL) was added. After stirring at room temperature overnight, the reaction mixture was poured into a 1 N hydrochloric acid solution, and extracted with ethyl acetate. The organic phase was washed sequentially with a 1 N aqueous hydrochloric acid solution, water, and a saturated, aqueous, sodium chloride solution. After drying over anhydrous sodium sulfate, the organic phase was filtered and the solvent evaporated in vacuo to yield a crude yellow solid (3.4 g, 21%). The crude solid (1.0 g) was purified by reverse phase preparative chromatography on a Primesphere® 10 C-18 column (25 cm×5 cm), eluting with 56% acetonitrile in water with 0.1% trifluoroacetic acid at a flow rate of 90 mL/min. After evaporation of the acetonitrile solvent, the aqueous phase was extracted with ethyl acetate. The organic phase was washed sequentially with water and a saturated, aqueous, sodium chloride solution, dried over anhydrous sodium sulfate, and the solvent evaporated in vacuo to a colorless solid. Crystallization of the colorless solid from a mixture of diethyl ether-hexane yielded the title compound (0.46 g, 1.16 mmol) as a homogeneous, colorless, crystalline solid, m.p. 225–230° C.;

MS [(−ESI), m/z]: 394 [M−H]$^-$;

IR (Solid), $\nu_{max}$: 3300 (br), 1670, 1605, 1580, 1480, 1440, 1250, 1175, 1080, 775, 730 cm$^{-1}$;

$^1$H NMR (500 MHz, DMSO-d$_6$) δ: 7.77 (dd, J=7.6, 0.9 Hz, 1H, ArH-1), 7.61 (dd, J=7.8, 0.9 Hz, 1H, ArH-4), 7.45 (td, J=7.5, 1.4 Hz, 1H, ArH-3), 7.41–7.39 (m, 3H, ArH-2,10, ArH'-2'), 7.24 (dd, J=7.8, 0.9 Hz, 1H, ArH-7), 7.13 (td, J=7.3, 0.9 Hz, 1H, ArH-8), 7.10 (td, J=7.3, 1.4 Hz, 1H, ArH-9), 6.93 (dd, J=8.7, 2.4 Hz, 1H, ArH'-6'), 6.51 (d, J=8.9 Hz, 1H, ArH'-5'), 5.41 (q, J=7.0 Hz, 1H, H-6), 1.13 (d, J=7.0 Hz, 3H, —CH$_3$-6);

$^{13}$C NMR (125 MHz, DMSO-d$_6$) δ: 170.2 (s, 1C, —C═O-4'), 163.8 (s, 1C, ArC'-4'), 136.0 (s, 1C, ArC-6a), 132.8 (s, 1C, ArC'-6'), 132.3 (s, 1C, ArC-4a), 130.0 (s, 1C, ArC'-2'), 129.6 (s, 1C, ArC-10b), 129.1 (s, 1C, ArC-10a), 128.4 (s, 1C, ArC'-1'), 128.2 (s, 1C, ArC-3), 128.1 (s, 1C, ArC-8), 127.9 (s, 1C, ArC-2), 127.3 (s, 1C, ArC-9), 126.5 (s, 1C, ArC-4), 126.1 (s, 1C, ArC-7), 123.8 (s, 1C, ArC-1), 123.1 (s, 1C, ArC-10), 116.9 (s, 1C, ArC'-3'), 112.5 (s, 1C, ArC'-5'), 54.1 (s, 1C, C-6), 21.6 (s, 1C, —CH$_3$-6);

Anal. calcd for $C_{21}H_{17}NO_5S$: C, 63.79; H, 4.33; N, 3.54. Found: C, 63.40; H, 4.29; N, 3.39

EXAMPLE 25

Ethyl 2-ethoxy-5-[(6-methylphenanthridin-5(6H)-yl) sulfonyl]benzoate

A stirred suspension of 2-hydroxy-5-[(6-methylphenanthridin-5(6H)-yl)sulfonyl]benzoic acid (0.5 g, 1.26 mmol) and anhydrous potassium carbonate (0.36 g, 2.6 mmol) in anhydrous N,N-dimethylformamide (5 mL) was treated drop-wise at room temperature under nitrogen with a solution of iodoethane (0.405 g, 2.6 mmol) in anhydrous N,N-dimethylformamide (1 mL). The mixture was stirred at room temperature overnight. The reaction was diluted with diethyl ether and water. The organic phase was separated and washed sequentially with a 1 N hydrochloric acid solution and water. After drying over anhydrous sodium sulfate, the organic phase was filtered through a short column of silica gel, and the filtrate evaporated in vacuo to yield a crude product (0.5 g). The crude product was purified by preparative chromatography on a Biotage® 40 Mi column of pre-packed silica gel (90 g), eluting with a mixture of methyl tert-butyl ether-hexane (15:85) at a flow rate of 40 mL/min to afford, after evaporation of the solvent, a colorless solid. Crystallization of the colorless solid from a mixture of diethyl ether-hexane yielded the title compound (0.239 g, 0.53 mmol, 42%) as a homogeneous, white powder, m.p. 113–115° C.;

MS [(+ESI), m/z]: 452 [M+H]$^+$;

IR (Solid), $\nu_{max}$: 1710, 1600, 1480, 1440, 1330, 1175, 1150, 1100, 1080, 770, 725 cm$^{-1}$;

$^1$H NMR (500 MHz, DMSO-d$_6$) δ: 7.72 (dd, J=7.5, 1.6 Hz, 1H, ArH-1), 7.58 (dd, J=7.9, 1.4 Hz, 1H, ArH-4), 7.41 (td, J=7.5, 1.6 Hz, 1H, ArH-3), 7.38–7.34 (m, 2H, ArH-2, 10), 7.18 (dd, J=7.5, 1.2 Hz, 1H, ArH-7), 7.12 (d, J=2.6 Hz, 1H, ArH'-2'), 7.10–7.05 (m, 2H, ArH-8,9), 7.02 (dd, J=8.8, 2.6 Hz, 1H, ArH'-6'), 6.69 (d, J=8.9 Hz, 1H, ArH'-5'), 5.37 (q, J=7.0 Hz, 1H, H-6), 4.11 (q, J=7.1 Hz, 2H, —C(O)CH$_2$CH$_3$-3'), 3.92 (dq, J=14.0, 7.1 Hz, 2H, —OCH$_2$CH$_3$-4') 1.21 (t, J=7.1 Hz, 3H, —C(O)CH$_2$CH$_3$-3'), 1.20 (t, J=7.0 Hz, 3H, —OCH$_2$CH$_3$-4'), 1.10 (d, J=7.0 Hz, 3H, —CH$_3$-6);

$^{13}$C NMR (125 MHz, DMSO-d$_6$) δ: 163.5 (s, 1C, —C═O), 160.5 (s, 1C, ArC'-4'), 135.9 (s, 1C, ArC-6a), 132.3, (s, 1C, ArC-4a), 131.7 (s, 1C, ArC'-6'), 129.7 (s, 1C, ArC'-2'), 129.5 (s, 1C, ArC-10b), 128.9 (s, 1C, ArC-10a or ArC'-1'), 128.4 (s, 1C, ArC-3), 128.1 (s, 1C, ArC-8), 127.8 (s, 1C, ArC-2), 127.5 (s, 1C, ArC-9), 127.3 (s, 1C, ArC-4), 126.0 (s, 1C, ArC-7), 123.8 (s, 1C, ArC-1), 123.0 (s, 1C, ArC-10), 119.5 (s, 2C, ArC'-3'), 112.9 (s, 1C, ArC'-5'), 64.6 (s, 1C, —C(O)CH$_2$CH$_3$-3'), 60.5 (s, 1C, —OCH$_2$CH$_3$-4'), 54.1 (s, 1C, C-6), 21.6 (s, 1C, —CH$_3$-6), 14.1 (s, 1C, —C(O)CH$_2$CH$_3$-3'), 14.0 (s, 1C, —OCH$_2$CH$_3$-4');

Anal. calcd for $C_{25}H_{25}NO_5S$: C, 66.50; H, 5.58; N, 3.10. Found: C, 66.70; H, 5.62; N, 2.84.

EXAMPLE 26

2-(Hydroxymethyl)-4-[(6-methylphenanthridin-5 (6H)-yl)sulfonyl]phenol

A stirred solution of crude 2-hydroxy-5-[(6-methylphenanthridin-5(6H)-yl)sulfonyl]benzoic acid (1.75 g, 4.43 mmol) in anhydrous tetrahydrofuran (20 mL) was treated drop-wise at room temperature under nitrogen via syringe with 10 M borane-methyl sulfide complex (1.5 mL, 15 mmol). After stirring four hours at room temperature, the reaction was quenched with methanol (20 mL), concentrated in vacuo, diluted with water, and extracted with ethyl acetate. The organic phase was washed sequentially with an aqueous solution of potassium carbonate, water, a saturated, aqueous, sodium chloride solution, a 1 N hydrochloric acid solution, and water. The organic phase was dried over anhydrous sodium sulfate, filtered through a short column of silica gel, and eluted with ethyl acetate. The ethyl acetate phase was evaporated in vacuo to a crude oil (1.2 g). The crude oil was purified by preparative chromatography on a Biotage® 40 Mi column of pre-packed silica gel (90 g) with gradient elution of between 10% to 55% methyl tert-butyl ether in hexane at a flow rate of 50 mL/min; and afforded, after evaporation of the solvent, a colorless oil (0.687 g, 1.8 mmol). Crystallization of the colorless oil from diethyl ether yielded the title compound (0.6 g, 1.57 mmol, 35%) as a homogeneous, colorless, crystalline, solid, m.p. 182–184° C.;

MS [(+ESI), m/z]: 382 [M+H]$^+$;

MS [(−ESI), m/z]: 380 [M−H]$^-$;

IR (Solid), $v_{max}$: 3520, 3400, 1600, 1590, 1500, 1480, 1440, 1305, 1280, 1155, 1120, 1075, 1010, 730 cm$^{-1}$;

$^1$H NMR (500 MHz, DMSO-d$_6$) δ: 10.14 (br s, 1H, —OH-4'), 7.76 (dd, J=7.6, 0.9 Hz, 1H, ArH-1), 7.58 (dd, J=7.8, 1.1 Hz, 1H, ArH-4), 7.45 (d, J=7.5 Hz, 1H, ArH-10), 7.40 (td, J=7.5, 1.2 Hz, 1H, ArH-3), 7.35 (td, J=7.5, 1.4 Hz, 1H, ArH-2), 7.18–7.09 (m, 4H, ArH-7,8,9, ArH'-2'), 6.71 (dd, J=8.5, 2.4 Hz, 1H, ArH'-6'), 6.34 (d, J=8.5 Hz, 1H, ArH'-5'), 5.35 (q, J=6.9 Hz, 1H, H-6), 4.87 (br s, 1H, —CH$_2$OH-3'), 4.16 (d, J=14.5 Hz, 1H, —CH$_2$OH-3'), 4.07 (d, J=14.5 Hz, 1H, —CH$_2$OH-3'), 1.12 (d, J=7.0 Hz, 3H, —CH$_3$-6);

$^{13}$C NMR (125 MHz, DMSO-d$_6$) δ: 157.7 (s, 1C, ArC'-4'), 136.5 (s, 1C, ArC-6a), 132.8, (s, 1C, ArC-4a), 129.3 (s, 1C, ArC-10b), 128.7 (s, 1C, ArC-4), 128.6 (s, 1C, ArC'-1'), 128.3 (s, 1C, ArC-10a) 128.1 (s, 1C, ArC-3), 127.8 (s, 1C, ArC-8), 127.3 (s, 1C, ArC-2), 127.2 (s, 1C, ArC-9), 126.7 (s, 1C, ArC'-6'), 126.6 (s, 1C, ArC'-2'), 126.4 (s, 1C, ArC'-3'), 126.0 (s, 1C, ArC-7), 123.6 (s, 1C, ArC-1), 123.0 (s, 1C, ArC-10), 113.5 (s, 1C, ArC'-5'), 57.2 (s, 1C, —CH$_2$OH-3'), 53.8 (s, 1C, C-6), 21.7 (s, 1C, —CH$_3$-6);

Anal. calcd for C$_{21}$H$_{19}$NO$_4$S: C, 66.12; H, 5.02; N, 3.67. Found: C, 65.84; H, 5.11; N, 3.45.

EXAMPLE 27

2-Hydroxy-5-[(6-methylphenanthridin-5(6H)-yl) sulfonyl]b nzald hyde

4-[(6-M thylphenanthridin-5(6H)-yl)sulfonyl]phenol (0.5 g, 1.42 mmol), prepared according to the procedure in Example 1, and hexamethylenetetramine (0.6 g, 4.28 mmol) were suspended in trifluoroacetic acid (5 mL) and reluxed under argon for two hours. The solid gradually dissolved. The reaction mixture was cooled to room temperature and quenched with water. Trifluoroacetic acid was removed in vacuo, and the aqueous phase was extracted with ethyl acetate. The organic phase was washed sequentially with water, a saturated, aqueous, sodium carbonate solution, and a saturated, aqueous, sodium chloride solution. After drying over anhydrous magnesium sulfate, the organic phase was evaporated in vacuo to yield a red-orange oil. The crude product was purified by flash column chromatography on silica gel, eluting with a mixture of ethyl acetate-hexane (1:3), to yield the title compound (0.17 g, 0.45 mmol, 31%) as a white solid, m.p. 143–145° C.;

MS [(−ESI), m/z]: 378 [M−H]$^-$;

$^1$H NMR (500 MHz, DMSO-d$_6$) δ: 11.41 (s, 1H, CHO), 9.94 (s, 1H, —OH-4'), 7.76 (d, J=7.6 Hz, 1H, ArH-1), 7.61 (d, J=7.8 Hz, 1H, ArH-4), 7.46–7.38 (m, 3H, ArH-2,3,10), 7.24 (d, J=2.5 Hz, 1H, ArH'-2'), 7.20 (d, J=7.8 Hz, 1H, ArH-7), 7.13–7.08 (m, 2H, ArH-8,9), 6.97 (dd, J=8.7, 2.6 Hz, 1H, ArH'-6'), 6.55 (d, J=8.7 Hz, 1H, ArH'-5'), 5.39 (q, J=7.0 Hz, 1H, H-6), 1.14 (d, J=7.0 Hz, 3H, —CH$_3$-6);

Anal. calcd for C$_{21}$H$_{17}$NO$_4$S.0.14H$_2$O: C, 66.04; H, 4.56; N, 3.67. Found: C, 66.05; H, 4.53; N, 3.54.

EXAMPLE 28

Step a)

4-[(2-Bromo-6-ethylphenanthridin-5(6H)-yl) sulfonyl]phenol

A stirred and cooled solution of 2-bromo-6-ethyl-5-[(4-methoxyphenyl)sulfonyl]-5,6-dihydrophenanthridine (1.13 g, 2.46 mmol) and cyclohexene (2.5 mL, 24.6 mmol) in dichloromethane (5 mL) was treated drop-wise under nitrogen at −30° C. with boron tribromide (2.5 mL, 24.6 mmol). After the addition was completed, the reaction mixture was allowed to warm to room temperature and stirred for four hours. The reaction was cooled to −30° C. and quenched with methanol (1 mL). The solvent was removed in vacuo to yield the title compound as a gray powder (0.982 g, 2.21 mmol, 90%), which was confirmed by LCMS (ES−, FA, CV=20 or 5).

Step b)

4-[(6-Ethyl-2-thi n-3-ylph nanthridin-5(6H)-yl) sulfonyl]phenol

A solution of 4-[(2-bromo-6-ethylphenanthridin-5(6H)-yl)sulfonyl]ph nol (0.982 g, 2.21 mmol) and 3-thiopheneboronic acid (0.565 g, 4.42 mmol) in 1,4-dioxane was treated with a freshly prepared and nitrogen purged solution of tetrakis(triphenylphosphine)palladium (0) (0.127 g, 0.110 mmol, 5 mole %) in 1,4-dioxane and a 2 M aqueous solution of sodium carbonate (3.31 mL, 6.63 mmol). The mixture was purged with argon for 30 minutes and heated to 100° C. for up to six hours. The reaction progress was monitored by high-pressure liquid chromatography. At completion, the reaction was cooled to room temperature, and diluted with dichloromethane (3 mL) and a 0.5 M aqueous sodium hydroxide solution (2 mL). After stirring for 30 minutes, the mixture was extracted with ethyl acetate. The organic phase was dried over anhydrous sodium sulfate and concentrated to a residue. The residue was purified by flash column chromatography on silica gel with gradient elution of between 10% to 20% ethyl acetate in hexane to yield the title compound (0.643 g, 1.44 mmol, 65%) as a purified product, which was characterized by LCMS (ES−, FA, CV=20 or 5), m.p. 174–176° C.;

MS [(−ESI), m/z]: 446 [M−H]$^-$;

HRMS [(+ESI), m/z]: 448.10296 [M+H]$^+$. Calcd. for C$_{25}$H$_{22}$NO$_3$S$_2$: 448.10356;

IR (Solid), $v_{max}$: 3410, 1600, 1590, 1495, 1490, 1450, 1325, 1150, 1080, 825 cm$^{-1}$;

$^1$H NMR (500 MHz, DMSO-d$_6$) δ: 10.14 (s, 1H, —OH-4'), 8.09 (d, J=1.8 Hz, 1H, ArH-1), 8.04 (dd, J=2.8, 1.4 Hz, 1H, 2-thiophene), 7.76 (dd, J=8.4, 1.8 Hz, 1H, ArH-3), 7.71–7.64 (m, 4H, ArH-4,10, 4,5-thiophene), 7.24–7.16 (m, 3H, ArH-7,8,9), 6.90 (d, J=8.7 Hz, 2H, ArH'-2',6'), 6.35 (d, J=8.7 Hz, 2H, ArH'-3',5'), 5.08 (dd, J=9.8, 5.5 Hz, 1H, H-6), 1.42 (d quintet, J=13.4, 7.2 Hz, 1H, —CH$_2$CH$_3$-6), 1.30 (ddq, J=13.4, 9.8, 7.2 Hz, 1H, —CH$_2$CH$_3$-6), 0.91 (t, J=7.2 Hz, 3H, —CH$_2$CH$_3$-6).

EXAMPLE 29

4-{[6-Ethyl-2-(3-methoxyphenyl)phenanthridin-5 (6H)-yl]sulfonyl}phenol

A solution of 4-[(2-bromo-6-ethylphenanthridin-5(6H)-yl)sulfonyl]phenol (1.25 g, 2.70 mmol) and 3-methoxyphenylboronic acid (0.822 g, 5.41 mmol) in 1,4-dioxane was treated with a solution of tetrakis (triphenylphosphine)palladium (0) (0.156 g, 0.135 mmol, 5 mole %) in 1,4-dioxane and a 2 M aqueous solution of sodium carbonate (4.0 mL, 8.0 mmol) according to the procedure and in the same manner as described in Example 28, step b; and yielded, after chromatographic purification, 4-{[6-ethyl-2-(3-methoxyphenyl)phenanthridin-5(6H)-yl]sulfonyl}phenol (1.05 g, 2.23 mmol, 83%) as a purified product, which was characterized by LCMS (ES+, FA, CV=20 or 5);

MS [(−ESI), m/z]: 470 [M−H]⁻;

¹H NMR (500 MHz, DMSO-d$_6$) δ: 10.19 (s, 1H, —OH-4'), 8.03 (s, 1H, ArH-1), 7.71 (m, 3H), 7.31–7.19 (m, 6H), 6.94 (d, 2H, ArH'-2',6'), 6.94 (d, 1H, ArH"-4"), 6.36 (d, 2H, ArH'-3',5'), 5.05 (dd, 1H, H-6), 3.84 (s, 3H, —OCH$_3$-3"), 1.60–1.20 (m, 2H, —CH$_2$CH$_3$-6), 0.91 (t, J=7.2 Hz, 3H, —CH$_2$CH$_3$-6).

EXAMPLE 30

3-{6-Ethyl-5-[(4-hydroxyphenyl)sulfonyl]-5,6-dihydrophenanthridine-2-yl}phenol

A stirred and cooled solution of 4-{[6-ethyl-2-(3-methoxyphenyl)phenanthridin-5(6H)-yl]sulfonyl}phenol (0.645 g, 1.36 mmol) and cyclohexene (1.1 mL, 10.9 mmol) in dichloromethane (5 mL) was treated drop-wise under nitrogen at −30° C. with boron tribromide (1.03 mL, 10.9 mmol). After the addition was completed, the reaction mixture was allowed to warm to room temperature and stirred for four hours. The reaction was cooled to −30° C. and quenched with methanol (1 mL). The solvent was removed in vacuo, and the residue was purified by flash column chromatography on silica gel, eluting with a mixture of ethyl acetate-hexane (1:3); to yield the title compound (0.473 g, 1.03 mmol, 76%), which was characterized by LCMS (ES+, FA, CV=20 or 5), m.p. 105° C.;

MS [(+ESI), m/z]: 458 [M+H]⁺;

MS [(−ESI), m/z]: 456 [M−H]⁻;

HRMS [(+ESI), m/z]: 458.14179 [M+H]⁺. Calcd. for C$_{27}$H$_{23}$NO$_4$S: 458.14206;

¹H NMR (500 MHz, DMSO-d$_6$) δ: 10.15 (s, 1H, —OH-4'), 9.53 (s, 1H, —OH-3"), 7.95 (d, J=1.7 Hz, 1H, ArH-1), 7.72–7.63 (m, 3H), 7.29–7.15 (m, 5H), 7.12 (s, 1H, ArH"-2"), 6.93 (d, J=8.7 Hz, 2H, ArH'-2',6'), 6.79 (dd, J=7.9, 2.1 Hz, 1H, ArH"-4"), 6.36 (d, J=8.7 Hz, 2H, ArH'-3',5'), 5.08 (dd, J=9.6, 5.5 Hz, 1H, H-6), 1.47–1.39 (d quintet, J=13.6, 7.2 Hz, 1H, —CH$_2$CH$_3$-6), 1.34–1.25 (ddq, J=13.6, 9.6, 7.2 Hz, 1H, —CH$_2$CH$_3$-6), 0.91 (t, J=7.2 Hz, 3H, —CH$_2$CH$_3$-6).

EXAMPLE 31

Step a)

2-(Dibenzo[b,d]furan-4-yl)-6-ethyl-5-[(4-meth xyph nyl)sulfonyl]-5,6-dihydrophenanthridine A solution of 2-bromo-6-ethyl-5-[(4-methoxyphenyl)sulfonyl]-5,6-dihydrophenanthridine (1.5 g, 3.1 mmol) and dibenzo[b,d]furan-4-ylboronic acid (1.34 g, 6.3 mmol) in 1,4-dioxane was treated with a solution of tetrakis (triphenylphosphine)palladium (0) (0.182 g, 0.15 mmol, 5 mole %) in 1,4-dioxane and a 2 M aqueous solution of sodium carbonate (4.74 mL, 9.4 mmol) according to the procedure and in the same manner as described in Example 28, step b; and yielded, after chromatographic purification on silica gel, eluting with a mixture of ethyl acetate in hexane (1:9), 2-(dibenzo[b,d]furan-4-yl)-6-ethyl-5-[(4-methoxyphenyl)sulfonyl]-5,6-dihydrophenanthridine (0.855 g, 1.56 mmol, 51%) as a purified product, which was characterized by LCMS (ES+, FA, CV=20 or 5);

Step b)

4-[(2-Dibenzo[b,d]furan-4-yl-6-ethylphenanthridin-5(6H)-yl)sulfonyl]phenol

A stirred and cooled solution of 2-(dibenzo[b,d]furan-4-yl)-6-ethyl-5-[(4-methoxyphenyl)sulfonyl]-5,6-dihydrophenanthridine (0.855 g, 1.56 mmol) and cyclohexene (1.26 mL, 12.5 mmol) in dichloromethane (5 mL) was treated drop-wise under nitrogen at −30° C. with boron tribromide (1.18 mL, 12.5 mmol). After the addition was completed, the reaction mixture was allowed to warm to room temperature and stirred for four hours. The reaction was cooled to −30° C. and quenched with methanol (1 mL). The solvent was removed in vacuo, and the residue was purified by flash column chromatography on silica gel to yield the title compound (0.756 g, 1.42 mmol, 91%), which was characterized by LCMS (ES+, FA, CV=20 or 5), m.p. 218–220° C.;

MS [(+ESI), m/z]: 532 [M+H]⁺;

MS [(−ESI), m/z]: 530 [M−H]⁻;

HRMS [(+ESI), m/z]: 532.15748 [M+H]⁺. Calcd. for C$_{33}$H$_{25}$NO$_4$S: 532.15771;

IR (Solid), $v_{max}$: 3400, 1600, 1580, 1500, 1490, 1450, 1190, 1170, 1080, 830, 755 cm⁻¹;

¹H NMR (500 MHz, DMSO-d$_6$) δ: 10.18 (s, 1H, —OH-4'), 8.28 (d, J=1.8 Hz, 1H, ArH-1), 8.22 (dd, J=7.6, 0.6 Hz, 1H, ArH"-9"), 8.19, (d, J=7.6 Hz, 1H, ArH"-1"), 8.02 (dd, J=8.4, 1.8 Hz, 1H, ArH-3), 7.85 (d, J=7.6 Hz, 1H, ArH"-3"), 7.81 (d, J=8.4 Hz, 1H, ArH-4), 7.80 (d, J=8.1 Hz, 1H, ArH"-6"), 7.68 (dd, J=8.4, 1.4 Hz, 1H, ArH-10), 7.55 (td, J=8.3, 0.9 Hz, 1H, ArH"-7"), 7.53 (t, J=7.6 Hz, 1H, ArH"-2"), 7.44 (t, J=7.5 Hz, 1H, ArH"-8"), 7.26–7.18 (m, 3H, ArH-7,8,9), 7.00 (dd, J=8.7, 2.8 Hz, 2H, ArH'-2',6'), 6.40 (dd, J=8.7, 2.8 Hz, 2H, ArH'-3',5'), 5.13 (dd, J=9.8, 5.5 Hz, 1H, H-6), 1.48 (d quintet, J=13.4, 7.2 Hz, 1H, —CH$_2$CH$_3$-6), 1.36 (ddq, J=13.4, 9.8, 7.2 Hz, 1H, —CH$_2$CH$_3$-6), 0.95 (t, J=7.2 Hz, 3H, —CH$_2$CH$_3$-6).

EXAMPLE 32

Method A

Step a)

N-(4'-Fluorobiphenyl-2-yl)acetamide

A stirred solution of 2-iodoaniline (32.6 g, 149 mmol) and 4-fluorophenylboronic acid (20.8 g, 149 mmol) in tetrahydrofuran (1.5 L) was treated under nitrogen with [1,1'-bis(diphenylphosphino)ferrocene]dichloropalladium (II) complex with dichloromethane (2.20 g, 2.69 mmol) and a 5 N sodium hydroxide solution (60 mL). The reaction mixture was heated at reflux for twelve hours, cooled to room temperature, and the solvent removed in vacuo. The residue was dissolved in ethyl acetate (250 mL) and extracted with a saturated, aqueous, sodium chloride solution (100 mL). The aqueous phase was further extracted with ethyl acetate (2×50 mL). The combined organic phase was dried over anhydrous magnesium sulfate, filtered, and concentrated in vacuo to a brown oil. The brown oil was filtered through a short column of silica gel, and eluted with a mixture of ethyl acetate-hexane (1:4). After evaporation of the solvent in vacuo, a solution of the crude 4'-fluoro-biphenyl-2-ylamine in dichloromethane (75 mL) was treated with pyridine (27.7 mL, 343 mmol), acetic anhydride (15.5 mL, 164 mmol), and 4-(N,N-dimethylamino)pyridine (0.55 g, 4.5 mmol). After stirring for twelve hours at room temperature, the reaction was quenched with a saturated, aqueous, ammonium chloride solution (250 mL). The separated aqueous phase was extracted with dichloromethane (3×75 mL), and the combined organic phase washed sequentially with a 0.1 N hydrochloric acid solution (2×50 mL), and a saturated, aqueous, sodium bicarbonate solution (50 mL). The organic phase was dried over anhydrous sodium sulfate, filtered and concentrated in vacuo to a second brown oil. After toluene was added and removed in vacuo (3×), the resulting brown solid was crystallized from ethyl acetate-hexane to yield a first crop of the desired product (19.0 g). The mother liquor was concentrated and purified by flash column chromatography on silica gel, eluting with ethyl acetate-hexane (1:4), to obtain a second crop (5.0 g). The combined crops afforded the title compound as a homogeneous, colorless, crystalline, solid (24.0 g, 70%). m.p. 123–124° C.;

MS [(+ESI), m/z]: 230 [M+H]$^+$;

$^1$H NMR (500 MHz, DMSO-d$_6$) δ: 9.24 (s, 1H), 7.44–7.23 (m, 8H), 1.87 (s, 3H); Anal. calcd for C$_{14}$H$_{12}$FNO: C, 73.35; H, 5.28; N, 6.11. Found: C, 73.09; H, 5.20; N, 5.89.

Step b)

8-Fluoro-6-methylphenanthridine

The N-(4'-fluorobiphenyl-2-yl)acetamide (18.5 g, 80.7 mmol) was mixed with polyphosphoric acid (250 g) and heated at 120° C. with vigorous stirring for 48 hours. The hot reaction mixture was poured onto ice and stirred vigorously until homogeneous. Ammonium hydroxide (28–30%, aqueous) was added until the pH was greater than eight. A white precipitate was filtered, dissolved in ethyl acetate (250 mL), and re-filtered. The combined filtrate was washed with a saturated, aqueous, sodium chloride solution, dried over anhydrous sodium sulfate, filtered, and evaporated in vacuo to a brown solid. The brown solid was purified by crystallization from a mixture of ethyl acetate-hexane to yield the title compound as a white, crystalline solid (15.9 g, 94%), m.p. 92–93° C.;

MS [(+ESI), m/z]: 212 [M+H]$^+$;

$^1$H NMR (500 MHz, CDCl$_3$) δ: 8.63 (dd, J=9.0, 5.4 Hz, 1H), 8.49 (dd, J=8.2, 1.0 Hz, 1H), 8.10 (dd, J=8.1, 1.1 Hz, 1H), 7.84 (dd, J=9.6, 2.6 Hz, 1H), 7.71 (m, 1H), 7.65–7.57 (m, 2H), 3.01 (s, 3H);

$^1$H NMR (400 MHz, DMSO-d$_6$) δ: 8.89 (dd, J=9.1, 5.6 Hz, 1H), 8.70 (dd, J=8.1, 1.3 Hz, 1H), 8.05 (dd, J=10.1, 2.5 Hz, 1H), 7.97 (dd, J=8.1, 1.3 Hz, 1H), 7.80 (m, 1H), 7.70 (m, 1H), 7.63 (m, 1H), 3.01 (s, 3H);

Anal. calcd for C$_{14}$H$_{10}$FN.0.10H$_2$O: C, 78.93; H, 4.83; N, 6.57. Found: C, 78.90; H, 4.57; N, 6.58.

Step c)

4-(Chlorosulfonyl)phenyl ethyl carbonate

A solution of sodium 4-hydroxybenzenesulfonate dihydrate (50.0 g, 215 mmol) in 1.25 N aqueous sodium hydroxide (170 mL, 213 mmol) was treated drop-wise with ethyl chloroformate (20.6 mL, 215 mmol). The reaction mixture was stirred for twelve hours at room temperature. After cooling the mixture to 0° C., a white precipitate, which formed under the reaction conditions, was filtered. The solid was dried in vacuo at 70° C. The white solid (40.0 g) was suspended in toluene (350 mL) and treated with N,N-dimethylformamide (6.0 mL) and thionyl chloride (22.0 mL, 298 mmol), and the resulting mixture was heated at 100° C. for twelve hours. After cooling to room temperature, the reaction mixture was filtered through diatomaceous earth. The filtrate was concentrated in vacuo, and the resulting oil solidified upon standing. The solidified oil was dissolved in ethyl acetate-hexane (1:4), filtered through a short column of silica gel, and the solvent removed in vacuo to yield the sulfonyl chloride as a white solid (34.8 g, 61%), m.p. 74–76° C.;

$^1$H NMR (400 MHz, DMSO-d$_6$) δ: 7.60 (d, J=8.7 Hz, 2H), 7.14 (d, J=8.8 Hz, 2H), 4.23 (q, J=7.1 Hz, 2H), 1.26 (t, J=7.1 Hz, 3H).

Step d)

Ethyl 4-[(8-fluoro-6-methylphenanthridin-5(6H)-yl)sulfonyl]phenyl carbonate

A stirred solution of 8-fluoro-6-methylphenanthridine (8.00 g, 37.9 mmol) in tetrahydrofuran (152 mL) was treated with freshly crushed sodium borohydride (7.16 g, 189 mmol). Trifluoroacetic acid (11.7 mL, 152 mmol) was added drop-wise at a rate suitable to control gas evolution and exothermic reaction conditions. After the trifluoroacetic acid addition was completed, the heterogeneous reaction mixture was stirred until the reaction returned to room temperature; then was re-heated to reflux for 14 hours. After cooling to room temperature, a saturated, aqueous, sodium bicarbonate solution (250 mL) was slowly added. The mixture was filtered through a plug of glass wool, and extracted with diethyl ether (4×75 mL). The combined organic extract was dried over anhydrous sodium sulfate, filtered, and concentrated in vacuo to afford the dihydrophenanthridine as a light-brown paste. A solution of the crude dihydrophenanthridine in dichloromethane (38 mL) was treated with triethylamine (31.7 mL, 227 mmol) and 4-(chlorosulfonyl) phenyl ethyl carbonate (12.0 g, 45.3 mmol), and stirred at room temperature for 14 hours. The reaction was quenched with a 0.1 N sodium hydroxide solution (150 mL) and extracted with dichloromethane (6×50 mL). The combined organic extract was washed with a 2 N hydrochloric acid solution (2×40 mL), dried over anhydrous sodium sulfate, filtered, and concentrated in vacuo to a viscous, brown oil. The brown oil was triturated with hexane (25 mL) to afford a light-brown solid. The light-brown solid was purified by cystallization from a mixture of ethyl acetate-hexane to yield a first crop of the desired product. The mother liquor was concentrated in vacuo, and purified by filtration through a plug of silica gel, eluting with ethyl acetate-hexane (1:4), to obtain a second crop. The combined crops afforded the title compound as a white, crystalline solid (15.2 g, 91%), m.p. 136–138° C.;

MS [(+ESI), m/z]: 442 [M+H]$^+$;

$^1$H NMR (500 MHz, DMSO-d$_6$) δ: 7.77 (d, J=7.6 Hz, 1H), 7.63 (d, J=7.8 Hz, 1H), 7.48–7.39 (m, 3H), 7.19 (dd, J=9.0, 2.6 Hz, 1H), 7.09 (d, J=8.7 Hz, 2H), 6.98 (d, J=8.7 Hz, 2H), 6.93 (td, J=8.7, 2.6 Hz, 1H), 5.48 (q, J=7.0 Hz, 1H), 4.21 (q, J=7.1 Hz, 2H), 1.25 (t, J=7.1 Hz, 3H), 1.15 (t, J=7.0 Hz, 3H);

Anal. calcd for C$_{23}$H$_{20}$FNO$_5$S: C, 62.57; H, 4.57; N, 3.17. Found: C, 62.51; H, 4.47; N, 2.96.

Step e)

4-[(8-Fluoro-6-methylphenanthridin-5(6H)-yl)sulfonyl]phenol

A solution of ethyl 4-[(8-fluoro-6-methylphenanthridin-5(6H)-yl)sulfonyl]phenyl carbonate (0.45 g, 1.02 mmol) in methanol (5.0 mL) was treated with a 1 N sodium hydroxide (5.1 mL) solution, and heated at 75° C. for 14 hours. After cooling to room temperature, the methanol was evaporated in vacuo. The resulting aqueous mixture was acidified with a 1 N hydrochloric acid solution, diluted with a saturated, aqueous, sodium chloride solution (100 mL), and extracted with dichloromethane (5×15 mL). The combined organic phase was dried over anhydrous sodium sulfate, filtered, and concentrated in vacuo to a white solid. The solid was purified by filtration through a short column of silica gel, eluting with ethyl acetate, to yield the title compound as a homogeneous, white, crystalline, solid (0.34 g, 89%), m.p. 188° C.;

MS [(−ESI), m/z]: 368 [M−H]−;

$^1$H NMR (500 MHz, DMSO-$d_6$) δ: 10.24 (br s, 1H), 7.76 (dd, J=7.6 Hz, 1.5, 1H), 7.60 (dd, J=7.8, 1.4 Hz, 1H), 7.52 (dd, J=8.7, 5.0 Hz, 1H), 7.41 (m, 1H), 7.37 (m, 1H), 7.17 (dd, J=9.2, 2.7 Hz, 1H), 6.96 (td, J=8.7, 2.7 Hz, 1H), 6.86 (d, J=8.9 Hz, 2H), 6.38 (d, J=8.9 Hz, 2H), 5.41 (q, J=7.0 Hz, 1H), 1.13 (d, J=7.0 Hz, 3H);

Anal. calcd for $C_{20}H_{16}FNO_3S$: C, 65.03; H, 4.37; N, 3.79. Found: C, 64.77; H, 4.31; N, 3.76.

Method B
Step a)

8-Fluoro-5-(4-m thoxyph nylsulfonyl)-6-methyl-5,6-dihydrophenanthridin

The title compound was prepared from 8-fluoro-6-methylphenanthridine (5.27 g, 25.0 mmol), sodium borohydride (4.72 g, 125 mmol), and trifluoroacetic acid (8 mL, 100 mmol), in tetrahydrofuran (100 mL); followed by triethylamine (20 mL, 150 mmol) and 4-methoxybenzenesulfonyl chloride (5.67 g, 27.5 mmol) in dichloromethane (20 mL), according to the procedure and in the same manner as described in Example 32, Method A, Step d, to afford the crude product as a brown solid. The crude product was purified by re-crystallization from a mixture of dichloromethane-hexane to yield 8-fluoro-5-(4-methoxyphenylsulfonyl)-6-methyl-5,6-dihydrophenanthridine, as a homogeneous, white, crystalline, solid (8.31 g, 87%), m.p. 132–136° C.;

MS [(+ESI), m/z]: 384 [M+H]+;

$^1$H NMR (500 MHz, DMSO-$d_6$) δ: 7.75 (dd, J=7.7, 1.1 Hz, 1H), 7.61 (m, 1H), 7.48 (dd, J=8.6, 5.4 Hz, 1H), 7.43 (m, 1H), 7.38 (m, 1H), 7.16 (dd, J=9.2, 2.8 Hz, 1H), 6.98–6.92 (m, 3H), 6.59 (d, J=8.8 Hz, 2H), 5.43 (q, J=7.0 Hz, 1H), 3.64 (s, 3H), 1.13 (d, J=7.0 Hz, 3H);

Anal. calcd for $C_{21}H_{18}FNO_3S$: C, 65.78; H, 4; 3.65. Found: C, 65.64; H, 4.90; N, 3.51.

Step b)

4-[(8-Fluoro-6-methylphenanthridin-5(6H)-yl)sulfonyl]phenol

A stirred suspension of 8-fluoro-5-(4-methoxyphenylsulfonyl)-6-methyl-5,6-dihydrophenanthridine (1.26 g, 3.29 mmol) and cyclohexene (6.0 mL, 59 mmol) was treated drop-wise with a solution of 1 M boron tribromide (20 mL, 20 mmol) in dichloromethane at room temperature under nitrogen. After stirring for 20 hours at room temperature, a saturated, aqueous, sodium bicarbonate solution (300 mL) was added drop-wise, and the resulting mixture extracted with dichloromethane (6×20 mL). The combined organic phase was dried over anhydrous sodium sulfate, filtered, and concentrated in vacuo. The crude material was purified by flash column chromatography on silica gel, eluting with a mixture of ethyl acetate-hexane (1:19 to 1:4 gradient), followed by re-crystallization from a mixture of dichloromethane-hexane to yield the title compound as a homogeneous, white, crystalline, solid (1.1 g, 90%). The melting point, mass spectum, and NMR spectrum of this product were identical to the authentic material prepared in Example 32, Method A, Step e.

EXAMPLE 33

Method A
Step a)

Ethyl 4-{[(S)-8-flu ro-6-methylphenanthridin-5(6H)-yl]sulfonyl}phenyl carbonat *

The enantiomers of ethyl 4-[(-8-fluoro-6-methylphenanthridin-5(6H)-yl]sulfonyl]phenyl carbonate (Example 32, Method A, Step d) were separated by chiral stationary phase high-performance liquid chromatography (Chiralcel® OJ-25×5 cm column) on a Rainin Auto-Prep System®, eluting with ethanol at a flow rate of 10 mL/min. The first peak with a retention time at 8.5 minutes was the title compound;

$T_R$ 8.5 min;

m.p. 159° C.;

$[\alpha]_D^{25}$=+212.2° (c=1% solution, $CHCl_3$);

MS [(+ESI), m/z]: 442 [M+H]+;

$^1$H NMR (500 MHz, DMSO-$d_6$) δ: 7.77 (d, J=7.6 Hz, 1H), 7.63 (d, J=7.8 Hz, 1H), 7.48–7.39 (m, 3H), 7.19 (dd, J=9.0 Hz, 2.6, 1H), 7.09 (d, J=8.7 Hz, 2H), 6.98 (d, J=8.7 Hz, 2H), 6.93 (td, J=8.7 Hz, 2.6, 1H), 5.48 (q, J=7.0 Hz, 1H), 4.21 (q, J=7.1 Hz, 2H), 1.25(t, J=7.1 Hz, 3H), 1.15 (t, J=7.0 Hz, 3H);

Anal. calcd for $C_{23}H_{20}FNO_5S$: C, 62.57; H, 4.57; N, 3.17. Found: C, 62.44; H, 4.58; N, 3.03.

*The absolute configuration was assigned by conversion to 4-{[(S)-8-fluoro-6-methylphenanthridin-5(6H)-yl]sulfonyl}phenol.

Step b)

4-{[(S)-8-Fluoro-6-methylphenanthridin-5(6H)-yl]sulfonyl}phenol*

The title compound was prepared from ethyl 4-{[(S)-8-fluoro-6-methylphenanthridin-5(6H)-yl]sulfonyl}phenyl carbonate (0.05 g, 0.11 mmol), 2.5 N aqueous sodium hydroxide (2 mL, 5 mmol), and methanol (2 mL), according to the procedure and in the same manner as described in Example 32, Method A, Step e to yield 4-{[(S)-8-fluoro-6-methylphenanthridin-5(6H)-yl]sulfonyl}phenol as a solid (0.04 g, 100%), m.p. 193° C.;

$[\alpha]_D^{25}$=+267.2° (c=1% solution, $CHCl_3$);

MS [(−ESI), m/z]: 368 [M−H]−;

$^1$H NMR (500 MHz, DMSO-$d_6$) δ: 10.24 (br s, 1H), 7.76 (dd, J=7.6 Hz, 1.5, 1H), 7.60 (dd, J=7.8 Hz, 1.4, 1H), 7.52 (dd, J=8.7 Hz, 5.0, 1H), 7.41 (m, 1H), 7.37 (m, 1H), 7.17 (dd, J=9.2, 2.7 Hz, 1H), 6.96 (td, J=8.7, 2.7 Hz, 1H), 6.86 (d, J=8.9 Hz, 2H), 6.38 (d, J=8.9 Hz, 2H), 5.41 (q, J=7.0 Hz, 1H), 1.13 (d, J=7.0 Hz, 3H);

Anal. calcd for $C_{20}H_{16}FNO_3S$: C, 65.03; H, 4.37; N, 3.79. Found: C, 64.82; H, 4.47; N, 3.71.

*The absolute configuration was assigned by analogy to (S)-8-fluoro-5-[(4-methoxyphenyl)sulfonyl]-6-methyl-5,6-dihydrophenanthridine. The absolute configuration of the above (S)-8-fluoro-5-[(4-methoxyphenyl)sulfonyl]-6-methyl-5,6-dihydrophenanthridine was determined by a single crystal x-ray diffraction experiment.

Method B
Step a)

(S)-8-Fluoro-5-[(4-methoxyphenyl)sulfonyl]-6-methyl-5,6-dihydrophenanthridin*

The enantiomers of 8-fluoro-5-[(4-methoxyphenyl)sulfonyl]-6-methyl-5,6-dihydrophenanthridine (Example 32, Method B, Step a) were separated by chiral stationary phase high-performance liquid chromatography (Chiralpak® AD-25×5 cm column) on a Rainin Auto-Prep System®, eluting with a mixture of 2-propanol-hexane (1:9) at a flow rate of 15 mL/min. The first peak with a retention time at 10.0 minutes was the title compound;

$T_R$ 10.0 minutes;
m.p. 181–182° C.;
$[\alpha]_D^{25}$=+239.3° (c=1% solution, CHCl$_3$);
MS [(+ESI), m/z]: 384 [M+H]$^+$;
$^1$H NMR (500 MHz, DMSO-d$_6$) δ: 7.75 (dd, J=7.7, 1.1 Hz, 1H), 7.61 (m, 1H), 7.48 (dd, J=8.6, 5.4 Hz, 1H), 7.43 (m, 1H), 7.38 (m, 1H), 7.16 (dd, J=9.2, 2.8 Hz, 1H), 6.98–6.92 (m, 3H), 6.59 (d, J=8.8 Hz, 2H), 5.43 (q, J=7.0 Hz, 1H), 3.64 (s, 3H), 1.13 (d, J=7.0 Hz, 3H).

*The absolute configuration of (S)-8-fluoro-5-[(4-methoxyphenyl)sulfonyl]-6-methyl-5,6-dihydrophenanthridine was determined by a single crystal x-ray diffraction experiment.

Step b)

4-{[(S)-8-Fluoro-6-methylphenanthridin-5(6H)-yl]sulfonyl}phenol*

The title compound was prepared from (S)-8-fluoro-5-[(4-methoxyphenyl)sulfonyl]-6-methyl-5,6-dihydrophenanthridine (0.75 g, 1.95 mmol), cyclohexene (7.1 mL, 70.1 mmol), and 1 M boron tribromide in dichoromethane (23 mL, 23 mmol) according to the procedure and in the same manner as described in Example 32, Method B, Step b. The crude product was purified by flash column chromatography on silica gel, eluting with a mixture of ethyl acetate-hexane (1:9 to 1:4 gradient) to yield, 4-{[(S)-8-fluoro-6-methylphenanthridin-5(6H)-yl]sulfonyl}phenol*, as a homogeneous solid (0.59 g, 82%), m.p. 193° C.

*The mass spectum and NMR spectrum of this material were identical to the mass spectum and NMR spectrum of authentic material prepared in Example 33, Method A, Step b;

$[\alpha]_D^{25}$=+263° (1% solution, CHCl$_3$).

Method C

Step a)

1-(2',4-Difluoro-1,1'-biphenyl-2-yl)ethanone

A stirred solution of 2-bromo-5-fluoroacetophenone (11.72 g, 54 mmol) and 2-fluorophenylboronic acid (7.55 g, 54 mmol) in tetrahydrofuran (600 mL) was treated under nitrogen with [1,1'-bis(diphenylphosphino)ferrocene] dichloropalladium (II) complex with dichloromethane (2.20 g, 2.69 mmol, 5 mole %) and a 5 N sodium hydroxide solution (21.6 mL, 108 mmol). The reaction was heated at 60° C. for twelve hours, cooled to room temperature, and the solvent removed in vacuo. The residue was dissolved in diethyl ether, filtered through a short column of silica gel, and the solvent evaporated in vacuo to a crude brown oil (11.72 g). The crude oil was purified by repetitive, preparative, liquid chromatography on a Biotage® 40 Mi column of pre-packed silica gel (90 g), eluting with a gradient of between 3% and 10% methyl tert-butylether in hexane at a flow rate of 50 mL/min to afford, after evaporation of the solvent, the title compound as a purified, colorless oil (10.2 g, 43.9 mmol, 81%).

Step b)

1-(2',4-Difluoro-1,1'-biphenyl-2-yl)ethylamine

A stirred solution of 1-(2',4-difluoro-1,1'-biphenyl-2-yl) ethanone (9.10 g, 39.0 mmol) in anhydrous methanol (800 mL) was treated with dried ammonium acetate (154.1 g, 2.0 mol) and sodium cyanoborohydride (5.00 g, 80 mmol). The reaction was heated under nitrogen at 60° C. for fifteen hours, cooled to room temperature, and the solvent removed in vacuo. The residue was treated with a saturated, aqueous, ammonia solution and extracted with diethyl ether (2×). The combined organic phase was washed sequentially with water and eight times (or until the amine was no longer present in the organic layer) with a 2 N aqueous hydrochloric acid solution. The combined acidic aqueous layer was filtered to afford a dialkyated dimer, N,N-bis[1-(2',4-difluoro-1,1'-biphenyl-2-yl)ethyl]amine hydrochloride (1:1) (0.68 g 1.40 mmol, 7.2%), as a colorless solid, m.p. 190–193° C. The aqueous filtrate was extracted with diethyl ether (1×) and neutralized to pH 10 with a 2.5 N aqueous sodium hydroxide solution. The aqueous phase was extracted with diethyl ether (3×). The combined organic phase was washed with water, dried over anhydrous sodium sulfate, filtered, and the solvent removed in vacuo below room temperature to afford the title compound as a homogeneous, clear, colorless oil (5.5 g, 23.6 mmol, 60%), which solidified in the freezer, m.p. 38–40° C.;

MS [(+ESI), m/z]: 234 [M+H]$^+$;
IR (Film), $\nu_{max}$: 2967, 1606, 1476, 1447, 1370, 1257, 1199, 1107, 871, 813, 757 cm$^{-1}$;
$^1$H NMR (400 MHz, DMSO-d$_6$) δ: 1.08 (broad d, J=6.9 Hz, 3H), 1.82 (broad s, 2H), 3.82 (q, J=6.3 Hz, 1H), 7.10 (td, J=8.3, 2.7 Hz, 1H), 7.15 (t, J=6.1 Hz, 1H), 7.27–7.35 (m, 3H), 7.44 (m, 1H), 7.54 (d, J=10.4 Hz, 1H);
Anal. calcd for C$_{14}$H$_{13}$F$_2$N: C, 72.09; H, 5.62; N, 6.00. Found: C, 71.51; H, 5.72; N, 6.08.

Step c)

(1S)-1-(2',4-Difluoro-1,1'-biphenyl-2-yl) ethanaminium(4R)-4-(2-methoxyphenyl)-5,5-dimethyl-1,3,2-dioxaphosphinan-2-olate 2-oxide A solution of 1-(2',4-difluoro-1,1'-biphenyl-2-yl) ethylamine (2.78, 11.9 mmol) in 2-butanone (15 mL) was added to a stirred slurry of (R)-(+)-2-hydroxy-4-(2-methoxyphenyl)-5,5-dimethyl-1,3,2-dioxaphosphorinane (3.27 g, 12 mmol) in 2-butanone (100 mL). The mixture was heated to reflux until a homogeneous solution was obtained. After cooling to room temperature, the flask was covered and allowed to stand undisturbed for 64 hours. The white precipitate (2.74 g, 90.9% based upon theoretical 50% resolution) was collected by filtration. The chiral purity of the white precipate was determined by chiral LC (98.4% (+)::1.6% (−)), then the solid resuspended in 2-butanone (100 mL) and heated vigorously. The heterogenous mixture was filtered while warm, the solid rinsed with additional warm 2-butanone, and dried to a constant weight (2.66 g, 97%), m.p. 269.9–272° C.;

MS [(+ESI), m/z]: 234 [M+H]$^+$;
$^1$H NMR (400 MHz, DMSO-d$_6$) δ: 0.54 (s, 3H), 0.83 (s, 3H), 1.41 (d, J=6.5 Hz, 3H), 3.41 (dd, J=23.1, 10.7 Hz, 1H), 3.73 (s, 3H), 3.97 (m, 2H), 5.50 (d, J=2.9 Hz, 1H), 6.95 (dd, J=14.4, 7.7 Hz, 2H), 7.25 (m, 2H), 7.33 (m, 5H), 7.50 (m, 1H), 7.78 (d, J=10.4 Hz, 1H), 8.74 (s, 3H);
Anal. Calcd for C$_{14}$H$_{13}$F$_2$N.C$_{12}$H$_{17}$O$_5$P: C, 61.78; H, 5.98; N, 2.77. Found: C, 61.75; H, 5.70; N, 2.60.

Step d)
Part 1)

N-[(1S)-1-(2',4-Difluoro-1,1'-biphenyl-2-yl)ethyl]-4-methoxybenzenesulfonamide A stirred suspension of (1S)-1-(2',4-difluoro-1,1'-biphenyl-2-yl)ethanaminium (4R)-4-(2-methoxyphenyl)-5, 5-dimethyl-1,3,2-dioxaphosphinan-2-olate 2-oxide (2.53 g, 5.0 mmol) in acetonitrile (50 mL) was treated sequentially with triethylamine (1.39 mL, 10 mmol) and 4-methoxybenzenesulfonyl chloride (1.04 g, 5.05 mmol). The progress of the reaction was monitored by LCMS. After eight hours, approximately 5% of the starting amine was still present. An additional aliquot of 4-methoxybenzenesulfonyl chloride (52 mg, 0.25 mmol, 5 mole %) was added, and the reaction was stirred at ambient temperature for an additional 16 hours. Monitoring by LCMS indicated complete formation of a single product. The solvent was removed in vacuo. The residue was dissolved in dichloromethane and washed with a 5% aqueous sodium bicarbonate solution. The aqueous phase was extracted with dichloromethane. The combined organic phase was washed with a 2 N hydrochloric acid solution. The organic phase was dried over anhydrous sodium sulfate, filtered, and concentrated in vacuo to a residue. The residue was purified by preparative liquid chromatography on a Biotage® 40 Mi column of pre-packed silica gel (90 g), eluting with a gradient of 30%–50% methyl tert-butylether in hexane, to afford N-[(1S)-1-(2',4-difluoro-1,1'-biphenyl-2-yl)ethyl]-4-methoxybenzenesulfonamide (1.8 g, 89%, 99.2% ee), m.p. 133–135° C.;

$[\alpha]_D^{25}$=−17° (c=10.1 mg/mL in $CHCl_3$);

Chiral LC Purity: 99.2% ee;

HRMS [(+ESI), m/z]: 404.11224 [M+H]$^+$. Calcd for $C_{21}H_{19}F_2NO_3S$: 404.11265

$^1$H NMR (400 MHz, DMSO-$d_6$) δ: 1.13 (d, J=6.8 Hz, 3H), 3.79 (s, 3H), 4.05 (m, 1H), 6.92 (d, J=8.6 Hz, 2H), 7.05 (t, J=6.9 Hz, 1H), 7.11 (m, 1H), 7.20 (t, J=7.8 Hz, 2H), 7.29 (m, 2H), 7.40 (d, J=8.8 Hz, 2H), 7.48 (m, 1H), 8.10 (d, J=7.0 Hz, 1H).

Step d)
Part 2a)

N-[1-(2',4-Difluoro-1,1'-biphenyl-2-yl)ethyl]-4-methoxybenzenesulfonamide

A stirred solution of 1-(2',4-difluoro-1,1'-biphenyl-2-yl) ethylamine (0.26 g, 1.12 mmol) in dichloromethane (10 mL) was treated with 4-methoxybenzenesulfonyl chloride (0.23 g, 1.12 mmol), and pyridine (0.09 g, 1.12 mmol). The reaction was stirred at room temperature for twelve hours, diluted with dichloromethane, washed sequentially with a 1 N hydrochloric acid solution (2×) and a saturated, aqueous, sodium chloride solution. The organic phase was dried over anhydrous sodium sulfate, filtered through a short column of silica gel, and evaporated to a residue which, after crystallization from ethyl acetate-hexane, afforded the title compound (0.22 g, 0.53 mmol, 48%) as a racemic, homogeneous, colorless, crystalline solid, m.p. 182–184° C.;

MS [(+ESI), m/z]: 404 [M+H]$^+$;

MS [(−ESI), m/z]: 402 [M−H]$^-$;

IR (Solid), $v_{max}$: 3241, 1594, 1480, 1325, 1263, 1154, 1083, 1026, 917, 835, 768, 671 cm$^{-1}$;

$^1$H NMR (400 MHz, DMSO-$d_6$) δ: 1.13 (d, J=6.7 Hz, 3H), 3.79 (s, 3H), 4.05 (d, J=7.1 Hz, 1H, major rotamer), 4.10 (broad s, 1H, minor rotamer), 6.92 (d, J=8.5 Hz, 2H), 7.11 (t, J=8.3 Hz, 1H), 7.20 (m, 2H), 7.27 (t, J=89 Hz, 1H), 7.32 (t, J=7.4 Hz, 1H), 7.41 (d, J=8.8 Hz, 2H), 7.45–7.50 (m, 1H), 8.05 (broad s, 1H, minor rotamer), 8.09 (broad s, 1H, major rotamer), exists as approximately 2:1 ratio of rotamers;

Anal. calcd for $C_{21}H_{19}F_2NO_3S$: C, 62.52; H, 4.75; N, 3.47. Found: C, 62.54; H, 4.84; N, 3.24.

Step d)
Part 2b)

N-[(1R)-1-(2',4-Difluoro-1,1'-biphenyl-2-yl)ethyl]-4-methoxybenzenesulfonamid *

The enantiomers of N-[1-(2',4-difluoro-1,1'-biphenyl-2-yl)ethyl]-4-methoxybenzenesulfonamide were separated by automated, preparative, normal phase, chiral chromatography on a Chiralpak AD-H® column (2×25 cm) eluting with a mixture of 50% ethanol in hexane at a flow rate of 15 mL/min. After evaporation of the solvent in vacuo, peak one with a retention time at 5.4 minutes and monitored by ultraviolet detection yielded, N-[(1R)-1-(2',4-difluoro-1,1'-biphenyl-2-yl)ethyl]-4-methoxybenzenesulfonamide* (0.05 g, 0.13 mmol, 50%) as a homogeneous, colorless, amorphous solid, m.p. 133–135° C.;

$T_R$=5.4 minutes;

$[\alpha]_D^{25}$=+14.9° (c=10.0 mg/mL in $CHCl_3$);

HRMS [(+ESI), m/z]: 404.11216 [M+H]$^+$. Calcd. for $C_{21}H_{19}F_2NO_3S$: 404.11265;

$^1$H NMR (400 MHz, DMSO-$d_6$) δ: 1.13 (d, J=6.7 Hz, 3H, major rotamer), 3.79 (s, 3H), 4.05 (broad q, 1H, major rotamer), 4.10 (broad q, 1H, minor rotamer), 6.92 (d, J=8.5 Hz, 2H), 7.11 (t, J=8.3 Hz, 1H), 7.20 (m, 2H), 7.27 (t, J=8.9 Hz, 1H), 7.32 (t, J=7.4 Hz, 1H), 7.41 (d, J=8.9 Hz, 2H), 7.45–7.50 (m, 1H), 8.05 (d, J=7.0 Hz, 1H, minor rotamer), 8.10 (d, J=7.0 Hz, 1H, major rotamer), exists as approximately 2:1 ratio of rotamers.

*The stereochemical configuration is absolute and was assigned by conversion to (6R)-8-fluoro-5-[(4-methoxyphenyl)sulfonyl]-6-methyl-5,6-dihydrophenanthridine. The absolute configuration was determined by analogy to (6S)-8-fluoro-5-[(4-methoxyphenyl)sulfonyl]-6-methyl-5,6-dihydrophenanthridine which was determined by a single crystal x-ray diffraction experiment.

Step d)
Part 2c)

N-[(1S)-1-(2',4-Difluoro-1,1'-biphenyl-2-yl)ethyl]-4-methoxybenzenesulfonamide*

The enantiomers of N-[1-(2',4-difluoro-1,1'-biphenyl-2-yl)ethyl]-4-methoxybenzenesulfonamide were separated by automated, preparative, normal phase, chiral chromatography on a Chiralpak AD-H® column (2×25 cm) eluting with a mixture of 50% ethanol in hexane at a flow rate of 15 mL/min. After evaporation of the solvent in vacuo, peak two with a retention time at 6.7 minutes and monitored by ultraviolet detection yielded, N-[(1S)-1-(2',4-difluoro-1,1'-biphenyl-2-yl)ethyl]-4-methoxybenzenesulfonamide* (0.05 g, 0.13 mmol, 50%) as a homogeneous, colorless, amorphous solid, m.p. 133–135° C.;

$T_R$=6.7 minutes;

$[\alpha]_D^{25}$=−15.8° (c=10.0 mg/mL in $CHCl_3$);

HRMS [(+ESI), m/z]: 404.11224 [M+H]$^+$. Calcd. for $C_{21}H_{19}F_2NO_3S$: 404.11265;

$^1$H NMR (400 MHz, DMSO-$d_6$) δ: 1.08 (d, J=7.0 Hz, 3H, minor rotamer), 1.13 (d, J=6.7 Hz, 3H, major rotamer), 3.79 (s, 3H), 4.05 (broad s, 1H, major rotamer), 4.10 (broad s, 1H, minor rotamer), 6.92 (d, J=8.5 Hz, 2H), 7.11 (t, J=8.3 Hz, 1H), 7.20 (m, 2H), 7.27 (t, J=89 Hz, 1H), 7.32 (t, J=7.4 Hz, 1H), 7.41 (d, J=8.9 Hz, 2H), 7.45–7.50 (m, 1H), 8.05 (broad s, 1H, minor rotamer), 8.09 (broad s, 1H, major rotamer), exists as approximately 2:1 ratio of rotamers.

*The stereochemical configuration is absolute and was assigned by conversion to (6S)-8-fluoro-5-[(4-methoxyphenyl)sulfonyl]-6-methyl-5,6-dihydrophenanthridine. The absolute configuration was assigned by comparison to the authentic sample of (6S)-8-fluoro-5-[(4-methoxyphenyl)sulfonyl]-6-methyl-5,6-dihydrophenanthridine determined by a single crystal x-ray diffraction experiment.

Step e)

(6S)-8-Fluoro-5-[(4-m thoxyphenyl)sulf nyl]-6-methyl-5,6-dihydrophenanthridine*

A stirred suspension of N-[(1S)-1-(2',4-difluoro-1,1'-biphenyl-2-yl)ethyl]-4-methoxybenzenesulfonamide (1.7 g, 4.2 mmol) and potassium carbonate (1.16 g, 8.4 mmol) in N,N-dimethylformamide (25 mL) was heated at 100° C., and the reaction progress was monitored by LCMS. After 96 hours, water (300 mL) was added with stirring. A precipitate was filtered and washed with copious amounts of water. The product was purified by preparative liquid chromatography on a Biotage® 40 Mi column of pre-packed silica gel (90 g), eluting with a gradient of 30%–50% methyl tert-butylether in hexane, to afford a purified solid. Recrystallization of the solid afforded (6S)-8-fluoro-5-[(4-methoxyphenyl)sulfonyl]-6-methyl-5,6-dihydrophenanthridine* (1.4 g, 87%, >99.9% ee), m.p. 196.8–198° C.;

$[\alpha]_D^{25}$=+209° (c=11.0 mg/mL in $CHCl_3$);

Chiral LC Purity: >99.9% ee;

MS [(+ESI), m/z]: 384 $[M+H]^+$;

$^1$H NMR (400 MHz, DMSO-$d_6$): δ: 1.14 (d, J=7.0 Hz, 3H), 3.65 (s, 3H), 5.44 (q, J=6.8 Hz, 1H), 6.61 (m, 2H), 6.97 (m, 3H), 7.18 (dd, J=9.2, 2.7 Hz, 1H), 7.41 (m, 2H), 7.50 (dd, J=8.8, 5.5 Hz, 1H), 7.62 (dd, J=7.9, 1.4 Hz, 1H), 7.76 (dd, J=7.4, 2.0 Hz, 1H);

Anal. Calcd for $C_{21}H_{18}FNO_3S$: C, 65.78; H, 4.73; N, 3.65. Found: C, 65.65; H, 4.65; N, 3.65.

*The stereochemical configuration is absolute and was assigned by comparison to an authentic sample of (6S)-8-fluoro-5-[(4-methoxyphenyl)sulfonyl]-6-methyl-5,6-dihydrophenanthridine synthesized in Example 33, Method B, step a. The absolute configuration of the above (6S)-8-fluoro-5-[(4-methoxyphenyl)sulfonyl]-6-methyl-5,6-dihydrophenanthridine was determined by a single crystal x-ray diffraction experiment.

Step f)

4-{[(6S)-8-Fluoro-6-methylphenanthridin-5(6H)-yl]sulfonyl}phenol

The title compound can be obtained from N-[(1S)-1-(2',4-difluoro-1,1'-biphenyl-2-yl)ethyl]-4-methoxybenzenesulfonamide (Example 33, Method C, Step d, Parts 1 or 2c) by following first the procedure described in Example 33, Method C, Step e, followed by the demethylation procedure described in Example 33, Method B, Step b.

EXAMPLE 34

Method A

Step a)

Ethyl 4-{([(R)-8-flu ro-6-m thylph nanthridin-5(6H)-yl]sulfonyl}phenyl carb nate*

The enantiomers of ethyl 4-{[(R)-8-fluoro-6-methylphenanthridin-5(6H)-yl]sulfonyl}phenyl carbonate (Example 32, Method A, Step d) were separated by chiral stationary phase high-performance liquid chromatography (Chiralcel® OJ-25×5 cm column) on a Rainin Auto-Prep System®, eluting with ethanol at a flow rate of 10 mL/min. The second peak with a retention time at 12.6 minutes was the title compound;

$T_R$ 12.6 minutes;

m.p. 159° C.;

$[\alpha]_D^{25}$=−217.0° (c=1% solution, $CHCl_3$);

MS [(+ESI), m/z]: 442 $[M+H]^+$;

$^1$H NMR (500 MHz, DMSO-$d_6$) δ: 7.77 (d, J=7.6 Hz, 1H), 7.63 (d, J=7.8 Hz, 1H), 7.48–7.39 (m, 3H), 7.19 (dd, J=9.0, 2.6 Hz, 1H), 7.09 (d, J=8.7 Hz, 2H), 6.98 (d, J=8.7 Hz, 2H), 6.93 (td, J=8.7, 2.6 Hz, 1H), 5.48 (q, J=7.0 Hz, 1H), 4.21 (q, J=7.1 Hz, 2H), 1.25 (t, J=7.1 Hz, 3H), 1.15 (t, J=7.0 Hz, 3H);

Anal. calcd for $C_{23}H_{20}FNO_5S$: C, 62.57; H, 4.57; N, 3.17. Found: C, 62.50; H, 4.59; N, 3.06.

*The absolute configuration was assigned by conversion to 4-{[(R)-8-fluoro-6-methylphenanthridin-5(6H)-yl]sulfonyl}phenol.

Step b)

4-{[(R)-8-Fluoro-6-methylphenanthridin-5(6H)-yl]sulfonyl}phenol*

The title compound was prepared from ethyl 4-{[(R)-8-fluoro-6-methylphenanthridin-5(6H)-yl]sulfonyl}phenyl carbonate (0.05 g, 0.11 mmol), a 2.5 N aqueous sodium hydroxide solution (2 mL, 5 mmol), and methanol (2 mL), according to the procedure and in the same manner as described in Example 32, Method A, Step e to yield 4-{[(R)-8-fluoro-6-methylphenanthridin-5(6H)-yl]sulfonyl}phenol* as a solid (0.04 g, 100%), m.p. 193° C.;

$[\alpha]_D^{25}$=−263.0° (c=1% solution, $CHCl_3$);

MS [(−ESI), m/z]: 368 $[M-H]^-$;

$^1$H NMR (500 MHz, DMSO-$d_6$) δ: 10.24 (br s, 1H), 7.76 (dd, J=7.6 Hz, 1.5, 1H), 7.60 (dd, J=7.8, 1.4 Hz, 1H), 7.52 (dd, J=8.7, 5.0 Hz, 1H), 7.41 (m, 1H), 7.37 (m, 1H), 7.17 (dd, J=9.2, 2.7 Hz, 1H), 6.96 (td, J=8.7, 2.7 Hz, 1H), 6.86 (d, J=8.9 Hz, 2H), 6.38 (d, J=8.9 Hz, 2H), 5.41 (q, J=7.0 Hz, 1H), 1.13 (d, J=7.0 Hz, 3H);

Anal. calcd for $C_{20}H_{16}FNO_3S \cdot 0.30H_2O$: C, 64.09; H, 4.46; N, 3.74. Found: C, 63.88; H, 4.31; N, 3.59.

*The absolute configuration was assigned by analogy to (S)-8-fluoro-5-[(4-methoxyphenyl)sulfonyl]-6-methyl-5,6-dihydrophenanthridine. The absolute configuration of the above (S)-8-fluoro-5-[(4-methoxyphenyl)sulfonyl]-6-methyl-5,6-dihydrophenanthridine was determined by a single crystal x-ray diffraction experiment.

Method B

Step a)

(R)-8-Fluoro-5-[(4-methoxyphenyl)sulfonyl]-6-methyl-5,6-dihydrophenanthridine*

The enantiomers of 8-fluoro-5-[(4-methoxyphenyl)sulfonyl]-6-methyl-5,6-dihydrophenanthridine (Example 32, Method B, Step a) were separated by chiral stationary phase high-performace liquid chromatography (Chiralpak® AD-25×5 cm column) on a Rainin Auto-Prep System®, eluting with a mixture of 2-propanol-hexane (1:9) at a flow rate of 15 mL/min. The second peak with a retention time at 12.8 minutes was the title compound;

$T_R$ 12.8 minutes;

m.p. 181–182° C.;

$[\alpha]_D^{25}$=−251.0° (1% solution, $CHCl_3$);

MS [(+ESI), m/z]: 384 $[M+H]^+$;

$^1$H NMR (500 MHz, DMSO-$d_6$) δ: 7.75 (dd, J=7.7, 1.1 Hz, 1H), 7.61 (m, 1H), 7.48 (dd, J=8.6, 5.4 Hz, 1H), 7.43 (m, 1H), 7.38 (m, 1H), 7.16 (dd, J=9.2, 2.8 Hz, 1H), 6.98–6.92 (m, 3H), 6.59 (d, J=8.8 Hz, 2H), 5.43 (q, J=7.0 Hz, 1H), 3.64 (s, 3H), 1.13 (d, J=7.0 Hz, 3H).

*The absolute configuration was assigned by analogy to (S)-8-fluoro-5-[(4-methoxyphenyl)sulfonyl]-6-methyl-5,6-dihydrophenanthridine.

Step b)

4-{[(R)-8-Fluoro-6-methylphenanthridin-5(6H)-yl]sulfonyl}phenol*

The title compound was prepared from (R)-8-fluoro-5-[(4-methoxyphenyl)sulfonyl]-6-methyl-5,6-dihydrophenanthridine (0.74 g, 1.93 mmol), cyclohexene (7.0 mL, 70.0 mmol), and 1 M boron tribromide in dichloromethane (23 mL, 23 mmol) according to the procedure and in the same manner as described in Example 32, Method B, Step b. The crude product was purified by flash column chromatography on silica gel, eluting with a mixture of ethyl acetate-hexane (1:9 to 1:4 gradient), followed by trituration from hot hexane to yield 4-{[(R)-8-fluoro-6-methylphenanthridin-5(6H)-yl]sulfonyl}phenol* as a solid (0.52 g, 73%), m.p. 193° C.

*The mass and NMR spectra of this material were identical to the mass and NMR spectra of authentic material prepared in Example 34, Method A, Step b;

$[\alpha]_D^{25}$=−261° (1% solution, CHCl$_3$).

EXAMPLE 35

Step a)

8-Fluoro-5-[(4-methoxy-3-methylphenyl)sulfonyl]-6-methyl-5,6-dihydrophenanthridine The intermediate dihydrophenanthridine was prepared from 8-fluoro-6-methylphenanthridine, (Example 32, Method A, Step b, 0.7 g, 3.3 mmol), by treatment with sodium borohydride (0.5 g, 13.2 mmol) and trifluoroacetic acid (0.5 mL, 6.6 mmol) in tetrahydrofuran (35 mL). In a separate, second step, the dihydrophenanthridine was treated with triethylamine (1.0 mL, 7.4 mmol) and 4-methoxy-3-methylbenzenesulfonyl chloride (0.82 g, 3.7 mmol, 2 equivalents) in dichloromethane (10 mL) according to the procedure and in the same manner as described in Example 32, Method A, Step d. The crude product was purified by flash column chromatography on silica gel, eluting with a mixture of ethyl acetate-hexane (1:9 to 1:4 gradient) to yield, 8-fluoro-5-[(4-methoxy-3-methylphenyl)sulfonyl]-6-methyl-5,6-dihydrophenanthridine as a homogeneous, white solid (0.36 g, 49% from the dihydrophenanthridine);

MS [(+ESI), m/z]: 420 [M+Na]$^+$;

$^1$H NMR (400 MHz, CDCl$_3$) δ: 7.75 (dd, 1H), 7.50 (dd, 1H), 7.36 (td, 1H), 7.30 (td, 1H), 7.21 (m, 1H), 6.87 (m, 1H), 6.76–6.71 (m, 3H), 6.30 (d, 1H), 5.32 (q, 1H), 3.67 (s, 3H), 1.82 (s, 3H), 1.22 (d, 3H).

Step b)

4-[(8-Fluoro-6-methylphenanthridin-5(6H)-yl)sulfonyl]-2-methylphenol

A mixture of 8-fluoro-5-[(4-methoxy-3-methylphenyl)sulfonyl]-6-methyl-5,6-dihydrophenanthridine (0.30 g, 0.75 mmol) and tetrabutylammonium iodide (0.69 g, 1.9 mmol) was treated with 1 M boron trichloride in dichloromethane (1.9 mL, 1.9 mmol) at room temperature. After stirring for 24 hours at room temperature, the mixture was treated sequentially with water (20 mL), a saturated, aqueous, sodium bicarbonate solution (50 mL), and ether (20 mL). The separated aqueous phase was extracted with diethyl ether (3×25 mL). The combined organic phase was dried over anhydrous sodium sulfate, filtered, and concentrated in vacuo to a residue. The residue was purified by flash column chromatography on silica gel, eluting with a mixture of ethyl acetate-hexane (1:4 to 3:7 gradient) to yield, the title compound as a homogeneous solid (0.21 g, 73%), m.p. 196° C.;

MS [(+ESI), m/z]: 384 [M+H]$^+$;

$^1$H NMR (500 MHz, CDCl$_3$) δ: 7.78 (dd, 1H), 7.53 (dd, 1H), 7.39 (td, 1H), 7.33 (td, 1H), 7.23 (m, 1H), 6.82–6.75 (m, 3H), 6.28 (d, 2H), 5.36 (q, 1H), 4.88 (s, 1H), 1.90 (s, 3H), 1.25 (d, 3H);

Anal. calcd for C$_{21}$H$_{18}$FNO$_3$S: C, 65.78; H, 4.73; N, 3.65. Found: C, 65.66; H, 4.81; N, 3.50.

EXAMPLE 36

Step a)

N-(3'-Methoxy-1,1'-biphenyl-2-yl)acetamide

3'-Methoxy-1,1'-biphenyl-2-ylamine was prepared from 2-iodoaniline (3.64 g, 16.7 mmol), 3-methoxyphenylboronic acid (2.54 g, 16.7 mmol), [1,1'-bis(diphenylphosphino)ferrocene]dichloropalladium (II) complex with dichloromethane (0.41 g, 0.50 mmol), and a 5 N aqueous sodium hydroxide solution (6.7 mL, 33.5 mmol), according to the procedure and in the same manner as described in Example 32, Method A, Step a, to afford the intermediate biphenyl amine as an oil (2.79 g, 84%). The title compound was prepared from the above intermediate biphenyl amine (0.75 g, 3.8 mmol), acetic anhydride (1.4 mL, 15 mmol), 4-(N,N-dimethylamino)pyridine (0.05 g, 0.4 mmol), and pyridine (1.2 mL, 15 mmol) according to the same procedure as described in Example 32, Method A, Step a to yield N-(3'-methoxy-1,1'-biphenyl-2-yl)acetamide as a solid (0.60 g, 66%), m.p. 105–107° C.;

MS [(+ESI), m/z]: 242 [M+H]$^+$;

$^1$H NMR (500 MHz, CDCl$_3$) δ: 8.29 (d, J=8.1 Hz, 1H), 7.40–7.35 (m, 2H), 7.24 (d, J=7.3 Hz, 1H), 7.16 (m, 2H), 6.95 (m, 2H), 6.90 (s, 1H), 3.84 (s, 3H), 2.03 (s, 3H);

Anal. calcd for C$_{15}$H$_{15}$NO$_2$: C, 74.67; H, 6.27; N, 5.80. Found: C, 74.35; H, 6.25; N, 5.63.

Step b)

7-Methoxy-6-methylphenanthridine and 9-Methoxy-6-methylphenanthridine

A stirred solution of N-(3'-methoxy-1,1'-biphenyl-2-yl)acetamide (2.04 g, 10.2 mmol) in acetonitrile (205 mL) was treated with phosphorous oxychloride (4.8 mL, 51 mmol) and heated at reflux for 14 hours. After cooling to room temperature, the reaction was diluted with a saturated, aqueous, ammonium chloride solution (500 mL), ammonium hydroxide (until pH>10), and ethyl acetate (200 mL). The separated aqueous phase was extracted with ethyl acetate (3×100 mL). The combined organic phase was dried over anhydrous sodium sulfate, filtered, and concentrated in vacuo to a crude product. Analysis of the crude product by liquid chromatography with a mass spectrum detector indicated a 2:1 mixture of regioisomers. The crude product was purified by flash column chromatography on silica gel, eluting with a mixture of ethyl acetate-hexane (0:1 to 3:7 gradient), to yield the separated regioisomers, both as homogeneous solids: 7-methoxy regioisomer A (0.61 g, 24%), and 9-methoxy regioisomer B (1.19 g, 52%);

Regioisomer A: 7-Methoxy-6-methylphenanthridine, m.p. 85° C.;

MS [(+ESI), m/z]: 224 [M+H]$^+$;

$^1$H NMR (500 MHz, CDCl$_3$) δ: 8.48 (d, J=7.9 Hz, 1H), 8.21 (d, J=8.0 Hz, 1H), 8.04 (dd, J=8.3, 0.8 Hz, 1H), 7.73 (t, J=8.2, 1H), 7.68 (m, 1H), 7.58 (m, 1H), 7.09 (d, J=8.0 Hz, 1H), 4.03 (s, 3H), 3.18 (s, 3H);

Anal. calcd for C$_{15}$H$_{13}$NO.0.60H$_2$O: C, 76.97; H, 6.11; N, 5.98. Found: C, 76.98; H, 6.15; N, 5.80.

Regioisomer B: 9-Methoxy-6-methylphenanthridine, m.p. 85° C.;

MS [(+ESI), m/z]: 224 [M+H]$^+$;

$^1$H NMR (500 MHz, CDCl$_3$) δ: 8.46 (m, 1H), 8.15 (d, J=9.0 Hz, 1H), 8.07 (dd, J=8.1, 1.1 Hz, 1H), 7.95 (d, J=2.4 Hz, 1H), 7.70 (m, 1H), 7.59 (m, 1H), 7.29 (dd, J=8.9 Hz, 2.5, 1H), 4.05 (s, 3H), 3.00 (s, 3H);

Anal. calcd for $C_{15}H_{13}NO$: C, 80.69; H, 5.87; N, 6.27. Found: C, 80.71; H, 5.83; N, 6.20.

Step c)

9-Methoxy-5-[(4-methoxyphenyl)sulfonyl]-6-methyl-5,6-dihydrophenanthridin

The intermediate dihydrophenanthridine was prepared from 9-methoxy-6-methylphenanthridine (0.7 g, 3.1 mmol) by treatment with sodium borohydride (0.48 g, 12.6 mmol) and trifluoroacetic acid (0.5 mL, 6.3 mmol) in tetrahydrofuran (35 mL). In a separate, second step, the dihydrophenanthridine was treated with triethylamine (1.0 mL, 7.5 mmol) and 4-methoxybenzenesulfonyl chloride (0.77 g, 3.7 mmol, 2 equivalents) in dichloromethane (10 mL) according to the procedure and in the same manner as described in Example 32, Method A, Step d. The crude product was purified by flash column chromatography on silica gel, eluting with a mixture of ethyl acetate-hexane (1:9 to 1:4 gradient), to yield 9-methoxy-5-[(4-methoxyphenyl)sulfonyl]-6-methyl-5,6-dihydrophenanthridine as a homogeneous, white solid (0.45 g, 61% from the dihydrophenanthridine), m.p. 129–130° C.;

MS [(+ESI), m/z]: 396 [M+H]$^+$;

$^1$H NMR (500 MHz, CDCl$_3$) δ: 7.79 (dd, J=8.0 Hz, 1.4, 1H), 7.53 (dd, J=7.7, 1.4 Hz, 1H), 7.39 (m, 1H), 7.33 (m, 1H), 6.95 (m, 3H), 6.75 (d, J=2.4 Hz, 1H), 6.71 (dd, J=8.2, 2.4 Hz, 1H), 6.37 (m, 2H), 5.37 (q, J=7.0 Hz, 1H), 3.75 (s, 3H), 3.67 (s, 3H), 1.22 (d, J=7.0 Hz, 3H);

Anal. calcd for $C_{22}H_{21}NO_4S$: C, 66.82; H, 5.35; N, 3.54. Found: C, 66.79; H, 5.33; N, 3.44.

Step d)

5-[(4-Hydroxyphenyl)sulfonyl]-6-methyl-5,6-dihydrophenanthridin-9-ol

The title compound was prepared from 9-methoxy-5-[(4-methoxyphenyl)sulfonyl]-6-methyl-5,6-dihydrophenanthridine (0.35 g, 0.89 mmol), tetrabutylammonium iodide (0.82 g, 2.2 mmol), and 1 M boron trichloride in dichloromethane (4.44 mL, 4.44 mmol) according to the procedure and in the same manner as described in Example 35, Step b. The crude product was purified by flash column chromatography on silica gel, eluting with a mixture of ethyl acetate-hexane (3:7 to 1:1 gradient), to yield 5-[(4-hydroxyphenyl)sulfonyl]-6-methyl-5,6-dihydrophenanthridin-9-ol as a solid (0.18 g, 56%), m.p. 212° C.;

MS [(+ESI), m/z]: 368 [M+H]$^+$;

$^1$H NMR (500 MHz, CDCl$_3$) δ: 7.80 (dd, 1H), 7.51 (dd, 1H), 7.40 (td, 1H), 7.33 (td, 1H), 6.95–6.91 (m, 3H), 6.77 (d, 1H), 6.65 (dd, 1H), 6.36 (d, 2H), 5.37 (q, 1H), 5.05 (br s, 1H), 4.66 (br s, 1H), 1.23 (d, 3H);

Anal. calcd for $C_{20}H_{17}NO_4S$: C, 65.38; H, 4.66; N, 3.81. Found: C, 65.02; H, 4.88; N, 3.56.

EXAMPLE 37

Step a)

9-Methoxy-5-[(4-methoxy-3-methylphenyl)sulfonyl]-6-methyl-5,6-dihydrophenanthridine The intermediate dihydrophenanthridine was prepared from 9-methoxy-6-methylphenanthridine, (Example 36, Step b, 0.7 g, 3.1 mmol), by treatment with sodium borohydride (0.48 g, 12.6 mmol) and trifluoroacetic acid (0.5 mL, 6.3 mmol) in tetrahydrofuran (35 mL). In a separate, second step, the dihydrophenanthridine was treated with triethylamine (1.1 mL, 7.9 mmol) and 4-methoxy-3-methylbenzenesulfonyl chloride (0.87 g, 3.9 mmol, 2 equivalents) in dichloromethane (10 mL) according to the procedure and in the same manner as described in Example 32, Method A, Step d. The crude product was purified by flash column chromatography on silica gel, eluting with a mixture of ethyl acetate-hexane (1:9 to 3:7 gradient), to yield 9-methoxy-5-[(4-methoxy-3-methylphenyl)sulfonyl]-6-methyl-5,6-dihydrophenanthridine as a homogeneous, white solid (0.27 g, 33% from the dihydrophenanthridine);

$^1$H NMR (400 MHz, CDCl$_3$) δ: 7.75 (dd, 1H), 7.51 (dd, 1H), 7.37 (td, 1H), 7.29 (td, 1H), 6.94 (m, 1H), 6.82 (dd, 1H), 6.70–6.66 (m, 3H), 6.26 (d, 1H), 5.33 (q, 1H), 3.72 (s, 3H), 3.66 (s, 3H), 1.80 (s, 3H), 1.20 (d, 3H).

Step b)

5-[(4-Hydroxy-3-methylphenyl)sulfonyl]-6-methyl-5,6-dihydrophenanthridin-9-ol The title compound was prepared from 9-methoxy-5-[(4-methoxy-3-methylphenyl)sulfonyl]-6-methyl-5,6-dihydrophenanthridine (0.27 g, 0.66 mmol), tetrabutylammonium iodide (0.61 g, 1.7 mmol), and 1 M boron trichloride in dichloromethane (3.3 mL, 3.3 mmol) according to the procedure and in the same manner as described in Example 35, Step b. The crude product was purified by flash column chromatography on silica gel, eluting with a mixture of ethyl acetate-hexane (3:7 to 1:1 gradient), followed by re-crystallization from a mixture of dichloromethane-hexane, to yield 5-[(4-hydroxy-3-methylphenyl)sulfonyl]-6-methyl-5,6-dihydrophenanthridin-9-ol as a homogeneous solid (0.10 g, 40%);

MS [(−ESI), m/z]: 380 [M−H]$^-$;

$^1$H NMR (500 MHz, DMSO-d$_6$) δ: 10.07 (s, 1H), 9.31 (s, 1H), 7.59 (d, 1H), 7.56 (d, 1H), 7.37 (t, 1H), 7.32 (t, 1H), 7.02 (d, 1H), 6.78 (s, 1H), 6.72 (s, 1H), 6.65 (d, 1H), 6.60 (d, 1H), 6.37 (d, 1H), 5.30 (q, 1H), 1.78 (s, 3H), 1.07 (d, 3H);

Anal. calcd for $C_{21}H_{19}NO_4S \cdot 0.20H_2O$: C, 65.51; H, 5.08; N, 3.64. Found: C, 65.49; H, 4.84; N, 3.51.

EXAMPLE 38

Step a)

7-Methoxy-5-[(4-methoxy-3-methylphenyl)sulfonyl]-6-methyl-5,6-dihydrophenanthridine The intermediate dihydrophenanthridine was prepared from 7-methoxy-6-methylphenanthridine, (Example 36, Step b, 0.61 g, 2.7 mmol), by treatment with sodium borohydride (0.62 g, 16 mmol) and trifluoroacetic acid (0.84 mL, 10.8 mmol) in tetrahydrofuran (12 mL). In a separate, second step, the dihydrophenanthridine was treated with triethylamine (0.85 mL, 6.1 mmol) and 4-methoxy-3-methylbenzenesulfonyl chloride (0.67 g, 3.0 mmol, 2 equivalents) in dichloromethane (3 mL) according to the procedure and in the same manner as described in Example 32, Method A, Step d. The crude product was purified by flash column chromatography on silica gel, eluting with a mixture of ethyl acetate-hexane (1:9 to 1:4 gradient), to yield 7-methoxy-5-[(4-methoxy-3-methylphenyl)sulfonyl]-6-methyl-5,6-dihydrophenanthridine as a homogeneous, white solid (0.21 g, 34% from the dihydrophenanthridine);

$^1$H NMR (400 MHz, DMSO-d$_6$) δ: 7.70 (dd, 1H), 7.54 (dd, 1H), 7.40–7.31 (m, 2H), 7.02 (m, 2H), 6.80 (dd, 1H), 6.75 (dd, 1H), 6.70 (d, 1H), 6.53 (d, 1H), 5.58 (q, 1H), 3.83 (s, 3H), 3.62 (s, 3H), 1.76 (s, 3H), 1.03 (d, 3H).

Step b)

5-[(4-Hydroxy-3-methylphenyl)sulfonyl]-6-methyl-5,6-dihydrophenanthridin-7-ol The title compound was prepared from 7-methoxy-5-[(4-methoxy-3-methylphenyl)sulfonyl]-6-methyl-5,6- dihydrophenanthridine (0.21 g, 0.51 mmol), tetrabutylammonium iodide (0.47 g, 1.3 mmol), and 1 M boron trichloride in dichloromethane (3.1 mL, 3.1 mmol) according to the procedure and in the same manner as described in Example 35, Step b. The crude product was purified by flash column chromatography on silica gel, eluting with a mixture of ethyl acetate-hexane (3:7 to 3:2 gradient), followed by trituration from dichloromethane, to yield 5-[(4-hydroxy-3-methylphenyl)sulfonyl]-6-methyl-5,6-dihydrophenanthridin-7-ol as a homogeneous solid (0.10 g, 53%), m.p. 258° C.;

MS [(−ESI), m/z]: 380 [M−H]$^-$;

$^1$H NMR (500 MHz, DMSO-d$_6$) δ: 10.03 (s, 1H), 9.75 (s, 1H), 7.68 (d, 1H), 7.56 (d, 1H), 7.37 (t, 1H), 7.31 (t, 1H), 6.91 (m, 2H), 6.78 (s, 1H), 6.67 (d, 1H), 6.63 (d, 1H), 6.34 (d, 1H), 5.64 (q, 1H), 1.77 (s, 3H), 1.07 (d, 3H);

Anal. calcd for C$_{21}$H$_{19}$NO$_4$S 0.5H$_2$O: C, 64.60; H, 5.16; N, 3.59. Found: C, 64.64; H, 4.93; N, 3.55.

EXAMPLE 39

Step a)

7-Methoxy-5-[(4-methoxyphenyl)sulfonyl]-6-methyl-5,6-dihydrophenanthridin

The intermediate dihydrophenanthridine was prepared from 7-methoxy-6-methylphenanthridine, (Example 36, Step b, 0.61 g, 2.7 mmol), by treatement with sodium borohydride (0.62 g, 16 mmol) and trifluoroacetic acid (0.84 mL, 10.8 mmol) in tetrahydrofuran (12 mL). In a separate, second step, the dihydrophenanthridine was treated with triethylamine (0.77 mL, 5.5 mmol) and 4-methoxybenzenesulfonyl chloride (0.57 g, 2.8 mmol, 2 equivalents) in dichloromethane (3 mL) according to the procedure and in the same manner as described in Example 32, Method A, Step d. The crude product was purified by flash column chromatography on silica gel, eluting with a mixture of ethyl acetate-hexane (1:9 to 1:4 gradient), to yield 7-methoxy-5-[(4-methoxyphenyl)sulfonyl]-6-methyl-5,6-dihydrophenanthridine as a white solid (0.17 g, 33% from the dihydrophenanthridine);

$^1$H NMR (400 MHz, DMSO-d$_6$) δ: 7.71 (dd, 1H), 7.56 (dd, 1H), 7.40–7.31 (m, 2H), 7.04 (m, 2H), 6.89 (m, 2H), 6.79 (dd, 1H), 6.53 (m, 2H), 5.59 (q, 1H), 3.83 (s, 3H), 3.60 (s, 3H), 1.03 (d, 3H).

Step b)

5-[(4-Hydroxyphenyl)sulfonyl]-6-methyl-5,6-dihydrophenanthridin-7-ol

The title compound was prepared from 7-methoxy-5-[(4-methoxyphenyl)sulfonyl]-6-methyl-5,6-dihydrophenanthridine (0.17 g, 0.43 mmol), tetrabutylammonium iodide (0.39 g, 1.1 mmol), and 1 M boron trichloride in dichloromethane (2.6 mL, 2.6 mmol) according to the procedure and in the same manner as described in Example 35, Step b. The crude product was purified by flash column chromatography on silica gel, eluting with a mixture of ethyl acetate-hexane (1:1), followed by trituration from dichloromethane, to yield 5-[(4-hydroxyphenyl)sulfonyl]-6-methyl-5,6-dihydrophenanthridin-7-ol as a homogenous solid (0.096 g, 61%);

MS [(−ESI), m/z]: 366 [M−H]$^-$;

$^1$H NMR (500 MHz, DMSO-d$_6$) δ: 10.15 (br s, 1H), 9.72 (br s, 1H), 7.70 (dd, 1H), 7.59 (dd, 1H), 7.37 (td, 1H), 7.33 (td, 1H), 6.92 (m, 2H), 6.86 (d, 2H), 6.67 (dd, 1H), 6.35 (d, 2H), 5.64 (q, 1H), 1.07 (d, 3H);

Anal. calcd for C$_{20}$H$_{17}$NO$_4$S.0.20H$_2$O: C, 64.74; H, 4.73; N, 3.78. Found: C, 64.79; H, 4.64; N, 3.69.

EXAMPLE 40

Step a)

N-(4'-Fluoro-1,1'-biphenyl-2-yl)propanamide

The intermediate 1,1'-biphenylamine was prepared from 2-iodoaniline (16.5 g, 75.3 mmol), 4-fluorophenylboronic acid (10.5 g, 75.3 mmol), [1,1'-bis(diphenylphosphino)ferrocene]dichloropalladium (II) complex with dichloromethane (0.60 g, 0.73 mmol), and a 5 N aqueous sodium hydroxide solution (30 mL, 150 mmol). In a separate, second step the 1,1'-biphenylamine was treated with propionic anhydride (10.6 mL, 82.8 mmol), 4-(N,N-dimethylamino)pyridine (0.46 g, 3.8 mmol), and pyridine (24.0 mL, 301 mmol) in dichloromethane, according to the procedure and in the same manner as described in Example 32, Method A, Step a, to yield N-(4'-fluoro-1,1'-biphenyl-2-yl)propanamide as a solid (10.6 g, 58%), m.p. 101° C.;

MS [(+ESI), m/z]: 244 [M+H]$^+$;

$^1$H NMR (400 MHz, DMSO-d$_6$) δ: 9.12 (s, 1H), 7.40–7.18 (m, 8H), 2.10 (q, J=7.5 Hz, 2H), 0.93 (t, J=7.5 Hz, 3H);

Anal. calcd for C$_{15}$H$_{14}$FNO: C, 74.06; H, 5.80; N, 5.76. Found: C, 73.91; H, 5.83; N, 5.63.

Step b)

6-Ethyl-8-fluorophenanthridine

The title compound was prepared from N-(4'-fluoro-1,1'-biphenyl-2-yl)propanamide (5.00 g, 20.6 mmol) and phosphorous oxychloride (9.6 mL, 103 mmol), according to the procedure and in the same manner as described in Example 36, Step b to yield, after purification by re-crystallization from a mixture of ethyl acetate-hexane, 6-ethyl-8-fluorophenanthridine as a white solid (1.43 g, 31%, m.p. 105–106° C.;

MS [(+ESI), m/z]: 226 [M+H]$^+$;

$^1$H NMR (500 MHz, DMSO-d$_6$) δ: 8.93 (dd, J=9.1, 5.6 Hz, 1H), 8.74 (d, J=7.8 Hz, 1H), 8.13 (dd, J=10.3, 2.6 Hz, 1H), 8.03 (dd, J=8.1, 0.8 Hz, 1H), 7.82 (m, 1H), 7.74 (m, 1H), 7.68 (m, 1H), 3.34 (q, J=7.5 Hz, 2H), 1.40 (t, J=7.5 Hz, 3H);

Anal. calcd for C$_{15}$H$_{12}$FN: C, 79.98; H, 5.37; N, 6.22. Found: C, 79.71; H, 5.20; N, 6.09.

Step c)

6-Ethyl-8-fluoro-5-[(4-methoxyphenyl)sulfonyl]-5,6-dihydrophenanthridine

The intermediate dihydrophenanthridine was prepared from 6-ethyl-8-fluorophenanthridine (1.10 g, 4.88 mmol) by treatment with sodium borohydride (1.11 g, 29.3 mmol) and trifluoroacetic acid (1.50 mL, 19.5 mmol) in tetrahydrofuran (18 mL). In a separate, second step, the dihydrophenanthridine was treated with triethylamine (4.1 mL, 29.3 mmol) and 4-methoxybenzenesulfonyl chloride (1.11 g, 5.37 mmol) in dichloromethane (5 mL) according to the procedure and in the same manner as described in Example 32, Method A, Step d. The crude product was purified by flash column chromatography on silica gel, eluting with a mixture of ethyl acetate-hexane (1:9 to 3:7 gradient), to yield 6-ethyl-8-fluoro-5-[(4-methoxyphenyl)sulfonyl]-5,6-dihydrophenanthridine as a homogeneous, white, crystalline, solid (1.67 g, 87%), m.p. 153–156° C.;

MS [(+ESI), m/z]: 398 [M+H]$^+$;

¹H NMR (500 MHz, DMSO-d₆) δ: 7.74 (m, 1H), 7.62 (d, 1H), 7.49 (dd, 1H), 7.43–7.35 (m, 2H), 7.16 (dd, 1H), 6.98 (d, 2H), 6.96 (m, 1H), 6.60 (d, 2H), 5.12 (dd, 1H), 3.64 (s, 3H), 1.42 (m, 1H), 1.22 (m, 1H), 0.90 (t, 3H);

Anal. calcd for $C_{22}H_{20}FNO_3S$: C, 66.48; H, 5.07; N, 3.52. Found: C, 66.25; H, 4.96; N, 3.45.

Step d)

4-[(6-Ethyl-8-fluorophenanthridin-5(6H)-yl)sulfonyl]phenol

The title compound was prepared from 6-ethyl-8-fluoro-5-[(4-methoxyphenyl)sulfonyl]-5,6-dihydrophenanthridine (0.51 g, 1.3 mmol), tetrabutylammonium iodide (1.2 g, 3.2 mmol), and 1 M boron trichloride in dichloromethane (9.0 mL, 9.0 mmol) according to the procedure and in the same manner as described in Example 35, Step b. The crude product was purified by flash column chromatography on silica gel, eluting with a mixture of ethyl acetate-hexane (1:9 to 2:3 gradient), followed by re-crystallization from a mixture of dichloromethane-hexane, to yield 4-[(6-ethyl-8-fluorophenanthridin-5(6H)-yl)sulfonyl]phenol as a solid (0.36 g, 94%), m.p. 151° C.;

MS [(+ESI), m/z]: 384 [M+H]⁺;

¹H NMR (500 MHz, DMSO-d₆) δ: 10.21 (s, 1H), 7.74 (m, 1H), 7.60 (m, 1H), 7.52 (dd, 1H), 7.41–7.34 (m, 2H), 7.16 (dd, 1H), 6.96 (td, 1H), 6.87 (d, 2H), 6.37 (d, 2H), 5.09 (dd, 1H), 1.42 (m, 1H), 1.23 (m, 1H), 0.89 (t, 3H);

Anal. calcd for $C_{21}H_{18}FNO_3S$: C, 65.78; H, 4.73; N, 3.65. Found: C, 65.55; H, 4.64; N, 3.56.

EXAMPLE 41

Step a)

6-Ethyl-8-fluoro-5-[(4-methoxy-3-methylphenyl)sulfonyl]-5,6-dihydrophenanthridine The intermediate dihydrophenanthridine was prepared from 6-ethyl-8-fluoro-phenanthridine, (Example 40, Step b, 0.79 g, 3.48 mmol), by treatment with sodium borohydride (0.79 g, 21 mmol) and trifluoroacetic acid (1.1 mL, 14 mmol) in tetrahydrofuran (18 mL). In a separate, second step, the dihydrophenanthridine was treated with triethylamine (0.8 mL, 6 mmol) and 4-methoxy-3-methylbenzenesulfonyl chloride (0.66 g, 3.0 mmol, 2 equivalents) in dichloromethane (5 mL) according to the procedure and in the same manner as described in Example 32, Method A, Step d. The crude product was purified by flash column chromatography on silica gel, eluting with a mixture of ethyl acetate-hexane (1:19 to 3:7 gradient), to yield 6-ethyl-8-fluoro-5-[(4-methoxy-3-methylphenyl)sulfonyl]-5,6-dihydrophenanthridine as a homogeneous, white solid (0.57 g, 92% from the dihydrophenanthridine), m.p. 140° C.;

MS [(+ESI), m/z]: 434 [M+Na]⁺;

¹H NMR (500 MHz, DMSO-d₆) δ: 7.72 (m, 1H), 7.59 (dd, 1H), 7.46 (dd, 1H), 7.42–7.35 (m, 2H), 7.16 (dd, 1H), 6.93 (td, 1H), 6.82 (m, 2H), 6.59 (d, 1H), 5.09 (dd, 1H), 3.67 (s, 3H), 1.82 (s, 3H), 1.42 (m, 1H), 1.22 (m, 1H), 0.90 (t, 3H).

Step b)

4-[(6-Ethyl-8-fluorophenanthridin-5(6H)-yl)sulfonyl]-2-methylphenol

The title compound was prepared from 6-ethyl-8-fluoro-5-[(4-methoxy-3-methylphenyl)sulfonyl]-5,6-dihydrophenanthridine (0.53 g, 1.3 mmol), tetrabutylammonium iodide (1.2 g, 3.2 mmol), and 1 M boron trichloride in dichloromethane (8.9 mL, 8.9 mmol) according to the procedure and in the same manner as described in Example 35, Step b. The crude product was purified by flash column chromatography on silica gel, eluting with a mixture of ethyl acetate-hexane (1:9 to 1:1 gradient), followed by re-crystallization from a mixture of dichloromethane-hexane to yield 4-[(6-ethyl-8-fluorophenanthridin-5(6H)-yl)sulfonyl]-2-methylphenol as a homogeneous solid (0.25 g, 50%), m.p. 181° C.;

MS [(-ESI), m/z] 396 [M-H]⁻;

¹H NMR (500 MHz, DMSO-d₆) δ: 10.11 (s, 1H), 7.74 (d, 1H), 7.72 (d, 1H), 7.58 (dd, 1H), 7.49–7.33 (m, 2H), 7.17 (dd, 1H), 6.95 (td, 1H), 6.77 (d, 1H), 6.66 (dd, 1H), 6.37 (d, 1H), 5.09 (dd, 1H), 1.78 (s, 3H), 1.56 (m, 1H), 1.22 (m, 1H), 0.89 (t, 3H);

Anal. calcd for $C_{22}H_{20}FNO_3S \cdot 0.50H_2O$: C, 65.01; H, 5.21; N, 3.45. Found: C, 65.23; H, 4.97; N, 3.40.

EXAMPLE 42

Step a)

N-(3'-Methyl-1,1'-biphenyl-2-yl)propanamide

3'-Methyl-1,1'-biphenyl-2-ylamine was prepared from from 2-iodoaniline (2.97 g, 13.5 mmol), 3-methylphenylboronic acid (1.84 g, 13.5 mmol), [1,1'-bis(diphenylphosphino)ferrocene]dichloropalladium (II) complex with dichloromethane (0.33 g, 0.41 mmol), and a 5 N aqueous sodium hydroxide solution (5.4 mL, 27 mmol), according to the procedure and in the same manner as described in Example 32, Method A, Step a, to afford the intermediate biphenylamine as an oil (2.05 g, 83%). The title compound was prepared from the above intermediate biphenylamine (1.89 g, 10.3 mmol), propionic anhydride (2.64 mL, 20.6 mmol), 4-(N,N-dimethylamino)pyridine (0.12 g, 1.0 mmol), and pyridine (3.3 mL, 41 mmol), according to the same procedure, to yield N-(3'-methyl-1,1'-biphenyl-2-yl)propanamide as a solid (2.45 g, 99%), m.p. 83° C.;

MS [(-ESI), m/z]: 238 [M-H]⁻;

¹H NMR (500 MHz, DMSO-d₆) δ: 9.08 (s, 1H), 7.44 (d, J=7.8 Hz, 1H), 7.34–7.24 (m, 4H), 7.13 (t, J=8.4 Hz, 3H), 2.33 (s, 3H), 2.14 (q, J=7.4 Hz, 2H), 0.98 (t, J=7.4 Hz, 3H);

Anal. calcd for $C_{16}H_{17}NO$: C, 80.30; H, 7.16; N, 5.85. Found: C, 80.47; H, 7.12; N, 5.78.

Step b)

6-Ethyl-7-m thylphenanthridin and 6-Ethyl-9-m thylphenanthridine

The title compounds were prepared from N-(3'-methyl-1,1'-biphenyl-2-yl)propanamide (2.35 g, 9.82 mmol) and phosphorous oxychloride (4.6 mL, 49 mmol) according to the procedure and in the same manner as described in Example 36, Step b. The regioisomers were purified by flash column chromatography on silica gel, eluting with ethyl acetate-hexane (1:9) to yield the separated regioisomers as white solids: 7-methyl regioisomer A (0.25 g, 12%) and 9-methyl regioisomer B (1.59 g, 73%); Regioisomer A: 6-Ethyl-7-methylphenanthridine, MS [(+ESI), m/z]: 222 [M+H]⁺;

¹H NMR (400 MHz, CDCl₃) δ: 8.53 (dd, J=8.2, 0.5 Hz, 1H), 8.49 (m, 1H), 8.04 (dd, J=8.2 Hz, 1.0, 1H), 7.67–7.62 (m, 1H), 7.57–7.49 (m, 2H), 7.47 (d, J=7.2 Hz, 1H), 3.50 (q, J=7.4 Hz, 2H), 2.98 (s, 3H), 1.41 (t, J=7.4 Hz, 3H).

Regioisomer B: 6-Ethyl-9-methylphenanthridine,

MS [(+ESI), m/z]: 222 [M+H]⁺;

¹H NMR(400 MHz, CDCl₃) δ: 8.50 (dd, J=8.2, 1.3 Hz, 1H), 8.40 (s, 1H), 8.12 (d, J=8.4 Hz, 1H), 8.07 (dd, J=8.2, 1.2 Hz, 1H), 7.66 (m, 1H), 7.57 (m, 1H), 7.48 (dd, J=8.4, 1.5 Hz, 1H), 3.36 (q, J=7.5 Hz, 2H), 2.62 (s, 3H), 1.47 (t, J=7.5 Hz, 3H).

Step c)

6-Ethyl-5-[(4-methoxyphenyl)sulfonyl]-7-methyl-5,6-dihydrophenanthridine

The intermediate dihydrophenanthridine was prepared from 6-ethyl-7-methylphenanthridine (0.25 g, 1.1 mmol) by treatment with sodium borohydride (0.26 g, 6.8 mmol) and trifluoroacetic acid (0.35 mL, 4.6 mmol) in tetrahydrofuran (6 mL). In a separate, second step, the dihydrophenanthridine was treated with triethylamine (1.0 mL, 6.8 mmol) and 4-methoxybenzenesulfonyl chloride (0.47 g, 2.3 mmol) in dichloromethane (4 mL) according to the procedure and in the same manner as described in Example 32, Method A, Step d. The crude product was utilized without further purification.

MS [(+ESI), m/z]: 416 [M+Na]$^+$;

$^1$H NMR (400 MHz, DMSO-$d_6$) δ: 7.71 (dd, 1H), 7.58 (dd, 1H), 7.40–7.31 (m, 2H), 7.24 (m, 1H), 6.98 (m, 2H), 6.88 (m, 2H), 6.50 (m, 2H), 5.10 (dd, 1H), 3.58 (s, 3H), 2.27 (s, 3H), 1.40 (m, 1H), 1.08 (m, 1H), 0.90 (t, 3H).

Step d)

4-[(6-Ethyl-7-m thylphenanthridin-5(6H)-yl)sulfonyl]phenol

The title compound was prepared from 6-ethyl-5-[(4-methoxyphenyl)sulfonyl]-7-methyl-5,6-dihydrophenanthridine (0.45 g, 1.1 mmol), tetrabutylammonium iodide (1.00 g, 2.71 mmol), and 1 M boron trichloride in dichloromethane (8.0 mL, 8.0 mmol) according to the procedure and in the same manner as described in Example 35, Step b. The crude product was purified by flash column chromatography on silica gel, eluting with a mixture of ethyl acetate-hexane (3:7 to 1:1 gradient), followed by re-crystallization from a mixture of ethyl acetate-hexane, to yield 4-[(6-ethyl-7-methylphenanthridin-5(6H)-yl)sulfonyl]phenol as a homogeneous solid (0.11 g, 25%), m.p. 167–169° C.;

MS [(−ESI), m/z]: 378 [M−H]$^−$;

$^1$H NMR (500 MHz, DMSO-$d_6$) δ: 10.17 (br s, 1H), 7.75 (d, 1H), 7.60 (dd, 1H), 7.41–7.31 (m, 3H), 7.05–7.01 (m, 2H), 6.82 (d, 2H), 6.33 (d, 2H), 5.13 (dd, 1H), 2.30 (s, 3H), 1.43 (m, 1H), 1.12 (m, 1H), 0.93 (t, 3H);

Anal. calcd for $C_{22}H_{21}NO_3S$: C, 69.63; H, 5.58; N, 3.69. Found: C, 69.35; H, 5.67; N, 3.63.

EXAMPLE 43

Step a)

6-Ethyl-5-[(4-methoxyphenyl)sulfonyl]-9-methyl-5,6-dihydrophenanthridine

The intermediate dihydrophenanthridine was prepared from 6-ethyl-9-methylphenanthridine, (Example 42, Step b, 0.50 g, 2.3 mmol), by treatement with sodium borohydride (0.51 g, 13.5 mmol) and trifluoroacetic acid (0.7 mL, 9 mmol) in tetrahydrofuran (11 mL). In a separate, second step, the dihydrophenanthridine was treated with triethylamine (1.9 mL, 14 mmol) and 4-methoxybenzenesulfonyl chloride (0.93 g, 4.50 mmol) in dichloromethane (11 mL) according to the procedure and in the same manner as described in Example 32, Method A, Step d. The crude product was purified by re-crystallization from a mixture of ethyl acetate-hexane to yield 6-ethyl-5-[(4-methoxyphenyl)sulfonyl]-9-methyl-5,6-dihydrophenanthridine as a homogeneous, white, crystalline, solid, m.p. 133° C.;

MS [(+ESI), m/z]: 394 [M+H]$^+$;

$^1$H NMR (500 MHz, DMSO-$d_6$) δ: 7.72 (d, J=7.4 Hz, 1H), 7.59 (m, 1H), 7.41–7.33 (m, 2H), 7.22 (s, 1H), 7.07 (d, J=7.6 Hz, 1H), 6.98 (d, J=7.6 Hz, 1H), 6.90 (d, J=9.0 Hz, 2H), 6.53 (d, J=9.0 Hz, 2H), 5.02 (dd, J=9.5, 5.7 Hz, 1H), 3.63 (s, 3H), 2.21 (s, 3H), 1.36 (m, 1H), 1.23 (m, 1H), 0.88 (t, J=7.2 Hz, 3H);

Anal. calcd for $C_{23}H_{23}NO_3S \cdot 0.10H_2O \cdot 0.26C_6H_{15}N$: C, 69.97; H, 6.48; N, 4.19. Found: C, 69.79; H, 5.97; N, 3.57.

Step b)

4-[(6-Ethyl-9-methylphenanthridin-5(6H)-yl)sulfonyl]phenol

The title compound was prepared from 6-ethyl-5-[(4-methoxyphenyl)sulfonyl]-9-methyl-5,6-dihydrophenanthridine (0.67 g, 1.7 mmol), tetrabutylammonium iodide (1.5 g, 4.1 mmol), and 1 M boron trichloride in dichloromethane (11.9 mL, 11.9 mmol) according to the procedure and in the same manner as described in Example 35, Step b. The crude product was purified by flash column chromatography on silica gel, eluting with a mixture of ethyl acetate-hexane (3:7 to 1:1 gradient), followed by trituration from a mixture of ethyl acetate-hexane, to yield 4-[(6-ethyl-9-methylphenanthridin-5(6H)-yl)sulfonyl]phenol as a homogeneous solid (0.23 g, 36%), m.p. 167–170° C.;

MS [(+ESI), m/z]: 380 [M+H]$^+$;

$^1$H NMR (500 MHz, DMSO-$d_6$) δ: 10.17 (br s, 1H), 7.74 (d, 1H), 7.60 (d, 1H), 7.39–7.32 (m, 2H), 7.27 (s, 1H), 7.08 (d, 1H), 6.99 (d, 1H), 6.81 (d, 2H), 6.33 (d, 2H), 5.01 (dd, 1H), 2.23 (s, 3H), 1.36 (m, 1H), 1.23 (m, 1H), 0.87 (t, 3H);

Anal. calcd for $C_{22}H_{21}NO_3S$: C, 69.63; H, 5.58; N, 3.69. Found: C, 69.59; H, 5.47; N, 3.58.

EXAMPLE 44

Step a)

N-(5-Bromo-4'-fluoro-1,1'-biphenyl-2-yl)propanamide

A vigorously stirred suspension of 2-iodoaniline (10.0 g, 45.7 mmol), potassium bromide (6.52 g, 54.8 mmol), and ammonium molybdate tetrahydrate (0.57 g, 0.46 mmol) in acetic acid (54 mL) was cooled to 0° C., treated with sodium perborate (7.74 g, 50.3 mmol), and stirred for two hours as the reaction warmed to room temperature. After adding water and stirring one additional hour, the reaction mixture was poured into ice-water and filtered. The filtered solid was washed with water, dissolved in ethyl acetate (250 mL), and washed with a saturated, aqueous, potassium carbonate solution (2×75 mL). The organic phase was dried over anhydrous sodium sulfate, filtered, and concentrated in vacuo to afford the intermediate, 4 bromo-2-iodoaniline, as a red solid (12.56 g, 92%).

5-Bromo-4'-fluoro-1,1'-biphenyl-2-ylamine was prepared from the above intermediate, 4-bromo-2-iodoaniline (12.6 g, 42.2 mmol), 4-fluorophenylboronic acid (5.9 g, 42 mmol), [1,1'-bis(diphenylphosphino)ferrocene]dichloropalladium (II) complex with dichloromethane (0.69 g, 0.84 mmol), and a 5 N aqueous sodium hydroxide solution (85 mL, 425 mmol) according to the procedure and in the same manner as described in Example 32, Method A, Step a.

The title compound was prepared from the above 5-bromo-4'-fluoro-1,1'-biphenyl-2-ylamine (10.1 g, 37.8 mmol), propionic anhydride (5.33 mL, 41.6 mmol), 4-(N, N-dimethylamino)pyridine (0.46 g, 3.8 mmol), and pyridine (12.3 mL, 151 mmol), according to the same procedure, to yield N-(5-bromo-4'-fluoro-1,1'-biphenyl-2-yl)propanamide as a solid (7.74 g, 64% from 4-bromo-2-iodoaniline), m.p. 133° C.;

MS [(−ESI), m/z]: 320 [M−H]$^-$;

$^1$H NMR (500 MHz, DMSO-d$_6$) δ: 9.21 (s, 1H), 7.52 (dd, J=2.4, 8.5 Hz, 1H), 7.47 (d, J=2.2 Hz, 1H), 7.43–7.38 (m, 3H), 7.28–7.23 (m, 2H), 2.13 (q, J=7.5 Hz, 2H), 0.95 (t, J=7.5 Hz, 3H);

Anal. calcd for C$_{15}$H$_{13}$BrFNO: C, 55.92; H, 4.07; N, 4.35. Found: C, 55.79; H, 4.08; N, 4.31.

Step b)

2-Bromo-6-ethyl-8-fluorophenanthridine

The title compound was prepared from N-(5-bromo-4'-fluoro-1,1'-biphenyl-2-yl)propanamide (3.94 g, 12.2 mmol) and polyphosphoric acid (74 g), according to the procedure and in the same manner as described in Example 32, Method A, Step b, to yield, after re-crystallization from a mixture of ethyl acetate-hexane, 2-bromo-6-ethyl-8-fluorophenanthridine as a white solid (3.32 g, 89%), m.p. 111° C.;

MS [(+ESI), m/z]: 304 [M+H]$^+$;

$^1$H NMR (500 MHz, DMSO-d$_6$) δ: 8.99 (m, 2H), 8.15 (dd, J=10.2, 2.4 Hz, 1H), 7.95 (d, J=8.7 Hz, 1H), 7.87–7.81 (m, 2H), 3.33 (q, J=7.4 Hz, 2H), 1.39 (t, J=7.4 Hz, 3H);

Anal. calcd for C$_{15}$H$_{11}$BrFN: C, 59.23; H, 3.65; N, 4.60. Found: C, 59.00; H, 3.52; N, 4.44.

Step c)

2-Brom -6-ethyl-8-fluoro-5-[(4-methoxyphenyl) sulfonyl]-5,6-dihydrophenanthridine The intermediate dihydrophenanthridine was prepared from 2-bromo-6-ethyl-8-fluorophenanthridine (3.27 g, 10.8 mmol) by treatment with sodium borohydride (2.03 g, 53.8 mmol) and trifluoroacetic acid (3.31 mL, 43.0 mmol) in tetrahydrofuran (43 mL). In a separate, second step, the dihydrophenanthridine was treated with triethylamine (9.0 mL, 65 mmol) and 4-methoxybenzenesulfonyl chloride (2.44 g, 11.8 mmol) in dichloromethane (11 mL) according to the procedure and in the same manner as described in Example 32, Method A, Step d. The crude product was purified by flash column chromatography on silica gel, eluting with a mixture of ethyl acetate-hexane (1:9 to 1:4 gradient), to afford 2-bromo-6-ethyl-8-fluoro-5-[(4-methoxyphenyl)sulfonyl]-5,6-dihydrophenanthridine as a homogeneous, yellow, crystalline, solid, m.p. 133–136° C.;

MS [(+ESI), m/z]: 498/500 [M+Na]$^+$, contains one bromine atom;

$^1$H NMR (400 MHz, DMSO-d$_6$) δ: 7.94 (d, J=2.2 Hz, 1H), 7.65–7.47 (m, 3H), 7.15 (m, 1H), 7.00 (d, J=8.9 Hz, 2H), 6.93 (td, J=8.8, 2.8 Hz, 1H), 6.60 (d, J=8.9 Hz, 2H), 5.10 (dd, J=10.0, 5.5 Hz, 1H), 3.61 (s, 3H), 1.36 (m, 1H), 1.16 (m, 1H), 0.86 (t, J=7.3 Hz, 3H).

Step d)

4-[(2-Bromo-6-ethyl-8-fluorophenanthridin-5(6H)-yl)sulfonyl]phenol

The title compound was prepared from 2-bromo-6-ethyl-8-fluoro-5-[(4-methoxyphenyl)sulfonyl]-5,6-dihydrophenanthridine (0.61 g, 1.3 mmol), tetrabutylammonium iodide (1.1 g, 3.1 mmol), and 1 M boron trichloride in dichloromethane (9.0 mL, 9.0 mmol) according to the procedure and in the same manner as described in Example 35, Step b. The crude product was purified by flash column chromatography on silica gel, eluting with a mixture of ethyl acetate-hexane (3:7 to 1:1 gradient), followed by trituration from a mixture of ethyl acetate-hexane to yield 4-[(2-bromo-6-ethyl-8-fluorophenanthridin-5(6H)-yl)sulfonyl]phenol as a homogeneous solid (0.23 g, 38%), m.p. 220–221° C.;

MS [(−ESI), m/z]: 460 [M−H]$^-$;

$^1$H NMR (500 MHz, DMSO-d$_6$) δ: 10.27 (br s, 1H), 7.97 (d, 1H), 7.62–7.58 (m, 2H), 7.54 (d, 1H), 7.19 (dd, 1H), 6.97 (td, 1H), 6.92 (d, 2H), 6.41 (d, 2H), 5.11 (dd, 1H), 1.43 (m, 1H), 1.21 (m, 1H), 0.89 (t, 3H);

Anal. calcd for C$_{21}$H$_{17}$BrFNO$_3$S: C, 54.56; H, 3.71; N, 3.03. Found: C, 54.33; H, 3.77; N, 2.97.

EXAMPLE 45

4-[(2-Bromo-8-fluoro-6-methylphenanthridin-5(6H)-yl)sulfonyl]phenol

8-Fluoro-5-(4-methoxyphenylsulfonyl)-6-methyl-5,6-dihydrophenanthridine (0.64 g, 1.7 mmol) was treated with 1 M boron tribromide in dichloromethane (6.6 mL, 6.6 mmol) and stirred at room temperature for twelve hours. A solution of saturated, aqueous, sodium bicarbonate (50 mL) was added slowly to the reaction, followed by extraction of the mixture with dichloromethane (6×20 mL). The combined organic phase was dried over anhydrous sodium sulfate, filtered, and concentrated in vacuo to a crude material. The crude material was filtered through a short column of silica gel, eluted with a mixture of ethyl acetate-hexane (1:4), and the filtrate concentrated in vacuo to a solid. After trituration with dichloromethane and filtration, the title compound was obtained as a homogeneous solid (0.23 g, 37%), m.p. 237–239° C.;

MS [(−ESI), m/z]: 446 [M−H]$^-$;

$^1$H NMR (500 MHz, DMSO-d$_6$) δ: 10.30 (br s, 1H), 7.97 (d, J=2.1 Hz, 1H), 7.61–7.57 (m, 2H), 7.51 (d, J=8.6 Hz, 1H), 7.18 (dd, J=9.2, 2.7 Hz, 1H), 6.95 (td, J=8.8 Hz, 2.7, 1H), 6.90 (d, J=9.0 Hz, 2H), 6.40 (d, J=9.0 Hz, 2H), 5.41 (q, J=7.0 Hz, 1H), 1.11 (d, J=7.0 Hz, 3H);

Anal. calcd for C$_{20}$H$_{15}$BrFNO$_3$S: C, 53.58; H, 3.37; N, 3.12. Found: C, 53.29; H, 3.17; N, 2.97.

EXAMPLE 46

Step a)

3-Chloro-4-methoxybezenesulfonyl chloride

A stirred solution of 2-chloroanisole (8.90 mL, 70.1 mmol) in chloroform (100 mL) was cooled to 0° C., and treated drop-wise with chlorosulfonic acid (9.3 mL, 140 mmol). After stirring at room temperature for 14 hours, the reaction mixture was poured into ice-water (250 mL) and the separated, aqueous phase extracted with chloroform (2×50 mL). The combined organic phase was dried over anhydrous sodium sulfate, filtered, and concentrated in vacuo to a viscous oil which crystallized upon standing (8.58 g, 52%), m.p. 78° C.;

$^1$H NMR (400 MHz, DMSO-d$_6$) δ: 7.50–7.45 (m, 2H), 7.04 (d, J=8.4 Hz, 1H), 3.81 (s, 3H).

Step b)

6-Ethyl-8-fluor -5-[(3-chloro-4-methoxyphenyl) sulfonyl]-5,6-dihydrophenanthridine The intermediate dihydrophenanthridine was prepared from 6-ethyl-8-fluorophenanthridine, (Example 40, Step b, 0.40 g, 1.8 mmol), by treatment with sodium borohydride (0.40 g, 10.6 mmol) and trifluoroacetic acid (0.55 mL, 7.1 mmol) in tetrahydrofuran (7 mL). In a separate, second step, the dihydrophenanthridine was treated with triethylamine (0.9 mL, 6.4 mmol) and 3-chloro-4-methoxybenzenesulfonyl chloride (0.51 g, 2.1 mmol, 2.1 equivalents) in dichloromethane (5 mL), according to the procedure and in the same manner as described in Example 32, Method A, Step d, to afford 6-ethyl-8-fluoro-5-[(3-chloro-4-methoxyphenyl)sulfonyl]-5,6-dihydrophenanthridine as a crude product, which was utilized without further purification.

MS [(+ESI), m/z]: 454 [M+Na]$^+$;

$^1$H NMR (400 MHz, DMSO-d$_6$) δ: 7.72 (dd, 1H), 7.57 (dd, 1H), 7.48–7.35 (m, 3H), 7.18 (dd, 1H), 6.97 (d, 1H), 6.95–6.87 (m, 2H), 6.79 (d, 1H), 5.11 (dd, 1H), 3.71 (s, 3H), 1.38 (m, 1H), 1.19 (m, 1H), 0.87 (t, 3H).

Step c)

2-Chloro-4-[(6-ethyl-8-fluorophenanthridin-5(6H)-yl)sulfonyl]phenol

The title compound was prepared from 6-ethyl-8-fluoro-5-[(3-chloro-4-methoxyphenyl)sulfonyl]-5,6-dihydrophenanthridine (0.41 g, 0.96 mmol), tetrabutylammonium iodide (0.85 g, 2.3 mmol), and 1 M boron trichloride in dichloromethane (6.7 mL, 6.7 mmol) according to the procedure and in the same manner as described in Example 35, Step b. The crude product was purified by flash column chromatography on silica gel, eluting with a mixture of ethyl acetate-hexane (20:80 to 35:65 gradient), followed by re-crystallization from a mixture of ethyl acetate-hexane, to yield 2-chloro-4-[(6-ethyl-8-fluorophenanthridin-5(6H)-yl)sulfonyl]phenol as a homogeneous solid (0.16 g, 41%), m.p. 174–177° C.;

MS [(−ESI), m/z]: 416 [M−H]$^-$;

$^1$H NMR (500 MHz, DMSO-d$_6$) δ: 11.09 (s, 1H), 7.76 (dd, 1H), 7.59 (m, 1H), 7.51 (dd, 1H), 7.45–7.37 (m, 2H), 7.22 (dd, 1H), 7.00–6.92 (m, 2H), 6.77 (m, 1H), 6.56 (d, 1H), 5.12 (dd, 1H), 1.42 (m, 1H), 1.20 (m, 1H), 0.90 (t, 3H);

Anal. calcd for C$_{21}$H$_{17}$ClFNO$_3$S: C, 60.36; H, 4.10; N, 3.35. Found: C, 60.00; H, 4.09; N, 3.24.

EXAMPLE 47

Step a)

6-Ethyl-8-fluoro-5-[(4-methoxyphenyl)sulfonyl]-2-phenyl-5,6-dihydrophenanthridine A stirred solution of 2-bromo-6-ethyl-8-fluoro-5-[(4-methoxyphenyl)sulfonyl]-5,6-dihydrophenanthridine (Example 44, Step c, 0.25 g, 0.52 mmol) and phenylboronic acid (0.06 g, 0.52 mmol) in tetrahydrofuran (5 mL) was treated under nitrogen with [1,1'-bis(diphenylphosphino)ferrocene]dichloropalladium (II) complex with dichloromethane (0.01 g, 0.02 mmol) and a 5 N aqueous sodium hydroxide solution (0.2 mL, 1 mmol). The reaction mixture was heated at reflux for twelve hours, cooled to room temperature, and quenched with a saturated, aqueous, sodium chloride solution (10 mL) and diethyl ether (50 mL). The separated organic phase was dried over anhydrous magnesium sulfate, filtered, and concentrated in vacuo to a crude product. The crude product was purified by flash column chromatography on silica gel, eluting with a mixture of ethyl acetate-hexane (1:4) to yield the title compound as a solid (0.13 g, 50%);

MS [(+ESI), m/z]: 474 [M+H]$^+$;

$^1$H NMR (500 MHz, DMSO-d$_6$) δ: 8.02 (d, J=1.7 Hz, 1H), 7.81 (m, 2H), 7.72 (m, 3H), 7.49 (t, J=7.7 Hz, 2H), 7.39 (t, J=7.3 Hz, 1H), 7.18 (dd, J=9.2, 2.6 Hz, 1H), 7.07 (d, J=8.9 Hz, 2H), 6.98 (td, J=8.7, 2.6 Hz, 1H), 6.63 (d, J=8.9 Hz, 2H), 5.14 (dd, J=10.0, 5.4 Hz, 1H), 3.64 (s, 3H), 1.46 (m, 1H), 1.28 (m, 1H), 0.93 (t, J=7.3 Hz, 3H);

Anal. calcd for C$_{28}$H$_{24}$FNO$_3$S: C, 71.02; H, 5.11; N, 2.96. Found: C, 70.84; H, 5.24; N, 2.80.

Step b)

4-[(6-Ethyl-8-fluoro-2-phenylphenanthridin-5(6H)-yl)sulfonyl]phenol

A stirred suspension of 6-ethyl-8-fluoro-5-[(4-methoxyphenyl)sulfonyl]-2-phenyl-5,6-dihydrophenanthridine (0.13 g, 0.26 mmol) and cyclohexene (0.48 mL, 4.8 mmol) was treated drop-wise at room temperature under nitrogen with a solution of 1 M boron tribromide in dichloromethane (1.6 mL, 1.6 mmol). After stirring for 20 hours at room temperature, the reaction was quenched by the drop-wise addition of a saturated, aqueous, sodium bicarbonate solution (300 mL), followed by extraction with dichloromethane (6×20 mL). The combined organic phase was dried over anhydrous sodium sulfate, filtered, and concentrated in vacuo to a crude product. The crude product was purified by flash column chromatography on silica gel, eluting with a mixture of ethyl acetate-hexane (1:4 to 3:7 gradient), followed by re-crystallization from a mixture of ethyl acetate-hexane, to yield 4-[(6-ethyl-8-fluoro-2-phenylphenanthridin-5(6H)-yl)sulfonyl]phenol as a homogeneous solid (0.09 g, 71%), m.p. 207° C.;

MS [(−ESI), m/z]: 458 [M−H]$^-$;

$^1$H NMR (500 MHz, DMSO-d$_6$) δ: 10.22 (br s, 1H), 8.03 (d, 1H), 7.81 (m, 2H), 7.77–7.68 (m, 3H), 7.48 (t, 2H), 7.39 (t, 1H), 7.18 (dd, 1H), 7.01–6.96 (m, 3H), 6.41 (d, 2H), 5.13 (dd, 1H), 1.46 (m, 1H), 1.29 (m, 1H), 0.92 (t, 3H);

Anal. calcd for C$_{27}$H$_{22}$FNO$_3$S: C, 70.57; H, 4.83; N, 3.05. Found: C, 70.27; H, 4.69; N, 2.94.

EXAMPLE 48

Step a)

8-Fluoro-5-[(3-methoxyphenyl)sulfonyl]-6-methyl-5,6-dihydrophenanthridine

The intermediate dihydrophenanthridine was prepared from 8-fluoro-6-methylphenanthridine, (Example 32, Method A, Step b, 2.00 g, 9.45 mmol), by treatment with sodium borohydride (1.79 g, 47.4 mmol) and trifluoroacetic acid (2.9 mL, 37.9 mmol) in tetrahydrofuran (38 mL). In a separate, second step, the dihydrophenanthridine was treated with triethylamine (2.9 mL, 21 mmol) and 3-methoxybenzenesulfonyl chloride (0.78 g, 3.8 mmol, 1.1 equivalents) in dichloromethane (5 mL) according to the procedure and in the same manner as described in Example 32, Method A, Step d. The crude product was purified by re-crystallization from a mixture of ethyl acetate-hexane to yield 8-fluoro-5-[(3-methoxyphenyl)sulfonyl]-6-methyl-5,6-dihydrophenanthridine as a homogeneous solid (1.02 g, 78% from the dihydrophenanthridine), m.p. 130–131° C.;

MS [(+ESI), m/z]: 384 [M+H]$^+$;

$^1$H NMR (500 MHz, CDCl$_3$) δ: 7.81 (dd, J=8.0, 1.3 Hz, 1H), 7.55 (dd, J=7.8, 1.4 Hz, 1H), 7.41 (m, 1H), 7.34 (m, 1H), 7.25 (m, 1H), 6.86 (m, 1H), 6.80–6.74 (m, 2H), 6.71–6.67 (m, 2H), 6.52 (m, 1H), 5.38 (q, J=7.0 Hz, 1H), 3.48 (s, 3H), 1.27 (d, J=7.0 Hz, 3H);

Anal. calcd for C$_{21}$H$_{18}$FNO$_3$S.0.15C$_6$H$_{15}$N.0.50H$_2$O: C, 64.53; H, 5.25; N, 3.95. Found: C, 64.87; H, 5.05; N, 3.92.

Step b)

3-[(8-Fluor -6-methylphenanthridin-5(6H)-yl)sulfonyl]ph nol

The title compound was prepared from 8-fluoro-5-[(3-methoxyphenyl)sulfonyl]-6-methyl-5,6-dihydrophenanthridine (0.50 g, 1.3 mmol), cyclohexene (2.4 mL, 24 mmol), and 1 M boron tribromide in dichloromethane (7.8 mL, 7.8 mmol) according to the procedure and in the same manner as described in Example 47, Step b. The crude product was purified by flash column chromatography on silica gel, eluting with a mixture of ethyl acetate-hexane (1:4), followed by trituration from hexane, to yield 3-[(8-fluoro-6-methylphenanthridin-5(6H)-yl)sulfonyl]phenol as a homogeneous solid (0.37 g, 71%), m.p. 161° C.;

MS [(−ESI), m/z]: 368 [M−H]$^-$;

$^1$H NMR (500 MHz, DMSO-d$_6$) δ: 9.73 (br s, 1H), 7.78 (d, 1H), 7.60 (m, 1H), 7.53 (dd, 1H), 7.43–7.37 (m, 2H), 7.15 (dd, 1H), 6.95 (td, 1H), 6.89 (t, 1H), 6.65 (dd, 1H), 6.51 (d, 1H), 6.48 (s, 1H), 5.42 (q, 1H), 1.14 (d, 3H);

Anal. calcd for $C_{20}H_{16}FNO_3S \cdot 0.10C_4H_8O_2 \cdot 0.10H_2O$: C, 64.48; H, 4.51; N, 3.69. Found: C, 64.47; H, 4.29; N, 3.48.

EXAMPLE 49

Step a)

3-Fluoro-4-methoxybenzenesulfonyl chloride

A stirred solution of 2-fluoroanisole (33.7 mL, 301 mmol) in chloroform (250 mL) was cooled to 0° C. and treated drop-wise with chlorosulfonic acid (50.0 mL, 752 mmol). After stirring at room temperature for 14 hours, the reaction mixture was poured into ice-water (700 mL) and the separated, aqueous phase extracted with chloroform (2×200 mL). The combined organic phase was dried over anhydrous sodium sulfate, filtered, and concentrated in vacuo to yield 3-fluoro-4-methoxybenzenesulfonyl chloride as a fine, white solid (58.6 g, 87%), m.p. 80° C.;

$^1$H NMR (400 MHz, DMSO-d$_6$) δ: 7.32 (m, 1H), 7.25 (dd, J=11.5, 2.0 Hz, 1H), 7.05 (t, J=8.5 Hz, 1H), 3.78 (s, 3H).

Step b)

8-Fluoro-5-[(3-fluoro-4-methoxyphenyl)sulfonyl]-6-methyl-5,6-dihydrophenanthridine The intermediate dihydrophenanthridine was prepared from 8-fluoro-6-methylphenanthridine, (Example 32, Method A, Step b, 2.00 g, 9.45 mmol), by treatment with sodium borohydride (1.79 g, 47.4 mmol) and trifluoroacetic acid (2.9 mL, 37.9 mmol) in tetrahydrofuran (38 mL). In a separate, second step, the dihydrophenanthridine was treated with triethylamine (2.7 mL, 19 mmol) and 3-fluoro-4-methoxybenzenesulfonyl chloride (0.78 g, 3.5 mmol, 1.1 equivalents) in dichloromethane (5 mL) according to the procedure and in the same manner as described in Example 32, Method A, Step d. The crude product was purified by re-crystallization from a mixture of ethyl acetate-hexane to yield 8-fluoro-5-[(3-fluoro-4-methoxyphenyl)sulfonyl]-6-methyl-5,6-dihydrophenanthridine as a homogeneous solid (1.08 g, 84% from the dihydrophenanthridine), m.p. 146–147° C.;

MS [(−ESI), m/z]: 460 [M+AcO]$^-$;

$^1$H NMR (500 MHz, CDCl$_3$) δ: 7.77 (m, 1H), 7.56 (d, J=7.7 Hz, 1H), 7.38 (m, 2H), 7.31 (dd, J=8.1, 5.4 Hz, 1H), 6.89 (dt, J=8.7, 1.1 Hz, 1H), 6.82 (td, J=8.6, 2.6 Hz, 1H), 6.78 (dd, J=8.4, 2.6 Hz, 1H), 6.70 (dd, J=10.7, 2.2 Hz, 1H), 6.51 (m, 1H), 5.35 (q, J=7.0 Hz, 1H), 3.77 (s, 3H), 1.26 (d, J=7.0 Hz, 3H);

Anal. calcd for $C_{21}H_{17}F_2NO_3S$: C, 62.83; H, 4.27; N, 3.49. Found: C, 62.59; H, 4.46; N, 3.49.

Step c)

2-Fluoro-4-[(8-fluoro-6-methylphenanthridin-5(6H)-yl)sulfonyl]phenol

The title compound was prepared from 8-fluoro-5-[(3-fluoro-4-methoxyphenyl)sulfonyl]-6-methyl-5,6-dihydrophenanthridine (0.50 g, 1.3 mmol), cyclohexene (2.3 mL, 22 mmol), and 1 M boron tribromide in dichloromethane (7.5 mL, 7.5 mmol) according to the procedure and in the same manner as described in Example 47, Step b. The crude product was purified by flash column chromatography on silica gel, eluting with a mixture of ethyl acetate-hexane (1:4), followed by trituration from hexane, to yield 2-fluoro-4-[(8-fluoro-6-methylphenanthridin-5(6H)-yl)sulfonyl]phenol as a homogeneous solid (0.40 g, 82%), m.p. 191° C.;

MS [(−ESI), m/z]: 386 [M−H]$^-$;

$^1$H NMR (500 MHz, DMSO-d$_6$) δ: 10.79 (br s, 1H), 7.79 (dd, 1H), 7.59 (dd, 1H), 7.54 (dd, 1H), 7.45–7.38 (m, 2H), 7.21 (dd, 1H), 6.98 (td, 1H), 6.74 (dd, 1H), 6.67 (dd, 1H), 6.58 (t, 1H), 5.44 (q, 1H), 1.44 (d, 3H);

Anal. calcd for $C_{20}H_{15}F_2NO_3S$: C, 62.01; H, 3.90; N, 3.62. Found: C, 61.75; H, 3.80; N, 3.41.

EXAMPLE 50

Step a)

5-[(3,4-Dimethoxyph nyl)sulfonyl]-8-fluoro-6-methyl-5,6-dihydroph nanthridine

The intermediate dihydrophenanthridine was prepared from 8-fluoro-6-methylphenanthridine, (Example 32, Method A, Step b, 2.00 g, 9.45 mmol), by treatment with sodium borohydride (1.79 g, 47.4 mmol) and trifluoroacetic acid (2.9 mL, 37.9 mmol) in tetrahydrofuran (38 mL). In a separate, second step, the dihydrophenanthridine was treated with triethylamine (3.0 mL, 22 mmol) and 3,4-dimethoxybenzenesulfonyl chloride (0.94 g, 3.97 mmol, 1.1 equivalents) in dichloromethane (5 mL) according to the procedure and in the same manner as described in Example 32, Method A, Step d. The crude product was purified by re-crystallization from a mixture of ethyl acetate-hexane to yield 5-[(3,4-dimethoxyphenyl)sulfonyl]-8-fluoro-6-methyl-5,6-dihydrophenanthridine as a homogeneous solid (1.03 g, 69% from the dihydrophenanthridine), m.p. 152–153° C.;

MS [(+ESI), m/z]: 414 [M+H]$^+$;

$^1$H NMR (500 MHz, CDCl$_3$) δ: 7.82 (dd, 1H), 7.54 (dd, 1H), 7.40 (m, 1H), 7.33 (m, 1H), 7.27 (m, 1H), 6.81–6.75 (m, 3H), 6.41 (d, 1H), 6.36 (d, 1H), 5.38 (q, 1H), 3.75 (s, 3H), 3.46 (s, 3H), 1.26 (d, 3H);

Anal. calcd for $C_{22}H_{20}FNO_4S$: C, 63.91; H, 4.88; N, 3.39. Found: C, 63.54; H, 4.97; N, 3.30.

Step b)

4-[(8-Fluoro-6-methylphenanthridin-5(6H)-yl)sulfonyl]benzene-1,2-diol

The title compound was prepared from 5-[(3,4-dimethoxyphenyl)sulfonyl]-8-fluoro-6-methyl-5,6-dihydrophenanthridine (0.50 g, 1.2 mmol), cyclohexene (4.4 mL, 44 mmol), and 1 M boron tribromide in dichloromethane (14.5 mL, 14.5 mmol) according to the procedure and in the same manner as described in Example 47, Step b. The crude product was purified by flash column chromatography on silica gel, eluting with a mixture of ethyl acetate-hexane (1:1 to 7:3 gradient), followed by re-crystallization from a mixture of dichloromethane-hexane (2×), to yield 4-[(8-fluoro-6-methylphenanthridin-5(6H)-yl)sulfonyl]benzene-1,2-diol as a homogeneous solid (0.23 g, 50%), m.p. 165–170° C.;

MS [(−ESI), m/z]: 384 [M−H]$^-$;

$^1$H NMR (500 MHz, DMSO-d$_6$) δ: 9.64 (br s, 1H), 9.22 (br s, 1H), 7.77 (dd, 1H), 7.58 (dd, 1H), 7.55 (dd, 1H), 7.41–7.32 (m, 2H), 7.31 (dd, 1H), 6.95 (td, 1H), 6.44–6.41 (m, 2H), 6.36 (d, 1H), 5.37 (q, 1H), 1.13 (d, 3H);

Anal. calcd for $C_{20}H_{16}FNO_4S \cdot 0.50CH_2Cl_2$: C, 57.55; H, 4.00; N, 3.27. Found: C, 57.18; H, 4.14; N, 3.21.

EXAMPLE 51

Step a)

6-Ethyl-8-fluoro-5-[(4-methoxyphenyl)sulfonyl]-2-methyl-5,6-dihydrophenanthridine A stirred solution of 2-bromo-6-ethyl-8-fluoro-5-[(4-methoxyphenyl)sulfonyl]-5,6-dihydrophenanthridine (Example 44, Step c, 0.30 g, 0.63 mmol) in tetrahydrofuran (7 mL) was cooled to −78° C., and treated drop-wise under nitrogen with a solution of 1.4 M n-butyllithium in hexane (0.9 mL, 1.26 mmol). After stirring for 10 min, iodomethane (0.08 mL, 1.26 mmol) was added, and the reaction stirred until room temperature was reached. The reaction was quenched with a 0.1 N hydrochloric acid solution (15 mL, 1.5 mmol), and a saturated, aqueous, sodium chloride solution (150 mL). The separated aqueous phase was extracted with diethyl ether (3×20 mL). The combined organic phase was dried over anhydrous sodium sulfate, filtered, and concentrated in vacuo to a crude product, which was used without further purification;

MS [(+ESI), m/z]: 434 [M+Na]$^+$;

$^1$H NMR (400 MHz, DMSO-d$_6$) δ: 7.51 (s, 1H), 7.47–7.41 (m, 2H), 7.18 (dd, 1H), 7.10 (dd, 1H), 6.97–6.89 (m, 3H), 6.56 (d, 2H), 5.04 (dd, 1H), 3.60 (s, 3H), 2.32 (s, 3H), 1.37 (m, 1H), 1.19 (m, 1H), 0.85 (t, 3H).

Step b)

4-[(6-Ethyl-8-fluoro-2-methylphenanthridin-5(6H)-yl)sulfonyl]phenol

The title compound was prepared from 6-ethyl-8-fluoro-5-[(4-methoxyphenyl)sulfonyl]-2-methyl-5,6-dihydrophenanthridine (0.24 g, 0.58 mmol), cyclohexene (2.1 mL, 21 mmol), and 1 M boron tribromide in dichloromethane (7.0 mL, 7.0 mmol) according to the procedure and in the same manner as described in Example 47, Step b. The crude product was purified by flash column chromatography on silica gel, eluting with a mixture of ethyl acetate-hexane (1:4), followed by re-crystallization from a mixture of ethyl acetate-hexane (2×), to afford 4-[(6-ethyl-8-fluoro-2-methylphenanthridin-5(6H)-yl)sulfonyl]phenol as a homogeneous solid (0.14 g, 59%), m.p. 197–200° C.;

MS [(−ESI), m/z]: 396 [M−H]$^-$;

$^1$H NMR (500 MHz, DMSO-d$_6$) δ: 10.18 (br s, 1H), 7.56 (s, 1H), 7.51–7.47 (m, 2H), 7.21 (d, 1H), 7.14 (dd, 1H), 6.95 (td, 1H), 6.88 (d, 2H), 6.38 (d, 2H), 5.07 (dd, 1H), 2.35 (s, 3H), 1.40 (m, 1H), 1.21 (m, 1H), 0.88 (t, 3H);

Anal. calcd for $C_{22}H_{20}FNO_3S \cdot 0.50H_2O$: C, 65.01; H, 5.21; N, 3.45. Found: C, 64.98; H, 5.08; N, 3.26.

EXAMPLE 52

Step a)

6-Ethyl-8-fluoro-5-[(4-methoxyphenyl)sulfonyl]-2-thien-3-yl-5,6-dihydrophenanthridine The title compound was prepared from 2-bromo-6-ethyl-8-fluoro-5-[(4-methoxyphenyl)sulfonyl]-5,6-dihydrophenanthridine (Example 44, Step c, 0.35 g, 0.73 mmol), 3-thiopheneboronic acid (0.09 g, 0.73 mmol), [1,1'-bis(diphenylphosphino)ferrocene]dichloropalladium (II) complex with dichloromethane (0.02 g, 0.02 mmol), and a 5 N aqueous sodium hydroxide solution (0.3 mL, 1.5 mmol) according to the procedure and in the same manner as described in Example 47, Step a. The crude material was purified by flash column chromatography on silica gel, eluting with a mixture of ethyl acetate-hexane (1:4) to yield 6-ethyl-8-fluoro-5-[(4-methoxyphenyl)sulfonyl]-2-thien-3-yl-5,6-dihydrophenanthridine as a solid (0.18 g, 51%);

MS [(+ESI), m/z]: 480 [M+H]$^+$;

$^1$H NMR (500 MHz, DMSO-d$_6$) δ: 8.06 (m, 2H), 7.78 (dd, 1H), 7.72 (m, 2H), 7.68 (m, 1H), 7.64 (d, 1H), 7.15 (dd, 1H), 7.04 (d, 2H), 6.99 (td, 1H), 6.62 (d, 2H), 5.13 (dd, 1H), 3.64 (s, 3H), 1.45 (m, 1H), 1.27 (m, 1H), 0.93 (t, 3H);

Anal. calcd for $C_{26}H_{22}FNO_3S_2 \cdot 0.10C_6H_{14}$: C, 65.44; H, 4.83; N, 2.87. Found: C, 65.74; H, 5.05; N, 2.73.

Step b)

4-[(6-Ethyl-8-fluoro-2-thien-3-ylphenanthridin-5(6H)-yl)sulfonyl]phenol

The title compound was prepared from 6-ethyl-8-fluoro-5-[(4-methoxyphenyl)sulfonyl]-2-thien-3-yl-5,6-dihydrophenanthridine (0.28 g, 0.58 mmol), cyclohexene (13 mL, 10.5 mmol), and 1 M boron tribromide in dichloromethane (3.5 mL, 3.5 mmol) according to the procedure and in the same manner as described in Example 47, Step b. The crude product was purified by flash column chromatography on silica gel, eluting with a mixture of ethyl acetate-hexane (1:4) to yield 4-[(6-ethyl-8-fluoro-2-thien-3-ylphenanthridin-5(6H)-yl)sulfonyl]phenol as a homogeneous solid (0.17 g, 63%);

MS [(−ESI), m/z]: 464 [M−H]$^-$;

$^1$H NMR (500 MHz, DMSO-d$_6$) δ: 10.20 (br s, 1H), 8.06 (m, 2H), 7.78–7.66 (m, 4H), 7.63 (d, 1H), 7.17 (dd, 1H), 7.00 (td, 1H), 6.94 (d, 2H), 6.40 (d, 2H), 5.11 (dd, 1H), 1.44 (m, 1H), 1.26 (m, 1H), 0.91 (t, 3H).

EXAMPLE 53

4-[(6-Ethyl-8-fluorophenanthridin-5(6H)-yl)sulfonyl]phenyl 3,3-dimethylbutanoate A stirred solution of 4-[(6-ethyl-8-fluorophenanthridin-5(6H)-yl)sulfonyl]phenol (Example 40, Step d, 0.05 g, 0.13 mmol) in dichloromethane (2 mL) was treated sequentially with pyridine (0.04 mL, 0.52 mmol) and t-butylacetyl chloride (0.04 mL, 0.26 mmol). After stirring for twelve hours at room temperature, the reaction was quenched with a saturated, aqueous, sodium bicarbonate solution (50 mL). The separated aqueous phase was extracted with dichloromethane (3×10 mL). The combined organic phase was dried over anhydrous sodium sulfate, filtered, and concentrated in vacuo to a crude product. The crude product was purified by flash column chromatography on silica gel, eluting with a mixture of ethyl acetate-hexane (1:9 to 1:4 gradient) to yield the title compound as a white solid (0.05 g, 71%), m.p. 128° C.;

MS [(+ESI), m/z]: 482 [M+H]+;

$^1$H NMR (500 MHz, DMSO-d$_6$) δ: 7.75 (d, 1H), 7.63 (d, 1H), 7.48–7.39 (m, 3H), 7.17 (dd, 1H), 7.11 (d, 2H), 6.89 (m, 1H), 6.85 (d, 2H), 5.14 (dd, 1H), 2.29 (s, 2H), 1.44 (m, 1H), 1.23 (m, 1H), 1.02 (s, 9H), 0.91 (t, 3H);

Anal. calcd for C$_{27}$H$_{28}$FNO$_4$S.0.15C$_6$H$_{14}$.0.30H$_2$O: C, 67.03; H, 6.19; N, 2.80. Found: C, 67.15; H, 6.40; N, 2.40.

EXAMPLE 54

4-[(6-Ethyl-8-fluorophenanthridin-5(6H)-yl)sulfonyl]phenyl propionate

A stirred solution of 4-[(6-ethyl-8-fluorophenanthridin-5(6H)-yl)sulfonyl]phenol (Example 40, Step d, 0.06 g, 0.16 mmol) in dichloromethane (2 mL) was treated sequentially with pyridine (0.05 mL, 0.63 mmol) and propionyl chloride (0.03 mL, 0.3 mmol). After stirring for twelve hours at room temperature, the reaction was quenched with a saturated, aqueous, sodium bicarbonate solution (50 mL). The separated aqueous phase was extracted with dichloromethane (3×10 mL). The combined organic phase was dried over anhydrous sodium sulfate, filtered, and concentrated in vacuo to a crude product. The crude product was purified by flash column chromatography on silica gel, eluting with a mixture of ethyl acetate-hexane (1:9 to 1:4 gradient) to yield the title compound as a white solid (0.05, 77%), m.p. 111–112° C.;

MS [(+ESI), m/z]: 440 [M+H]+;

$^1$H NMR (500 MHz, DMSO-d$_6$) δ: 7.76 (d, 1H), 7.65 (dd, 1H), 7.48 (dd, 1H), 7.45–7.37 (m, 2H), 7.19 (dd, 1H), 7.09 (d, 2H), 6.93 (m, 1H), 6.86 (d, 2H), 5.16 (dd, 1H), 2.54 (q, 2H), 1.44 (m, 1H), 1.24 (m, 1H), 1.07 (t, 3H), 0.91 (t, 3H);

Anal. calcd for C$_{24}$H$_{22}$FNO$_4$S: C, 65.59; H, 5.05; N, 3.19. Found: C, 65.20; H, 4.98; N, 3.00.

EXAMPLE 55

4-[(6-Ethyl-8-fluorophenanthridin-5(6H)-yl)sulfonyl]phenyl benzoate

A stirred solution of 4-[(6-ethyl-8-fluorophenanthridin-5(6H)-yl)sulfonyl]phenol (Example 40, Step d, 0.05 g, 0.13 mmol) in dichloromethane (2 mL) was treated sequentially with pyridine (0.04 mL, 0.52 mmol) and benzoyl chloride (0.03 mL, 0.26 mmol). After stirring for twelve hours and room temperature, the reaction was quenched with a saturated, aqueous sodium bicarbonate solution (50 mL). The separated aqueous phase was extracted with dichloromethane (3×10 mL). The combined organic phase was dried over anhydrous sodium sulfate, filtered, and concentrated in vacuo to a crude product. The crude product was purified by flash column chromatography on silica gel, eluting with a mixture of ethyl acetate-hexane (1:9 to 1:4 gradient), followed by re-crystallization from a mixture of ethyl acetate-hexane, to yield the title compound as a white solid (0.04 g, 59%);

MS [(+ESI), m/z]: 488 [M+H]+;

$^1$H NMR (500 MHz, DMSO-d$_6$) δ: 8.06 (m, 2H), 7.78 (d, 1H), 7.74 (m, 1H), 7.66 (m, 1H), 7.59 (t, 2H), 7.53 (dd, 1H), 7.46–7.39 (m, 2H), 7.22 (dd, 1H), 7.15 (d, 2H), 7.06 (d, 2H), 6.97 (td, 1H), 5.20 (dd, 1H), 1.46 (m, 1H), 1.25 (m, 1H), 0.93 (t, 3H);

Anal. calcd for C$_{28}$H$_{22}$FNO$_4$S.0.10H$_2$O: C, 68.73; H, 4.57; N, 2.86. Found: C, 68.56; H, 4.30; N, 2.71.

EXAMPLE 56

Step a)

5-[(3-Fluoro-4-methoxyphenyl)sulfonyl]-6-methyl-5,6-dihydrophenanthridine

The title compound was prepared from phenanthridine (7.17 g, 40 mmol), 1.4 M methyllithium in diethyl ether (29 mL, 40.6 mmol), and 3-fluoro-4-methoxybenzenesulfonyl chloride (8.99 g, 40 mmol) according to the procedure and in the same manner as described in Example 1, step a. The crude product was purified by re-crystallization from a mixture of ethyl acetate-cyclohexane to yield 5-[(3-fluoro-4-methoxyphenyl)sulfonyl]-6-methyl-5,6-dihydrophenanthridine (6.79 g, 17.7 mmol, 44%) as an off-white solid;

MS [(EI), m/z]: 383 [M]+;

$^1$H NMR (500 MHz, DMSO-d$_6$) δ: 7.79 (dd, J=7.5, 1.5 Hz, 1H, ArH-1), 7.60 (dd, J=7.6, 1.5 Hz, 1H, ArH-4), 7.39–7.47 (m, 3H, ArH-2,3,10), 7.26 (d, J=6.6 Hz, 1H, ArH-7), 7.12–7.21 (m, 2H, ArH-8,9), 6.73–6.82 (m, 3H, ArH'), 5.42 (q, J=7 Hz, 1H, H-6), 3.71 (s, 3H, —OCH$_3$-4'), 1.11 (d, J=7 Hz, 3H, —CH$_3$-6);

Anal. calcd for C$_{21}$H$_{18}$FNO$_3$S: C, 65.78; H, 4.73; N, 3.65. Found: C, 65.84; H, 4.69; N, 3.57.

Step b)

2-Fluoro-4-[(6-methylphenanthridin-5(6H)-yl)sulfonyl]phenol

The title compound was prepared from 5-[(3-fluoro-4-methoxyphenyl)sulfonyl]-6-methyl-5,6-dihydrophenanthridine (0.5 g, 1.3 mmol), cyclohexene (0.33 mL, 3.25 mmol) and 1.0 M boron tribromide in dichloromethane (7.8 mL, 7.8 mmol) according to the procedure and in the same manner as described in Example 1, step b. The crude product was purified by flash column chromatography on silica gel, eluting sequentially with dichloromethane and ethyl acetate to yield 2-fluoro-4-[(6-methylphenanthridin-5(6H)-yl)sulfonyl]phenol (0.35 g, 0.96 mmol, 74%) as a light-yellow solid, m.p. 172–174° C.;

MS [(-ESI) m/z]: 368 [M-H]−;

$^1$H NMR (500 MHz, DMSO-d$_6$) δ: 10.71(s, 1H, —OH-4'), 7.79 (dd, J=7.5, 1.7 Hz, 1H, ArH-1), 7.60 (dd, J=7.6, 1.5 Hz, 1H, ArH-4), 7.48 (d, J=7.3 Hz, 1H, ArH-10), 7.37–7.45 (m, 2H, ArH-2,3), 7.25 (d, J=7.5, 1.4 Hz, 1H, ArH-7), 7.13–7.21 (m, 2H, ArH-8,9), 6.68 (dd, J=10.7, 2.1 Hz, 1H, ArH'-2'), 6.63 (dd, J=8.9, 2.1 Hz, 1H, ArH-6'), 6.53 (dd, J=10.7, 8.9 Hz, 1H, ArH'-5'), 5.41(q, J=7.0 Hz, 1H, H-6), 1.11(d, J=7.0 Hz, 3H, —CH$_3$-6);

Anal. calcd for C$_{20}$H$_{16}$FNO$_3$S.0.15H$_2$O: C, 64.56; H, 4.42; N, 3.76. Found: C, 64.31; H, 4.17; N, 3.56.

EXAMPLE 57

Step a)

2-Bromo-5-[(3-fluoro-4-methoxyphenyl)sulfonyl]-6-methyl-5,6-dihydrophenanthridine The title compound was prepared from 5-[(3-fluoro-4-methoxyphenyl)sulfonyl]-6-methyl-5,6-dihydrophenanthridine (1.15 g, 3.0 mmol), bromine (0.61 mL, 12.0 mmol), and acetic acid (30 mL) according to the procedure and in the same manner as described in Example 4, step a. The crude product was purified by re-crystallization from ethyl acetate to yield 2-bromo-5-[(3-fluoro-4-methoxyphenyl)sulfonyl]-6-methyl-5,6-dihydrophenanthridine (1.03 g, 2.22 mmol, 74%);

MS [(+ESI), m/z]: 461 [M+H]$^+$;

$^1$H NMR (500 MHz, DMSO-d$_6$) δ: 8.00 (d, J=2.3 Hz, 1H, ArH-1), 7.63 (dd, J=8.6, 2.3 Hz, 1H, ArH-3), 7.53–7.55 (m, 2H, ArH-4,10), 7.28 (d, J=7.5 Hz, 1H, ArH-7), 7.22 (t, J=7.5 Hz, 1H, ArH-8), 7.15 (t, J=Hz, 1H, ArH-9), 6.80–6.87 (m, 3H, ArH'-2',5',6'), 5.44 (q, J=7.0 Hz, 1H, H-6), 3.72 (s, 3H, —OCH$_3$-4'), 1.14 (d, J=7.0 Hz, 3H, —CH$_3$-6);

Step b)

4-[(2-Bromo-6-methylphenanthridin-5(6H)-yl) sulfonyl]-2-fluorophenol

The title compound was prepared from 2-bromo-5-[(3-fluoro-4-methoxyphenyl)sulfonyl]-6-methyl-5,6-dihydrophenanthridine (0.5 g, 1.08 mmol), cyclohexene, (0.27 mL, 3.58 mmol), and 1.0 M boron tribromide in dichloromethane (6.49 mL, 6.49 mmol) according to the procedure and in the same manner as described in Example 4, step b. The crude product was purified by re-crystallization from dichloromethane to yield 4-[(2-bromo-6-methylphenanthridin-5(6H)-yl)sulfonyl]-2-fluorophenol (0.15 g, 0.34 mmol, 31%) as an off-white solid, m.p. 203–206° C.;

MS [(–ESI), m/z]: 446 [M–H]$^-$;

$^1$H NMR (500 MHz, DMSO-d$_6$) δ: 10.77 (s, 1H, —OH-4'), 8.01 (d, J=2.2 Hz, 1H, ArH-1), 7.62 (dd, J=8.6, 2.3 Hz, 1H, ArH-4), 7.52–7.57 (m, 2H, ArH-3,10), 7.28 (d, J=7.3 Hz, 1H, ArH-7), 7.23 (t, J=7.3 Hz, 1H, ArH-8), 7.16 (t, J=7.3 Hz, 1H, ArH-9), 6.79 (dd, J=10.7, 2.1 Hz, 1H, ArH'-2'), 6.67 (dd, J=8.6, 2.1 Hz, 1H, ArH'-6'), 6.57 (t, J=8.6 Hz, 1H, ArH'-5'), 5.43 (q, J=7.0 Hz, 1H, H-6), 1.14 (d, J=7.0 Hz, 3H, —CH$_3$-6);

Anal. calcd for C$_{20}$H$_{15}$BrFNO$_3$S.0.35H$_2$O: C, 52.84; H, 3.48; N, 3.08. Found: C, 52.76; H, 3.33; N, 2.98.

EXAMPLE 58

Step a)

1-Methoxy-2-(trifluoromethyl)benzene

A stirred solution of 2-hydroxybenzotrifluoride (23.0 g, 142 mmol) in 2-butanone (107 mL) was treated with potassium carbonate (25.51 g, 185 mmol) and iodomethane (13.3 mL, 213 mmol). The mixture was heated at reflux overnight under argon until the thin-layer chromatography showed a completed reaction. The mixture was cooled to room temperature and filtered through diatomaceous earth. The filtered solid was washed with acetone and the filtrate concentrated carefully in vacuo without heating. The resulting crude liquid was purified by vacuum distillation to yield the title compound (21.79 g, 0.124 mol, 87%) as a colorless liquid.

7.56 (m, 2H, ArH-4,5), 7.20 (m, 1H, ArH-6), 7.03 (m, 1H, ArH-3), 3.83 (s, 3H, —OCH$_3$-1);

Step b)

4-Methoxy-3-(trifluoromethyl)benzenesulfonyl chloride

A solution of 1-methoxy-2-(trifluoromethyl)benzene (10.0 g, 56.8 mmol) in dry chloroform (76 mL) was cooled to 0° C. and treated with chlorosulfonic acid (7.55 mL, 113.5 mmol) drop-wise under argon. After the addition was completed, the reaction mixture was gradually warmed to room temperature and stirred overnight. The reaction was quenched by pouring the mixture slowly onto ice. The separated, aqueous phase was extracted with chloroform (3×). The combined organic phase was washed sequentially with a saturated, aqueous sodium chloride solution (2×) and water. The organic phase was dried over anhydrous magnesium sulfate and concentrated in vacuo to yield the title compound (8.77 g. 31.9 mmol, 56%) as a gray solid;

MS [(+ESI), m/z]: 274 [M+H]$^+$;

$^1$H NMR (500 MHz, DMSO-d$_6$) δ: 7.81 (dd, J=8.6, 2.0 Hz, 1H, ArH-6), 7.75 (d, 1H, J=2.1 Hz, ArH-2), 7.20(d, 1H, J=8.7 Hz, ArH-5), 3.89 (s, 3H, —OCH$_3$-4);

Anal. calcd for C$_8$H$_6$ClF$_3$O$_3$S: C, 34.99; H, 2.2. Found: C, 34.98, H, 2.1.

Step c)

5-{[4-M thoxy-3-(triflu romethyl)phenyl]sulfonyl}-6-methyl-5,6-dihydrophenanthridine The title compound was prepared from phenanthridine (5.38 g, 30 mmol), 1.4 M methyllithium in diethyl ether (21.8 mL, 30.5 mmol), and 4-methoxy-3-(trifluoromethyl) benzenesulfonyl chloride (8.24 g, 30 mmol) according to the procedure and in the same manner as described in Example 1, step a. The crude product was purified by flash column chromatography on silica gel, eluting with a mixture of ethyl acetate-hexane (1:8) to yield 5-{[4-methoxy-3-(trifluoromethyl)phenyl]sulfonyl}-6-methyl-5,6-dihydrophenanthridine (5.75 g, 13.27 mmol, 44%) as a white solid;

MS [(+ESI), m/z]: 434 [M+H]$^+$;

$^1$H NMR (500 MHz, DMSO-d$_6$) δ: 7.77 (d, J=7.8 Hz, 1H, ArH-1), 7.63 (d, J=7.7 Hz, 1H, ArH-4), 7.49–7.36 (m, 3H, ArH-2,3,10), 7.25 (d, J=7.3 Hz, 1H, ArH-7), 7.18–7.09 (m, 3H, ArH-8,9, ArH'-6'), 6.98 (d, J=2.1 Hz, 1H, ArH'-2'), 6.88 (d, J=9.0 Hz, 1H, ArH'-5'), 5.43 (q, J=7.0 Hz, 1H, H-6), 3.77 (s, 3H, —OCH$_3$-4'), 1.14 (d, J=7.0 Hz, 3H, —CH$_3$-6);

Anal. calcd for C$_{22}$H$_{18}$F$_3$NO$_3$S: C, 60.96; H, 4.19; N, 3.23. Found: C, 60.88; H, 4.1; N, 3.03.

Step d)

4-[(6-Methylphenanthridin-5(6H)-yl)sulfonyl]-2-(trifluoromethyl)phenol

The title compound was prepared from 5-{[4-methoxy-3-(trifluoromethyl)phenyl]sulfonyl}-6-methyl-5,6-dihydrophenanthridine (0.5 g, 1.15 mmol), cyclohexene (0.29 mL, 2.88 mmol), and 1.0 M boron tribromide in dichloromethane (6.92 mL, 6.92 mmol) according to the procedure and in the same manner as described in Example 1, step b. The crude product was purified by flash column chromatography on silica gel, eluting with dichloromethane to yield 4-[(6-methylphenanthridin-5(6H)-yl)sulfonyl]-2-(trifluoromethyl)phenol (0.044 g, 0.104 mmol, 9%) as an off-white solid, m.p. 213–215° C.;

MS [(–ESI) m/z]: 418 [M–H]$^-$;

$^1$H NMR (500 MHz, DMSO-d$_6$) δ: 11.44 (s, 1H, OH-4'), 7.78 (d, J=7.5 Hz, 1H, ArH-1), 7.62 (d, J=7.6 Hz, 1H, ArH-4), 7.47–7.40 (m, 3H, ArH-2,3,10), 7.24 (d, J=7.3 Hz, 1H, ArH-7), 7.18–7.10 (m, 2H, ArH-8,9), 6.99 (dd, J=8.7, 2.0 Hz, 1H, ArH'-6'), 6.94 (s, 1H, ArH'-2'), 6.56 (d, J=8.7 Hz, 1H, ArH'-5'), 5.41 (q, J=6.9 Hz, 1H, H-6), 1.14 (d, J=7.0 Hz, 3H, —CH$_3$-6);

Anal. calcd for C$_{21}$H$_{16}$F$_3$NO$_3$S.0.20CH$_2$Cl$_2$.0.20H$_2$O: C, 57.87; H, 3.85; N, 3.18. Found: C, 57.75; H, 3.91; N, 3.05.

EXAMPLE 59

Step a)

4-Methoxy-3,5-dimethylbenzenesulfonyl chloride

The title compound was prepared from 2-methoxy-1,3-dimethylbenzene (6.81 g, 50 mmol) and chlorosulfonic acid (6.65 mL, 100 mmol), according to the procedure and in the same manner as described in Example 58, step b to yield 4-methoxy-3,5-dimethylbenzenesulfonyl chloride (7.43 g, 31.3 mmol, 63%) as a white solid;

MS [(+ESI), m/z]: 234 [M+H]$^+$;

$^1$H NMR (500 MHz, DMSO-d$_6$) δ: 7.24 (s, 2H, ArH-2,6), 3.62 (s, 3H, —OCH$_3$-4), 2.19 (s, 6H, —CH$_3$-3,5);

Anal. calcd for C$_9$H$_{11}$ClO$_3$S.0.3H$_2$O: C, 45.02; H, 4.87. Found: C, 44.92; H, 4.78.

Step b)

5-[(4-Methoxy-3,5-dimethylphenyl)sulfonyl]-6-methyl-5,6-dihydrophenanthridin The title compound was prepared from phenanthridine (3.58 g, 20 mmol), 1.4 M methyllithium in diethyl ether (14.5 mL, 20.3 mmol), and 4-methoxy-3,5-dimethylbenzenesulfonyl chloride (4.69 g, 20 mmol) according to the procedure and in the same manner as described in Example 1, step a. The crude product was purified by flash column chromatography on silica gel, eluting with a mixture of ethyl acetate-hexane (1:8) to yield 5-[(4-methoxy-3,5-dimethylphenyl)sulfonyl]-6-methyl-5,6-dihydrophenanthridine (4.86 g, 12.4 mmol, 62%) as a white solid;

MS [(+ESI), m/z]: 394 [M+H]$^+$;

$^1$H NMR (500 MHz, DMSO-d$_6$) δ: 7.78 (d, J=7.5 Hz, 1H, ArH-1), 7.59 (d, J=7.8 Hz, 1H, ArH-4), 7.45–7.38 (m, 3H, ArH-2,3,10), 7.21–7.16 (m, 2H, ArH-7,8), 7.10 (t, J=7.3 Hz, 1H, ArH-9), 6.60 (s, 2H, ArH'-2',6'), 5.35 (q, J=7.1 Hz, 1H, H-6), 3.48 (s, 3H, —OCH$_3$-4'), 1.85 (s, 6H, —CH$_3$-3',5'), 1.13 (d, J=7.1 Hz, 3H, —CH$_3$-6);

Anal. calcd for C$_{23}$H$_{23}$NO$_3$S: C, 70.20; H, 5.89; N, 3.56. Found: C, 80.08; H, 5.84; N, 3.45.

Step c)

2,6-Dimethyl-4-[(6-methylphenanthridin-5(6H)-yl)sulfonyl]phenol

The title compound was prepared from 5-[(4-methoxy-3,5-dimethylphenyl)sulfonyl]-6-methyl-5,6-dihydrophenanthridine (1.0 g, 2.54 mmol), cyclohexene (0.64 mL, 6.36 mmol) and 1.0 M boron tribromide in dichloromethane (15.3 mL, 15.3 mmol) according to the procedure and in the same manner as described in Example 1, step b. The crude product was purified by flash column chromatography on silica gel, eluting with dichloromethane to yield 2,6-dimethyl-4-[(6-methylphenanthridin-5(6H)-yl)sulfonyl]phenol (0.79 g, 2.08 mmol, 82%) as a white solid, m.p. 211–213° C.;

MS [(+ESI), m/z]: 380 [M+H]$^+$;

$^1$H NMR (500 MHz, DMSO-d$_6$) δ: 8.93 (s, 1H, —OH-4'), 7.76 (d, J=7.5 Hz, 1H, ArH-1), 7.58 (d, J=7.8 Hz, 1H, ArH-4), 7.44–7.34 (m, 3H, ArH-2,3,10), 7.22–7.17 (m, 2H, ArH-7,8), 7.11 (t, J=7.2 Hz, 1H, ArH-9), 6.52 (s, 2H, ArH'-2',6'), 5.36 (q, J=7.0 Hz, 1H, H-6), 1.79 (s, 6H, —CH$_3$-3',5'), 1.12 (d, J=7.0 Hz, 3H, —CH$_3$-6);

Anal. calcd for C$_{22}$H$_{21}$NO$_3$S.0.65H$_2$O: C, 67.55; H, 5.75; N, 3.58. Found: C, 67.43; H, 5.55; N, 3.44.

EXAMPLE 60

Step a)

4'-Methyl-1,1'-biphenyl-2-amine

A stirred solution of 2-iodoaniline (5.0 g, 22.8 mmol), and 4-methylphenylboronic acid (3.1 g, 22.8 mmol) in tetrahydrofuran was treated under argon with [1,1'-bis(diphenylphosphino)ferrocene]dichloropalladium (II) complex with dichloromethane (1:1) (0.37 g, 0.46 mmol), and a 5.0 N sodium hydroxide solution (9.1 mL, 45.7 mmol). The reaction mixture was heated under reflux for 24 hours, cooled to room temperature, and washed with a saturated, aqueous, sodium chloride solution. The aqueous phase was further extracted with ethyl acetate (3×). The combined organic phase was dried over anhydrous magnesium sulfate, and the solvent evaporated in vacuo. The crude product was purified by flash column chromatography on silica gel, eluting with a mixture of ethyl acetate-hexane (1:12) to yield the title compound (3.26 g, 17.8 mmol, 78%) as an orange oil;

MS [(+ESI), m/z]: 184 [M+H]$^+$;

$^1$H NMR (500 MHz, DMSO-d$_6$) δ: 7.29 (d, J=7.9 Hz, 2H, ArH'-2',6'), 7.24 (d, J=7.9 Hz, 2H, ArH'-3',5'), 7.02 (t, 1H, ArH-5), 6.95 (d, J=7.6, 1H, ArH-6), 6.74 (d, J=7.9 Hz, 1H, ArH-3), 6.61 (t, J=7.4 Hz, 1H, ArH-4), 4.69 (s, 2H, —NH$_2$-2), 2.33 (s, 3H, —CH$_3$-4');

Anal. calcd for C$_{13}$H$_{13}$N: C, 85.21; H, 7.15; N, 7.64. Found: C, 85.0, H, 7.15; N, 7.55.

Step b)

N-(4'-Methyl-1,1'-biphenyl-2-yl)acetamide

A stirred solution of 4'-methyl-1,1'-biphenyl-2-amine (3.09 g, 16.87 mmol) in dichloromethane was treated with acetic anhydride (1.75 mL, 18.6 mmol), pyridine (3.14 mL, 38.8 mmol), and 4-(N,N-dimethylamino)pyridine (0.062 g, 0.506 mmol). After stirring under argon for 16 hours, a saturated, aqueous, ammonium chloride solution (5 mL) was added to the reaction mixture and stirring continued another 30 minutes. The reaction mixture was poured into a 0.1 N hydrochloric acid solution. The separated aqueous phase was further extracted with dichloromethane (3×). The combined organic phase was washed sequentially with a 0.1 N hydrochloric acid solution and a saturated aqueous, sodium bicarbonate solution. After drying over anhydrous magnesium sulfate, the solvent was removed in vacuo. The crude product was purified by re-crystallization from a mixture of ethyl acetate-hexane to yield the title compound (3.17 g, 14.1 mmol, 83%) as a white, crystalline solid;

MS [(+ESI), m/z]: 226 [M+H]$^+$;

$^1$H NMR (500 MHz, DMSO-d$_6$) δ: 9.16 (s, 1H, NH), 7.45–7.22 (m, 8H, ArH), 2.34 (s, 3H, CH$_3$-3',5'), 1.88 (s, 3H, —C(O)CH$_3$);

Anal. calcd for C$_{15}$H$_{15}$NO: C, 79.97; H, 6.71; N, 6.22. Found: C, 80.13; H, 6.76; N, 6.11.

Step c)

6,8-Dimethylphenanthridine

The title compound was prepared from N-(4'-methyl-1,1'-biphenyl-2-yl)acetamide (3.05 g, 13.5 mmol) and polyphosphoric acid (40 g) according to the procedure and in the same manner as described in Example 32, Method A, step b. The crude product was purified by re-crystallization from a mixture of ethyl acetate-hexane to yield 6,8-dimethylphenanthridine (2.04 g, 9.82 mmol, 73%) as a light-yellow solid;

MS [(+ESI), m/z]: 208 [M+H]$^+$;

$^1$H NMR (500 MHz, DMSO-d$_6$) δ: 8.72 (d, J=8.4 Hz, 1H, ArH-1), 8.69 (d, J=8.1 Hz, 1H, ArH-4), 8.11 (s, 1H, ArH-7), 7.97 (d, J=8.1, 1H, ArH-10), 7.77 (d, J=8.4 Hz, 1H, ArH-9), 7.71–7.67 (t, J=8.0 Hz, 1H, ArH-2), 7.63 (t, J=8.1 Hz, 1H, ArH-3), 2.94 (s, 3H, —CH$_3$-6), 2.58 (s, 3H, —CH$_3$-8);

Anal. calcd for $C_{15}H_{13}N$: C, 86.92; H, 6.32; N, 6.76. Found: C, 86.65; H, 6.35; N, 6.62.

Step d)

5-[(4-Methoxyphenyl)sulfonyl]-6,8-dimethyl-5,6-dihydroph nanthridin

A stirred solution of 6,8-dimethylphenanthridine (1.95 g, 9.41 mmol) in tetrahydrofuran (90 mL) was treated with sodium borohydride (1.42 g, 37.6 mmol) and trifluoroacetic acid (0.72 mL, 9.41 mmol). After stirring overnight under argon, another equivalent of sodium borohydride was added, and the mixture heated at reflux for five hours. After cooling to room temperature, the reaction was quenched with a mixture of a saturated, aqueous, sodium bicarbonate solution and a saturated, aqueous, sodium chloride solution. The aqueous phase was extracted with diethyl ether (3×). The combined organic phase was dried over anhydrous magnesium sulfate, filtered, and evaporated in vacuo to a crude dihydrophenanthridine. A solution of the crude dihydrophenanthridine in dichloromethane (25 mL) was treated with triethylamine (5.25 mL, 37.63 mmol) and 4-methoxybenzenesulfonyl chloride (2.14 g, 10.3 mmol). After stirring for 18 hours under argon at room temperature, the reaction mixture was quenched with a 1 N sodium hydroxide solution and extracted with dichloromethane (2×). The combined organic phase was washed with a 2 N hydrochloric acid solution, dried over anhydrous magnesium sulfate, and evaporated in vacuo to an orange solid. The orange solid was purified by flash column chromatography on silica gel, eluting with a mixture of ethyl acetate-hexane (1:8) to yield the title compound (1.61 g, 4.24 mmol, 45%) as a white solid;

MS [(+ESI), m/z]: 380 [M+H]$^+$;

$^1$H NMR (500 MHz, DMSO-d$_6$) δ: 7.72 (d, J=7.5 Hz, 1H, ArH-1), 7.58 (d, J=7.9 Hz, 1H, ArH-4), 7.39–7.31 (m, 3H, ArH-2,3,10), 7.00 (s, 1H, ArH-7), 6.95 (d, J=8.9 Hz, 2H, ArH'-2',6'), 6.93 (d, J=8.1 Hz, 1H, ArH-9), 6.55 (d, J=8.9 Hz, 2H, ArH'-3',5'), 5.31 (q, J=6.9 Hz, 1H, H-6), 3.63 (s, 3H, —OCH$_3$-4'), 2.25 (s, 3H, —CH$_3$-8), 1.12 (d, J=7.0 Hz, 3H, —CH$_3$-6);

Anal. calcd for $C_{22}H_{21}NO_3S$: C, 69.63; H, 5.58; N, 3.69. Found: C, 69.31; H, 5.42; N, 3.57.

Step e)

4-[(6,8-Dimethylphenanthridin-5(6H)-yl)sulfonyl]phenol

The title compound was prepared from 5-[(4-methoxyphenyl)sulfonyl]-6,8-dimethyl-5,6-dihydrophenanthridine (0.6 g, 1.58 mmol), cyclohexene (0.4 mL, 3.95 mmol), and 1.0 M boron tribromide in dichloromethane (9.5 mL, 9.49 mmol) according to the procedure and in the same manner as described in Example 1, step b. The crude product was purified by flash column chromatography on silica gel, eluting with dichloromethane to yield 4-[(6,8-dimethylphenanthridin-5(6H)-yl)sulfonyl]phenol (0.31 g, 0.85 mmol, 54%) as a white solid, m.p. 111–113° C.;

MS [(−ESI), m/z]: 364 [M−H]$^-$;

$^1$H NMR (500 MHz, DMSO-d$_6$) δ: 10.20 (s, 1H, OH-4'), 7.73 (d, J=7.5 Hz, 1H, ArH-1), 7.57 (d, J=7.5 Hz, 1H, ArH-4), 7.38–7.31 (m, 3H, ArH-2,3,10), 7.01 (s, 1H, ArH-7), 6.95 (d, J=7.9 Hz, 1H, ArH-9), 6.84 (d, J=8.8 Hz, 2H, ArH'-2',6'), 6.34 (d, J=8.7 Hz, 2H, ArH'-3',5'), 5.31 (q, J=6.9 Hz, 1H, H-6), 2.25 (s, 3H, —CH$_3$-8), 1.11 (d, J=6.9 Hz, 3H, —CH$_3$-6);

Anal. calcd for $C_{21}H_{19}NO_3S \cdot 0.40H_2O$: C, 67.68; H, 5.36; N, 3.76. Found: C, 67.45; H, 5.16; N, 3.64.

EXAMPLE 61

Step a)

4'-Chloro-1,1'-biphenyl-2-amine

The title compound was prepared from 2-iodoaniline (5.0 g, 22.83 mmol), 4-chlorophenylboronic acid (3.57 g, 22.8 mmol), [1,1'-bis(diphenylphosphino)ferrocene] dichloropalladium (II) complex with dichloromethane (0.373 g, 0.46 mmol), and a 5.0 M sodium hydroxide solution (9.1 mL, 45.65 mmol) according to the procedure and in the same manner as described in Example 60, step a. The crude product was purified by flash column chromatography on silica gel, eluting with a mixture of ethyl acetate-hexane (1:12) to yield 4'-chloro-1,1'-biphenyl-2-amine (3.67 g, 18.0 mmol, 79%) as an orange oil;

MS [(+ESI), m/z]: 204 [M+H]$^+$;

$^1$H NMR (500 MHz, DMSO-d$_6$) δ: 7.47 (d, J=8.4 Hz, 2H, ArH'-3',5'), 7.42 (d, J=8.4 Hz, 2H, ArH'-2',6'), 7.04 (td, J=7.4, 1.1 Hz, 1H, ArH-5), 6.96 (d, J=7.5 Hz, 1H, ArH-6), 6.75 (d, J=8.1 Hz, 1H, ArH-3), 6.62 (t, J=7.5 Hz, 1H, ArH-4), 4.80 (s, 2H, NH$_2$-2);

Anal. calcd for $C_{12}H_{10}ClN \cdot 0.05H_2O$: C, 70.46; H, 4.98; N, 6.85. Found: C, 70.3; H, 4.88; N, 6.86.

Step b)

N-(4'-Chloro-1,1'-biphenyl-2-yl)acetamide

The title compound was prepared from 4'-chloro-1,1'-biphenyl-2-amine (3.5 g, 17.19 mmol), acetic anhydride (1.79 mL, 18.9 mmol), pyridine (3.2 mL, 39.5 mmol), and 4-(N,N-dimethylamino)pyridine (0.06 g, 0.52 mmol) according to the procedure and in the same manner as described in Example 60, step b. The crude product was purified by re-crystallization from a mixture of ethyl acetate-hexane to yield N-(4'-chloro-1,1'-biphenyl-2-yl)acetamide (2.16 g, 8.78 mmol, 51%) as a white solid;

MS [(−ESI,) m/z]: 244 [M−H]$^-$;

$^1$H NMR (500 MHz, DMSO-d$_6$) δ: 9.28 (s, 1H, —NH), 7.49–7.26 (m, 8H, ArH), 1.87 (s, 3H, —C(O)CH$_3$);

Anal. calcd for $C_{14}H_{12}ClNO$: C, 68.44; H, 4.92; N, 5.7. Found: C, 68.39; H, 4.92; N, 5.62.

Step c)

8-Chloro-6-methylphenanthridine

The title compound was prepared from N-(4'-chloro-1,1'-biphenyl-2-yl)acetamide (2.1 g, 8.55 mmol) and polyphosphoric acid (25.3 g) according to the procedure and in the same manner as described in Example 32, Method A, Step b. The crude product was re-crystallized from a mixture of hexane-ethyl acetate to yield 8-chloro-6-methylphenanthridine (1.66 g, 7.28 mmol, 85%) as an off-white solid;

MS [(+ESI), m/z]: 228 [M+H]$^+$;

$^1$H NMR (500 MHz, DMSO-d$_6$) δ: 8.87 (d, J=8.9 Hz, 1H, ArH-1), 8.74 (d, J=8.3 Hz, 1H, ArH-4), 8.35 (d, J=2.0 Hz, 1H, ArH-7), 8.01 (d, J=8.1 Hz, 1H, ArH-10), 7.95 (dd, J=8.7, 2.0 Hz, 1H, ArH-9), 7.76 (d, J=8.1 Hz, 1H, ArH-2), 7.68 (d, J=8.1 Hz, 1H, ArH-3), 2.96 (s, 3H, —CH$_3$-6);

Anal. calcd for $C_{14}H_{10}ClN$: C, 73.85; H, 4.43; N, 6.15. Found: C, 73.53; H, 4.37; N, 6.05.

Step d)

8-Chloro-5-[(4-methoxyphenyl)sulfonyl]-6-methyl-5,6-dihydrophenanthridine

A stirred solution of 8-chloro-6-methylphenanthridine (1.6 g, 7.03 mmol) in tetrahydrofuran (67 mL) was treated with sodium borohydride (2.13 g, 56.2 mmol) and trifluoroacetic acid (1.08 mL, 3.51 mmol) and heated at reflux for 5.5 hours. After cooling to room temperature, the reaction was quenched with a mixture of a saturated, aqueous, sodium bicarbonate solution and a saturated, aqueous, sodium chloride solution. The aqueous phase was extracted with diethyl ether (3×). The combined organic phase was dried over anhydrous magnesium sulfate, filtered, and evaporated in vacuo to a crude dihydrophenanthridine. A solution of the dihydrophenanthridine in dichloromethane (19 mL) was treated with triethylamine (3.9 mL, 28.1 mmol) and 4-methoxybenzenesulfonyl chloride (1.60 g, 7.73 mmol). After stirring for 18 hours under argon at room temperature, the reaction mixture was quenched with a 1 N aqueous sodium hydroxide solution, and extracted with dichloromethane (2×). The combined organic phase was washed with a 2 N hydrochloric acid solution, dried over anhydrous magnesium sulfate, and evaporated in vacuo to an orange solid. The orange solid was purified by flash column chromatography on silica gel, eluting with a mixture of ethyl acetate-hexane (1:8) to yield the title compound (1.65 g, 4.11 mmol, 59%) as a white solid;

MS [(+ESI), m/z]: 400 [M+H]$^+$;

$^1$H NMR (500 MHz, DMSO-d$_6$) δ: 7.78 (d, J=7.6 Hz, 1H, ArH-1), 7.61 (d, J=8.0 Hz, 1H, ArH-4), 7.48–7.36 (m, 4H, ArH-2,3,7,10), 7.16 (dd, J=8.4, 2.3 Hz, 1H, ArH-9), 6.99 (dd, J=11.7, 2.9 Hz, 2H, ArH'-2',6'), 6.60 (dd, J=11.6, 2.8 Hz, 2H, ArH'3',5'), 5.41 (q, J=7.0 Hz, 1H, H-6), 3.66 (s, 3H, —OCH$_3$-4'), 1.13 (d, J=7.0 Hz, 3H, —CH$_3$-6);

Anal. calcd for C$_{21}$H$_{18}$ClNO$_3$S: C, 63.07; H, 4.54; N, 3.5. Found: C, 62.96; H, 4.67; N, 3.34.

Step e)

4-[(8-Chloro-6-methylphenanthridin-5(6H)-yl)sulfonyl]phenol

The title compound was prepared from 8-chloro-5-[(4-methoxyphenyl)sulfonyl]-6-methyl-5,6-dihydrophenanthridine (0.6 g, 1.50 mmol), cyclohexene (0.304 mL, 3.75 mmol), and 1.0 M boron tribromide in dichloromethane (9.0 mL, 9.0 mmol) according to the procedure and in the same manner as described in Example 1, step b. The crude product was purified by flash column chromatography on silica gel, eluting with dichloromethane to yield 4-[(8-chloro-6-methylphenanthridin-5(6H)-yl)sulfonyl]phenol (0.24 g, 0.63 mmol, 42%) as a white solid, m.p. 176–178° C.;

MS [(-ESI), m/z]: 384 [M-H]$^-$;

$^1$H NMR (500 MHz, DMSO-d$_6$) δ: 10.23 (s, 1H, —OH-4'), 7.78 (dd, J=7.7, 1.6 Hz, 1H, ArH-1), 7.60 (dd, J=7.9, 1.2 Hz, 1H, ArH-4), 7.49 (d, J=8.5 Hz, 1H, ArH-10), 7.46–7.36 (m, 3H, ArH-2,3,7), 7.17 (dd, J=8.5, 2.2 Hz, 1H, ArH-9), 6.87 (d, J=8.9 Hz, 2H, ArH'-2',6'), 6.38 (d, J=8.9 Hz, 2H, ArH'-3',5'), 5.41 (q, J=7.0 Hz, 1H, H-6), 1.12 (d, J=7.0 Hz, 3H, —CH$_3$-6);

Anal. calcd for C$_{20}$H$_{16}$ClNO$_3$S.0.45H$_2$O: C, 60.97; H, 4.32; N, 3.56. Found: C, 60.95; H, 4.01; N, 3.43.

EXAMPLE 62

Step a)

2-Bromo-8-chloro-5-[(4-meth xyphenyl)sulfonyl]-6-m thyl-5,6-dihydrophenanthridin The title compound was prepared from 8-chloro-5-[(4-methoxyphenyl)sulfonyl]-6-methyl-5,6-dihydrophenanthridine (0.95 g, 2.38 mmol), bromine (0.12 mL, 9.50 mmol), and glacial acetic acid (24 mL) according to the procedure and in the same manner as described in Example 4, step a. The crude product was purified by flash column chromatography on silica gel, eluting with a mixture of ethyl acetate-hexane (1:3 to 1:1 gradient) to yield 2-bromo-8-chloro-5-[(4-methoxyphenyl)sulfonyl]-6-methyl-5,6-dihydrophenanthridine (0.70 g, 1.46 mmol, 61%) as a white solid;

MS [(+ESI), m/z]: 478 [M+H]$^+$;

$^1$H NMR (500 MHz, DMSO-d$_6$) δ: 8.01 (d, J=2.1 Hz, 1H, ArH-1), 7.64 (dd, J=8.6, 2.1 Hz, 1H, ArH-4), 7.56–7.53 (m, 2H, ArH-3,10), 7.38 (d, J=2.1 Hz, 1H, ArH-7), 7.16 (dd, J=8.4, 2.1 Hz, 1H, ArH-9), 7.05 (d, J=9.0 Hz, 2H, ArH'-2', 6'), 6.63 (d, J=8.9 Hz, 2H, ArH'-3',5'), 5.43 (q, J=7.0 Hz, 1H, H-6), 3.67 (s, 3H, —OCH$_3$-4'), 1.14 (d, J=7.0 Hz, 3H, —CH$_3$-6);

Anal. calcd for C$_{21}$H$_{17}$BrClNO$_3$S: C, 52.68; H, 3.58; N, 2.93. Found: C, 52.98; H, 3.71; N, 2.9.

Step b)

4-[(2-Bromo-8-chloro-6-methylphenanthridin-5(6H)-yl)sulfonyl]phenol

The title compound was prepared from 2-bromo-8-chloro-5-[(4-methoxyphenyl)sulfonyl]-6-methyl-5,6-dihydrophenanthridine (0.6 g, 1.25 mmol), cyclohexene (0.32 mL, 3.13 mmol), and 1.0 M boron tribromide in dichloromethane (7.52 mL, 7.52 mmol) according to the procedure and in the same manner as described in Example 1, step b. The crude product was purified by flash column chromatography on silica gel, eluting with dichloromethane to yield 4-[(2-bromo-8-chloro-6-methylphenanthridin-5(6H)-yl)sulfonyl]phenol (0.33 g, 0.71 mmol, 56%) as a light-yellow solid, m.p. 213–215° C.;

MS [(-ESI) m/z]: 462 [M-H]$^-$;

$^1$H NMR (500 MHz, DMSO-d$_6$) δ: 10.29 (s, 1H, —OH-4'), 8.01 (d, J=2.0 Hz, 1H, ArH-1), 7.63–7.52 (m, 3H, ArH-3,4,10), 7.41 (d, J=1.9 Hz, 1H, ArH-7), 7.18 (dd, J=8.4, 2.0 Hz, 1H, ArH-9), 6.92 (d, J=8.7 Hz, 2H, ArH'-2',6'), 6.41 (d, J=8.7 Hz, 2H, ArH'-3',5'), 5.43 (q, J=6.9 Hz, 1H, H-6), 1.13 (d, J=6.9 Hz, 3H, —CH$_3$-6);

Anal. calcd for C$_{20}$H$_{15}$BrClNO$_3$S: C, 51.69; H, 3.25; N, 3.01. Found: C, 51.53; H, 3.26; N, 2.93.

Examples 63 to 98 were synthesized as an automated directed array in an combinatorial manner according to General Procedure A described below.

General Procedure A

Step a)

A 0.25 M solution of 2-bromo-6-ethyl-5-[(4-methoxyphenyl)sulfonyl]-5,6-dihydrophenanthridine (400 µL, 45.8 mg, 100 µmol) in 1,4-dioxane and a 0.25 M solution of the aryl (or alkyl) boronic acid (800 µL, 200 µmol) in 1,4-dioxane were mixed together in a two dram vial and treated with a freshly prepared 0.05 M solution of tetrakis(triphenylphosphine)palladium (0) (300 µL, 5.78 mg, 15 µmol) and a 2 M aqueous solution of sodium carbonate (150 µL, 41.5 mg, 300 µmol). The mixture was purged with argon for 30 minutes and heated to 100° C. for up to six hours. The reaction progress was monitored by high-performance liquid chromatography. At completion, the reaction was cooled to room temperature and diluted with dichloromethane (3 mL) and a 0.5 M aqueous sodium hydroxide solution (2 mL). After shaking for 30 minutes and centrifugation, the organic phase was separated and concentrated to a residue in a clean vial, and the product confirmed by MS (APCI+).

Step b)

A shaken solution of the Suzuki coupled product of General Procedure A, Step a, and cyclohexene (100 μL, 1.0 mmol) in dichloromethane (600 μL) was treated under argon in a glove box at −30° C. with a solution of 1.0 M boron tribromide in dichloromethane (800 μL, 800 μmol). After the addition was completed, the reaction mixture was allowed to warm to room temperature for five hours. The reaction was cooled to −30° C., and quenched with methanol (200 μL) at a rate of 1 mL/min. The mixture was diluted with dichloromethane (2 mL) and water (2 mL), shaken; and the organic phase was separated and concentrated by centrifugation to a residue. The residue was diluted with dimethyl sulfoxide (800 μL) and purified by high-throughput purification techniques to yield the purified compound, which was confirmed by LCMS (ES−, FA, CV=20 or 5).

EXAMPLE 63

2-{6-Ethyl-5-[(4-hydroxyph nyl)sulfonyl]-5,6-dihydr ph nanthridin-2-yl}ph nol

HRMS [(+ESI), m/z]: 458.14151 [M+H]$^+$. Calcd. for $C_{27}H_{23}NO_4S$: 458.14206.

EXAMPLE 64

4-{[6-Ethyl-2-[4-(methylthio)phenyl]phenanthridin-5(6H)-yl]sulfonyl}phenol

HRMS [(+ESI), m/z]: 488.13407 [M+H]$^+$. Calcd. for $C_{28}H_{25}NO_3S_2$: 488.13487.

EXAMPLE 65

4-{[6-Ethyl-2-[(E)-2-phenylethenyl]phenanthridin-5(6H)-yl]sulfonyl}phenol

HRMS [(+ESI), m/z]: 468.16250 [M+H]$^+$. Calcd. for $C_{29}H_{25}NO_3S$: 468.16279.

EXAMPLE 66

4-{[2-(1,1'-Biphenyl-4-yl)-6-ethylphenanthridin-5(6H)-yl]sulfonyl}phenol

HRMS [(+ESI), m/z]: 518.17747 [M+H]$^+$. Calcd. for $C_{33}H_{27}NO_3S$: 518.17844.

EXAMPLE 67

4-{[2-(3-Chlorophenyl)-6-ethylphenanthridin-5(6H)-yl]sulfonyl}phenol

HRMS [(+ESI), m/z]: 476.10774 [M+H]$^+$. Calcd. for $C_{27}H_{22}ClNO_3S$: 476.10817.

EXAMPLE 68

4-[(6-Ethyl-2-quinolin-8-ylphenanthridin-5(6H)-yl)sulfonyl]phenol

HRMS [(+ESI), m/z]: 493.15815 [M+H]$^+$. Calcd. for $C_{30}H_{24}N_2O_3S$: 493.15804.

EXAMPLE 69

4-[(6-Ethyl-2-ph nylphenanthridin-5(6H)-yl)sulfonyl]phenol

HRMS [(+ESI), m/z]: 442.14691 [M+H]$^+$. Calcd. for $C_{27}H_{23}NO_3S$: 442.14714.

EXAMPLE 70

4-{[6-Ethyl-2-(2-m thylph nyl)phenanthridin-5(6H)-yl]sulfonyl}phenol

HRMS [(+ESI), m/z]: 456.16263 [M+H]$^+$. Calcd. for $C_{28}H_{25}NO_3S$: 456.16279.

EXAMPLE 71

4-[(6-Ethyl-2-thianthren-1-ylphenanthridin-5(6H)-yl)sulfonyl]phenol

HRMS [(+ESI), m/z]: 580.10708 [M+H]$^+$. Calcd. for $C_{33}H_{25}NO_3S_3$: 580.10694.

EXAMPLE 72

4-{[2-(1-Benzofuran-2-yl)-6-ethylphenanthridin-5(6H)-yl]sulfonyl}phenol

HRMS [(+ESI), m/z]: 482.14186 [M+H]$^+$. Calcd. for $C_{29}H_{23}NO_4S$: 482.14206.

EXAMPLE 73

4-{[6-Ethyl-2-(4-hydroxyphenyl)phenanthridin-5(6H)-yl]sulfonyl}phenol

HRMS [(+ESI), m/z]: 458.14136 [M+H]$^+$. Calcd. for $C_{27}H_{23}NO_4S$: 458.14206.

EXAMPLE 74

4-{[2-(2-Chlorophenyl)-6-ethylphenanthridin-5(6H)-yl]sulfonyl}phenol

HRMS [(+ESI), m/z]: 476.10818 [M+H]$^+$. Calcd. for $C_{27}H_{22}ClNO_3S$: 476.10817.

EXAMPLE 75

4-{[6-Ethyl-2-(4-ethylphenyl)phenanthridin-5(6H)-yl]sulfonyl}phenol

HRMS [(+ESI), m/z]: 470.17797 [M+H]$^+$. Calcd. for $C_{29}H_{27}NO_3S$: 470.17844.

EXAMPLE 76

1-(5-{6-Ethyl-5-[(4-hydroxyph nyl)sulfonyl]-5,6-dihydroph nanthridin-2-yl}thi n-2-yl)ethanone HRMS [(+ESI), m/z]: 490.11440 [M+H]$^+$. Calcd. for $C_{27}H_{23}NO_4S_2$: 490.11413.

EXAMPLE 77

5-{6-Ethyl-5-[(4-hydroxyphenyl)sulfonyl]-5,6-dihydrophenanthridin-2-yl}pyrimidine-2,4-diol HRMS [(+ESI), m/z]: 476.12804 [M+H]$^+$. Calcd. for $C_{25}H_{21}N_3O_5S$: 476.12747.

EXAMPLE 78

4-{[6-Ethyl-2-(2-hydroxyphenyl)phenanthridin-5(6H)-yl]sulfonyl}-2-methylphenol

HRMS [(+ESI), m/z]: 472.15783 [M+H]$^+$. Calcd. for $C_{28}H_{25}NO_4S$: 472.15771.

EXAMPLE 79

4-[(6-Ethyl-2-thien-3-ylphenanthridin-5(6H)-yl)sulfonyl]-2-methylphenol

HRMS [(+ESI), m/z]: 462.11896 [M+H]$^+$. Calcd. for $C_{26}H_{23}NO_3S_2$: 462.11921.

EXAMPLE 80

4-{[6-Ethyl-2-[4-(methylthio)phenyl]phenanthridin-5(6H)-yl]sulfonyl}-2-methylphenol HRMS [(+ESI), m/z]: 502.15006 [M+H]$^+$. Calcd. for $C_{29}H_{27}NO_3S_2$: 502.15052.

EXAMPLE 81

4-{[6-Ethyl-2-[(E)-2-phenylethenyl]phenanthridin-5(6H)-yl]sulfonyl}-2-methylphenol HRMS [(+ESI), m/z]: 482.17829 [M+H]$^+$. Calcd. for $C_{30}H_{27}NO_3S$: 482.17844.

EXAMPLE 82

4-{6-Ethyl-5-[(4-hydroxy-3-methylphenyl)sulfonyl]-5,6-dihydroph nanthridin-2-yl}b nz ne-1,2-di l HRMS [(+ESI), m/z]: 488.15249 [M+H]$^+$. Calcd. for $C_{28}H_{25}NO_5S$: 488.15262.

EXAMPLE 83

4-{[2-(1,1'-Biphenyl-4-yl)-6-ethylphenanthridin-5(6H)-yl]sulfonyl}-2-methylphenol HRMS [(+ESI), m/z]: 532.19391 [M+H]$^+$. Calcd. for $C_{34}H_{29}NO_3S$: 532.19409.

EXAMPLE 84

4-{[6-Ethyl-2-(3-hydroxyphenyl)phenanthridin-5(6H)-yl]sulfonyl}-2-methylphenol

HRMS [(+ESI), m/z]: 472.15779 [M+H]$^+$. Calcd. for $C_{28}H_{25}NO_4S$: 472.15771.

EXAMPLE 85

4-{[2-(3-Chlorophenyl)-6-ethylphenanthridin-5(6H)-yl]sulfonyl}-2-methylphenol

HRMS [(+ESI), m/z]: 490.12370 [M+H]$^+$. Calcd. for $C_{28}H_{24}ClNO_3S$: 490.12382.

EXAMPLE 86

4-{[6-Ethyl-2-[(E)-hept-1-enyl]phenanthridin-5(6H)-yl]sulfonyl}-2-methylphenol

HRMS [(+ESI), m/z]: 476.22567 [M+H]$^+$. Calcd. for $C_{29}H_{33}NO_3S$: 476.22539.

EXAMPLE 87

4-[(6-Ethyl-2-pyridin-4-ylphenanthridin-5(6H)-yl)sulfonyl]-2-methylphenol

HRMS [(+ESI), m/z]: 457.15770 [M+H]$^+$. Calcd. for $C_{27}H_{24}N_2O_3S$: 457.15804.

EXAMPLE 88

4-[(6-Ethyl-2-quinolin-8-ylphenanthridin-5(6H)-yl)sulfonyl]-2-methylphenol

HRMS [(+ESI), m/z]: 507.17306 [M+H]$^+$. Calcd. for $C_{31}H_{26}N_2O_3S$: 507.17369.

EXAMPLE 89

4-{[6-Ethyl-2-(2-methylphenyl)phenanthridin-5(6H)-yl]sulfonyl}-2-methylphenol

HRMS [(+ESI), m/z]: 470.17835 [M+H]$^+$. Calcd. for $C_{29}H_{27}NO_3S$: 470.17844.

EXAMPLE 90

4-{[2-(1-Benzothien-2-yl)-6-ethylphenanthridin-5(6H)-yl]sulfonyl}-2-methylphenol HRMS [(+ESI), m/z]: 512.13482 [M+H]$^+$. Calcd. for $C_{30}H_{25}NO_3S_2$: 512.13487.

EXAMPLE 91

4-{[2-(1-Benzothien-3-yl)-6-ethylphenanthridin-5(6H)-yl]sulfonyl}-2-methylphenol HRMS [(+ESI), m/z]: 512.13470 [M+H]$^+$. Calcd. for $C_{30}H_{25}NO_3S_2$: 512.13487.

EXAMPLE 92

4-[(2-Dibenzo[b,d]furan-4-yl-6-ethylphenanthridin-5(6H)-yl)sulfonyl]-2-methylphenol HRMS [(+ESI), m/z]: 546.17342 [M+H]$^+$. Calcd. for $C_{34}H_{27}NO_4S$: 546.17336.

EXAMPLE 93

4-{[2-(1-Benzofuran-2-yl)-6-ethylphenanthridin-5(6H)-yl]sulfonyl}-2-methylphenol HRMS [(+ESI), m/z]: 496.15765 [M+H]$^+$. Calcd. for $C_{30}H_{25}NO_4S$: 496.15771.

EXAMPLE 94

4-{[6-Ethyl-2-(4-hydroxyph nyl)phenanthridin-5(6H)-yl]sulf nyl}-2-methylph n l

HRMS [(+ESI), m/z]: 472.15758 [M+H]$^+$. Calcd. for $C_{28}H_{25}NO_4S$: 472.15771.

EXAMPLE 95

4-{[2-(2-Chlorophenyl)-6-ethylphenanthridin-5(6H)-yl]sulfonyl}-2-methylphenol

HRMS [(+ESI), m/z]: 490.12405 [M+H]$^+$. Calcd. for $C_{28}H_{24}ClNO_3S$: 490.12382.

EXAMPLE 96

4-{[6-Ethyl-2-(4-ethylphenyl)phenanthridin-5(6H)-yl]sulfonyl}-2-methylphenol

HRMS [(+ESI), m/z]: 484.19412 [M+H]$^+$. Calcd. for $C_{30}H_{29}NO_3S$: 484.19409.

EXAMPLE 97

1-(5-{6-Ethyl-5-[(4-hydroxy-3-methylphenyl)sulfonyl]-5,6-dihydrophenanthridin-2-yl}thien-2-yl)ethanone HRMS [(+ESI), m/z]: 504.12969 [M+H]$^+$. Calcd. for $C_{28}H_{25}NO_4S_2$: 504.12978.

EXAMPLE 98

5-{6-Ethyl-5-[(4-hydroxy-3-methylphenyl)sulfonyl]-5,6-dihydrophenanthridin-2-yl}pyrimidine-2,4-diol HRMS [(+ESI), m/z]: 490.14349 [M+H]$^+$. Calcd. for $C_{26}H_{23}N_3O_5S$: 490.14312.

EXAMPLE 99

Step a)

1-(2',4,4'-Trifluoro-1,1'-biphenyl-2-yl)ethanone

A stirred solution of 2-bromo-5-fluoroacetophenone (11.72 g, 54 mmol) and 2,4-difluorophenylboronic acid (8.53 g, 54 mmol) in tetrahydrofuran (600 mL) was treated under nitrogen with [1,1'-bis(diphenylphosphino)ferrocene] dichloropalladium (II) complex with dichloromethane (2.20 g, 2.69 mmol, 5 mole %) and a 5 N sodium hydroxide solution (21.6 mL, 108 mmol). The reaction was heated at 60° C. for twelve hours, cooled to room temperature, and the solvent removed in vacuo. The residue was dissolved in diethyl ether, filtered through a short column of silica gel, and the solvent evaporated in vacuo to a crude brown oil (11.72 g). The crude oil was purified by preparative liquid chromatography on a Biotage® 40 Mi column of pre-packed silica gel (90 g), eluting with a gradient of between 3% and 10% methyl tert-butyl ether in hexane at a flow rate of 50 mL/min to afford, after evaporation of the solvent, the title compound as a purified, colorless oil (7.11 g, 28.4 mmol, 52%);

HRMS [(+ESI), m/z]: 251.06705 [M+H]$^+$. Calcd for $C_{14}H_9F_3O$: 251.06783;

IR (Film), $v_{max}$: 2918, 1695, 1604, 1481, 1424, 1267, 1186, 1139, 1100, 962, 850, 814 cm$^{-1}$;

$^1$H NMR (400 MHz, DMSO-d$_6$) δ: 2.44 (s, 3H), 7.16 (tdd, J=8.5, 2.5, 0.9 Hz, 1H), 7.28 (ddd, J=10.5, 9.4, 2.6 Hz, 1H), 7.37–7.45 (m, 2H), 7.50 (td, J=8.5, 2.7 Hz, 1H), 7.75 (dd, J=9.4, 2.7 Hz, 1H);

Anal. calcd for $C_{14}H_9F_3O$: C, 67.20; H, 3.63; N, 0.00. Found: C, 67.37; H, 3.46; N, 0.00.

Step b)

1-(2',4,4'-Trifluoro-1,1'-biphenyl-2-yl)ethylamine

A stirred solution of 1-(2',4,4'-trifluoro-1,1'-biphenyl-2-yl)ethanone (6.80 g, 27.2 mmol) in anhydrous methanol (560 mL) was treated with dried ammonium acetate (108 g, 1.4 mol) and sodium cyanoborohydride (3.64 g, 56 mmol). The reaction was heated under nitrogen at 60° C. for fifteen hours, cooled to room temperature, and the solvent removed in vacuo. The residue was treated with a saturated, aqueous ammonia solution and extracted twice with diethyl ether. The combined organic phase was washed sequentially with water and eight times (or until the amine was no longer present in the organic layer) with a 2 N aqueous hydrochloric acid solution. The combined acidic aqueous layer was filtered to afford a dialkyated dimer, N,N-bis[1-(2',4,4'-trifluoro-1,1'-biphenyl-2-yl)ethyl]amine hydrochloride (1:1) (0.86 g 1.77 mmol, 13%), as a colorless solid, m.p. 285° C. The aqueous filtrate was extracted with diethyl ether (1×) and neutralized to pH 10 with a 2.5 N aqueous sodium hydroxide solution. The aqueous phase was extracted with diethyl ether (3×). The combined organic phase was washed with water, dried over anhydrous sodium sulfate, filtered, and the solvent removed in vacuo below room temperature to afford the title compound, as a homogeneous, clear, colorless oil (4.30 g, 17.1 mmol, 61%);

HRMS [(+ESI), m/z]: 252.09935 [M+H]$^+$. Calcd. for $C_{14}H_{12}F_3N$: 252.09946;

$^1$H NMR (400 MHz, DMSO-d$_6$) δ: 1.07 (broad s, 3H), 2.01 (broad s, 2H), 3.77 (q, J=6.2 Hz, 1H), 7.07–7.18 (m, 3H), 7.32–7.46 (m, 2H), 7.53 (d, J=10.5 Hz, 1H).

Step c)

4-Methoxy-N-[1-(2',4,4'-trifluoro-1,1'-biphenyl-2-yl) thyl]benz nesulfonamide A stirred solution of 1-(2',4,4'-trifluoro-1,1'-biphenyl-2-yl)ethylamine (0.71 g, 2.84 mmol) in dichloromethane (5 mL) was treated with 4-methoxybenzenesulfonyl chloride (0.62 g, 3.0 mmol), and N,N-diisopropylethylamine (0.77 g, 6.0 mmol). The reaction was stirred at room temperature for twelve hours, and the solvent evaporated in vacuo to a crude oil. The crude oil was purified by preparative liquid chromatography on a Biotage® 40 Mi column of pre-packed silica gel (90 g), eluting with a gradient of between 5% and 50% methyl tert-butyl ether in hexane at a flow rate of 40 mL/min, to afford, after evaporation of the solvent, a colorless oil. Crystallization of the colorless oil from diethyl ether-hexane yielded the title compound (0.80 g, 1.90 mmol, 67%) as a homogeneous, colorless, crystalline solid, m.p. 178–180° C.;

MS [(+ESI), m/z]: 422 [M+H]$^+$;

MS [(–ESI), m/z]: 420 [M–H]$^-$;

IR (Solid), $v_{max}$: 3241, 1594, 1481, 1425, 1325, 1264, 1145, 1024, 835, 670 cm$^{-1}$;

$^1$H NMR (400 MHz, DMSO-d$_6$) δ: 1.16 (d, J=6.9 Hz, 3H), 3.79 (s, 3H), 4.04 (m, 1H), 6.93 (d, J=8.7 Hz, 2H), 7.05–7.38 (m, 6H), 7.42 (ddd, J=8.9, 2.8, 2.2 Hz, 2H), 8.06 (d, J=5.4 Hz, 1H, major rotamer), 8.11 (d, J=4.9 Hz, 1H, minor rotamer), exists as approximately 2:1 ratio of rotamers;

Anal. calcd for $C_{21}H_{18}F_3NO_3S$: C, 59.85; H, 4.31; N, 3.32. Found: C, 59.93; H, 4.33 N, 3.34.

Step d)

3,8-Difluoro-5-[(4-methoxyphenyl)sulfonyl]-6-methyl-5,6-dihydrophenanthridin A stirred suspension of 4-methoxy-N-[1-(2',4,4'-trifluoro-1,1'-biphenyl-2-yl)ethyl]benzenesulfonamide (0.74 g, 1.74 mmol) and potassium carbonate (0.48 g, 3.50 mmol) in N,N-dimethylformamide (5 mL) was heated for twelve hours at 100° C. The reaction mixture was cooled and poured into distilled water. After stirring overnight at room temperature, a precipitate was filtered and dried under high vacuum. The precipitate was purified by preparative liquid chromatography on a Biotage® 40 Mi column of pre-packed silica gel (90 g), eluting with a mixture of 15% methyl tert-butyl ether in hexane at a flow rate of 50 mL/min to afford, after evaporation of the solvent, a colorless solid. Crystallization from diethyl ether-hexane yielded the title compound (0.67 g, 1.65 mmol, 95%) as a homogeneous, colorless, crystalline solid, m.p. 141–143° C.;

MS [(+ESI), m/z]: 402 [M+H]$^+$;

IR (Solid), $v_{max}$: 1593, 1479, 1340, 1240, 1150, 1071, 960, 811, 699 cm$^{-1}$;

$^1$H NMR (400 MHz, DMSO-d$_6$) δ: 1.16 (d, J=7.0 Hz, 3H), 3.66 (s, 3H), 5.46 (q, J=6.9 Hz, 1H), 6.64 (ddd, J=9.1, 3.1, 2.1 Hz, 2H), 6.97 (td, J=8.8, 2.6 Hz, 1H), 7.06 (ddd, J=9.1, 3.1, 2.1 Hz, 2H), 7.19 (dd, J=9.2, 2.7 Hz, 1H), 7.27 (td, J=8.6, 2.7 Hz, 1H), 7.41 (dd, J=10.0, 2.7 Hz, 1H), 7.50 (dd, J=8.8, 5.4 Hz, 1H), 7.84 (dd, J=8.8, 6.2 Hz, 1H);

Anal. calcd for $C_{21}H_{17}F_2NO_3S$: C, 62.83; H, 4.27; N, 3.49. Found: C, 63.07; H, 4.22; N, 3.39.

Step e)

4-{[(6R)-3,8-Difluoro-6-methylphenanthridin-5 (6H)-yl]sulfonyl}phenol*

A stirred suspension of 3,8-difluoro-5-[(4-methoxyphenyl)sulfonyl]-6-methyl-5,6-dihydrophenanthridine (0.73 g, 1.74 mmol) and cyclohexene (4.10 g, 50.0 mmol) was treated at room temperature under nitrogen with a solution of 1.0 M boron tribromide in dichloromethane (15 mL, 15.0 mmol). After stirring for approximately four hours at room temperature, the reaction was cooled to −20° C. and quenched with methanol (5 mL). The solvent was evaporated in vacuo to a dark oil. The dark oil was purified by preparative liquid chromatography on a Biotage 40 Mi column of pre-packed silica gel (90 g), eluting with a gradient of between 5% and 30% methyl tert-butyl ether in hexane at a flow rate of 50 mL/min to afford, after evaporation of the solvent in vacuo and trituration with hexane, 4-[(3,8-difluoro-6-methylphenanthridin-5(6H)-yl)sulfonyl]phenol as a colorless racemic solid (0.44 g, 1.13 mmol, 65%).

The enantiomers of 4-[(3,8-difluoro-6-methylphenanthridin-5(6H)-yl)sulfonyl]phenol were separated by automated, preparative, normal phase, chiral chromatography on a Chiralpak AD-H® column (2×25 cm) eluting with a mixture of 10% 2-propanol in hexane at a flow rate of 20 mL/min. After evaporation of the solvent in vacuo, peak one with a retention time at 13.2 minutes and monitored by ultraviolet detection yielded, after trituration with 2-propanol-hexane, 4-{[(6R)-3,8-difluoro-6-methylphenanthridin-5(6H)-yl]sulfonyl}phenol* (0.15 g, 0.40 mmol, 23%) as a homogeneous, colorless, amorphous solid, m.p. 194–195° C.;

$T_R$=13.2 minutes;

$[\alpha]_D^{25}$=−225° (c=11.7 mg/mL in MeOH);

MS [(+ESI), m/z]: 388 [M+H]$^+$;

MS [(−ESI), m/z]: 386 [M−H]$^-$;

IR (Solid), $\nu_{max}$: 3397, 3320, 1586, 1482, 1440, 1241, 1147, 952, 812, 70 cm$^{-1}$;

$^1$H NMR (400 MHz, DMSO-d$_6$) δ: 1.15 (d, J=7.0 Hz, 3H), 5.45 (q, J=7.0 Hz, 1H), 6.43 (ddd, J=8.8, 2.8, 2.1 Hz, 2H), 6.95 (ddd, J=6.7, 2.8, 2.1 Hz, 2H), 6.98 (td, J=8.8, 2.6 Hz, 1H), 7.19 (dd, J=9.2, 2.7 Hz, 1H), 7.26 (td, J=8.7, 2.8 Hz, 1H), 7.40 (dd, J=10.0, 2.7 Hz, 1H), 7.53 (dd, J=8.8, 5.4 Hz, 1H), 7.85 (dd, J=8.8, 6.2 Hz, 1H), 10.29 (s, 1H);

Anal. calcd for C$_{20}$H$_{15}$F$_2$NO$_3$S: C, 62.01; H, 3.90; N, 3.62. Found: C, 61.67; H, 3.72; N, 3.59.

*The stereochemical configuration is not absolute and was assigned arbitrarily.

EXAMPLE 100

4-{[(6S)-3,8-Difluoro-6-methylphenanthridin-5(6H)-yl]sulfonyl}phenol*

The enantiomers of 4-[(3,8-difluoro-6-methylphenanthridin-5(6H)-yl)sulfonyl]phenol were separated by automated, preparative, normal phase, chiral chromatography on a Chiralpak AD-H® column (2×25 cm) eluting with a mixture of 10% 2-propanol in hexane at a flow rate of 20 mL/min. After evaporation of the solvent in vacuo, peak two with a retention time at 17.6 minutes and monitored by ultraviolet detection yielded, after trituration with 2-propanol-hexane, 4-{[(6S)-3,8-difluoro-6-methylphenanthridin-5(6H)-yl]sulfonyl}phenol* (0.15 g, 0.39 mmol, 22%) as a homogeneous, colorless, amorphous solid, m.p. 194–196° C.;

$T_R$=17.6 minutes;

$[\alpha]_D^{25}$=+233° (c=11.0 mg/mL in MeOH);

MS [(+ESI), m/z]: 388 [M+H]$^+$;

MS [(−ESI), m/z]: 386 [M−H]$^-$;

IR (Solid), $\nu_{max}$: 3396, 3329, 1586, 1481, 1439, 1327, 1241, 1147, 951, 812, 701 cm$^{-1}$;

$^1$H NMR (400 MHz, DMSO-d$_6$) δ: 1.15 (d, J=7.0 Hz, 3H), 5.45 (q, J=7.0 Hz, 1H), 6.43 (ddd, J=8.8, 2.8, 1.8 Hz, 2H), 6.96 (ddd, J=8.8, 2.8, 2.1 Hz, 2H), 6.98 (td, J=8.8, 2.8 Hz, 1H), 7.19 (dd, J=9.2, 2.7 Hz, 1H), 7.26 (td, J=8.6, 2.7 Hz, 1H), 7.40 (dd, J=10.0, 2.7 Hz, 1H), 7.53 (dd, J=8.5, 5.4 Hz, 1H), 7.85 (dd, J=8.8, 6.2 Hz, 1H), 10.29 (s, 1H);

Anal. calcd for C$_{20}$H$_{15}$F$_2$NO$_3$S: C, 62.01; H, 3.90; N, 3.62. Found: C, 60.94; H, 3.52; N, 3.50.

*The stereochemical configuration is not absolute and was assigned arbitrarily.

EXAMPLE 101

Step a)

3-M thoxy-N-[1-(2',4,4'-triflu ro-1,1'-biph nyl-2-yl) ethyl]benz n sulfonamid

The title compound was prepared from 1-(2',4,4'-trifluoro-1,1'-biphenyl-2-yl)ethylamine (0.71 g, 2.84 mmol), 3-methoxybenzenesulfonyl chloride (0.62 g, 3.0 mmol), and N,N-diisopropylethylamine (0.77 g, 6.0 mmol) in dichloromethane (5 mL) according to the procedure and in the same manner as described in Example 99, step c. The crude product was purified by preparative liquid chromatography on a Biotage® 40 Mi column of pre-packed silica gel (90 g), eluting with a gradient of between 5% and 50% methyl tert-butyl ether in hexane at a flow rate of 40 mL/min to afford, after evaporation of the solvent, a colorless oil. Crystallization of the colorless oil from ethyl acetate-hexane yielded the title compound (0.96 g, 2.28 mmol, 80%) as a homogeneous, colorless, crystalline solid, m.p. 129–130° C.;

MS [(+ESI), m/z]: 422 [M+H]$^+$;

MS [(−ESI), m/z]: 420 [M−H]$^-$;

IR (Solid), $\nu_{max}$: 3260, 1594, 1479, 1426, 1325, 1248, 1153, 1079, 917, 866, 681 cm$^{-1}$;

$^1$H NMR (400 MHz, DMSO-d$_6$) δ: 1.18 (d, J=6.7 Hz, 3H), 3.71, (s, 3H, minor rotamer), 3.74 (s, 3H, major rotamer), 4.04–4.11 (m, 1H), 6.98–7.38 (m, 10H), 8.25 (broad s, 1H, minor rotamer), 8.28 (broad s, 1H, major rotamer), exists as approximately 2:1 mixture of rotamers;

Anal. calcd for C$_{21}$H$_{18}$F$_3$NO$_3$S: C, 59.85; H, 4.31; N, 3.32. Found: C, 59.67; H, 4.11; N, 3.17.

Step b)

3,8-Difluoro-5-[(3-methoxyphenyl)sulfonyl]-6-methyl-5,6-dihydrophenanthridin

A stirred suspension of 3-methoxy-N-[1-(2',4,4'-trifluoro-1,1'-biphenyl-2-yl)ethyl]benzenesulfonamide (0.88 g, 2.1 mmol) and potassium carbonate (0.58 g, 4.2 mmol) in N,N-dimethylformamide (5 mL) was heated for twelve hours at 100° C. The reaction mixture was cooled and poured into distilled water. After stirring overnight at room temperature, a precipitate was filtered and dried under high vacuum. The title compound (0.81 g, 2.0 mmol, 96%) was obtained as a colorless, fine, crystalline powder, m.p. 147–149° C.;

MS [(+ESI), m/z]: 402 [M+H]$^+$;

IR (Solid), $\nu_{max}$: 1597, 1477, 1342, 1241, 1160, 1046, 955, 815, 705 cm$^{-1}$;

$^1$H NMR (400 MHz, DMSO-d$_6$) δ: 1.17 (d, J=7.0 Hz, 3H), 3.6 (s, 3H), 5.53 (q, J=7.0 Hz, 1H), 6.65 (dd, J=3.8, 1.4 Hz, 1H), 6.67 (dt, J=7.8, 1.2 Hz, 1H), 6.88 (ddd, J=8.3, 2.5, 0.8 Hz, 1H), 6.95 (td, J=8.8, 2.8 Hz, 1H), 7.04 (t, J=8.0 Hz, 1H), 7.23 (dd, J=9.2, 2.7 Hz, 1H), 7.30 (td, J=8.7, 2.8 Hz, 1H), 7.44 (dd, J=10.0, 2.7 Hz, 1H), 7.49 (dd, J=8.8, 5.4 Hz, 1H), 7.86 (dd, J=8.8, 6.2 Hz, 1H);

Anal. calcd for C$_{21}$H$_{17}$F$_2$NO$_3$S: C, 62.83; H, 4.27; N, 3.49. Found: C, 62.65; H, 3.92; N, 3.44.

Step c)

3-{[(6R)-3,8-Difluoro-6-methylphenanthridin-5(6H)-yl]sulfonyl}phenol*

A stirred suspension of 3,8-difluoro-5-[(3-methoxyphenyl)sulfonyl]-6-methyl-5,6-dihydrophenanthridine (0.90 g, 2.24 mmol) and cyclohexene (4.10 g, 50.0 mmol) was treated at room temperature under nitrogen with a solution of 1.0 M boron tribromide in dichloromethane (15 mL, 15.0 mmol). After stirring for approximately four hours at room temperature, the reaction was cooled to −20° C. and quenched with methanol (5 mL). The solvent was evaporated in vacuo to a dark oil. The dark oil was purified by preparative liquid chromatography on a Biotage® 40 Mi column of pre-packed silica gel (90 g), eluting with a gradient of between 5% and 30% methyl tert-butyl ether in hexane at a flow rate of 50 mL/min to afford, after evaporation of the solvent in vacuo and trituration with hexane, 4-[(3,8-difluoro-6-methylphenanthridin-5(6H)-yl)sulfonyl]phenol, as a colorless racemic solid (0.55 g, 1.42 mmol, 63%).

The enantiomers of 3-[(3,8-difluoro-6-methylphenanthridin-5(6H)-yl)sulfonyl]phenol were separated by automated, preparative, normal phase, chiral chromatography on a Chiralpak AS-H® column (2×25 cm) eluting with a mixture of 15% 2-propanol in hexane at a flow rate of 20 mL/min. After evaporation of the solvent in vacuo, peak one with a retention time at 18.1 minutes and monitored by ultraviolet detection yielded, after trituration with diethyl ether-hexane, 3-{[(6R)-3,8-difluoro-6-methylphenanthridin-5(6H)-yl]sulfonyl}phenol* (0.08 g, 0.20 mmol, 8.9%) as a homogeneous, colorless, amorphous solid, m.p. 181–183° C.;

$T_R$=18.1 minutes;

$[\alpha]_D^{25}$=−218° (c=10.5 mg/mL in MeOH);

MS [(+ESI), m/z]: 388 [M+H]$^+$;

MS [(−ESI), m/z]: 386 [M−H]$^-$;

IR (Solid), $v_{max}$: 3404, 1605, 1478, 1446, 1305, 1239, 1158, 1067, 959, 822, 709 cm$^{-1}$;

$^1$H NMR (400 MHz, DMSO-d$_6$) δ: 1.17 (d, J=7.0 Hz, 3H), 5.46 (q, J=6.8 Hz, 1H), 6.53 (t, J=2.1 Hz, 1H), 6.59 (ddd, J=7.8, 1.6, 0.9 Hz, 1H), 6.68 (ddd, J=8.1, 2.5, 0.8 Hz, 1H), 6.93 (t, J=8.0 Hz, 1H), 6.93 (td, J=8.7, 2.8 Hz, 1H), 7.17 (dd, J=9.2, 2.7 Hz, 1H), 7.28 (td, J=8.6, 2.7 Hz, 1H), 7.41 (dd, J=10.1, 2.6 Hz, 1H), 7.53 (dd, J=8.8, 5.4 Hz, 1H), 7.87 (dd, J=8.8, 6.2 Hz, 1H), 9.8 (s, 1H);

Anal. calcd for $C_{20}H_{15}F_2NO_3S$: C, 62.01; H, 3.90; N, 3.62. Found: C, 61.60; H, 3.76; N, 3.31.

*The stereochemical configuration is not absolute and was assigned arbitrarily.

EXAMPLE 102

3-{[(6S)-3,8-Difluoro-6-methylphenanthridin-5(6H)-yl]sulfonyl}phenol*

The enantiomers of 3-[(3,8-difluoro-6-methylphenanthridin-5(6H)-yl)sulfonyl]phenol were separated by automated, preparative, normal phase, chiral chromatography on a Chiralpak AS-H® column (2×25 cm) eluting with a mixture of 15% 2-propanol in hexane at a flow rate of 20 mL/min. After evaporation of the solvent in vacuo, peak two with a retention time at 19.6 minutes and monitored by ultraviolet detection yielded, after trituration with diethyl ether-hexane, 3-{[(6S)-3,8-difluoro-6-methylphenanthridin-5(6H)-yl]sulfonyl}phenol* (0.08 g, 0.20 mmol, 8.9%) as a homogeneous, colorless, amorphous solid, m.p. 181–182° C.;

$T_R$=19.6 minutes;

$[\alpha]_D^{25}$=+241° (c=10.0 mg/mL in CHCl$_3$);

MS [(−ESI), m/z]: 386 [M−H]$^-$;

IR (Solid), $v_{max}$: 3406, 1606, 1479, 1446, 1259, 1160, 1068, 823, 711 cm$^{-1}$;

$^1$H NMR (400 MHz, DMSO-d$_6$) δ: 1.17 (d, J=7.0 Hz, 3H), 5.46 (q, J=6.8 Hz, 1H), 6.53 (t, J=2.1 Hz, 1H), 6.59 (ddd, J=7.8, 1.6, 0.9 Hz, 1H), 6.68 (ddd, J=8.1, 2.5, 0.8 Hz, 1H), 6.93 (t, J=8.0 Hz, 1H), 6.93 (td, J=8.7, 2.8 Hz, 1H), 7.17 (dd, J=9.2, 2.7 Hz, 1H), 7.28 (td, J=8.6, 2.7 Hz, 1H), 7.41 (dd, J=10.1, 2.6 Hz, 1H), 7.53 (dd, J=8.8, 5.4 Hz, 1H), 7.87 (dd, J=8.8, 6.2 Hz, 1H), 9.8 (s, 1H);

Anal. calcd for $C_{20}H_{15}F_2NO_3S$: C, 62.01; H, 3.90; N, 3.62. Found: C, 61.83; H, 3.87; N, 3.51.

*The stereochemical configuration is not absolute and was assigned arbitrarily.

EXAMPLE 103

Step a)

2,4-Dimethoxy-N-[1-(2',4,4'-trifluoro-1,1'-biphenyl-2-yl)ethyl]benzen sulfonamide A stirred solution of 1-(2',4,4'-trifluoro-1,1'-biphenyl-2-yl)ethylamine (0.71 g, 2.84 mmol) in dichloromethane (5 mL) was treated with 2,4-dimethoxybenzenesulfonyl chloride (0.71 g, 3.0 mmol), and N,N-diisopropylethylamine (0.77 g, 6.0 mmol). The reaction was stirred at room temperature for twelve hours, and the solvent was evaporated in vacuo to a crude oil. The crude oil was purified by preparative liquid chromatography on a Biotage® 40 Mi column of pre-packed silica gel (90 g), eluting with a gradient of between 5% and 50% methyl tert-butyl ether in hexane at a flow rate of 40 mL/min to afford, after evaporation of the solvent, a colorless oil. Crystallization of the colorless oil from ethyl acetate-hexane yielded the title compound (0.93 g, 2.07 mmol, 73%) as a homogeneous, colorless, crystalline solid, m.p. 192–194° C.;

MS [(+ESI), m/z]: 452 [M+H]$^+$;

MS [(−ESI), m/z]: 450 [M−H]$^-$;

IR (Solid), $v_{max}$: 3281, 1592, 1470, 1421, 1319, 1136, 1022, 817, 681 cm$^{-1}$;

$^1$H NMR (400 MHz, DMSO-d$_6$) δ: 1.18 (d, J=6.7 Hz, 3H), 3.79 (s, 6H), 4.05 (m, 1H), 6.36–6.56 (m, 2H), 6.98–7.14 (m, 3H), 7.22 (broad t, 1H), 7.26–7.42 (m, 3H), 7.81 (broad d, J=8.0 Hz, 1H), exists as approximately 1:1 mixture of rotamers;

Anal. calcd for $C_{22}H_{20}F_3NO_4S$: C, 58.53; H, 4.47; N, 3.10. Found: C, 58.52; H, 4.45 N, 3.13.

Step b)

5-[(2,4-Dimethoxyphenyl)sulfonyl]-3,8-difluoro-6-methyl-5,6-dihydrophenanthridine A stirred suspension of 2,4-dimethoxy-N-[1-(2',4,4'-trifluoro-1,1'-biphenyl-2-yl)ethyl]benzenesulfonamide (0.86 g, 1.91 mmol) and potassium carbonate (0.53 g, 3.82 mmol) in N,N-dimethylformamide (5 mL) was heated for twelve hours at 100° C. The reaction mixture was cooled and poured into distilled water. After stirring overnight at room temperature, a precipitate was filtered and dried under high vacuum. The title compound (0.75 g, 1.74 mmol, 91%) was obtained as a colorless, fine, crystalline powder, m.p. 112–115° C.;

MS [(+ESI), m/z]: 432 [M+H]$^+$;

IR (Solid), $v_{max}$: 1596, 1480, 1345, 1163, 1067, 965, 811, 699 cm$^{-1}$;

$^1$H NMR (400 MHz, DMSO-d$_6$) δ: 1.19 (d, J=7.0 Hz, 3H), 3.15 (s, 3H), 3.71 (s, 3H), 5.35 (q, J=6.9 Hz, 1H), 6.20 (d, J=2.3 Hz, 1H), 6.47 (dd, J=9.1, 2.3 Hz, 1H), 7.06 (dd, J=9.3, 2.6 Hz, 1H), 7.08 (td, J=8.8, 2.6 Hz, 1H), 7.16 (td, J=8.6, 2.7 Hz, 1H), 7.34 (dd, J=10.6, 2.6 Hz, 1H), 7.57 (d, J=8.8 Hz, 1H), 7.76 (dd, J=8.5, 5.4 Hz, 1H), 7.91 (dd, J=8.8, 6.2 Hz, 1H);

Anal. calcd for $C_{22}H_{19}F_2NO_4S$: C, 61.24; H, 4.44; N, 3.25. Found: C, 61.20; H, 4.42; N, 3.24.

Step c)

4-{[(6S)-3,8-Difluoro-6-methylphenanthridin-5(6H)-yl]sulfonyl}benzene-1,3-diol*

A stirred suspension of 5-[(2,4-dimethoxyphenyl)sulfonyl]-3,8-difluoro-6-methyl-5,6-dihydrophenanthridine (0.69 g, 1.60 mmol) and cyclohexene (4.10 g, 50.0 mmol) was treated at room temperature under nitrogen with a solution of 1.0 M boron tribromide in dichloromethane (15 mL, 15.0 mmol). After stirring for approximately four hours at room temperature, the reaction was cooled to −20° C. and quenched with methanol (5 mL). The solvent was evaporated in vacuo to a dark oil. The dark oil was purified by preparative liquid chromatography on a Biotage® 40 Mi column of pre-packed silica gel (90 g), eluting with a gradient of between 5% to 30% methyl tert-butyl ether in hexane at a flow rate of 50 mL/min to afford, after evaporation of the solvent in vacuo and trituration with hexane, 4-[(3,8-difluoro-6-methylphenanthridin-5(6H)-yl)sulfonyl]benzene-1,3-diol, as a colorless racemic solid (0.55 g, 1.42 mmol, 63%).

The enantiomers of 4-[(3,8-difluoro-6-methylphenanthridin-5(6H)-yl)sulfonyl]benzene-1,3-diol were separated by automated, preparative, normal phase, chiral chromatography on a Chiralpak AS-H® (2×25 cm) column eluting with a mixture of hexane-2-propanol-ethanol in a ratio of 72/18/10% at a flow rate of 20 mL/min. After evaporation of the solvent in vacuo, peak one with a retention time at 11.2 minutes and monitored by ultraviolet detection yielded, after trituration with hexane, 4-{[(6S)-3,8-difluoro-6-methylphenanthridin-5(6H)-yl]sulfonyl}benzene-1,3-diol* (0.07 g, 0.17 mmol, 10.8%) as a homogeneous, colorless, amorphous solid, m.p. 163–165° C.;

$T_R$=11.2 minutes;

$[α]_D^{25}$=+197° (c=10.4 mg/mL in CHCl$_3$);

HRMS [(+ESI), m/z]: 404.07690 [M+H]$^+$. Calcd for $C_{20}H_{15}F_2NO_4S$: 404.07627;

IR (Solid), $v_{max}$: 3394, 1596, 1475, 1404, 1337, 1255, 1145, 1061, 957, 811, 715 cm$^{-1}$;

$^1$H NMR (400 MHz, DMSO-d$_6$) δ: 1.15 (d, J=7.0 Hz, 3H), 5.40 (q, J=6.9 Hz, 1H), 6.05 (d, J=2.3 Hz, 1H), 6.13 (dd, J=8.8, 2.3 Hz, 1H), 7.06–7.15 (m, 3H), 7.28 (d, J=8.8 Hz, 1H), 7.37 (dd, J=10.7, 2.7 Hz, 1H), 7.75 (dd, J=8.5, 5.4 Hz, 1H), 7.88 (dd, J=8.8, 6.5 Hz, 1H), 10.13 (s, 1H), 10.20 (s, 1H).

*The stereochemical configuration is not absolute and was assigned arbitrarily.

EXAMPLE 104

4-{[(6R)-3,8-Difluoro-6-methylphenanthridin-5(6H)-yl]sulfonyl}benzene-1,3-diol*

The enantiomers of 4-[(3,8-difluoro-6-methylphenanthridin-5(6H)-yl)sulfonyl]benzene-1,3-diol were separated by automated, preparative, normal phase, chiral chromatography on a Chiralpak AS-H® (2×25 cm) column eluting with a mixture of hexane-2-propanol-ethanol in a ratio of 72/18/10% at a flow rate of 20 mL/min. After evaporation of the solvent in vacuo, peak two with a retention time at 15.7 minutes and monitored by ultraviolet detection yielded, after trituration with diethyl ether-hexane, 4-{[(6R)-3,8-difluoro-6-methylphenanthridin-5(6H)-yl]sulfonyl}benzene-1,3-diol* (0.07 g, 0.17 mmol, 10.8%) as a homogeneous, colorless, amorphous solid, m.p. 153–156° C.;

$T_R$=15.7 minutes;

$[α]_D^{25}$=−199° (c=10.1 mg/mL in CHCl$_3$);

MS [(+ESI), m/z]: 404 [M+H]$^+$;

MS [(−ESI), m/z]: 402 [M−H]$^−$;

IR (Solid), $v_{max}$: 3393, 1596, 1475, 1337, 1239, 1145, 1061, 957, 840 cm$^{-1}$;

$^1$H NMR (400 MHz, DMSO-d$_6$) δ: 1.15 (d, J=7.0 Hz, 3H), 5.40 (q, J=6.9 Hz, 1H), 6.05 (d, J=2.3 Hz, 1H), 6.13 (dd, J=8.8, 2.3 Hz, 1H), 6.05–7.15 (m, 3H), 7.28 (d, J=8.8 Hz, 1H), 7.37 (dd, J=10.7, 2.7 Hz, 1H), 7.75 (dd, J=8.8, 5.4 Hz, 1H), 7.88 (dd, J=8.8, 6.5 Hz, 1H), 10.13 (s, 1H), 10.20 (s, 1H);

Anal. calcd for $C_{20}H_{15}F_2NO_4S$: C, 59.55; H, 3.75; N, 3.47. Found: C, 58.82; H, 3.54; N, 2.34.

*The stereochemical configuration is not absolute and was assigned arbitrarily.

EXAMPLE 105

Step a)

1-(2',4'-Difluoro-1,1'-biphenyl-2-yl)ethanone 2,4-Difluorophenylboronic acid (9.47 g, 60 mmol), tetrabutylammonium bromide (16.1 g, 50 mmol), and potassium carbonate (20.7 g, 150 mmol) were added to a flask followed by water (50 mL). The contents were mixed until most of the dissolvable solids were in solution. To the remaining slurry was added 2'-bromoacetophenone (9.95 g, 50 mmol) and palladium acetate (1.12 g, 5 mmol). The stirred contents were heated to 70° C. under a nitrogen atmosphere for 12 hours. Thin layer chromatography analysis indicated the formation of a single product. The reaction was allowed to cool to room temperature. Ethyl acetate (500 mL) was added and the organic phase was extracted with water (3×100 mL). The combined aqueous phase was extracted once with additional ethyl acetate and the organic phases were combined, dried over anhydrous sodium sulfate, filtered, and concentrated to provide a crude oil. The product was purified by preparative liquid chromatography on a Biotage® 40 Mi column of prepacked silica gel (90 g), eluting with a gradient of 5%–20% methyl tert-butyl ether in hexane, to afford the title compound (5.7 g, 49%) as a yellow oil;

MS [(+ESI), m/z]: 233 [M+H]$^+$;

$^1$H NMR (400 MHz, DMSO-d$_6$) δ: 2.42 (s, 3H), 7.16 (m, J=8.5, 8.5, 2.6, 1.0 Hz, 1H), 7.27 (m, 1H), 7.39 (m, 2H), 7.56 (td, J=7.6, 1.5 Hz, 1H), 7.64 (td, J=7.5, 1.4 Hz, 1H), 7.86 (m, J=7.6, 0.7, 0.7, 0.4 Hz, 1H);

Step b)

1-(2',4'-Difluoro-1,1'-biphenyl-2-yl)ethylamine

To a stirred solution of 1-(2',4'-difluoro-1,1'-biphenyl-2-yl)ethanone (3.67 g, 15.8 mmol) in anhydrous methanol (200 mL) was added solid ammonium acetate (12.2 g, 158 mmol). The reaction mixture was heated at 60° C. for one hour, followed by the addition of a methanolic solution of sodium cyanoborohydride (5 mL, 1.99 g, 31.6 mmol). After 16 hours, the methanol was removed in vacuo and aqueous ammonium hydroxide was added. The aqueous phase was extracted with diethyl ether (3×200 mL) until the amine was no longer present in the aqueous phase. The combined organic phase was washed with 2 N aqueous hydrochloric acid (3×100 mL) and the aqueous phases combined. The solid formed during the acid wash was determined to be the dialkyated amine and was segregated from the aqueous phase. Aqueous sodium hydroxide was added to the acidic aqueous phase until the solution was neutralized to pH 8 to 9. The basic aqueous phase was extracted with diethyl ether until the primary amine was no longer detected in the aqueous phase. The combined organic phase was dried over anhydrous sodium sulfate, filtered, and concentrated to afford a clear oil that was used without further purification;

MS [(+ESI), m/z]: 217 [M+H-17]$^+$, benzylic cation as a result of the loss of $NH_3$;

$^1$H NMR (400 MHz, DMSO-d$_6$) δ: 1.10 (d, J=25.6 Hz, 3H) 3.80 (q, J=6.5 Hz, 1H), 7.10 (d, J=7.5 Hz, 1H), 7.17 (m, 1H), 7.27 (td, J=7.5, 1.3 Hz, 1H), 7.34 (td, J=9.7, 2.6 Hz, 2H), 7.43 (td, J=7.6, 1.0 Hz, 1H), 7.71 (dd, J=6.1, 2.7 Hz, 1H);

Step c)

N-[1-(2',4'-Difluoro-1,1'-biphenyl-2-yl)ethyl]-4-methoxybenzenesulfonamide

4-Methoxybenzenesulfonyl chloride (341 mg, 1.7 mmol) was added to a solution of 1-(-2',4'-difluoro-biphenyl-2-yl)ethylamine (350 mg, 1.5 mmol) and triethylamine (418 μL, 3 mmol) in acetonitrile. The reaction progress was monitored by LCMS and after 2 hours the reaction appeared to be complete. Water was added and the resulting solid was collected by filtration. The solid was dissolved in dichloromethane and purified by preparative liquid chromatography on a Biotage® 40 Mi column of prepacked silica gel (90 g), eluting with a gradient of 30%–50% methyl tert-butyl ether in hexane (35 min), to afford the title compound (473 mg, 78%) as a white solid, m.p. 154–155° C.;

MS [(EI), m/z]: 403.11 (M+);

MS [(+ESI), m/z]: 404 [M+H]$^+$);

MS [(−ESI), m/z]: 402 [M−H]$^-$;

$^1$H NMR (400 MHz, DMSO-d$_6$) δ: 1.12 (d, J=7.0 Hz, 3H), 3.80 (s, 3H), 3.99 (m, 1H), 6.91 (t, J=8.8 Hz, 2H), 7.07 (m, 1H), 7.23 (m, 4H), 7.32 (m, 1H), 7.42 (d, J=8.8 Hz, 3H), 8.06 (d, J=6.7 Hz, 1H);

Anal. Calcd for $C_{21}H_{19}F_2NO_3S$: C, 62.52; H, 4.75; N, 3.47. Found: C, 62.37; H, 4.80; N, 3.25.

Step d)

3-Fluoro-5-[(4-methoxyphenyl)sulfonyl]-6-methyl-5,6-dihydrophenanthridine

N-[1-(2',4'-Difluoro-1,1'-biphenyl-2-yl)ethyl]4-methoxybenzenesulfonamide (347 mg, 0.86 mmol) was dissolved in anhydrous N,N-dimethylformamide (2 mL) and potassium carbonate (238 mg, 1.72 mmol) was added as a solid in one portion. The mixture was heated at 100° C. with stirring until a single product had formed as gauged by LCMS (5–6 hours). Water (10 mL) was added and a white solid precipitated from the cloudy solution. The mixture was allowed to stand until the solution was clear, and the precipitated solid was filtered and washed with additional water to afford the desired compound (324 mg, 98%) as a white solid, m.p. 137.5–139° C.;

MS [(EI), m/z]: 383.1 (M+.);

MS [(+ESI), m/z]: 384 [M+H]$^+$;

$^1$H NMR (400 MHz, DMSO-d$_6$): δ: 1.16 (d, J=7.0 Hz, 3H), 3.64 (s, 3H), 5.44 (q, J=7.0 Hz, 1H), 6.58 (m, 2H), 7.03 (m, 2H), 7.16 (m, J=19.6, 7.3, 7.3, 1.4 Hz, 2H), 7.26 (m, 2H), 7.42 (dd, J=10.1, 2.9 Hz, 1H), 7.45 (dd, J=7.6, 1.2 Hz, 1H), 7.86 (dd, J=8.8, 6.2 Hz, 1H);

Anal. Calcd for $C_{21}H_{18}FNO_3S$: C, 65.78; H, 4.73; N, 3.65. Found: C, 65.67; H, 4.68; N, 3.52.

Step e)

4-[(3-Fluoro-6-methylphenanthridin-5(6H)-yl)sulfonyl]phenol

To a stirred slurry of 3-fluoro-5-[(4-methoxyphenyl)sulfonyl]-6-methyl-5,6-dihydrophenanthridine (262 mg, 0.68 mmol) in cyclohexene (1.38 mL, 14 mmol) under an inert atmosphere of nitrogen was added a 1 M solution of boron tribromide in dichloromethane (4.1 mL). The progress of the reaction was monitored by thin-layered chromatography and after 2.5 hours the reaction was deemed complete. The reaction contents were cooled to 0° C. and methanol was added slowly. The volatile components were removed in vacuo and the crude residue was purified by preparative liquid chromatography on a Biotage® 40 Mi column of prepacked silica gel (90 g), eluting with a gradient of 30%–50% methyl tert-butyl ether in hexane, to afford the title compound (77 mg, 30%) as a solid, m.p. 162–165° C.;

MS [(+ESI), m/z]: 370 [M+H]$^+$;

MS [(−ESI), m/z]: 368 [M−H]$^-$;

$^1$H NMR (400 MHz, DMSO-d$_6$) δ: 1.15 (d, J=7.0 Hz, 3H), 5.43 (q, J=7.0 Hz, 1H), 6.38 (ddd, J=9.4, 2.9, 2.5 Hz, 2H), 6.93 (m, 2H), 7.17 (ddd, J=8.6, 7.2, 1.6 Hz, 2H), 7.24 (m, 2H), 7.41 (dd, J=10.1, 2.9 Hz, 1H), 7.48 (dd, J=7.4, 1.4 Hz, 1H), 7.86 (dd, J=8.8, 6.2 Hz, 1H), 10.23 (s, 1H), Small impurities.

EXAMPLE 106

Step a)

N-[1-(2',4'-Difluoro-1,1'-biphenyl-2-yl)ethyl]-3-methoxybenzenesulfonamide

The title compound was prepared from 3-methoxybenzenesulfonyl chloride (341 mg, 1.7 mmol), 1-(-2',4'-difluoro-biphenyl-2-yl)ethylamine (350 mg, 1.5 mmol), and triethylamine (418 μL, 3 mmol) according to the procedure and in the same manner as described in Example 105, step c. The solid was purified by preparative liquid chromatography on a Biotage® 40 Mi column of prepacked silica gel (90 g), eluting with a gradient of 30%–50% methyl tert-butyl ether in hexane (35 min), and the product (473 mg, 78%) isolated as a white solid, m.p. 127.5–129° C.;

MS [(+ESI), m/z]: 404 [M+H]$^+$;

MS [(−ESI), m/z]: 402 [M−H]$^-$);

$^1$H NMR (400 MHz, DMSO-d$_6$) δ: 1.15 (br d, J=7.0 Hz, 3H), 3.71 (m, J=13.5 Hz, 3H), 4.05 (m, 1H), 7.0 (s, 1H), 7.07 (m, 3H), 7.15 (br m, 1H), 7.23 (t, J=7.4 Hz, 2H) 7.31 (br m, 3H), 7.47 (d, J=7.8 Hz, 1H), 8.24 (br d, J=6.7 Hz, 1H);

Anal. Calcd for $C_{21}H_{19}F_2NO_3S$: C, 62.52; H, 4.75; N, 3.47. Found: C, 62.34; H, 4.75; N, 3.23.

Step b)

3-Fluoro-5-[(3-methoxyphenyl)sulfonyl]-6-methyl-5,6-dihydrophenanthridine

The title compound was prepared from N-[1-(2',4'-difluoro-1,1'-biphenyl-2-yl)ethyl]-3- methoxybenzenesulfonamide (454 mg, 1.12 mmol), anhydrous N,N-dimethylformamide (2 mL), and potassium carbonate (311 mg, 2.25 mmol) according to the procedure and in the same manner as described in Example 105, step d, and the product (426 mg, 99%) isolated as a white solid, m.p. 115–117° C.;

MS [(+ESI), m/z]: 384 [M+H]$^+$;

$^1$H NMR (400 MHz, DMSO-d$_6$) δ: 1.17 (d, J=7.0 Hz, 3H), 3.51 (s, 3H), 5.49 (q, J=6.8 Hz, 1H), 6.59 (dd, J=2.6, 1.8 Hz, 1H), 6.67 (ddd, J=7.7, 1.8, 0.9 Hz, 1H), 6.84 (ddd, J=8.4, 2.6, 0.9 Hz, 1H), 7.00 (m, 1H), 7.15 (m, 2H), 7.27 (dt, J=5.8, 1.7 Hz, 1H), 7.30 (m, 1H), 7.45 (ddd, J=7.2, 5.0, 2.2 Hz, 2H), 7.88 (dd, J=8.8, 6.2 Hz, 1H);

Anal. Calcd for C$_{21}$H$_{18}$FNO$_3$S: C, 65.78; H, 4.73; N, 3.65. Found: C, 65.54; H, 4.83; N, 3.52.

Step c)

3-[(3-Fluoro-6-methylphenanthridin-5(6H)-yl)sulfonyl]phenol

The title compound was prepared from 3-fluoro-5-[(3-methoxyphenyl)sulfonyl]-6-methyl-5,6-dihydrophenanthridine (350 mg, 0.91 mmol), cyclohexene (1.85 mL, 18 mmol), and 1.0 M solution of boron tribromide in dichloromethane (5.5 mL) according to the procedure and in the same manner as described in Example 105, step e. The volatile components were removed in vacuo and the crude residue was purified by preparative liquid chromatography on a Biotage® 40 Mi column of prepacked silica gel (90 g), eluting with a gradient of 30%–50% methyl tert-butyl ether in hexane, to afford the desired compound (77 mg, 30%) as a solid, m.p. 164–167° C.;

MS [(+ESI), m/z]: 370 [M+H]$^+$;

MS [(–ESI), m/z]: 368 [M–H]$^-$;

$^1$H NMR (400 MHz, DMSO-d$_6$) δ: 1.17 (d, J=7.0 Hz, 3H), 5.43 (q, J=6.9 Hz, 1H), 6.53 (m, 1H), 6.57 (m, 1H), 6.65 (ddd, J=8.2, 2.5, 0.9 Hz, 1H), 6.88 (t, J=8.0 Hz, 1H), 7.19 (m, 3H), 7.27 (m, 1H), 7.42 (dd, J=10.1, 2.9 Hz, 1H), 7.50 (dd, J=7.2, 1.6 Hz, 1H), 7.89 (dd, J=8.8, 6.2 Hz, 1H), 9.73 (s, 1H);

Anal. Calcd for C$_{20}$H$_{16}$FNO$_3$S: C, 65.03; H, 4.37; N, 3.79. Found: C, 64.85; H, 4.35; N, 3.51.

EXAMPLE 107

3-{[(6R)-3-Fluoro-6-methylphenanthridin-5(6H)-yl]sulfonyl}phenol

The enantiomers of 3-[(3-fluoro-6-methylphenanthridin-5(6H)-yl)sulfonyl]phenol (200 mg, 0.54 mmol) were separated by automated, preparative, normal phase, chiral chromatography on a Chiralpak AS (20 mm×250 mm) column eluting with a mixture of hexane-2-propanol-ethanol (85:10:5) at a flow rate of 20 mL/min. The fractions were combined and evaporated in vacuo, and one peak (99.8%) with a retention time of 9.18 minutes was isolated as a white solid (55 mg, 55% based upon a 1:1 ratio of enantiomers with a theoretical maximum amount of 100 mg);

[α]$_D^{25}$=–233° (c=10.0 mg/mL, CHCl$_3$);

MS [(+ESI) m/z]: 370 [M+H]$^+$;

MS [(–ESI), m/z]: 368 [M–H]$^-$;

$^1$H NMR (400 MHz, DMSO-d$_6$) δ: 1.17 (d, J=7.0 Hz, 3H), 5.43 (q, J=6.8 Hz, 1H), 6.53 (m, 1H), 6.57 (ddd, J=7.8, 1.8, 1.0 Hz, 1H), 6.65 (ddd, J=8.2, 2.5, 0.8 Hz, 1H), 6.88 (t, J=8.0 Hz, 1H), 7.18 (m, 3H), 7.27 (td, J=8.6, 2.7 Hz, 1H), 7.42 (dd, J=10.1, 2.6 Hz, 1H), 7.50 (dd, J=7.5, 1.6 Hz, 1H), 7.89 (dd, J=8.8, 6.2 Hz, 1H), 9.73 (s, 1H);

Anal. Calcd for C$_{20}$H$_{16}$FNO$_3$S: C, 65.03; H, 4.37; N, 3.79. Found: C, 65.35; H, 4.77; N, 3.47.

EXAMPLE 108

3-{[(6S)-3-Fluoro-6-methylphenanthridin-5(6H)-yl]sulfonyl}phenol

The enantiomers of 3-[(3-fluoro-6-methylphenanthridin-5(6H)-yl)sulfonyl]phenol (200 mg, 0.54 mmol) were separated by automated, preparative, normal phase, chiral chromatography on a Chiralpak AS (20 mm×250 mm) column eluting with a mixture of hexane-2-propanol-ethanol (85:10:5) at a flow rate of 20 mL/min. The fractions were combined and evaporated in vacuo, and one peak (99.9%) with a retention time of 11.154 minutes was isolated as a white solid (60 mg, 60% based upon a 1:1 ratio of enantiomers with a theoretical maximum amount of 100 mg);

[α]$_D^{25}$=+218° (c=10.0 mg/mL, CHCl$_3$);

MS [(+ESI), m/z]: 370 [M+H]$^+$;

MS [(–ESI), m/z]: 368 [M–H]$^-$;

$^1$H NMR (400 MHz, DMSO-d$_6$) δ: 1.17 (d, J=7.0 Hz, 3H), 5.43 (q, J=7.0 Hz, 1H), 6.53 (m, 1H), 6.57 (ddd, J=7.8, 1.7, 0.9 Hz, 1H), 6.65 (ddd, J=8.2, 2.5, 0.8 Hz, 1H), 6.88 (t, J=8.0 Hz, 1H), 7.18 (m, 3H), 7.27 (td, J=8.6, 2.7 Hz, 1H), 7.42 (dd, J=10.1, 2.6 Hz, 1H), 7.50 (dd, J=7.4, 1.7 Hz, 1H), 7.89 (dd, J=8.8, 6.2 Hz, 1H), 9.73 (s, 1H).

[α]$_D^{25}$=+249° (c=10.0 mg/mL, CHCl$_3$);

MS [(+ESI), m/z]: 370 [M+H]$^+$;

MS [(–ESI), m/z]: 368 [M–H]$^-$;

$^1$H NMR (400 MHz, DMSO-d$_6$) δ: 1.17 (d, J=7.0 Hz, 3H), 5.43 (q, J=7.0 Hz, 1H), 6.53 (m, 1H), 6.57 (ddd, J=7.8, 1.7, 0.9 Hz, 1H), 6.65 (ddd, J=8.2, 2.5, 0.8 Hz, 1H), 6.88 (t, J=8.0 Hz, 1H), 7.18 (m, 3H), 7.27 (td, J=8.6, 2.7 Hz, 1H), 7.42 (dd, J=10.1, 2.6 Hz, 1H), 7.50 (dd, J=7.4, 1.7 Hz, 1H), 7.89 (dd, J=8.8, 6.2 Hz, 1H), 9.73 (s, 1H).

EXAMPLE 109

Step a)

N-[1-(2',4'-Difluoro-1,1'-biphenyl-2-yl)ethyl]-2,4-dimethoxybenzenesulfonamide The title compound was prepared from 2,4-dimethoxybenzenesulfonyl chloride (473 mg, 2.0 mmol), 1-(2',4'-difluoro-1,1'-biphenyl-2-yl)ethylamine (466 mg, 2.0 mmol), and triethylamine (334 μL, 2.2 mmol) according to the procedure and in the same manner as described in Example 105, step c. The product was purified by preparative liquid chromatography on a Biotage® 40Mi column of prepacked column of silica gel (90 g), eluting with a gradient of 30%–50% methyl tert-butyl ether in hexane (35 min), to afford the desired compound (600 mg, 69%) as a white solid;

MS [(+ESI), m/z]: 434 [M+H]$^+$;

MS [(–ESI), m/z]: 432 [M–H]$^-$;

$^1$H NMR (400 MHz, DMSO-d$_6$) δ: 1.16 (d, J=6.7 Hz, 3H), 3.75 (s, 3H), 3.78 (s, 3H), 4.05 (m, 1H), 6.49 (m, 2H), 6.96 (d, J=7.5 Hz, 1H), 7.05 (m, 2H), 7.20 (t, J=7.6 Hz, 2H), 7.34 (m, 2H), 7.60 (d, J=7.8 Hz, 1H), 7.71 (d, J=7.8 Hz, 1H);

Anal. Calcd for C$_{22}$H$_{21}$F$_2$NO$_4$S: C, 60.96; H, 4.88; N, 3.23. Found: C, 60.74; H, 4.82; N, 3.05.

Step b)

3-Fluoro-5-[(2,4-dimethoxyphenyl)sulfonyl]-6-methyl-5,6-dihydrophenanthridin The title compound was prepared from N-[1-(2',4'-difluoro-1,1'-biphenyl-2-yl)ethyl]-2,4- dimethoxybenzenesulfonamide (550 mg, 1.27 mmol), anhydrous N,N-dimethylformamide (1 mL), and potassium carbonate (351 mg, 2.5 mmol) according to the procedure and in the same manner as described in Example 105, step d, and the product (525 mg, 99%) isolated as a white solid;

MS [(+ESI), m/z]: 414 [M+H]$^+$;
MS [(−ESI), m/z]: 412 [M−H]$^-$;
$^1$H NMR (400 MHz, DMSO-d$_6$) δ: 1.19 (d, J=7.0 Hz, 3H), 3.11 (s, 3H), 3.70 (s, 3H), 5.32 (q, J=7.0 Hz, 1H), 6.18 (d, J=2.3 Hz, 1H), 6.46 (dd, J=9.0, 2.5 Hz, 1H), 7.15 (m, 3H), 7.26 (td, J=7.5, 1.4 Hz, 1H), 7.35 (dd, J=10.7, 2.6 Hz, 1H), 7.59 (d, J=8.8 Hz, 1H), 7.72 (d, J=7.0 Hz, 1H), 7.93 (dd, J=8.8, 6.2 Hz, 1H).

Step c)

4-[3-Fluoro-6-methylphenanthridin-5(6H)-yl]sulfonyl]benzene-1,3-diol

The title compound was prepared from 3-fluoro-5-[(2,4-dimethoxyphenyl)sulfonyl]-6-methyl-5,6-dihydrophenanthridine (490 mg, 1.2 mmol), cyclohexene (1.08 mL, 10.7 mmol), and 1.0 M solution of boron tribromide in dichloromethane (8.3 mL) according to the procedure and in the same manner as described in Example 105, step e. The volatile components were removed in vacuo and the crude residue was purified by preparative liquid chromatography on a Biotage® 40 Mi column of prepacked silica gel (90 g), eluting with a gradient of 30%–50% methyl tert-butyl ether in hexane, to afford the product (252 mg, 55%) as a solid;

MS [(+ESI), m/z]: 386 [M+H]$^+$;
MS [(−ESI), m/z]: 384 [M−H]$^-$.

EXAMPLE 110

4-{[(6R)-3-Fluoro-6-methylphenanthridin-5(6H)-yl]sulfonyl}benzene-1,3-diol

The enantiomers of 4-[3-fluoro-6-methylphenanthridin-5(6H)-yl]sulfonyl]benzene-1,3-diol (252 mg, 0.65 mmol) were separated by automated, preparative, normal phase, chiral chromatography on a Chiralpak AS (20 mm×250 mm) column eluting with 30% ethanol in hexane at a flow rate of 20 mL/min. The fractions were combined and evaporated in vacuo, and one peak (99.8%) with a retention time of 6.00 minutes with a negative optical rotation was isolated as a white solid (78 mg, 61% based upon a 1:1 ratio of enantiomers with a theoretical maximum amount of 126 mg), m.p. 150–152° C.;

[α]$_D^{25}$=−221° (c=10.7 mg/mL, CHCl$_3$);
MS [(+ESI), m/z]: 386 [M+H]$^+$;
MS [(−ESI), m/z]: 384 [M−H]$^-$;
HRMS [(+ESI_FT), m/z]: 386.08530 [M+H]$^+$. Calcd for C$_{20}$H$_{16}$FNO$_4$S: 386.08569;
$^1$H NMR (400 MHz, DMSO-d$_6$) δ: 1.13 (d, J=7.0 Hz, 3H), 5.36 (q, J=6.8 Hz, 1H), 6.07 (d, J=2.3 Hz, 1H), 6.15 (dd, J=8.8, 2.3 Hz, 1H), 7.11 (td, J=8.5, 2.6 Hz, 1H), 7.24 (m, 3H), 7.36 (m, 2H), 7.72 (d, J=7.5 Hz, 1H), 7.91 (dd, J=8.8, 6.5 Hz, 1H), 10.13 (s, 1H), 10.23 (s, 1H).

EXAMPLE 111

4-{[(6S)-3-Fluoro-6-methylphenanthridin-5(6H)-yl]sulfonyl}benzene-1,3-diol

The enantiomers of 4-[3-fluoro-6-methylphenanthridin-5(6H)-yl]sulfonyl]benzene-1,3-diol (252 mg, 0.65 mmol) were separated by automated, preparative, normal phase, chiral chromatography on a Chiralpak AS (20 mm×250 mm) column eluting with 30% ethanol in hexane at a flow rate of 20 mL/min. The fractions were combined and evaporated in vacuo, and one peak (99.5%) with a retention time of 6.80 minutes with a positive optical rotation was isolated as a white solid (76 mg, 60% based upon a 1:1 ratio of enantiomers with a theoretical maximum amount of 126 mg), m.p. 151–153° C.;

[α]$_D^{25}$=+247° (c=11.1 mg/mL, CHCl$_3$);
MS [(+ESI), m/z]: 386 [M+H]$^+$;
MS [(−ESI), m/z]: 384 [M−H]$^-$;
HRMS [(+ESI_FT), m/z]: 386.08511 [M+H]$^+$. Calcd for C$_{20}$H$_{16}$FNO$_4$S: 386.08569;
$^1$H NMR (400 MHz, DMSO-d$_6$) δ: 1.13 (d, J=7.0 Hz, 3H), 5.36 (m, 1H), 6.07 (d, J=2.1 Hz, 1H), 6.15 (dd, J=8.8, 2.3 Hz, 1H), 7.11 (td, J=8.6, 2.7 Hz, 1H), 7.24 (m, 3H), 7.34 (d, J=8.8 Hz, 1H), 7.37 (dd, J=10.9, 2.6 Hz, 1H), 7.72 (d, J=7.5 Hz, 1H), 7.91 (dd, J=8.8, 6.5 Hz, 1H), 10.13 (s, 1H), 10.23 (s, 1H);

EXAMPLE 112

Step a)

1-(2′,5′-Difluoro-1,1′-biphenyl-2-yl) thanon

The title compound was prepared from 2,5-difluorophenylboronic acid (1.74 g, 11 mmol), tetrabutylammonium bromide (3.22 g, 10 mmol), potassium carbonate (4.15 g, 30 mmol), 2′-bromoacetophenone (1.99 g, 10 mmol), and palladium acetate (224 mg, 1.0 mmol) according to the procedure and in the same manner as described in Example 99, step a. The product was purified by preparative liquid chromatography on a Biotage® 40 Mi column of prepacked silica gel (90 g), eluting with a gradient of 10%–30% methyl tert-butyl ether in hexane, to afford the desired compound (2.31 g, 99%) as a yellow oil;

MS [(EI), m/z]: 232.07 (M$^+$);
$^1$H NMR (400 MHz, DMSO-d$_6$) δ: 2.46 (s, 3H), 7.25 (m, 3H), 7.41 (dd, J=7.4, 1.3 Hz, 1H), 7.58 (td, J=7.6, 1.3 Hz, 1H), 7.65 (td, J=7.5, 1.4 Hz, 1H), 7.89 (dt, J=7.7, 0.8 Hz, 1H).

Step b)

1-(2′,5′-Difluoro-1,1′-biphenyl-2-yl)ethylamine

The title compound was prepared from 1-(2′,5′-difluoro-1,1′-biphenyl-2-yl)ethanone (2.0 g, 8.6 mmol), anhydrous methanol (100 mL), ammonium acetate (13.3 g, 172 mmol), and sodium cyanoborohydride (1.08 g, 17.2 mmol) according to the procedure and in the same manner as described in Example 105, step b;

MS [(+ESI), m/z]: 234 [M+H]$^+$;
$^1$H NMR (400 MHz, DMSO-d$_6$) δ: 1.10 (d, J=19.1 Hz, 3H), 1.81 (s, 2H), 3.83 (q, J=6.5 Hz, 1H), 7.13 (dd, J=7.5, 1.3 Hz, 1H), 7.30 (m, 4H), 7.44 (td, J=7.6, 1.3 Hz, 1H), 7.71 (d, J=5.7 Hz, 1H).

Step c)

N-[1-(2′,5′-Difluoro-1,1′-biphenyl-2-yl)ethyl]-4-methoxybenzenesulfonamide

4-Methoxybenzenesulfonyl chloride (326 mg, 1.6 mmol) was added to a solution of 1-(2′,5′-difluoro-1,1′-biphenyl-2-yl)ethylamine (350 mg, 1.5 mmol) and triethylamine (418 uL, 3 mmol) in acetonitrile. The reaction was stirred at ambient temperature for 16 hours, whereupon dichloromethane was added and the reaction washed with water. The organic phase was dried over anhydrous sodium sulfate, filtered, concentrated, and purified by preparative liquid chromatography on a Biotage® 40 Mi column of prepacked silica gel (90 g), eluting with a gradient of 30%–50% methyl tert-butyl ether in hexane (35 min), to afford the product (540 mg, 89%) as a white solid, m.p. 143–144° C.;

MS [(−ESI), m/z]: 402 [M−H]⁻;

$^1$H NMR (400 MHz, DMSO-d$_6$) δ: 1.12 (d, J=6.7 Hz, 3H), 3.8 (s, 3H), 3.98 (m, 1H), 6.88 (d, J=8.5 Hz, 2H), 7.06 (d, J=7.50 Hz, 1H), 7.26 (m, 5H), 7.35 (m, 2H), 7.45 (d, J=7.8 Hz, 1H), 8.05 (d, J=6.5 Hz, 1H), exists as a mixture of rotomers;

Anal. Calcd for C$_{21}$H$_{19}$F$_2$NO$_3$S: C, 62.52; H, 4.75; N, 3.47. Found: C, 62.44; H, 4.61; N, 3.45.

Step d)

2-Fluoro-5-[(4-methoxyphenyl)sulfonyl]-6-methyl-5,6-dihydrophenanthridine

The title compound was prepared from N-[1-(2',5'-difluoro-1,1'-biphenyl-2-yl)ethyl]-4-methoxybenzenesulfonamide (450 mg, 1.1 mmol), anhydrous N,N-dimethylformamide (2 mL), and potassium carbonate (304 mg, 2.2 mmol) according to the procedure and in the same manner as described in Example 105, step d. The product was purified by preparative column chromatography on a Biotage® 40 Mi column of prepacked silica gel (90 g), eluting with a gradient of 30%–50% methyl tert-butyl ether in hexane (35 min), to afford the desired compound (280 mg, 65%) as a white solid, m.p. 167–168° C.;

MS [(+ESI), m/z]: 384 [M+H]⁺;

$^1$H NMR (400 MHz, DMSO-d$_6$) δ: 1.11 (d, J=7.0 Hz, 3H), 3.60 (s, 3H), 5.39 (q, J=6.8 Hz, 1H), 6.52 (m, 2H), 6.91 (m, 2H), 7.09 (td, J=7.5, 1.6 Hz, 1H), 7.22 (m, 3H), 7.43 (d, J=7.8 Hz, 1H), 7.62 (m, 2H).

Step e)

4-[(2-Fluoro-6-methylphenanthridin-5(6H)-yl) sulfonyl]phenol

The title compound was prepared from 2-fluoro-5-[(4-methoxyphenyl)sulfonyl]-6-methyl-5,6-dihydrophenanthridine (220 mg, 0.57 mmol), cyclohexene (1.2 mL, 11.5 mmol), and 1.0 M solution of boron tribromide in dichloromethane (3.4 mL) according to the procedure and in the same manner as described in Example 105, step e. The volatile components were removed in vacuo, and the crude residue was purified by preparative liquid chromatography on a Biotage® 40 Mi column of prepacked silica gel (90 g), eluting with a gradient of 5%–30% methyl tert-butyl ether in hexane, to afford the product (164 mg, 77%) as a solid, m.p. 216–218° C.;

$^1$H NMR (400 MHz, DMSO-d$_6$) δ: 1.11 (d, J=7.0 Hz, 3H), 5.38 (q, J=6.8 Hz, 1H), 6.31 (m, 2H), 6.81 (ddd, J=9.4, 2.9, 2.5 Hz, 2H), 7.11 (td, J=7.3, 1.7 Hz, 1H), 7.21 (m, 3H), 7.46 (d, J=7.8 Hz, 1H), 7.60 (dd, J=8.0, 4.7 Hz, 1H), 7.63 (dd, J=9.3, 2.1 Hz, 1H), 10.15 (s, 1H);

Anal. Calcd for C$_{20}$H$_{16}$FNO$_3$S: C, 65.03; H, 4.37; N, 3.79. Found: C, 65.01; H, 4.19; N, 3.53.

EXAMPLE 113

Step a)

N-[1-(2',5'-Difluoro-1,1'-biphenyl-2-yl)ethyl]-3-methoxybenzenesulfonamide

The title compound was prepared from 3-methoxybenzenesulfonyl chloride (326 mg, 1.6 mmol), 1-(-2',5'-difluoro-biphenyl-2-yl)ethylamine (350 mg, 1.5 mmol), and triethylamine (418 µL, 3 mmol) according to the procedure and in the same manner as described in Example 112, step c. The product was purified by preparative liquid chromatography on a Biotage® 40 Mi column of prepacked silica gel (90 g), eluting with a gradient of 30%–50% methyl tert-butyl ether in hexane (35 min), to afford the desired compound (570 mg, 94%) as a clear glass;

MS [(+ESI), m/z]: 404 [M+H]⁺;

MS [(−ESI), m/z]: 402 [M−H]⁻;

$^1$H NMR (400 MHz, DMSO-d$_6$) δ: 1.15 (br d, J=6.7 Hz, 3H), 3.67 (br s, 3H), 4.04 (m, J=3.1 Hz, 1H), 6.80 (m, 1H), 6.95 (d, J=1.0 Hz, 1H), 7.03 (m, 3H), 7.21 (d, J=7.0 Hz, 1H), 7.27 (m, 4H), 7.46 (d, J=7.8 Hz, 1H), 8.25 (s, 1H).

Step b)

2-Fluoro-5-[(3-methoxyphenyl)sulfonyl]-6-methyl-5,6-dihydrophenanthridine

The title compound was prepared from N-[1-(2',5'-difluoro-1,1'-biphenyl-2-yl)ethyl]-3-methoxybenzenesulfonamide (440 mg, 1.1 mmol), anhydrous N,N-dimethylformamide (2 mL), and potassium carbonate (301 mg, 2.2 mmol) according to the procedure and in the same manner as described in Example 105, step d. The product was purified by preparative liquid chromatography on a Biotage® 40 Mi column of prepacked silica gel (90 g), eluting with a gradient of 30%–50% methyl tert-butyl ether in hexane (35 min), to afford the desired compound (100 mg, 24%) as a white solid;

MS [(+ESI), m/z]: 384 [M+H]⁺;

MS [(−ESI), m/z]: 382 [M−H]⁻.

Step c)

3-[(2-Fluoro-6-methylphenanthridin-5(6H)-yl) sulfonyl]phenol

The title compound was prepared from 2-fluoro-5-[(3-methoxyphenyl)sulfonyl]-6-methyl-5,6-dihydrophenanthridine (100 mg, 0.26 mmol), cyclohexene (528 µL, 5.2 mmol), and 1.0 M solution of boron tribromide in dichloromethane (1.6 mL) according to the procedure and in the same manner as described in Example 105, step e. The volatile components were removed in vacuo, and the crude residue was purified by preparative liquid chromatography on a Biotage® 40 Mi column of prepacked silica gel (90 g), eluting with a gradient of 5%–30% methyl tert-butyl ether in hexane, to afford the desired compound (86 mg, 89%) as a solid, m.p. 195–196° C.;

MS [(+ESI), m/z]: 370 [M+H]⁺;

MS [(−ESI), m/z]: 368 [M−H]⁻;

$^1$H NMR (400 MHz, DMSO-d$_6$) δ: 1.12 (d, J=7.0 Hz, 3H), 5.37 (q, J=6.9 Hz, 1H), 6.41 (m, 1H), 6.45 (m, 1H), 6.59 (ddd, J=8.2, 2.5, 0.9 Hz, 1H), 6.82 (t, J=8.0 Hz, 1H), 7.09 (ddd, J=7.8, 6.6, 2.2 Hz, 1H), 7.18 (ddd, J=14.4, 7.8, 1.7 Hz, 2H), 7.25 (td, J=8.7, 2.9 Hz, 1H), 7.48 (d, J=7.5 Hz, 1H), 7.60 (dd, J=8.8, 5.4 Hz, 1H), 7.65 (dd, J=10.1, 2.9 Hz, 1H), 9.66 (s, 1H).

EXAMPLE 114

Step a)

1-(2',4',5-Trifluoro-1,1'-biphenyl-2-yl)ethanone

The title compound was prepared from 2,4-difluorophenylboronic acid (2.0 g, 12.7 mmol), tetrabutylammonium bromide (3.71 g, 11.5 mmol), potassium carbonate (4.78 g, 34.6 mmol), 2'-bromo-4'-fluoroacetophenone (2.5 g, 11.5 mmol), and palladium acetate (259 mg, 1.15 mmol) according to the procedure and in the same manner as described in Example 105, step a. The product was purified by preparative liquid chromatography on a Biotage® 40 Mi column of prepacked silica gel (90 g), eluting with a gradient of 10%–30% methyl tert-butyl ether in hexane, to afford the desired compound (850 mg, 30%) as a clear yellow oil;

MS [(EI), m/z]: 250.1 (M$^+$.);

$^1$H NMR (400 MHz, DMSO-d$_6$) δ: 2.42 (s, 3H), 7.17 (m, J=8.5, 8.5, 2.6, 0.9 Hz, 1H), 7.29 (m, 2H), 7.43 (m, 2H), 7.97 (dd, J=8.7, 5.8 Hz, 1H).

Step b)

1-(2',4',5-Trifluoro-1,1'-biphenyl-2-yl)ethylamine

The title compound was prepared from 1-(2',4',5-trifluoro-1,1'-biphenyl-2-yl)ethanone (720 mg, 2.9 mmol), anhydrous methanol (10 mL), ammonium acetate (4.44 g, 58 mmol), and sodium cyanoborohydride (362 g, 5.8 mmol) according to the procedure and in the same manner as described in Example 105, step b. The crude amine was immediately used without further purification in Example 114, step c;

MS [(+ESI), m/z]: 252 [M+H]$^+$, 235 [M+H–17]$^+$, benzylic cation as a result of the loss of NH$_3$.

Step c)

N-[1-(2',4',5-Trifluoro-1,1'-biphenyl-2-yl)ethyl]-4-methoxybenzenesulfonamide

The title compound was prepared from 4-methoxybenzenesulfonyl chloride (146 mg, 0.7 mmol), 1-(-2',4',5-trifluoro-1,1'-biphenyl-2-yl)ethylamine (169 mg, 0.67 mmol), and triethylamine (187 μL, 1.3 mmol) according to the procedure and in the same manner as described in Example 105, step c. The product was purified by preparative liquid chromatography on a Biotage® 40 Mi column of prepacked silica gel (90 g), eluting with a gradient of 30%–50% methyl tert-butyl ether in hexane (35 min), to afford the desired compound (197 mg, 70%) as a white solid;

MS [(+ESI), m/z]: 422 [M+H]$^+$;

MS [(–ESI), m/z]: 420 [M–H]$^-$.

Step d)

3,9-Difluoro-5-[(4-methoxyphenyl)sulfonyl]-6-methyl-5,6-dihydrophenanthridine

The title compound was prepared from N-[1-(2',4',5-trifluoro-1,1'-biphenyl-2-yl)ethyl]-4-methoxybenzenesulfonamide (161 mg, 0.38 mmol), anhydrous N,N-dimethylformamide (1 mL), and potassium carbonate (106 mg, 0.76 mmol) according to the procedure and in the same manner as described in Example 105, step d resulting in the isolation of 143 mg (93%) of a white solid. This material was used without further purification in Example 114, step e;

MS [(+ESI), m/z]: 402 [M+H]$^+$;

$^1$H NMR (400 MHz, DMSO-d$_6$) δ: 1.14 (d, J=7.0 Hz, 3H), 3.66 (s, 3H), 5.48 (q, J=6.9 Hz, 1H), 6.63 (m, 2H), 7.03 (m, 2H), 7.30 (m, 2H), 7.43 (dd, J=10.0, 2.7 Hz, 1H), 7.89 (dd, J=8.8, 6.2 Hz, 1H).

Step e)

4-[(3,9-Difluoro-6-m thylphenanthridin-5(6H)-yl)sulfonyl]ph nol

The title compound was prepared from 3,9-difluoro-5-[(4-methoxyphenyl)sulfonyl]-6-methyl-5,6-dihydrophenanthridine (130 mg, 0.32 mmol), cyclohexene (656 μL, 6.5 mmol), and 1.0 M solution of boron tribromide in dichloromethane (1.94 mL) according to the procedure and in the same manner as described in Example 105, step e. The volatile components were removed in vacuo and the crude residue was purified by preparative liquid chromatography on a Biotage® 40 Mi column of prepacked silica gel (90 g), eluting with a gradient of 5%–50% methyl. tert-butyl ether in hexane, to afford the product (98 mg, 78%) as a solid, m.p. 178.5–186° C.;

MS [(+ESI), m/z]: 388 [M+H]$^+$;

MS [(–ESI), m/z]: 386 [M–H]$^-$;

$^1$H NMR (400 MHz, DMSO-d$_6$) δ: 1.14 (d, J=6.7 Hz, 3H), 5.46 (q, J=6.9 Hz, 1H), 6.42 (m, 2H), 6.93 (m, 2H), 7.03 (td, J=8.7, 2.6 Hz, 1H), 7.29 (m, 2H), 7.36 (dd, J=10.4, 2.6 Hz, 1H), 7.42 (dd, J=10.1, 2.9 Hz, 1H), 7.91 (dd, J=8.8, 6.2 Hz, 1H), 10.30 (s, 1H).

EXAMPLE 115

Step a)

N-[1-(2',4',5-Trifluoro-1,1'-biphenyl-2-yl)ethyl]-3-methoxybenzenesulfonamide

The title compound was prepared from 3-methoxybenzenesulfonyl chloride (146 mg, 0.7 mmol), 1-(-2',4',5-trifluoro-1,1'-biphenyl-2-yl)ethylamine (169 mg, 0.67 mmol), and triethylamine (187 μL, 1.3 mmol) according to the procedure and in the same manner as described in Example 105, step c. The product was purified by preparative liquid chromatography on a Biotage® 40 Mi column of prepacked silica gel (90 g), eluting with a gradient of 30%–50% methyl tert-butyl ether in hexane (35 min), to afford the desired compound (235 mg, 83%) as a white solid;

MS [(+ESI), m/z]: 422 [M+H]$^+$;

MS (–ESI), m/z]: 420 [M–H]$^-$.

Step b)

3,9-Difluoro-5-[(3-methoxyphenyl)sulfonyl]-6-methyl-5,6-dihydrophenanthridine

The title compound was prepared from N-[1-(2',4',5-trifluoro-1,1'-biphenyl-2-yl)ethyl]-3-methoxybenzenesulfonamide (234 mg, 0.55 mmol), anhydrous N,N-dimethylformamide (1 mL), and potassium carbonate (154 mg, 1.1 mmol) according to the procedure and in the same manner as described in Example 105, step d resulting in the isolation of 211 mg (95%) of a white solid. This material was used without further purification in Example 115, step c;

MS [(+ESI), m/z]: 402 [M+H]$^+$;

$^1$H NMR (400 MHz, DMSO-d$_6$) δ: 1.16 (d, J=7.0 Hz, 3H) 3.55 (s, 3H), 5.53 (q, J=7.0 Hz, 1H), 6.60 (dd, J=2.3, 1.8 Hz, 1H), 6.66 (ddd, J=7.7, 1.8, 0.9 Hz, 1H), 6.91 (ddd, J=8.4, 2.6, 0.9 Hz, 1H), 7.02 (m, 2H), 7.32 (m, 3H), 7.46 (dd, J=10.0, 2.7 Hz, 1H), 7.92 (dd, J=8.8, 6.2 Hz, 1H).

Step c)

3-[(3,9-Difluoro-6-methylphenanthridin-5(6H)-yl) sulfonyl]phenol

The title compound was prepared from 3,9-difluoro-5-[(3-methoxyphenyl)sulfonyl]-6-methyl-5,6-dihydrophenanthridine (150 mg, 0.37 mmol), cyclohexene (757 μL, 7.5 mmol), and 1.0 M solution of boron tribromide in dichloromethane (2.24 mL) according to the procedure and in the same manner as described in Example 105, step e. The volatile components were removed in vacuo, and the crude residue was purified by preparative liquid chromatography on a Biotage® 40 Mi column of prepacked silica gel (90 g), eluting with a gradient of 5%–50% methyl tert-butyl ether in hexane, to afford the product (98 mg, 78%) as a solid, m.p. 167.2–173° C.;

MS [(+ESI), m/z]: 388 [M+H]$^+$;

MS [(-ESI), m/z]: 386 [M-H]$^-$;

$^1$H NMR (400 MHz, DMSO-d$_6$) δ: 1.15 (d, J=7.0 Hz, 3H), 5.46 (q, J=6.9 Hz, 1H), 6.50 (m, 1H), 6.57 (ddd, J=7.8, 1.8, 1.0 Hz, 1H), 6.70 (ddd, J=8.2, 2.5, 0.9 Hz, 1H), 6.93 (t, J=8.0 Hz, 1H), 7.00 (td, J=8.7, 2.6 Hz, 1H), 7.30 (m, 2H), 7.36 (dd, J=10.4, 2.6 Hz, 1H), 7.43 (dd, J=10.1, 2.6 Hz, 1H), 7.93 (dd, J=8.8, 6.2 Hz, 1H), 9.78 (s, 1H).

EXAMPLE 116

Step a)

1-(2',5',5-Trifluoro-1,1'-biphenyl-2-yl)ethanone

The title compound was prepared from 2,5-difluorophenylboronic acid (2.0 g, 12.7 mmol), tetrabutylammonium bromide (3.71 g, 11.5 mmol), potassium carbonate (4.78 g, 34.6 mmol), 2'-bromo-4'-fluoroacetophenone (2.5 g, 11.5 mmol), and palladium acetate (259 mg, 1.15 mmol) according to the procedure and in the same manner as described in Example 105, step a. The product was purified by preparative liquid chromatography on a Biotage® 40 Mi column of prepacked silica gel (90 g), eluting with a gradient of 10%–30% methyl tert-butyl ether in hexane, to afford the desired compound (784 mg, 27%) as a clear yellow oil.

Step b)

1-(2',5',5-Trifluoro-1,1'-biphenyl-2-yl)ethylamine

The title compound was prepared from 1-(2',5',5-trifluoro-1,1'-biphenyl-2-yl)ethanone (650 mg, 2.6 mmol), anhydrous methanol (10 mL), ammonium acetate (4.0 g, 52 mmol), and sodium cyanoborohydride (326 g, 5.2 mmol) according to the procedure and in the same manner as described in Example 105, step b. The crude amine was immediately used without further purification in Example 116, step c;

MS [(+ESI), m/z]: 252 [M+H]$^+$, 235 [M+H-17]$^+$, benzylic cation as a result of the loss of NH$_3$.

Step c)

N-[1-(2',5',5-Trifluoro-1,1'-biphenyl-2-yl)ethyl]-4-methoxybenzenesulfonamide

The title compound was prepared from 4-methoxybenzenesulfonyl chloride (153 mg, 0.74 mmol), 1-(-2',5',5-trifluoro-1,1'-biphenyl-2-yl)ethylamine (177 mg, 0.70 mmol), and triethylamine (147 μL, 1.1 mmol) according to the procedure and in the same manner as described in Example 105, step c. The product was purified by preparative liquid chromatography on a Biotage® 40 Mi column of prepacked silica gel (90 g), eluting with a gradient of 30%–50% methyl tert-butyl ether in hexane (35 min), to afford the desired compound (259 mg, 91%) as a white solid;

MS [(+ESI), m/z]: 422 [M+H]$^+$;

MS [(-ESI), m/z]: 420 [M-H]$^-$.

Step d)

2,9-Difluoro-5-[(4-methoxyphenyl)sulfonyl]6-methyl-5,6-dihydrophenanthridine

The title compound was prepared from N-[1-(2',4',5-trifluoro-1,1'-biphenyl-2-yl)ethyl]-4-methoxybenzenesulfonamide (210 mg, 0.50 mmol), anhydrous N,N-dimethylformamide (1 mL), and potassium carbonate (138 mg, 1.0 mmol) according to the procedure and in the same manner as described in Example 105, step d resulting in the isolation of 200 mg (99%) of a white solid. This material was used without further purification in Example 116, step e;

MS [(+ESI), m/z]: 402 [M+H]$^+$;

$^1$H NMR (400 MHz, DMSO-d$_6$) δ: 1.13 (d, J=7.0 Hz, 3H), 3.66 (s, 3H), 5.46 (q, J=7.0 Hz, 1H), 6.61 (m, 2H), 6.94 (m, 2H), 7.06 (td, J=8.7, 2.6 Hz, 1H), 7.34 (m, 3H), 7.65 (dd, J=9.1, 5.4 Hz, 1H), 7.72 (dd, J=10.0, 3.0 Hz, 1H).

Step e)

4-[(2,9-Difluoro-6-methylphenanthridin-5(6H)-yl)sulfonyl]phenol

The title compound was prepared from 2,9-difluoro-5-[(4-methoxyphenyl)sulfonyl]-6-methyl-5,6-dihydrophenanthridine (150 mg, 0.37 mmol), cyclohexene (757 μL, 7.5 mmol), and 1.0 M solution of boron tribromide in dichloromethane (2.24 mL) according to the procedure and in the same manner as described in Example 105, step e. The volatile components were removed in vacuo and the crude residue was purified on a Biotage® 40 Mi column of prepacked silica gel (90 g), eluting with a gradient of 5%–50% methyl tert-butyl ether in hexane, to afford the desired compound (117 mg, 81%) as a white solid, m.p. 194–196° C.;

MS [(+ESI), m/z]: 388 [M+H]$^+$;

MS [(-ESI), m/z]: 386 [M-H]$^-$;

$^1$H NMR (400 MHz, DMSO-d$_6$) δ: 1.13 (d, J=7.0 Hz, 3H), 5.45 (q, J=7.0 Hz, 1H), 6.40 (m, 2H), 6.85 (ddd, J=9.4, 2.9, 2.5 Hz, 2H), 7.06 (td, J=8.7, 2.6 Hz, 1H), 7.31 (qd, J=5.7, 2.9 Hz, 2H), 7.40 (dd, J=10.4, 2.6 Hz, 1H), 7.64 (dd, J=8.9, 5.3 Hz, 1H), 7.74 (dd, J=9.8, 2.9 Hz, 1H), 10.27 (s, 1H).

EXAMPLE 117

Step a)

N-[1-(2',5',5-Trifluoro-1,1'-biphenyl-2-yl)ethyl]-3-methoxybenzenesulfonamide

The title compound was prepared from 3-methoxybenzenesulfonyl chloride (153 mg, 0.74 mmol), 1-(-2',5',5-trifluoro-1,1'-biphenyl-2-yl)ethylamine (177 mg, 0.70 mmol), and triethylamine (147 uL, 1.1 mmol) according to the procedure and in the same manner as described in Example 105, step c. The product was purified by preparative liquid chromatography on a Biotage® 40 Mi column of prepacked silica gel (90 g), eluting with a gradient of 30%–50% methyl tert-butyl ether in hexane (35 min), to afford the desired compound (295 mg, 100%) as a white solid;

MS [(+ESI), m/z]: 422 [M+H]$^+$;

MS [(-ESI), m/z]: 420 [M-H]$^-$.

Step b)

2,9-Difluoro-5-[(3-methoxyphenyl)sulfonyl]-6-methyl-5,6-dihydrophenanthridine

The title compound was prepared from N-[1-(2',4',5-trifluoro-1,1'-biphenyl-2-yl)ethyl]-3-methoxybenzenesulfonamide (221 mg, 0.52 mmol), anhydrous N,N-dimethylformamide (1 mL), and potassium carbonate (138 mg, 1.0 mmol) according to the procedure and in the same manner as described in Example 105, step d resulting in the isolation of 208 mg (99%) of a white solid.

This material was used without further purification in Example 117, step c;

MS [(+ESI), m/z]: 402 [M+H]$^+$;

$^1$H NMR (400 MHz, DMSO-d$_6$) δ: 1.15 (d, J=7.0 Hz, 3H), 3.55 (s, 3H), 5.52 (q, J=6.8 Hz, 1H), 6.54 (m, 1H), 6.57 (ddd, J=7.6, 1.7, 1.0 Hz, 1H), 6.89 (ddd, J=8.4, 2.6, 0.9 Hz, 1H), 7.04 (m, 2H), 7.35 (m, 3H), 7.67 (dd, J=8.8, 5.4 Hz, 1H), 7.75 (dd, J=9.8, 2.9 Hz, 1H).

Step c)

3-[(2,9-Difluoro-6-methylphenanthridin-5(6H)-yl) sulfonyl]phenol

The title compound was prepared from 2,9-difluoro-5-[(3-methoxyphenyl)sulfonyl]-6-methyl-5,6-dihydrophenanthridine (156 mg, 0.39 mmol), cyclohexene (760 μL, 7.7 mmol), and 1.0 M solution of boron tribromide in dichloromethane (2.33 mL) according to the procedure and in the same manner as described in Example 105, step e. The volatile components were removed in vacuo and the crude residue was purified by preparative liquid chromatography on a Biotage® 40 Mi column of prepacked silica gel (90 g), eluting with a gradient of 5%–50% methyl tert-butyl ether in hexane, to afford the desired product (139 mg, 92%) as a white solid, m.p. 165.5–171° C.;

MS [(+ESI), m/z]: 388 [M+H]$^+$;

MS [(−ESI), m/z]: 386 [M−H]$^−$;

$^1$H NMR (400 MHz, DMSO-d$_6$) δ: 1.14 (d, J=7.0 Hz, 3H), 5.44 (q, J=6.9 Hz, 1H), 6.42 (m, 1H), 6.49 (ddd, J=7.8, 1.8, 1.0 Hz, 1H), 6.68 (ddd, J=8.2, 2.5, 0.8 Hz, 1H), 6.90 (t, J=8.0 Hz, 1H), 7.04 (td, J=8.7, 2.6 Hz, 1H), 7.32 (m, 2H), 7.39 (dd, J=10.4, 2.6 Hz, 1H), 7.65 (dd, J=9.1, 5.4 Hz, 1H), 7.76 (dd, J=9.8, 2.9 Hz, 1H), 9.65 (br s, 1H).

EXAMPLE 118

Method A

Step a)

4-Chloro-1,1'-biphenyl-2-ylamine

A stirred solution of 2-bromo-5-chloronitrobenzene (5.00 g, 21.2 mmol) and phenylboronic acid (2.58 g, 21.2 mmol) in tetrahydrofuran (85 mL) was treated under nitrogen with [1,1'-bis(diphenylphosphino)ferrocene]dichloropalladium (II) complex with dichloromethane (0.52 g, 0.63 mmol, 3 mole %) and a 5 N sodium hydroxide solution (8.5 mL, 42.5 mmol). The reaction was heated at 60° C. for twelve hours, cooled to room temperature, and the solvent removed in vacuo. The residue was treated with ethyl acetate (200 mL) and a saturated aqueous sodium chloride solution (100 mL). The phases were separated and the aqueous phase was extracted with ethyl acetate (2×50 mL). The combined organic phase was dried over anhydrous magnesium sulfate, filtered, and the solvent concentrated in vacuo. The resulting brown oil was filtered through a plug of silica gel (20:80 ethyl acetate:hexane). After concentration of the solvent in vacuo, the resulting, pure 4-chloro-2-nitro-biphenyl (4.66 g, 19.0 mmol, 94%) was dissolved in acetic acid (13.2 mL) and ethanol (13.2 mL). Iron granules (15.6 g, 278 mmol) were added and the mixture was stirred with a mechanical stirrer for 12 hours. The mixture was diluted with ethanol and then filtered through Celite® filter aid. The resulting solution was concentrated in vacuo, diluted with toluene and concentrated in vacuo (×3) to afford a viscous oil. The viscous oil was purified by flash column chromatography, eluting with a mixture of ethyl acetate-hexane (1:4), to afford the title compound as a homogeneous oil (3.46 g, 85%);

$^1$H NMR (400 MHz, DMSO-d$_6$) δ: 7.45–7.30 (m, 5H), 6.94 (d, J=8.0 Hz, 1H), 6.78 (d, J=2.1 Hz, 1H), 6.61 (dd, J=8.0, 2.1 Hz, 1H), 5.07 (s, 2H).

Step b)

N-(4-Chloro-1,1'-biphenyl-2-yl)acetamide

A stirred solution of 4-chloro-1,1'-biphenyl-2-ylamine (3.46 g, 17.0 mmol) in dichloromethane (8.5 mL) was treated with pyridine (3.2 mL, 39 mmol), acetic anhydride (1.77 mL, 18.7 mmol), and 4-(dimethylamino)pyridine (0.62 g, 0.51 mmol) and stirred at room temperature for 12 hours. A saturated, aqueous solution of ammonium chloride (150 mL) was added, and the layers were separated. The aqueous phase was extracted with dichloromethane (3×75 mL). The combined organic phase was washed sequentially with a 0.1 N hydrochloric acid solution (2×50 mL) and a saturated, aqueous sodium bicarbonate solution (50 mL), dried over anhydrous sodium sulfate, filtered and the solvent evaporated in vacuo to yield a brown oil. Toluene was added and removed in vacuo (×3) to afford a brown solid which, upon trituration with ethyl acetate/hexane, afforded the title compound as a homogeneous, colorless, crystalline solid (2.28 g, 93%), m.p. 125–127° C.;

MS [(−ESI), m/z]: 244 [M−H]$^−$;

$^1$H NMR (500 MHz, DMSO-d$_6$) δ: 9.27 (s, 1H), 7.58 (s, 1H), 7.43–7.28 (m, 7H), 1.86 (s, 3H);

Anal. calcd for C$_{14}$H$_{12}$ClNO: C, 68.44; H, 4.92; N, 5.70. Found: C, 68.25; H, 4.73; N, 5.37.

Step c)

3-Chloro-6-methylphenanthridine

N-(4-Chloro-1,1'-biphenyl-2-yl)acetamide (2.65 g, 10.8 mmol) was mixed with polyphosphoric acid (50 g) and heated to 120° C. with vigorous stirring for 12 hours. The hot reaction mixture was poured into a beaker containing ice and stirred vigorously until homogeneous. The solution was neutralized to a pH>8 with concentrated aqueous ammonia. A white precipitate formed and was filtered. The white solid was dissolved in ethyl acetate (250 mL) and re-filtered. The filtrate was washed with a saturated aqueous sodium chloride solution, dried over anhydrous sodium sulfate, filtered and the solvent concentrated in vacuo to a brown solid. The brown solid was purified by trituration with ethyl acetate/hexane to afford the title compound as white crystals (2.28 g, 93%), m.p. 129–131° C.;

MS [(+ESI), m/z]: 228 [M+H]$^+$;

$^1$H NMR (500 MHz, DMSO-d$_6$) δ: 8.78 (d, J=8.2 Hz, 1H), 8.73 (d, J=8.8 Hz, 1H), 8.30 (dd, J=8.2, 0.6 Hz, 1H), 7.98 (d, J=2.2 Hz, 1H), 7.92 (m, 1H), 7.78 (m, 1H), 7.64 (dd, J=8.7, 2.2 Hz, 1H), 2.93 (s, 3H);

Anal. calcd for C$_{14}$H$_{10}$ClN: C, 73.85; H, 4.43; N, 6.15. Found: C, 73.53; H, 4.10; N, 5.83.

Step d)

3-Chloro-5-[(3-methoxyphenyl)sulfonyl]-6-methyl-5,6-dihydrophenanthridine

A stirred solution of 3-chloro-6-methylphenanthridine (0.40 g, 1.76 mmol) in tetrahydrofuran (7 mL) was treated with freshly crushed sodium borohydride (0.33 g, 8.8 mmol). Trifluoroacetic acid (0.54 mL, 7.0 mmol) was added dropwise at a rate to keep the exothermic reaction and gas evolution under control. After the addition was complete the heterogeneous reaction mixture was stirred until the temperature returned to 23° C. The mixture was then heated at reflux for 14 hours. The reaction was cooled to room temperature and neutralized with a saturated, aqueous sodium bicarbonate solution (150 mL). The mixture was filtered through a plug of glass wool into a separatory funnel and extracted with diethyl ether (4×50 mL). The combined organic phase was dried over anhydrous sodium sulfate, filtered, and concentrated in vacuo to a light brown paste. The crude 3-chloro-6-methyl-5,6-dihydrophenanthridine was dissolved in pyridine (12 mL), treated with 3-methoxybenzenesulfonyl chloride (0.55 g, 2.64 mmol) and 4-(dimethylamino)pyridine (0.01 g, 0.08 mmol), and stirred at 80° C. for 14 hours. The reaction mixture cooled to room temperature, treated with a 0.1 N aqueous sodium hydroxide solution (100 mL, 10 mmol), and extracted with dichloromethane (6×50 mL). The combined organic phase was washed with a 2 N hydrochloric acid solution (2×40 mL), dried over anhydrous sodium sulfate, filtered, and concentrated in vacuo to a brown solid. The brown solid was purified by flash column chromatography, eluting with a mixture of ethyl acetate:hexane (1:4), followed by crystallization from ethyl acetate-hexane, to afford the title compound as a homogeneous, white, crystalline solid (0.38 g, 54%), m.p. 117–118° C.;

MS [(−ESI), m/z]: 398 [M−H]$^-$;

$^1$H NMR (500 MHz, DMSO-d$_6$) δ: 7.85 (d, J=8.6 Hz, 1H), 7.65 (d, J=2.3 Hz, 1H), 7.47 (m, 2H), 7.27 (dd, J=7.5, 1.2 Hz, 1H), 7.19 (m, 1H), 7.13 (td, J=7.6, 1.4 Hz, 1H), 6.99 (t, J=8.0 Hz, 1H), 6.83 (m, 1H), 6.64 (m, 1H), 6.58 (m, 1H), 5.49 (q, J=7.0 Hz, 1H), 3.51 (s, 3H), 1.17 (d, J=7.0 Hz, 3H);

Anal. calcd for $C_{21}H_{18}ClNO_3S \cdot 0.20H_2O$: C, 62.51; H, 4.60; N, 3.47. Found: C, 62.19; H, 4.46; N, 3.28.

Step e)

3-[(3-Chloro-6-methylphenanthridin-5(6H)-yl) sulfonyl]phenol

A stirred suspension of 3-chloro-5-[(3-methoxyphenyl) sulfonyl]-6-methyl-5,6-dihydrophenanthridine (0.38 g, 0.95 mmol) and cyclohexene (1.73 mL, 17.1 mmol) was treated dropwise at room temperature under nitrogen with a solution of 1.0 M boron tribromide (5.7 mL, 5.7 mmol) in dichloromethane. After stirring for 20 hours at room temperature, the reaction was quenched with a saturated, aqueous sodium bicarbonate solution (50 mL), and extracted with dichloromethane (6×20 mL). The combined organic phase was dried over anhydrous sodium sulfate, filtered, and concentrated in vacuo to a crude residue. The crude residue was triturated with hexane and purified by flash column chromatography, eluting with a mixture of ethyl acetate-hexane (30:70), to afford the title compound as a homogeneous, white, crystalline solid (0.17 g, 73%), m.p. 215° C.;

MS [(−ESI), m/z]: 384 [M−H]$^-$;

$^1$H NMR (500 MHz, DMSO-d$_6$) δ: 9.73 (s, 1H), 7.87 (d, J=8.6 Hz, 1H), 7.62 (d, J=2.3 Hz, 1H), 7.51 (d, J=7.3 Hz, 1H), 7.46 (dd, J=8.5, 2.2 Hz, 1H), 7.23–7.12 (m, 3H), 6.87 (t, J=7.9 Hz, 1H), 6.64 (t, J=7.9 Hz, 1H), 6.55 (m, 1H), 6.50 (t, J=2.0 Hz, 1H), 5.41 (q, J=6.9 Hz, 1H), 1.16 (d, J=6.9 Hz, 3H);

Anal. calcd for $C_{20}H_{16}ClNO_3S$: C, 62.25; H, 4.18; N, 3.63. Found: C, 61.88; H, 4.31; N, 3.49.

Method B
Step a)

1-(4'-Chloro-2'-fluoro-1,1'-biphenyl-2-yl)ethanone

2-Acetylphenylboronic acid (5 g, 30.5 mmol) and 4-chloro-2-fluoroiodobenzene (8.6 g, 33.5 mmol) were dissolved in a toluene/ethanol mixture (6:1, 175 mL). An aqueous solution of potassium carbonate (2 M, 60 mL) and tetrakis(triphenylphosphine)palladium (0) (1.06 g, 0.91 mmol) were added to the solution and the entire mixture was degassed using vacuum and stirring with intermittent nitrogen purge. The mixture was heated at 85° C. with stirring for 14 hours. The mixture was allowed to cool and then water was added. The organic phase was separated from the aqueous phase and the aqueous phase was extracted with ethyl acetate (3×100 mL). The organic phases were combined, dried over anhydrous sodium sulfate, filtered, and concentrated to a crude oil. The crude oil was purified by preparative liquid chromatography on a Biotage® 40 Mi column of prepacked silica gel (90 g), eluting with a gradient of 5%–20% methyl tert-butyl ether in hexane, to afford the desired product (4.07 g, 54%) as a yellow oil;

MS [(EI), m/z]: 248.0/250.0 [M$^+$.], contains one chlorine atom pattern;

$^1$H NMR (400 MHz, DMSO-d$_6$) δ: 2.45 (s, 3H), 7.37 (m, 3H), 7.44 (m, 1H), 7.57 (td, J=7.6, 1.3 Hz, 1H), 7.65 (td, J=7.6, 1.4 Hz, 1H), 7.90 (ddd, J=7.6, 1.4, 0.5 Hz, 1H).

Step b)

1-(4'-Chloro-2'-fluoro-1,1'-biphenyl-2-yl)ethylamine

To a stirred solution of 1-(4'-chloro-2'-fluoro-1,1'-biphenyl-2-yl)ethanone (3.2 g, 12.9 mmol) in anhydrous methanol (200 mL) was added solid ammonium acetate (19.8 g, 257 mmol). The reaction mixture was heated at 60° C. for one hour, followed by the addition of a methanolic solution of sodium cyanoborohydride (1.62 g, 25.8 mmol). After 16 hours, the methanol was removed in vacuo and aqueous ammonium hydroxide was added. The aqueous phase was extracted with diethyl ether (3×200 mL) until the amine was no longer present in the aqueous phase. The organic phase was then washed with 2 N aqueous hydrochloric acid (3×100 mL) and the aqueous phases combined. The solid formed during the acid wash was determined to be the dialkyated amine and was segregated from the aqueous phase. Aqueous sodium hydroxide was added to the acidic aqueous phase until the solution was neutralized to pH 8 to 9. The basic aqueous phase was extracted with diethyl ether until the primary amine was no longer detected in the aqueous phase. The combined organic phases were dried over anhydrous sodium sulfate, filtered, and concentrated to afford a clear oil that was used without further purification;

MS [(+ESI), m/z]: 233 [M+H−17]$^+$, benzylic cation as a result of loss of $NH_3$;

Step c)

N-[1-(4'-Chloro-2'-fluoro-1,1'-biphenyl-2-yl)ethyl]-3-methoxybenzenesulfonamid

3-Methoxybenzenesulfonyl chloride (331 mg, 1.6 mmol) was added to a solution of 1-(4'-chloro-2'-fluoro-1,1'-biphenyl-2-yl)ethylamine (400 mg, 1.6 mmol) and triethylamine (246 μL, 1.7 mmol) in acetonitrile. The reaction was mixed at room temperature for 24 hours, afterwhich the acetonitrile was removed in vacuo. The remaining solid was dissolved in dichloromethane and purified by preparative liquid chromatogrpahy on a Biotage® 40 Mi column of prepacked silica gel (90 g), eluting with a gradient of 5%–50% methyl tert-butyl ether in hexane (35 min), to afford the the desired product (694 mg, 99%) as a white solid;

MS [(+ESI), m/z]: 420/422 [M+H]$^+$, contains one chlorine atom pattern;

MS [(−ESI), m/z]: 418/420 [M−H]$^-$, contains one chlorine atom pattern;

$^1$H NMR (400 MHz, DMSO-d$_6$) δ: 1.16 (d, J=7.0 Hz, 3H), 3.72 (m, J=13.5 Hz, 3H), 4.03 (m, 1H), 6.97 (dd, J=2.5, 1.7

Hz, 1H), 7.09 (m, 3H), 7.24 (t, J=7.2 Hz, 2H), 7.36 (m, 3H), 7.50 (m, 2H), 8.25 (d, J=7.0 Hz, 1H).

Step d)

3-Chloro-5-[(3-methoxyphenyl)sulfonyl]-6-methyl-5,6-dihydrophenanthridine

The title compound was prepared from N-[1-(4'-chloro-2'-fluoro-1,1'-biphenyl-2-yl)ethyl]-3-methoxybenzenesulfonamide (686 mg, 1.6 mmol), anhydrous N,N-dimethylformamide (2 mL), and potassium carbonate (442 mg, 3.2 mmol) according to the procedure and in the same manner as described in Example 105, step d resulting in the isolation of 547 mg (84%) of a white solid that was used without further purification;

MS [(+ESI), m/z]: 400/402 [M+H]$^+$, contains one chlorine atom pattern;

MS [(-ESI), m/z]: 398/400 [M-H]$^-$, contains one chlorine atom pattern.

Step e)

3-[(3-Chloro-6-methylphenanthridin-5(6H)-yl)sulfonyl]phenol

The title compound was prepared from 3-chloro-5-[(3-methoxyphenyl)sulfonyl]-6-methyl-5,6-dihydrophenanthridine according to the procedure and in the same manner as described in Example 118, Method A, step e. The resulting racemic product was optically resolved in Examples 119 and 120.

EXAMPLE 119

3-{[(6R)-3-Chloro-6-methylphenanthridin-5(6H)-yl]sulfonyl}phenol

The enantiomers of 3-[(3-chloro-6-methylphenanthridin-5(6H)-yl)sulfonyl]phenol (280 mg, 0.73 mmol) were separated by automated, preparative, normal phase, chiral chromatography on a Chiralpak® AS (20 mm×250 mm) column eluting with 20% 2-propanol in hexane at a flow rate of 20 mL/min. After combination of fractions and evaporation of the solvent in vacuo, one peak (99.8%) with a retention time of 6.94 minutes was isolated as a white solid (122 mg, 44% based upon a 1:1 ratio of enantiomers with a theoretical maximum amount of 140 mg), m.p. 220.9–223° C.;

$[\alpha]_D^{25}$=-100.6° (c=10.0 mg/mL, CHCl$_3$);

MS [(+ESI), m/z]: 386/388 [M+H]$^+$, contains one chlorine atom pattern;

MS [(-ESI), m/z]: 384/386 [M-H]$^-$, contains one chlorine atom pattern;

$^1$H NMR (400 MHz, DMSO-d$_6$) δ: 1.17 (d, J=7.0 Hz, 3H), 5.42 (q, J=7.0 Hz, 1H), 6.51 (m, 1H), 6.57 (m, 1H), 6.65 (ddd, J=8.2, 2.4, 1.0 Hz, 1H), 6.89 (t, J=8.0 Hz, 1H), 7.16 (m, 1H), 7.22 (m, 2H), 7.47 (dd, J=8.4, 2.2 Hz, 1H), 7.52 (dd, J=7.6, 0.9 Hz, 1H), 7.63 (d, J=2.1 Hz, 1H), 7.87 (d, J=8.5 Hz, 1H), 9.74 (s, 1H);

Anal. Calcd for C$_{20}$H$_{16}$ClNO$_3$S: C, 62.25; H, 4.18; N, 3.63. Found: C, 61.86; H, 4.28; N, 3.44.

EXAMPLE 120

3-{[(6S)-3-Chloro-6-m thylphenanthridin-5(6H)-yl]sulfonyl}ph nol

The enantiomers of 3-[(3-chloro-6-methylphenanthridin-5(6H)-yl)sulfonyl]phenol (280 mg, 0.73 mmol) were separated by automated, preparative, normal phase, chiral chromatography on a Chiralpak® AS (20 mm×250 mm) column eluting with 20% 2-propanol in hexane at a flow rate of 20 mL/min. After combination of fractions and evaporation of the solvent in vacuo, one peak (99.9%) with a retention time of 9.38 minutes was isolated as a white solid (120 mg, 43% based upon a 1:1 ratio of enantiomers with a theoretical maximum amount of 140 mg), m.p. 219–223° C.;

$[\alpha]_D^{25}$=+91.6° (c=10.0 mg/mL, CHCl$_3$);

MS [(+ESI), m/z]: 386/388 [M+H]$^+$, contains one chlorine atom pattern;

MS [(-ESI), m/z]: 384/386 [M-H]$^-$, contains one chlorine atom pattern;

$^1$H NMR (400 MHz, DMSO-d$_6$) δ: 1.17 (d, J=7.0 Hz, 3H), 5.42 (q, J=6.8 Hz, 1H), 6.51 (m, 1H), 6.57 (ddd, J=7.8, 1.8, 1.0 Hz, 1H), 6.65 (ddd, J=8.3, 2.5, 0.9 Hz, 1H), 6.89 (t, J=8.0 Hz, 1H), 7.14 (dd, J=7.0, 1.8 Hz, 1H), 7.17 (m, 1H), 7.22 (m, 1H), 7.47 (dd, J=8.4, 2.2 Hz, 1H), 7.52 (dd, J=7.5, 1.0 Hz, 1H), 7.63 (d, J=2.1 Hz, 1H), 7.87 (d, J=8.5 Hz, 1H), 9.74 (s, 1H);

Anal. Calcd for C$_{20}$H$_{16}$ClNO$_3$S: C, 62.25; H, 4.18; N, 3.63. Found: C, 62.14; H, 4.45; N, 3.54.

EXAMPLE 121

Method A

4-[(3-Chloro-6-methylphenanthridin-5(6H)-yl)sulfonyl]phenol

A stirred solution of 3-chloro-6-methylphenanthridine (0.40 g, 1.76 mmol) in tetrahydrofuran (7 mL) was treated with freshly crushed sodium borohydride (0.33 g, 8.8 mmol). Trifluoroacetic acid (0.54 mL, 7.0 mmol) was added dropwise at a rate to keep the exothermic reaction and gas evolution under control. After the addition was complete, the heterogeneous reaction mixture was stirred until the temperature returned to 23° C. The mixture was then heated at reflux for 14 hours. The reaction was cooled to room temperature and neutralized with a saturated, aqueous sodium bicarbonate solution (150 mL). The mixture was filtered through a plug of glass wool into a separatory funnel and extracted with diethyl ether (4×50 mL). The combined organic phase was dried over anhydrous sodium sulfate, filtered, and concentrated in vacuo to a light brown paste. The crude 3-chloro-6-methyl-5,6-dihydrophenanthridine was dissolved in pyridine (12 mL), treated with carbonic acid 4-chlorosulfonyl-phenyl ester ethyl ester (0.699 g, 2.64 mmol) and 4-(dimethylamino)pyridine (0.01 g, 0.08 mmol), and stirred at 80° C. for 14 hours. The reaction was cooled to room termperature, treated with a 0.1 N aqueous sodium hydroxide solution (100 mL, 10 mmol), and extracted with dichloromethane (6×50 mL). The combined organic phase was washed with a 2 N hydrochloric acid solution (2×40 mL), dried over anhydrous sodium sulfate, filtered, and concentrated in vacuo to a viscous, brown oil. The viscous oil was purified by filtration through a plug of silica gel, eluting with a mixture of ethyl acetate-hexane (1:4). Concentration of the filtrate in vacuo, followed by trituration with ethyl acetate-hexane afforded the title compound as a homogeneous, white crystalline solid (0.25 g, 37%), m.p. 204° C.;

MS [(-ESI), m/z]: 384 [M-H]$^-$;

$^1$H NMR (500 MHz, DMSO-d$_6$) δ: 10.25 (br s, 1H), 7.83 (d, J=8.6 Hz, 1H), 7.61 (d, J=2.3 Hz, 1H), 7.50 (d, J=7.5 Hz, 1H), 7.44 (dd, J=8.6, 2.2 Hz, 1H), 7.25–7.13 (m, 3H), 6.91 (d, J=8.9 Hz, 2H), 6.37 (d, J=8.9 Hz, 2H), 5.41 (q, J=7.0 Hz, 1H), 1.14 (d, J=7.0 Hz, 3H);

Anal. calcd for C$_{20}$H$_{16}$ClNO$_3$S: C, 62.25; H, 4.18; N, 3.63. Found: C, 62.03; H, 4.06; N, 3.42.

Method B
Step a)

N-[1-(4'-Chloro-2'-fluoro-1,1'-biphenyl-2-yl)ethyl]-4-methoxybenzenesulfonamid The title compound was prepared from 4-methoxybenzenesulfonyl chloride (331 mg, 1.6 mmol), 1-(4'chloro-2'-fluoro-1,1'-biphenyl-2-yl)ethylamine (400 mg, 1.6 mmol), and triethylamine (246 µL, 1.7 mmol) according to the procedure and in the same manner as described in Example 105, step c resulting in the isolation of 644 mg (96%) of a white solid;

MS [(+ESI), m/z]: 420/422 [M+H]$^+$, contains one chlorine atom pattern;

MS [(−ESI), m/z]: 418/420 [M−H]$^-$, contains one chlorine atom pattern;

$^1$H NMR (400 MHz, DMSO-d$_6$) δ: 1.14 (d, J=7.0 Hz, 3H), 3.80 (s, 3H), 3.96 (m, 1H), 6.91 (t, J=8.0 Hz, 2H), 7.09 (m, 1H), 7.21 (m, 3H), 7.33 (m, 1H), 7.41 (d, J=8.8 Hz, 2H), 7.51 (m, 2H), 8.06 (d, J=6.5 Hz, 1H).

Step b)

3-Chloro-5-[(4-methoxyphenyl)sulfonyl]-6-methyl-5,6-dihydrophenanthridine

The title compound was prepared from N-[1-(4'-chloro-2'-fluoro-1,1'-biphenyl-2-yl)ethyl]-4-methoxybenzenesulfonamide (617 mg, 1.5 mmol), anhydrous N,N-dimethylformamide (2 mL), and potassium carbonate (414 mg, 3.0 mmol) according to the procedure and in the same manner as described in Example 105, step d resulting in the isolation of 607 mg (93%) of a white solid that was used without further purification;

MS [(+ESI), m/z]: 400/402 [M+H]$^+$, contains one chlorine atom pattern;

MS [(−ESI), m/z]: 398/400 [M−H]$^-$, contains one chlorine atom pattern.

Step c)

4-[(3-Chloro-6-methylphenanthridin-5(6H)-yl)sulfonyl]phenol

The title compound was prepared from 3-chloro-5-[(4-methoxyphenyl)sulfonyl]-6-methyl-5,6-dihydrophenanthridine according to the procedure and in the same manner as described in Example 118, Method A, step e. The resulting racemic product was optically resolved in Examples 122 and 123.

EXAMPLE 122

4-{[(6R)-3-Chloro-6-methylphenanthridin-5(6)-yl]sulfonyl}phenol

The enantiomers of 4-[(3-chloro-6-methylphenanthridin-5(6H)-yl)sulfonyl]phenol (400 mg, 1.0 mmol) were separated by automated, preparative, normal phase, chiral chromatography on a Chiralpak® AS (20 mm×250 mm) column eluting with 15% 2-propanol in hexane at a flow rate of 20 mL/min. After combination of fractions and evaporation of the solvent in vacuo, one peak (99.9%) with a retention time of 10.25 minutes was isolated as a white solid (151 mg, 43% based upon a 1:1 ratio of enantiomers with a theoretical maximum amount of 200 mg), m.p. 217.5–221° C.;

$[α]_D^{25}$=−103.6° (c=10.0 mg/mL, CHCl$_3$);

MS [(+ESI), m/z]: 386/388 [M+H]$^+$, contains one chlorine atom pattern;

MS [(−ESI), m/z]: 384/386 [M−H]$^-$, contains one chlorine atom pattern;

$^1$H NMR (400 MHz, DMSO-d$_6$) δ: 1.15 (d, J=7.0 Hz, 3H), 5.42 (m, 1H), 6.38 (m, 2H), 6.92 (m, 2H), 7.17 (ddd, J=14.1, 6.6, 1.6 Hz, 1H), 7.24 (ddd, J=12.7, 7.3, 1.4 Hz, 2H), 7.45 (dd, J=8.4, 2.2 Hz, 1H), 7.51 (d, J=7.5 Hz, 1H), 7.62 (d, J=2.3 Hz, 1H), 7.84 (d, J=8.5 Hz, 1H), 10.23 (s, 1H).

EXAMPLE 123

4-{[(6S)-3-Chloro-6-methylphenanthridin-5(6H)-yl]sulfonyl}phenol

The enantiomers of 4-[(3-chloro-6-methylphenanthridin-5(6H)-yl)sulfonyl]phenol (400 mg, 1.0 mmol) were separated by automated, preparative, normal phase, chiral chromatography on a Chiralpak® AS (20 mm×250 mm) column eluting with 15% 2-propanol in hexane at a flow rate of 20 mL/min. After combination of fractions and evaporation of the solvent in vacuo, one peak (98.9%) with a retention time of 13.90 minutes was isolated as a white solid (151 mg, 43% based upon a 1:1 ratio of enantiomers with a theoretical maximum amount of 200 mg), m.p. 213.5–220° C.;

$[α]_D^{25}$=+96.4° (c=10.0 mg/mL, CHCl$_3$);

MS [(+ESI), m/z]: 386/388 [M+H]$^+$, contains one chlorine atom pattern;

MS [(−ESI), m/z]: 384/386 [M−H]$^-$, contains one chlorine atom pattern;

$^1$H NMR (400 MHz, DMSO-d$_6$) δ: 1.15 (d, J=7.0 Hz, 3H), 5.42 (q, J=6.9 Hz, 1H), 6.38 (ddd, J=9.4, 2.9, 2.5 Hz, 2H), 6.92 (m, 2H), 7.17 (ddd, J=14.1, 6.5, 1.7 Hz, 1H), 7.24 (ddd, J=12.7, 7.3, 1.4 Hz, 2H), 7.45 (dd, J=8.5, 2.3 Hz, 1H), 7.50 (dd, J=7.6, 0.9 Hz, 1H), 7.62 (d, J=2.1 Hz, 1H), 7.84 (d, J=8.5 Hz, 1H), 10.24 (s, 1H).

EXAMPLE 124

Step a)

N-[1-(4'-Chloro-2'-fluoro-1,1'-biphenyl-2-yl)ethyl]-2,4-dimethoxybenzenesulfonamide The title compound was prepared from 2,4-dimethoxybenzenesulfonyl chloride (379 mg, 1.6 mmol), 1-(4'-chloro-2'-fluoro-1,1'-biphenyl-2-yl)ethylamine (400 mg, 1.6 mmol), and triethylamine (246 µL, 1.7 mmol) according to the procedure and in the same manner as described in Example 105, step c resulting in the isolation of 480 mg (67%) of a white solid;

MS [(+ESI), m/z]: 450/452 [M+H]$^+$, contains one chlorine atom pattern;

MS [(−ESI), m/z]: 448/450 [M−H]$^-$, contains one chlorine atom pattern;

$^1$H NMR (400 MHz, DMSO-d$_6$) δ: 1.17 (d, J=7.0 Hz, 3H), 3.75 (br s, 3H), 3.79 (br s, 3H), 4.02 (m, 1H), 6.47 (m, 2H), 7.01 (m, 2H), 7.20 (t, J=7.0 Hz, 1H), 7.32 (d, J=8.5 Hz, 1H), 7.38 (m, 2H), 7.47 (d, J=8.5 Hz, 1H), 7.60 (d, J=7.8 Hz, 1H), 7.71 (d, J=7.5 Hz, 1H).

Step b)

3-Chloro-5-[(2,4-dimethoxyphenyl)sulfonyl]-6-methyl-5,6-dihydrophenanthridin The title compound was prepared from N-[1-(4'-chloro-2'-fluoro-1,1'-biphenyl-2-yl)ethyl]-2,4-dimethoxybenzenesulfonamide (470 mg, 1.04 mmol), anhydrous N,N-dimethylformamide (2 mL), and potassium carbonate (287 mg, 2.0 mmol) according to the procedure and in the same manner as described in Example 105, step d resulting in the isolation of 447 mg (100%) of a white solid that was used without further purification;

MS [(+ESI), m/z]: 430/432 [M+H]⁺, contains one chlorine atom pattern.

Step c)

4-{[-3-Chloro-6-methylphenanthridin-5(6H)-yl]sulfonyl}b nzen -1,3-diol

The title compound was prepared from 3-chloro-5-[(2,4-dimethoxyphenyl)sulfonyl]-6-methyl-5,6-dihydrophenanthridine (429 mg, 1.0 mmol), cyclohexene (3.0 mL, 30 mmol), and 1.0 M solution of boron tribromide in dichloromethane (6.0 mL) according to the procedure and in the same manner as described in Example 105, step e. The volatile components were removed in vacuo and the crude residue was purified by preparative liquid chromatography on a Biotage® 40 Mi column of prepacked silica gel (90 g), eluting with a gradient of 30%–50% methyl tert-butyl ether in hexane, to afford the desired compound (400 mg, 99%) as a solid; MS [(−ESI), m/z]: 400/402 [M−H]⁻, contains one chlorine atom pattern.

Step d)

4-{[(6R)-3-Chloro-6-methylphenanthridin-5(6H)-yl]sulfonyl}benzene-1,3-diol

The enantiomers of 4-{[3-chloro-6-methylphenanthridin-5(6H)-yl]sulfonyl}benzene-1,3-diol (340 mg, 0.85 mmol) were separated by automated, preparative, normal phase, chiral chromatography on a Chiralpak AS (20 mm×250 mm) column eluting with a mixture of ethanol and hexane (1:1) at a flow rate of 14 mL/min. After combination of fractions and evaporation of the solvent in vacuo, one peak (99.9%) with a retention time of 4.36 minutes was isolated as a white solid (103 mg, 30% based upon a 1:1 ratio of enantiomers with a theoretical maximum amount of 170 mg), m.p. 178.2–182° C.;

$[\alpha]_D^{25}$=−72.01° (c=10.0 mg/mL, CHCl₃);

MS [(+ESI), m/z]: 402/404 [M+H]⁺, contains one chlorine atom pattern;

MS [(−ESI), m/z]: 400/402 [M−H]⁻, contains one chlorine atom pattern;

¹H NMR (400 MHz, DMSO-d₆) δ: 1.13 (d, J=7.0 Hz, 3H), 5.32 (m, 1H), 6.07 (d, J=2.1 Hz, 1H), 6.15 (dd, J=8.8, 2.3 Hz, 1H), 7.21 (m, 2H), 7.27 (m, 1H), 7.32 (td, J=5.7, 3.1 Hz, 2H), 7.61 (d, J=2.3 Hz, 1H), 7.75 (dd, J=7.8, 1.0 Hz, 1H), 7.89 (d, J=8.5 Hz, 1H), 10.13 (s, 1H), 10.24 (s, 1H);

Anal. Calcd for C₂₀H₁₆ClNO₄S: C, 59.78; H, 4.01; N, 3.49. Found: C, 59.99; H, 3.86; N, 3.24.

EXAMPLE 125

4-{[(6S)-3-Chl ro-6-methylphenanthridin-5(6H)-yl]sulfonyl}b nz ne-1,3-diol

The enantiomers of 4-{[3-chloro-6-methylphenanthridin-5(6H)-yl]sulfonyl}benzene-1,3-diol (340 mg, 0.85 mmol) were separated by automated, preparative, normal phase, chiral chromatography on a Chiralpak® AS (20 mm×250 mm) column eluting with a mixture of ethanol and hexane (1:1) at a flow rate of 14 mL/min. After combination of fractions and evaporation of the solvent in vacuo, one peak (99.7%) with a retention time of 5.42 minutes was isolated as a white solid (100 mg, 29% based upon a 1:1 ratio of enantiomers with a theoretical maximum amount of 170 mg), m.p. 180.2–183.1° C.;

$[\alpha]_D^{25}$=+66.7° (c=10.0 mg/mL, CHCl₃);

MS [(+ESI), m/z]: 402/404 [M+H]⁺, contains one chlorine atom pattern;

MS [(−ESI), m/z]: 400/402 [M−H]⁻, contains one chlorine atom pattern;

¹H NMR (400 MHz, DMSO-d₆) δ: 1.13 (d, J=7.0 Hz, 3H), 5.32 (m, 1H), 6.07 (d, J=2.3 Hz, 1H), 6.15 (dd, J=8.8, 2.3 Hz, 1H), 7.21 (ddd, J=13.4, 7.2, 1.4 Hz, 2H), 7.27 (m, 1H), 7.32 (td, J=5.6, 2.6 Hz, 2H), 7.61 (d, J=2.1 Hz, 1H), 7.75 (dd, J=7.8, 1.0 Hz, 1H), 7.89 (d, J=8.5 Hz, 1H), 10.13 (s, 1H), 10.24 (s, 1H).

EXAMPLE 126

4-{[(6S)-8-Fluoro-6-methylphenanthridin-5(6H)-yl]sulfonyl}phenyl sulfamate

To a stirred solution of 4-{[(6S)-8-fluoro-6-methylphenanthridin-5(6H)-yl]sulfonyl}phenol (1.11 g, 3.0 mmol) in dimethyacetamide (10 mL), cooled to 0° C., was added sulfamoyl chloride (1.39 g, 12.0 mmol). The mixture was allowed to warm to room temperature and stirring continued for 16 hours. Water (100 mL) was added and a white precipitate deposited on the inside of the reaction vessel. The water was removed and the flask was washed with additional water. The white solid was dissolved in dichloromethane and purified by preparative liquid chromatography on a Biotage® 40 Mi column of prepacked silica gel (90 g), eluting with a gradient of 30%–50% methyl tert-butyl ether in hexane, to afford the title compound (1.16 g, 87%) as a white solid, m.p. 166.5–167° C.;

MS [(+ESI), m/z]: 449 [M+H]⁺;

MS [(−ESI), m/z]: 447 [M−H]⁻;

¹H NMR (400 MHz, DMSO-d₆) δ: 1.16 (d, J=7.0 Hz, 3H), 5.49 (q, J=7.0 Hz, 1H), 6.97 (m, 3H), 7.14 (ddd, J=9.2, 2.9, 2.5 Hz, 2H), 7.20 (dd, J=9.2, 2.7 Hz, 1H), 7.45 (m, 3H), 7.63 (dd, J=7.8, 1.3 Hz, 1H), 7.77 (dd, J=7.6, 1.7 Hz, 1H), 8.13 (s, 2H);

Anal. Calcd for C₂₀H₁₇FN₂O₅S₂: C, 53.56; H, 3.82; N, 6.25. Found: C, 53.47; H, 3.82; N, 6.10.

m.p. 165.5–167.3° C.;

$[\alpha]_D^{25}$=+211° (c=10.0 g/mL, CHCl₃);

MS [(+ESI), m/z]: 449 [M+H]⁺;

MS [(−ESI), m/z]: 447 [M−H]⁻;

HRMS [(+ESI), m/z]: 449.06289 [M+H]⁺. Calcd for C₂₀H₁₇FN₂O₅S₂: 449.06357;

¹H NMR (400 MHz, CDCl₃) δ: CONSISTENT;

Anal. Calcd for C₂₀H₁₇FN₂O₅S₂: C, 53.56; H, 3.82; N, 6.25. Found: C, 52.70; H, 3.55; N, 6.14.

m.p. 148–150° C.;

$[\alpha]_D^{25}$=+188° (c=10.0 mg/mL, CHCl₃);

MS [(+ESI), m/z]: 449 [M+H]⁺;

MS [(−ESI), m/z]: 447 [M−H]⁻;

¹H NMR (400 MHz, CDCl₃) δ: CONSISTENT;

Anal. Calcd for C₂₀H₁₇FN₂O₅S₂: C, 53.56; H, 3.82; N, 6.25. Found: C, 53.27; H, 3.58; N, 6.15.

m.p. 148–150° C.;

$[\alpha]_D^{25}$=+154° (c=10.0 mg/mL, CHCl₃);

MS [(+ESI), m/z]: 449 [M+H]⁺;

MS [(−ESI), m/z]: 447 [M−H]⁻;

¹H NMR (400 MHz, CDCl₃) δ: CONSISTENT;

Anal. Calcd for C₂₀H₁₇FN₂O₅S₂: C, 53.56; H, 3.82; N, 6.25. Found: C, 53.42; H, 3.58; N, 6.23.

m.p. 151° C.;

$^1$H NMR (400 MHz, CDCl$_3$) δ: CONSISTENT, trace impurities might include ethyl acetate, but well below quantifiable 0.1 mole equiv minimum.

EXAMPLE 127

Step a)

6-Ethyl-8-fluoro-5-[(4-m thoxyphenyl)sulfonyl]-2-pyridin-3-yl-5,6-dihydrophenanthridine A stirred solution of 2-bromo-6-ethyl-8-fluoro-5-[(4-methoxyphenyl)sulfonyl]5,6-dihydrophenanthridine (0.35 g, 0.73 mmol) and 3-pyridineboronic acid (0.09 g, 0.73 mmol) in tetrahydrofuran (8.0 mL) was treated under nitrogen with [1,1'-bis(diphenylphosphino)ferrocene]dichloropalladium (II) complex with dichloromethane (18.0 mg, 0.02 mmol) and a 5 N sodium hydroxide solution (0.29 mL, 1.46 mmol). The reaction mixture was heated at reflux for twelve hours, cooled to room temperature, and the solvent removed in vacuo. The residue was dissolved in ethyl acetate (25 mL) and extracted with a saturated, aqueous, sodium chloride solution (10 mL). The aqueous phase was further extracted with ethyl acetate (2×25 mL). The combined organic phase was dried over anhydrous magnesium sulfate, filtered, and concentrated in vacuo to a brown oil. The brown oil was purified by preparative liquid chromatography on a Biotage® 40 Mi column of prepacked silica gel (90 g), eluting with a gradient of 20%–75% ethyl acetate in hexane, to afford the title compound (0.26 g, 75%) as a homogeneous white solid;

MS [(+ESI), m/z]: 475 [M+H]$^+$;

$^1$H NMR (500 MHz, DMSO-d$_6$) δ: 0.89 (t, J=7.2 Hz, 3H), 1.13–1.27 (m, 1H), 1.39–1.45 (m, 1H), 3.61 (s, 3H), 5.12 (dd, J=10.0, 5.5 Hz, 1H), 6.60 (ddd, J=8.9, 3.0, 2.1 Hz, 2H), 6.95 (td, J=8.9, 3.1 Hz, 1H), 7.05 (ddd, J=8.9, 3.0, 2.0 Hz, 2H), 7.14 (dd, J=9.3, 2.8 Hz, 1H), 7.46 (dd, J=7.2, 4.8 Hz, 1H), 7.70 (d, J=8.3 Hz, 1H), 7.73 (dd, J=8.6, 5.6 Hz, 1H), 7.77 (dd, J=8.5, 2.1 Hz, 1H), 8.09 (d, J=2.1 Hz, 1H), 8.19 (ddd, J=8.1, 2.4, 1.5 Hz, 1H), 8.55 (dd, J=4.8, 1.5 Hz, 1H), 9.00 (d, J=1.9 Hz, 1H);

Anal. calcd for C$_{27}$H$_{23}$FN$_2$O$_3$S: C, 68.34; H, 4.89; N, 5.90. Found: C, 68.05; H, 5.01; N, 5.63.

Step b)

4-[(6-Ethyl-8-fluoro-2-pyridin-3-ylphenanthridin-5(6H)-yl)sulfonyl]phenol

A stirred suspension of 6-ethyl-8-fluoro-5-[(4-methoxyphenyl)sulfonyl]-2-pyridin-3-yl-5,6-dihydrophenanthridine (0.24 g, 0.51 mmol) and cyclohexene (11.4 mL), 9.22 mmol) was treated at room temperature under nitrogen with a solution of 1.0 boron tribromide in dichloromethane (3.1 mL, 3.1 mmol). After stirring for 20 hours at room temperature, the reaction was quenched with a saturated, aqueous sodium bicarbonate solution (100 mL), and extracted with dichloromethane (6×20 mL). The combined organic phase was dried over anhydrous sodium sulfate, filtered, and the solvent concentrated in vacuo. The crude residue was triturated with hexane, filtered, and recrystallized from dichloromethane-methanol to afford the title compound as a homogeneous, white, crystalline solid (0.17 g, 73%), m.p. 195–200° C.;

MS [(+ESI), m/z]: 461 [M+H]$^+$;

$^1$H NMR (500 MHz, DMSO-d$_6$) δ: 10.22 (br s, 1H), 9.27 (d, J=2.0 Hz, 1H), 8.78 (m, 2H), 8.22 (d, J=2.1 Hz, 1H), 7.94 (dd, J=8.1, 5.5 Hz, 1H), 7.86 (dd, J=8.4, 2.2 Hz, 1H), 7.79 (dd, J=8.8, 5.5 Hz, 1H), 7.75 (d, J=8.4 Hz, 1H), 7.17 (dd, J=9.2, 2.7 Hz, 1H), 7.01 (td, J=8.8, 2.7 Hz, 1H), 6.96 (d, J=8.9 Hz, 2H), 6.39 (d, J=8.9 Hz, 2H), 5.13 (dd, J=9.9, 5.4 Hz, 1H), 1.43 (m, 1H), 1.23 (m, 1H), 0.88 (t, J=7.2 Hz, 3H).

What is claimed is:

1. A compound of formulae (I) or (II) having the structure

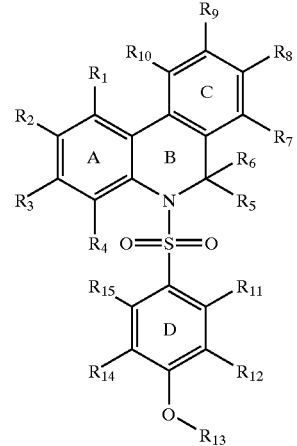

(I)

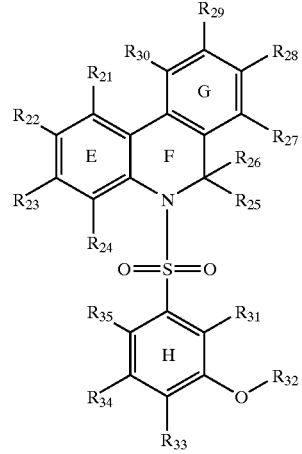

(II)

wherein

R$_1$, R$_2$, R$_3$, R$_4$, R$_7$, R$_8$, R$_9$, R$_{10}$, R$_{11}$, R$_{12}$, R$_{14}$, and R$_{15}$ are each, independently, hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, R$_{17}$—S(O)—, R$_{17}$—S(O)$_2$—, R$_{17}$—SO$_3$—, R$_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent R$_{p+1}$ or R$_{p-1}$ linked with an -alkylene-, or —X-alkylene- group;

R$_5$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, —CR(O), —CO$_2$R, or —C(O)N(R)$_2$; or R$_5$ may be taken together with either R$_6$ or R$_7$ and linked with an -alkylene- or —X-alkylene- group;

R$_6$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, —CR(O), —CO$_2$R, or —C(O)N(R)$_2$; or R$_6$ may be taken together with either R$_5$ or R$_7$ and linked with an -alkylene- or —X-alkylene- group;

$R_{13}$ is R, $R_{17}$—X—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_2$–C$_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

X is O, —NR—, —S(O)$_m$—, —C(O)—, —OC(O)—, —C(O)O—, —NRC(O)—, or —C(O)NR—;

m is 0, 1, or 2;

p is 2, 3, 6, 7, 8, 9, 12, 13, or 14;

$R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent $R_{q+1}$ or $R_{q-1}$ linked with an -alkylene-, or —Y-alkylene- group;

$R_{25}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{25}$ may be taken together with either $R_{26}$ or $R_{27}$ and linked with an -alkylene- or —Y-alkylene- group;

$R_{26}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{26}$ may be taken together with either $R_{25}$ or $R_{27}$ and linked with an -alkylene- or —Y-alkylene- group;

$R_{32}$ is R, $R_{17}$—Y—$R_{16}$—, $R_{17}$—S(O)—, $R_{17}$—S(O)$_2$—, —SO$_3$R, —S(O)$_2$N(R)$_2$, or D-glucuronidate;

Y is O, —NR—, —S(O)$_n$—, —C(O)—, —OC(O)—, —C(O)O—, —NRC(O)—, or —C(O)NR—;

n is 0, 1, or 2;

q is 22, 23, 26, 27, 28, 29, 32, 33, or 34;

or a pharmaceutically acceptable salt thereof.

2. The compound according to claim 1, wherein the compound is of formula (I) or a pharmaceutical acceptable salt thereof.

3. The compound according to claim 2, wherein $R_{13}$ is hydrogen, or a pharmaceutically acceptable salt thereof.

4. The compound according to claim 3, wherein $R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, aryl-$R_{16}$—, $R_{17}$—X—$R_{16}$—, hydroxyalkyl, HO—$R_{16}$—, halogen, —OR, —COR, or —CO$_2$R;

$R_5$ and $R_6$ are each, independently, hydrogen or $R_{17}$;

$R_{16}$ is -alkylene-;

$R_{17}$ is alkyl, aryl, heteroaryl, or perfluoroalkyl;

R is hydrogen or alkyl; or a pharmaceutically acceptable salt thereof.

5. The compound according to claim 1, wherein the compound is of formula (II) or a pharmaceutical acceptable salt thereof.

6. The compound according to claim 5, wherein $R_{32}$ is hydrogen, or a pharmaceutically acceptable salt thereof.

7. The compound according to claim 6, wherein $R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are each, independently, hydrogen, $R_{17}$, aryl-$R_{16}$—, $R_{17}$—Y—$R_{16}$—, hydroxyalkyl, HO—$R_{16}$—, halogen, —OR, —COR, or —CO$_2$R;

$R_{25}$ and $R_{26}$ are each, independently, hydrogen or $R_{17}$;

$R_{16}$ is -alkylene-;

$R_{17}$ is alkyl, aryl, heteroaryl, or perfluoroalkyl;

R is hydrogen or alkyl; or a pharmaceutically acceptable salt thereof.

8. The compound according to claim 1, which is

4-[(6-methylphenanthridin-5(6H)-yl)sulfonyl]phenol;

4-{[(S)-6-methylphenanthridin-5(6H)-yl]sulfonyl}phenol;

4-{[(R)-6-methylphenanthridin-5(6H)-yl]sulfonyl}phenol;

4-[(2-bromo-6-methylphenanthridin-5(6H)-yl)sulfonyl]phenol;

2-methyl-4-[(6-methylphenanthridin-5(6H)-yl)sulfonyl]phenol;

4-[(2-bromo-6-methylphenanthridin-5(6H)-yl)sulfonyl]-2-methylphenol;

4-[(6-butylphenanthridin-5(6H)-yl)sulfonyl]phenol;

4-[(2-bromo-6-butylphenanthridin-5(6H)-yl)sulfonyl]phenol;

4-[(6-phenylphenanthridin-5(6H)-yl)sulfonyl]phenol;

4-{[(S)-6-phenylphenanthridin-5(6H)-yl]sulfonyl}phenol;

4-{[(R)-6-phenylphenanthridin-5(6H)-yl]sulfonyl}phenol;

4-[(2-bromo-6-phenylphenanthridin-5(6H)-yl)sulfonyl]phenol;

2-bromo-4-[(2-bromo-6-phenylphenanthridin-5(6H)-yl)sulfonyl]phenol;

4-[(6-tert-butylphenanthridin-5(6H)-yl)sulfonyl]phenol;

4-{[(R)-6-tert-butylphenanthridin-5(6H)-yl]sulfonyl}phenol;

4-{[(S)-6-tert-butylphenanthridin-5(6H)-yl]sulfonyl}phenol;

4-[(2-bromo-6-tert-butylphenanthridin-5(6H)-yl)sulfonyl]phenol;

4-[(6-ethylphenanthridin-5(6H)-yl)sulfonyl]phenol;

4-[(2-bromo-6-ethylphenanthridin-5(6H)-yl)sulfonyl]phenol;

4-[(6-ethylphenanthridin-5(6H)-yl)sulfonyl]-2-methylphenol;

4-[(2-bromo-6-ethylphenanthridin-5(6H)-yl)sulfonyl]-2-methylphenol;

4-{[(S*)-6-[(R*)-1-methylpropyl]phenanthridin-5(6H)-yl]sulfonyl}phenol;

4-[(6-methylphenanthridin-5(6H)-yl)sulfonyl]benzene-1,2-diol;

2-hydroxy-5-[(6-methylphenanthridin-5(6H)-yl)sulfonyl]benzoic acid;

ethyl 2-ethoxy-5-[(6-methylphenanthridin-5(6H)-yl)sulfonyl]benzoate;

2-(hydroxymethyl)₄-[(6-methylphenanthridin-5(6H)-yl)sulfonyl]phenol;
2-hydroxy-5-[(6-methylphenanthridin-5(6H)-yl)sulfonyl]benzaldehyde;
4-[(6-ethyl-2-thien-3-ylphenanthridin-5(6H)-yl)sulfonyl]phenol;
4-{[6-ethyl-2-(3-methoxyphenyl)phenanthridin-5(6H)-yl]sulfonyl}phenol;
3-{6-ethyl-5-[(4-hydroxyphenyl)sulfonyl]-5,6-dihydrophenanthridin-2-yl}phenol;
4-[(2-dibenzo[b,d]furan-4-yl-6-ethylphenanthridin-5(6H)-yl)sulfonyl]phenol;
4-[(8-fluoro-6-methylphenanthridin-5(6H)-yl)sulfonyl]phenol;
4-{[(S)-8-fluoro-6-methylphenanthridin-5(6H)-yl]sulfonyl}phenol;
4-{[(R)-8-fluoro-6-methylphenanthridin-5(6H)-yl]sulfonyl}phenol;
4-[(8-fluoro-6-methylphenanthridin-5(6H)-yl)sulfonyl]-2-methylphenol;
5-[(4-hydroxyphenyl)sulfonyl]-6-methyl-5,6-dihydrophenanthridin-9-ol;
5-[(4-hydroxy-3-methylphenyl)sulfonyl]-6-methyl-5,6-dihydrophenanthridin-9-ol;
5-[(4-hydroxy-3-methylphenyl)sulfonyl]-6-methyl-5,6-dihydrophenanthridin-7-ol;
5-[(4-hydroxyphenyl)sulfonyl]-6-methyl-5,6-dihydrophenanthridin-7-ol;
4-[(6-ethyl-8-fluorophenanthridin-5(6H)-yl)sulfonyl]phenol;
4-[(6-ethyl-8-fluorophenanthridin-5(6H)-yl)sulfonyl]-2-methylphenol;
4-[(6-ethyl-7-methylphenanthridin-5(6H)-yl)sulfonyl]phenol;
4-[(6-ethyl-9-methylphenanthridin-5(6H)-yl)sulfonyl]phenol;
4-[(2-bromo-6-ethyl-8-fluorophenanthridin-5(6H)-yl)sulfonyl]phenol;
4-[(2-bromo-8-fluoro-6-methylphenanthridin-5(6H)-yl)sulfonyl]phenol;
2-chloro-4-[(6-ethyl-8-fluorophenanthridin-5(6H)-yl)sulfonyl]phenol;
4-[(6-ethyl-8-fluoro-2-phenylphenanthridin-5(6H)-yl)sulfonyl]phenol;
3-[(8-fluoro-6-methylphenanthridin-5(6H)-yl)sulfonyl]phenol;
2-fluoro-4-[(8-fluoro-6-methylphenanthridin-5(6H)-yl)sulfonyl]phenol;
4-[(8-fluoro-6-methylphenanthridin-5(6H)-yl)sulfonyl]benzene-1,2-diol;
4-[(6-ethyl-8-fluoro-2-methylphenanthridin-5(6H)-yl)sulfonyl]phenol;
4-[(6-ethyl-8-fluoro-2-thien-3-ylphenanthridin-5(6H)-yl)sulfonyl]phenol;
4-[(6-ethyl-8-fluorophenanthridin-5(6H)-yl)sulfonyl]phenyl 3,3-dimethylbutanoate;
4-[(6-ethyl-8-fluorophenanthridin-5(6H)-yl)sulfonyl]phenyl propionate;
4-[(6-ethyl-8-fluorophenanthridin-5(6H)-yl)sulfonyl]phenyl benzoate;
2-fluoro-4-[(6-methylphenanthridin-5(6H)-yl)sulfonyl]phenol;
4-[(2-bromo-6-methylphenanthridin-5(6H)-yl)sulfonyl]-2-fluorophenol;
4-[(6-methylphenanthridin-5(6H)-yl)sulfonyl]-2-(trifluoromethyl)phenol;
2,6-dimethyl-4-[(6-methylphenanthridin-5(6H)-yl)sulfonyl]phenol;
4-[(6,8-dimethylphenanthridin-5(6H)-yl)sulfonyl]phenol;
4-[(8-chloro-6-methylphenanthridin-5(6H)-yl)sulfonyl]phenol;
4-[(2-bromo-8-chloro-6-methylphenanthridin-5(6H)-yl)sulfonyl]phenol;
2-{6-ethyl-5-[(4-hydroxyphenyl)sulfonyl]-5,6-dihydrophenanthridin-2-yl}phenol;
4-{[6-ethyl-2-[4-(methylthio)phenyl]phenanthridin-5(6H)-yl]sulfonyl}phenol;
4-{[6-ethyl-2-[(E)-2-phenylethenyl]phenanthridin-5(6H)-yl]sulfonyl}phenol;
4-{[2-(1,1'-biphenyl-4-yl)-6-ethylphenanthridin-5(6H)-yl]sulfonyl}phenol;
4-{[2-(3-chlorophenyl)-6-ethylphenanthridin-5(6H)-yl]sulfonyl}phenol;
4-[(6-ethyl-2-quinolin-8-ylphenanthridin-5(6H)-yl)sulfonyl]phenol;
4-[(6-ethyl-2-phenylphenanthridin-5(6H)-yl)sulfonyl]phenol;
4-{[6-ethyl-2-(2-methylphenyl)phenanthridin-5(6H)-yl]sulfonyl}phenol;
4-[(6-ethyl-2-thianthren-1-ylphenanthridin-5(6H)-yl)sulfonyl]phenol;
4-{[2-(1-benzofuran-2-yl)-6-ethylphenanthridin-5(6H)-yl]sulfonyl}phenol;
4-{[6-ethyl-2-(4-hydroxyphenyl)phenanthridin-5(6H)-yl]sulfonyl}phenol;
4-{[2-(2-chlorophenyl)-6-ethylphenanthridin-5(6H)-yl]sulfonyl}phenol;
4-{[6-ethyl-2-(4-ethylphenyl)phenanthridin-5(6H)-yl]sulfonyl}phenol;
1-(5-{6-ethyl-5-[(4-hydroxyphenyl)sulfonyl]-5,6-dihydrophenanthridin-2-yl}thien-2-yl)ethanone;
5-{6-ethyl-5-[(4-hydroxyphenyl)sulfonyl]-5,6-dihydrophenanthridin-2-yl}pyrimidine-2,4-diol;
4-{[6-ethyl-2-(2-hydroxyphenyl)phenanthridin-5(6H)-yl]sulfonyl}-2-methylphenol;
4-[(6-ethyl-2-thien-3-ylphenanthridin-5(6H)-yl)sulfonyl]-2-methylphenol;
4-{[6-ethyl-2-[4-(methylthio)phenyl]phenanthridin-5(6H)-yl]sulfonyl}-2-methylphenol;
4-{[6-ethyl-2-[(E)-2-phenylethenyl]phenanthridin-5(6H)-yl]sulfonyl}-2-methylphenol;
4-{6-ethyl-5-[(4-hydroxy-3-methylphenyl)sulfonyl]-5,6-dihydrophenanthridin-2-yl}benzene-1,2-diol;
4-{[2-(1,1'-biphenyl-4-yl)-6-ethylphenanthridin-5(6H)-yl]sulfonyl}-2-methylphenol;
4-{[6-ethyl-2-(3-hydroxyphenyl)phenanthridin-5(6H)-yl]sulfonyl}-2-methylphenol;
4-{[2-(3-chlorophenyl)-6-ethylphenanthridin-5(6H)-yl]sulfonyl}-2-methylphenol;
4-{[6-ethyl-2-[(E)-hept-1-enyl]phenanthridin-5(6H)-yl]sulfonyl}-2-methylphenol;
4-[(6-ethyl-2-pyridin-4-ylphenanthridin-5(6H)-yl)sulfonyl]-2-methylphenol;

4-[(6-ethyl-2-quinolin-8-ylphenanthridin-5(6H)-yl)sulfonyl]-2-methylphenol;
4-{[6-ethyl-2-(2-methylphenyl)phenanthridin-5(6H)-yl]sulfonyl}-2-methylphenol;
4-{[2-(1-benzothien-2-yl)-6-ethylphenanthridin-5(6H)-yl]sulfonyl}-2-methylphenol;
4-{[2-(1-benzothien-3-yl)-6-ethylphenanthridin-5(6H)-yl]sulfonyl}-2-methylphenol;
4-[(2-dibenzo[b,d]furan-4-yl-6-ethylphenanthridin-5(6H)-yl)sulfonyl]-2-methylphenol;
4-{[2-(1-benzofuran-2-yl)-6-ethylphenanthridin-5(6H)-yl]sulfonyl}-2-methylphenol;
4-{[6-ethyl-2-(4-hydroxyphenyl)phenanthridin-5(6H)-yl]sulfonyl}-2-methylphenol;
4-{[2-(2-chlorophenyl)-6-ethylphenanthridin-5(6H)-yl]sulfonyl}-2-methylphenol;
4-{[6-ethyl-2-(4-ethylphenyl)phenanthridin-5(6H)-yl]sulfonyl}-2-methylphenol;
1-(5-{6-ethyl-5-[(4-hydroxy-3-methylphenyl)sulfonyl]-5,6-dihydrophenanthridin-2-yl}thien-2-yl)ethanone;
5-{6-ethyl-5-[(4-hydroxy-3-methylphenyl)sulfonyl]-5,6-dihydrophenanthridin-2-yl}pyrimidine-2,4-diol;
4-{[(6R)-3,8-difluoro-6-methylphenanthridin-5(6H)-yl]sulfonyl}phenol;
4-{[(6S)-3,8-difluoro-6-methylphenanthridin-5(6H)-yl]sulfonyl}phenol;
3-{[(6R)-3,8-difluoro-6-methylphenanthridin-5(6H)-yl]sulfonyl}phenol;
3-{[(6S)-3,8-difluoro-6-methylphenanthridin-5(6H)-yl]sulfonyl}phenol;
4-{[(6S)-3,8-difluoro-6-methylphenanthridin-5(6H)-yl]sulfonyl}benzene-1,3-diol;
4-{[(6R)-3,8-difluoro-6-methylphenanthridin-5(6H)-yl]sulfonyl}benzene-1,3-diol;
4-[(3-fluoro-6-methylphenanthridin-5(6H)-yl)sulfonyl]phenol;
3-[(3-fluoro-6-methylphenanthridin-5(6H)-yl)sulfonyl]phenol;
3-{[(6R)-3-fluoro-6-methylphenanthridin-5(6H)-yl]sulfonyl}phenol;
3-{[(6S)-3-fluoro-6-methylphenanthridin-5(6H)-yl]sulfonyl}phenol;
4-[3-fluoro-6-methylphenanthridin-5(6H)-yl]sulfonyl]benzene-1,3-diol;
4-{[(6R)-3-fluoro-6-methylphenanthridin-5(6H)-yl]sulfonyl}benzene-1,3-diol;
4-{[(6S)-3-fluoro-6-methylphenanthridin-5(6H)-yl]sulfonyl}benzene-1,3-diol;
4-[(2-fluoro-6-methylphenanthridin-5(6H)-yl)sulfonyl]phenol;
3-[(2-fluoro-6-methylphenanthridin-5(6H)-yl)sulfonyl]phenol;
4-[(3,9-difluoro-6-methylphenanthridin-5(6H)-yl)sulfonyl]phenol;
3-[(3,9-difluoro-6-methylphenanthridin-5(6H)-yl)sulfonyl]phenol;
4-[(2,9-difluoro-6-methylphenanthridin-5(6H)-yl)sulfonyl]phenol;
3-[(2,9-difluoro-6-methylphenanthridin-5(6H)-yl)sulfonyl]phenol;
3-[(3-chloro-6-methylphenanthridin-5(6H)-yl)sulfonyl]phenol;
3-{[(6R)-3-chloro-6-methylphenanthridin-5(6H)-yl]sulfonyl}phenol;
3-{[(6S)-3-chloro-6-methylphenanthridin-5(6H)-yl]sulfonyl}phenol;
4-[(3-chloro-6-methylphenanthridin-5(6H)-yl)sulfonyl]phenol;
4-{[(6R)-3-chloro-6-methylphenanthridin-5(6H)-yl]sulfonyl}phenol;
4-{[(6S)-3-chloro-6-methylphenanthridin-5(6H)-yl]sulfonyl}phenol;
4-{[(6R)-3-chloro-6-methylphenanthridin-5(6H)-yl]sulfonyl}benzene-1,3-diol;
4-{[(6S)-3-chloro-6-methylphenanthridin-5(6H)-yl]sulfonyl}benzene-1,3-diol;
4-{[(6R)-8-fluoro-6-methylphenanthridin-5(6H)-yl]sulfonyl}phenyl sulfamate;
4-[(6-ethyl-8-fluoro-2-pyridin-3-ylphenanthridin-5(6H)-yl)sulfonyl]phenol;

or a pharmaceutically acceptable salt thereof.

9. A pharmaceutical composition, which comprises a compound of formulae (I) or (II) having the structure

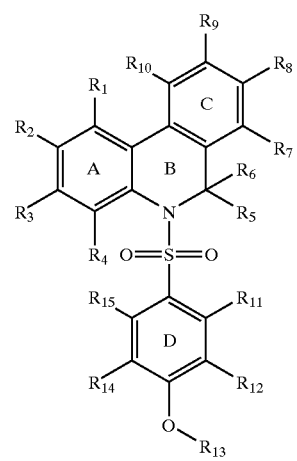

(I)

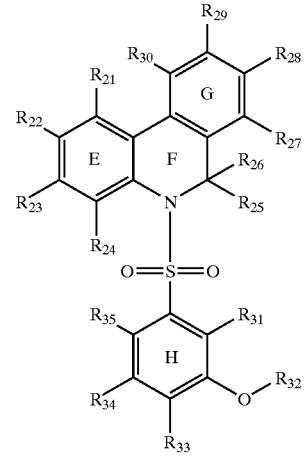

(II)

wherein $R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)

=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent R$_{p+1}$ or R$_{p-1}$ linked with an -alkylene-, or —X-alkylene- group;

R$_5$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, —CR(O), —CO$_2$R, or —C(O)N(R)$_2$; or R$_5$ may be taken together with either R$_6$ or R$_7$ and linked with an -alkylene- or —X-alkylene- group;

R$_6$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, —CR(O), —CO$_2$R, or —C(O)N(R)$_2$; or R$_6$ may be taken together with either R$_5$ or R$_7$ and linked with an -alkylene- or —X-alkylene- group;

R$_{13}$ is R, R$_{17}$—X—R$_{16}$—, R$_{17}$—S(O)—, R$_{17}$—S(O)$_2$—, —SO$_3$R, —S(O)$_2$N(R)$_2$, or D-glucuronidate;

R$_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

R$_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_2$–C$_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

X is O, —NR—, —S(O)$_m$—, —C(O)—, —OC(O)—, —C(O)O—, —NRC(O)—, or —C(O)NR—;

m is 0, 1, or 2;

p is 2, 3, 6, 7, 8, 9, 12, 13, or 14;

R$_{21}$, R$_{22}$, R$_{23}$, R$_{24}$, R$_{27}$, R$_{28}$, R$_{29}$, R$_{30}$, R$_{31}$, R$_{33}$, R$_{34}$, and R$_{35}$ are, independently, hydrogen, R$_{17}$; monofluoroalkyl, monofluoroalkenyl, aryl-R$_{16}$—, heteroaryl-R$_{16}$—, hydroxyalkyl, HO—R$_{16}$—, R$_{17}$—Y—R$_{16}$—, HS—R$_{16}$—, R$_{17}$—S(O)—, R$_{17}$—S(O)$_2$—, R$_{17}$—SO$_3$—, R$_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent R$_{q+1}$ or R$_{q-1}$ linked with an -alkylene-, or —Y-alkylene- group;

R$_{25}$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—Y—R$_{16}$—, HS—R$_{16}$—, —CR(O), —CO$_2$R, or —C(O)N(R)$_2$; or R$_{25}$ may be taken together with either R$_{26}$ or R$_{27}$ and linked with an -alkylene- or —Y-alkylene- group;

R$_{26}$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—Y—R$_{16}$—, HS—R$_{16}$—, —CR(O), —CO$_2$R, or —C(O)N(R)$_2$; or R$_{26}$ may be taken together with either R$_{25}$ or R$_{27}$ and linked with an -alkylene- or —Y-alkylene- group;

R$_{32}$ is R, R$_{17}$—Y—R$_{16}$—, R$_{17}$—S(O)—, R$_{17}$—S(O)$_2$—, —SO$_3$R, —S(O)$_2$N(R)$_2$, or D-glucuronidate;

Y is O, —NR—, —S(O)$_n$—, —C(O)—, —OC(O)—, —C(O)O—, —NRC(O)—, or —C(O)NR—;

n is 0, 1, or 2;

q is 22, 23, 26, 27, 28, 29, 32, 33, or 34;

or a pharmaceutically acceptable salt thereof, and a pharmaceutically acceptable carrier.

10. A method of treating chronic inflammatory disease in a mammal in need thereof, which comprises administering to said mammal an effective amount of a compound of claim 1.

11. A method of claim 10 wherein the said disease is rheumatoid arthritis, spondyloarthropathies, osteoarthritis, psoriatic arthritis, or juvenile arthritis.

12. A method of claim 10 wherein the said disease is inflammatory bowel disease, Crohn's disease, ulcerative colitis, or indeterminate colitis.

13. A method of claim 10 wherein the said disease is psoriasis.

14. A method of claim 10 wherein the said disease is asthma or chronic obstructive pulmonary disease.

15. A method of claim 10 wherein the said disease is sepsis.

16. The compound according to claim 2, wherein R$_{13}$ is —S(O)$_2$NH$_2$, or a pharmaceutically acceptable salt thereof.

17. The compound according to claim 5, wherein R$_{32}$ is —S(O)$_2$NH$_2$, or a pharmaceutically acceptable salt thereof.

18. A process comprising providing a sulfonamide of formula 37:

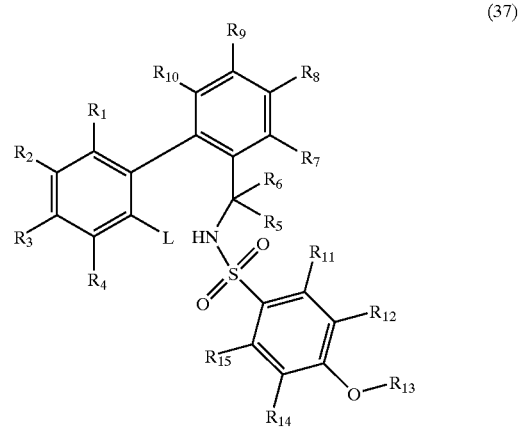

(37)

wherein

R$_1$, R$_2$, R$_3$, R$_4$, R$_7$, R$_8$, R$_9$, R$_{10}$, R$_{11}$, R$_{12}$, R$_{14}$, and R$_{15}$ are each, independently, hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, R$_{17}$—S(O)—, R$_{17}$—S(O)$_2$—, R$_{17}$—SO$_3$—, R$_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent R$_{p+1}$ or R$_{p-1}$ linked with an -alkylene-, or —X-alkylene- group;

R$_5$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—R$_{16}$—, —CR(O), —CO$_2$R, or —C(O)N(R)$_2$; or R$_5$ may be taken together with either R$_6$ or R$_7$ and linked with an -alkylene- or —X-alkylene- group;

R$_6$ is hydrogen, R$_{17}$, monofluoroalkyl, monofluoroalkenyl, aryl-R$_{16}$—, heteroaryl-R$_{16}$—, hydroxyalkyl, HO—R$_{16}$—, R$_{17}$—X—R$_{16}$—, HS—$R_{16}$—, —CR(O), —$CO_2R$, or —C(O)N(R)$_2$; or $R_6$ may be taken together with either $R_5$ or $R_7$ and linked with an -alkylene- or —X-alkylene- group;

$R_{13}$ is R, $R_{17}$—X—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-($C_2$-$C_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

X is O, —NR—, —S(O)$_m$—, —C(O)—, —OC(O)—, —C(O)O—, —NRC(O)—, or —C(O)NR—;

m is 0, 1, or 2; and p is 2, 3, 6, 7, 8, 9, 12, 13, or 14;

treating the sulfonamide of formula 37 with potassium carbonate to produce a phenanthridine of formula I:

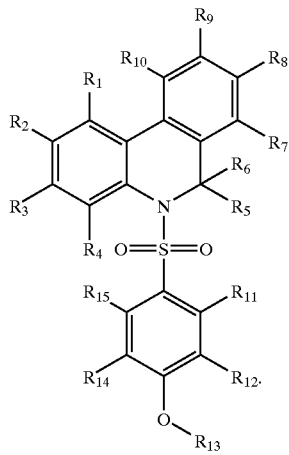

(I)

19. The process of claim 18 further comprising providing the S enantiomer of the biphenylamine of formula 36:

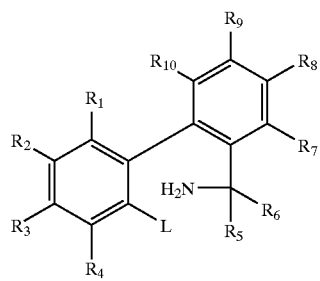

(36)

wherein
L is fluorine or chlorine; and
reacting the S enantiomer of the biphenylamine of formula 36 with a compound of formula 3 or an anhydride:

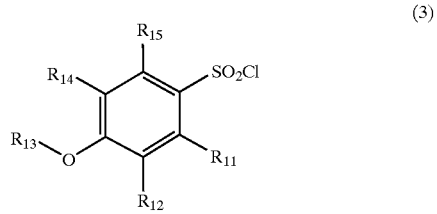

(3)

to produce a sulfonamide of formula 37.

20. The process of claim 19 further comprising providing a biphenylamine of formula 36:

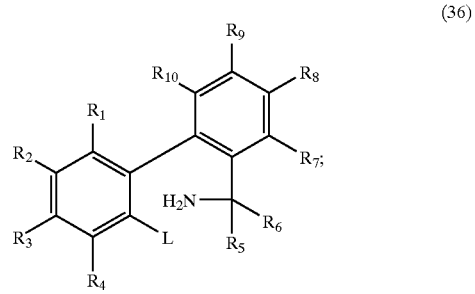

(36)

and
separating the biphenylamine of formula 36 into its respective enantiomers.

21. The process of claim 20 further comprising providing a compound of formula 35:

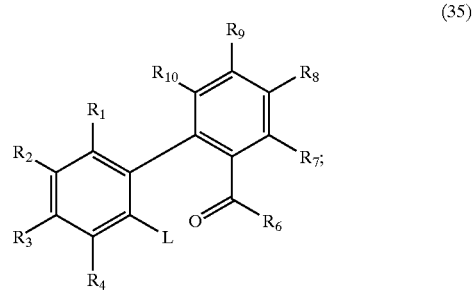

(35)

reacting the compound of formula 35 with an ammonium source optionally in the presence of an acid catalyst to produce an intermediate imine; and
reducing the intermediate imine with a hydride source to produce a biphenylamine of formula 36.

22. The process of claim 21 further comprising providing a compound of formula 33:

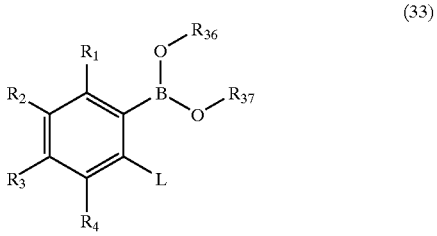

(33)

wherein
  $R_{36}$ and $R_{37}$ are, independently, hydrogen or ($C_1$–$C_4$) lower straight chain or ($C_3$–$C_6$) branched chain alkyl, or $R_{36}$ and $R_{37}$ are taken together to form a pinacol moiety; and reacting the compound of formula 33 in the presence of a coupling catalyst with a compound of formula 34:

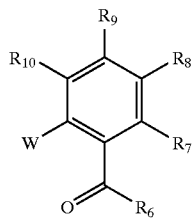

(34)

wherein
  W is a chlorine, bromine, or iodine atom, or a triflate (—$OSO_2CF_3$) moiety;
  to produce a compound of formula 35.

23. A process for preparing a compound of formula I:

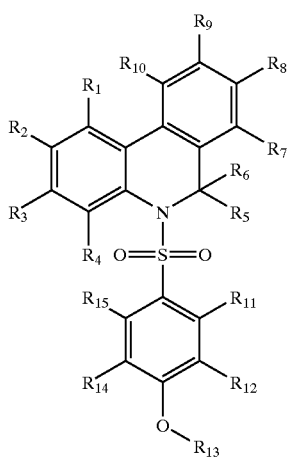

(I)

wherein
  $R_1$, $R_2$, $R_3$, $R_4$, $R_7$, $R_8$, $R_9$, $R_{10}$, $R_{11}$, $R_{12}$, $R_{14}$, and $R_{15}$ are each, independently, hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent $R_{p+1}$ or $R_{p-1}$ linked with an -alkylene-, or —X-alkylene- group;

$R_5$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, —CR(O), —CO$_2$R, or —C(O)N(R)$_2$; or $R_5$ may be taken together with either $R_6$ or $R_7$ and linked with an -alkylene- or —X-alkylene- group;

$R_6$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—X—$R_{16}$—, HS—$R_{16}$—, —CR(O), —CO$_2$R, or —C(O)N(R)$_2$; or $R_6$ may be taken together with either $R_5$ or $R_7$ and linked with an -alkylene- or —X-alkylene- group;

$R_{13}$ is R, $R_{17}$—X—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-($C_2$–$C_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

X is O, —NR—, —S(O)$_m$—, —C(O)—, —OC(O)—, —C(O)O—, —NRC(O)—, or —C(O)NR—;

m is 0, 1, or 2; and p is 2, 3, 6, 7, 8, 9, 12, 13, or 14;

comprising
  reacting a compound of formula 33:

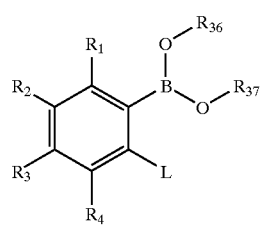

(33)

wherein
  L is fluorine or chlorine; and $R_{36}$ and $R_{37}$ are, independently, hydrogen or ($C_1$–$C_4$) lower straight chain or ($C_3$–$C_6$) branched chain alkyl, or $R_{36}$ and $R_{37}$ are taken together to form a pinacol moiety;

in the presence of a coupling catalyst with a compound of formula 34:

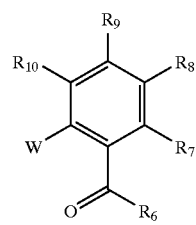

(34)

wherein
  W is a chlorine, bromine, or iodine atom, or a triflate (—$OSO_2CF_3$) moiety;

to produce a compound of formula 35:

(35)

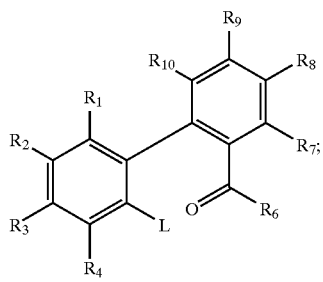

reacting the compound of formula 35 with an ammonium source optionally in the presence of an acid catalyst to produce an intermediate imine;
reducing the intermediate imine with a hydride source to produce a biphenylamine of formula 36:

(36)

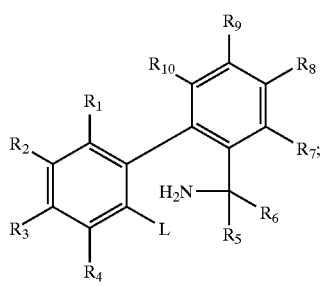

separating the biphenylamine of formula 36 into its respective enantiomers;
reacting the S enantiomer of the biphenylamine of formula 36 with a compound of formula 3 or an anhydride:

(3)

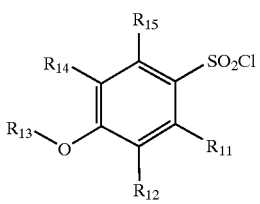

to produce a sulfonamide of formula 37:

(37)

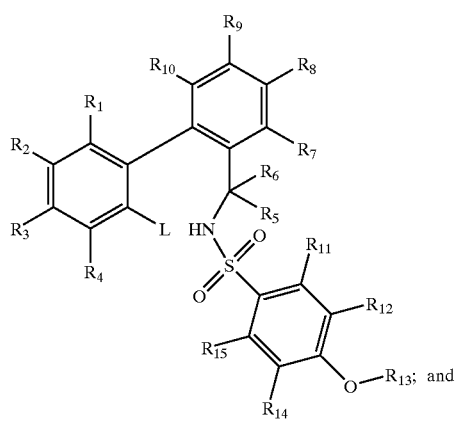

treating the sulfonamide of formula 37 with potassium carbonate to produce a phenanthridine of formula I:

(I)

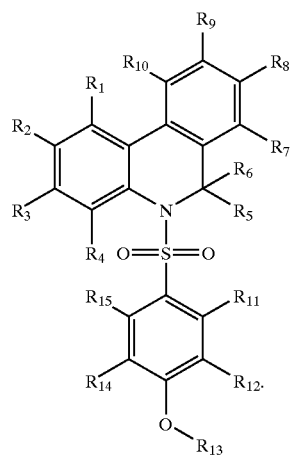

24. A process comprising providing a sulfonamide of formula 37a:

(37a)

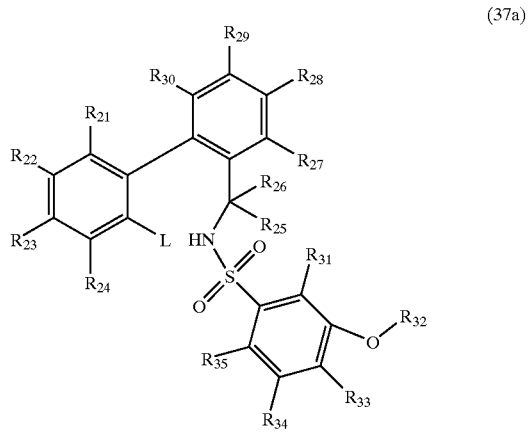

wherein $R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are, independently, hydrogen, $R_{17}$; monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent $R_{q+1}$ or $R_{q-1}$ linked with an -alkylene-, or —Y-alkylene- group;

$R_{25}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{25}$ may be taken together with either $R_{26}$ or $R_{27}$ and linked with an -alkylene- or —Y-alkylene- group;

$R_{26}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{26}$ may be taken together with either $R_{25}$ or $R_{27}$ and linked with an -alkylene- or —Y-alkylene- group;

$R_{32}$ is R, $R_{17}$—Y—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_2$–C$_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

Y is O, —NR—, —S(O)$_n$—, —C(O)—, —OC(O)—, —C(O)O—, —NRC(O)—, or —C(O)NR—;

n is 0, 1, or 2;

q is 22, 23, 26, 27, 28, 29, 32, 33, or 34; and
treating the sulfonamide of formula 37a with potassium carbonate to produce a phenanthridine of formula II:

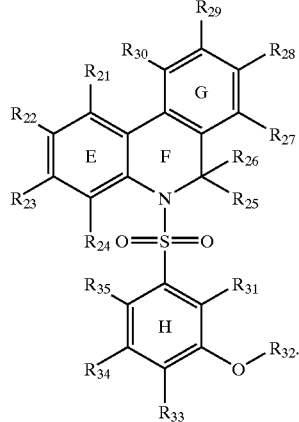

(II)

25. The process of claim 24 further comprising providing the S enantiomer of the biphenylamine of formula 36a:

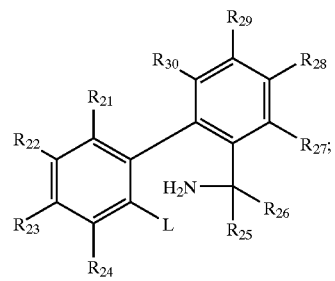

(36a)

wherein
L is fluorine or chlorine; and
reacting the S enantiomer of the biphenylamine of formula 36a with a compound of formula 32 or an anhydride:

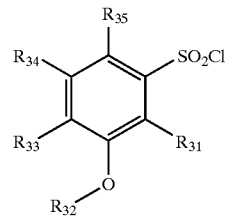

(32)

to produce a sulfonamide of formula 37a.

26. The process of claim 25 further comprising providing a biphenylamine of formula 36a:

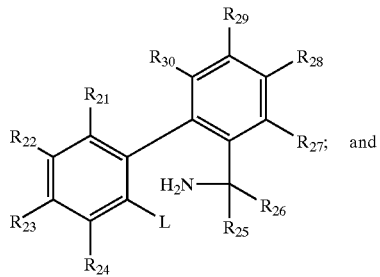

(36a)

and separating the biphenylamine of formula 36a into its respective enantiomers.

27. The process of claim 26 further comprising providing a compound of formula 35a:

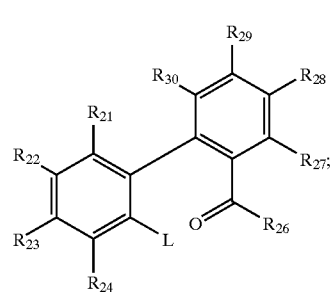

(35a)

reacting the compound of formula 35a with an ammonium source optionally in the presence of an acid catalyst to produce an intermediate imine; and reducing the intermediate imine with a hydride source to produce a biphenylamine of formula 36a.

28. The process of claim 27 further comprising providing a compound of formula 33a:

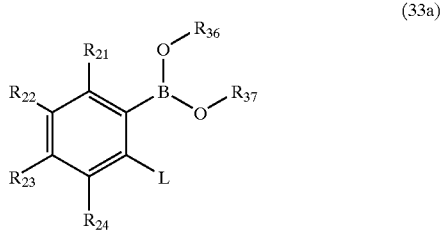

(33a)

wherein $R_{36}$ and $R_{37}$ are, independently, hydrogen or ($C_1$–$C_4$) lower straight chain or ($C_3$–$C_6$) branched chain alkyl, or $R_{36}$ and $R_{37}$ are taken together to form a pinacol moiety; and reacting the compound of formula 33a in the presence of a coupling catalyst with a compound of formula 34a:

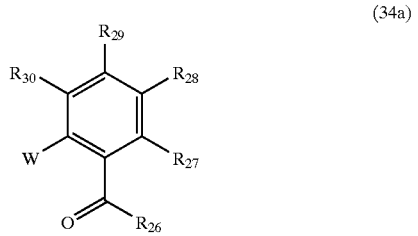

(34a)

wherein

W is a chlorine, bromine, or iodine atom, or a triflate (—OSO$_2$CF$_3$) moiety;

to produce a compound of formula 35a.

29. A process for preparing a compound of formula II:

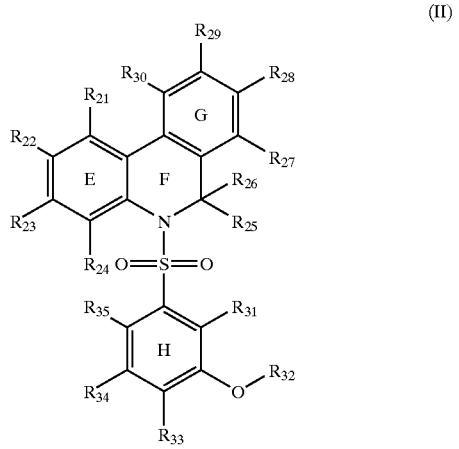

(II)

wherein $R_{21}$, $R_{22}$, $R_{23}$, $R_{24}$, $R_{27}$, $R_{28}$, $R_{29}$, $R_{30}$, $R_{31}$, $R_{33}$, $R_{34}$, and $R_{35}$ are, independently, hydrogen, $R_{17}$; monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, $R_{17}$—S(O)—, $R_{17}$—S(O)$_2$—, $R_{17}$—SO$_3$—, $R_{17}$—S(O)$_2$NR—, —N(R)$_2$, —NR—C(NH$_2$)=NR, cyano, nitro, halogen, —OR, —SR, —SO$_3$R, —S(O)$_2$N(R)$_2$, —C(O)R, —C(R)=N—OR, —C(NH$_2$)=NR, —CO$_2$R, —OC(O)R, or —C(O)N(R)$_2$; or are taken together with either an adjacent $R_{q+1}$ or $R_{q-1}$ linked with an -alkylene-, or —Y-alkylene- group;

$R_{25}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{25}$ may be taken together with either $R_{26}$ or $R_{27}$ and linked with an -alkylene- or —Y-alkylene- group;

$R_{26}$ is hydrogen, $R_{17}$, monofluoroalkyl, monofluoroalkenyl, aryl-$R_{16}$—, heteroaryl-$R_{16}$—, hydroxyalkyl, HO—$R_{16}$—, $R_{17}$—Y—$R_{16}$—, HS—$R_{16}$—, —CR(O), —CO$_2$R, or —C(O)N(R)$_2$; or $R_{26}$ may be taken together with either $R_{25}$ or $R_{27}$ and linked with an -alkylene- or —Y-alkylene- group;

$R_{32}$ is R, $R_{17}$—Y—$R_{16}$—, $R_{17}$—S(O)—, $R_{17}$—S(O)$_2$—, —SO$_3$R, —S(O)$_2$N(R)$_2$, or D-glucuronidate;

$R_{16}$ is -alkylene-, -cycloalkylene-, -alkylene-X-alkylene-, -alkylene-X-cycloalkylene-, -cycloalkylene-X-alkylene-, or -cycloalkylene-X-cycloalkylene-;

$R_{17}$ is alkyl, aryl, heteroaryl, cycloalkyl, alkenyl, cycloalkenyl, alkynyl, alkenyl-X-alkylene-, cycloalkenyl-X-alkylene-, or perfluoroalkyl;

R is, independently, hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-($C_2$–$C_6$)alkyl, alkoxyalkyl, alkylthioalkyl, formyl, acyl, alkoxycarbonyl, —C(O)NH$_2$, alkylaminocarbonyl, dialkylaminocarbonyl, alkylaminoalkyl, or dialkylaminoalkyl; or when an atom contains two R groups, the R groups may be taken together linked with an -alkylene- group;

Y is O, —NR—, —S(O)$_n$—, —C(O)—, —OC(O)—, —C(O)O—, —NRC(O)—, or —C(O)NR—;

n is 0, 1, or 2;

q is 22, 23, 26, 27, 28, 29, 32, 33, or 34; and comprising reacting a compound of formula 33a:

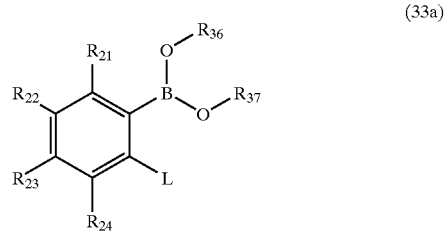

(33a)

wherein

L is fluorine or chlorine; and $R_{36}$ and $R_{37}$ are, independently, hydrogen or ($C_1$–$C_4$) lower straight chain or ($C_3$–$C_6$) branched chain alkyl, or $R_{36}$ and $R_{37}$ are taken together to form a pinacol moiety;

in the presence of a coupling catalyst with a compound of formula 34a:

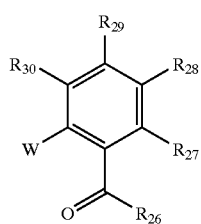
(34a)

wherein

W is a chlorine, bromine, or iodine atom, or a triflate (—OSO$_2$CF$_3$) moiety;

to produce a compound of formula 35a:

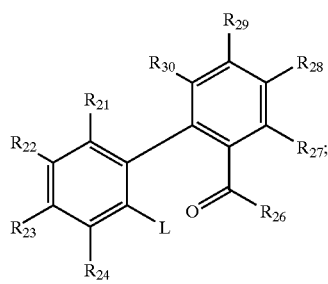
(35a)

reacting the compound of formula 35a with an ammonium source optionally in the presence of an acid catalyst to produce an intermediate imine;

reducing the intermediate imine with a hydride source to produce a biphenylamine of formula 36a:

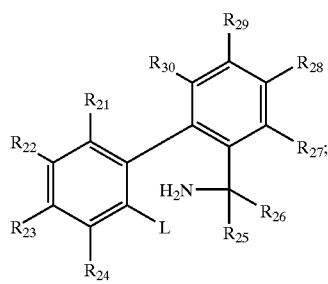
(36a)

separating the biphenyl amine of formula 36a into its respective enantiomers;

reacting the S enantiomer of the biphenylamine of formula 36a with a compound of formula 32 or an anhydride:

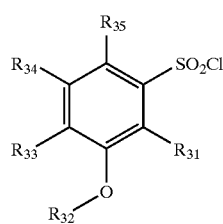
(32)

to produce a sulfonamide of formula 37a:

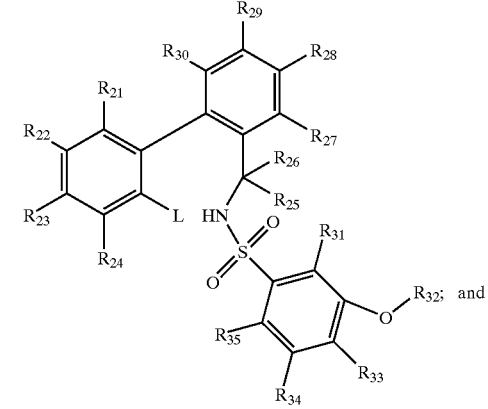
(37a)

treating the sulfonamide of formula 37a with potassium carbonate to produce a phenanthridine of formula II:

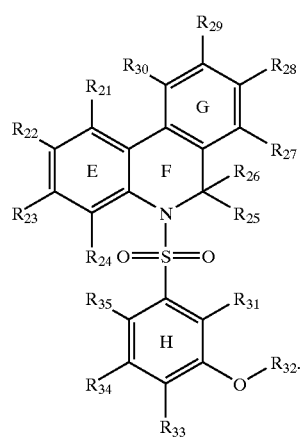
(II)

\* \* \* \* \*